US012560609B2

(12) United States Patent
Haq et al.

(10) Patent No.: US 12,560,609 B2
(45) Date of Patent: Feb. 24, 2026

(54) BIOMARKERS PREDICTIVE OF CANCER CELL RESPONSE TO ML329 OR A DERIVATIVE THEREOF

(71) Applicants: Dana-Farber Cancer Institute, Inc., Boston, MA (US); The General Hospital Corporation, Boston, MA (US); University of Kansas, Lawrence, KS (US)

(72) Inventors: Rizwan Haq, Boston, MA (US); David Fisher, Newton, MA (US); Frank Schoenen, Lawrence, KS (US)

(73) Assignees: Dana-Farber Cancer Institute, Inc., Boston, MA (US); The General Hospital Corporation, Boston, MA (US); University of Kansas, Lawrence, KS (US)

( * ) Notice: Subject to any disclaimer, the term of this patent is extended or adjusted under 35 U.S.C. 154(b) by 1180 days.

(21) Appl. No.: 17/294,475

(22) PCT Filed: Nov. 25, 2019

(86) PCT No.: PCT/US2019/063072

§ 371 (c)(1),
(2) Date: May 17, 2021

(87) PCT Pub. No.: WO2020/112672

PCT Pub. Date: Jun. 4, 2020

(65) Prior Publication Data

US 2022/0128562 A1 Apr. 28, 2022

Related U.S. Application Data

(60) Provisional application No. 62/935,386, filed on Nov. 14, 2019, provisional application No. 62/775,181, filed on Dec. 4, 2018, provisional application No. 62/771,429, filed on Nov. 26, 2018.

(51) Int. Cl.

| | |
|---|---|
| *G01N 33/574* | (2006.01) |
| *A61K 31/18* | (2006.01) |
| *G01N 33/68* | (2006.01) |

(52) U.S. Cl.
CPC ........... *G01N 33/574* (2013.01); *A61K 31/18* (2013.01); *G01N 33/6875* (2013.01); *G01N 2333/90209* (2013.01)

(58) Field of Classification Search
CPC ............. G01N 33/574; G01N 33/6875; G01N 2333/90209; G01N 2800/52; A61K 31/18
See application file for complete search history.

(56) References Cited

U.S. PATENT DOCUMENTS

| | | | |
|---|---|---|---|
| 6,406,699 | B1 | 6/2002 | Wood |
| 2017/0334842 | A1 | 11/2017 | Faloon et al. |
| 2022/0128562 | A1 | 4/2022 | Haq et al. |

FOREIGN PATENT DOCUMENTS

| | | | | |
|---|---|---|---|---|
| WO | WO-2014201016 A2 * | 12/2014 | | ......... A61K 31/4184 |
| WO | WO-2020/112672 A1 | 6/2020 | | |

OTHER PUBLICATIONS

Faloon et al., "A Small Molecule Inhibitor of the MITF Molecular Pathway." Probe Reports from the NIH Molecular Libraries Program. Bethesda (MD): National Center for Biotechnology Information (US) (Sep. 18, 2014).
Taguchi et al., "The KEAP1-NRF2 system in cancer." Frontiers in Oncology 7 (2017): 85.
Glorieux et al., "Overexpression of NAD(P)H:quinone oxidoreductase 1 (NQO1) and genomic gain of the NQO1 locus modulates breast cancer cell sensitivity to quinones," Life Sciences, 145:57-65 (2016).
International Search Report and Written Opinion for International Application No. PCT/US19/63072 dated Apr. 9, 2020.
Invitation to Pay Additional Fees for International Application No. PCT/US19/63072 dated Feb. 12, 2020.
Phillips et al., "Pharmacological and biological evaluation of a series of substituted 1,4-naphthoquinone bioreductive drugs," Biochemical Pharmacology, 68(11):2107-2116 (2004).

* cited by examiner

*Primary Examiner* — Shafiqul Haq
(74) *Attorney, Agent, or Firm* — Foley Hoag LLP; DeAnn F. Smith; Philip S. Choi

(57) ABSTRACT

The present invention is based in part on the identification of biomarkers, including NQO1, NRF2 and KEAP1, predictive of cancer cell responsiveness to treatment with ML 329 or a derivative thereof.

12 Claims, 60 Drawing Sheets

Specification includes a Sequence Listing.

| | pert_iname | Lineage | odds_ratio | adjusted_p_value |
|---|---|---|---|---|
| 1 | ML329 | skin | 4.2143102887163 | 0.0105206336188807 |

FIG. 7B

| | | Immobilized/Input (Fold Enrichment) | | Immobilized/(Immobilized+Soluble) (Fold Enrichment) | |
|---|---|---|---|---|---|
| Reference | Protein Description | Replicate 1 | Replicate 2 | Replicate 1 | Replicate 2 |
| PIR_HUMAN | Pirin | 3.5 | 4.3 | 17.6 | 21.8 |
| CSK2B_HUMAN | Casein kinase II subunit beta | 2.8 | 3.5 | 8.8 | 9.2 |
| CSK22_HUMAN | Casein kinase II subunit alpha | 2.6 | 3.5 | 5.6 | 5.8 |
| E9PG82_HUMAN | Sorcin | 2.0 | 2.2 | 1.7 | 1.6 |
| Cutoff | | ≥ 2.0 | | ≥ 2.0 | ≥ 2.0 |

Kinetic Analysis of Cylene Compounds CX-4945, CX-5011, and CX-5279[a]

| | | IC$_{50}$ (nM) | | | | | |
|---|---|---|---|---|---|---|---|
| compd | name | nCK2 | CK2$\alpha$ | CK2$\alpha$ dm (V66I174AA) | CK2$\alpha$ (V66A) | CK2$\alpha$ (I174A) | PIM1 |
| CX-4945 | sodium 5-(3-chloroanilino)pyrido[4,5-c]quinoline-8-carboxylic acid | 2.50 | 1.50 | 15.00 | 13.5 | 3.51 | 216.00 | quinone hydroquinone

ML329

| Protein Description | Immobilized/(Immobilized+Soluble) Replicate 2 | Replicate 3 |
|---|---|---|
| Pirin | 17.6 | 21.8 |
| Casein kinase II subunit beta | 8.8 | 9.2 |
| Casein kinase II subunit alpha | 5.6 | 5.8 |
| Sorcin | 1.7 | 1.6 |

ML329 (IC50 = 1.2 µM)

BRD-K45681478 (IC50 = 2.7 µM)

FIG. 28B

| | Reference | Protein Description | Immobilized/Input (Fold Enrichment) | | Immobilized/(Immobilized+Soluble) (Fold Enrichment) | |
|---|---|---|---|---|---|---|
| | | | Replicate 1 | Replicate 2 | Replicate 1 | Replicate 2 |
| | PIR_HUMAN | Pirin | 3.5 | 4.3 | 17.6 | 21.8 |
| CK2 complex | CSK2B_HUMAN | Casein kinase II subunit beta | 2.8 | 3.5 | 8.8 | 9.2 |
| CK2 complex | CSK22_HUMAN | Casein kinase II subunit alpha prime | 2.6 | 3.5 | 5.6 | 5.8 |
| CK2 complex | E9PG82_HUMAN | Sorcin | 2.0 | 2.2 | 1.7 | 1.6 |
| | Cutoff | | ≥ 2.0 | | ≥ 2.0 | ≥ 2.0 |

FIG. 29F

| Cell line | | Mutation | $IC_{50}$ | | | | |
|---|---|---|---|---|---|---|---|
| | | | ML-329 | KUC114361 | KUC114362 | KUC114363 | KUC114393 |
| SKMEL5 | Melanoma | BRAF V600E | ~ 200 nM | No effect | < 1 μM | ~ 500 nM | No effect |
| UACC257 | Melanoma | BRAF V600E | ~ 1 μM | No effect | ~ 2 μM | ~ 1 μM | No effect |
| MEWO | Melanoma | WT for BRAF/NRAS | ~ 3 μM | No effect | ~ 3 μM | No effect | No effect |
| IPC298 | Melanoma | NRAS Q61L | > 3 μM | No effect | ~ 3 μM | No effect | No effect |
| U2OS | non-melanoma (Sarcoma) | WT for BRAF/NRAS | No effect | No effect | No effect | No effect | No effect |

Napabucasin (STAT3i)

17-AAG (HSP90i)

FIG. 29V

| STRUCTURE | SMILES | Molecular Formula (including salts) | Molecular Weight |
|---|---|---|---|
| 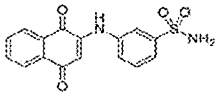 | O=C1C(NC2=CC=CC(S(N)(=O)=O)=C2)=CC (C3=CC=CC= C31)=O | C16H12N2O4S | 328.34 |
| 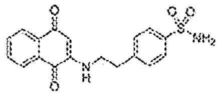 | O=C1C=C(NCCC2=CC=C(S( N)(=O)=O)C=C2)C(C3=CC= CC=C31)=O | C18H16N2O4S | 356.39 |
| 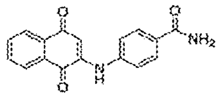 | O=C1C=C(NC2=CC=C(C(N)=O)C=C2)C( C3=CC=CC=C31 )=O | C17H12N2O3 | 292.29 |
| 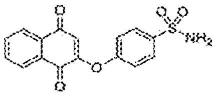 | O=C1C=C(OC2=CC=C(S( N)(=O)=O)C=C2)C(C3=CC=CC =C31)=O | C16H11NO5S | 329.32 |
| 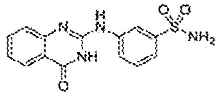 | O=C1C2=CC=CC=C2N=C(NC3=CC=CC(S( N)(=O)=O)=C3 )N1 | C14H12N4O3S | 316.33 |
| 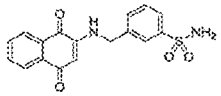 | O=C1C(NCC2=CC(S( N)(=O)=O)=CC=C2)=CC(C3=CC=C C=C3 1)=O | C17H14N2O4S | 342.37 |
| 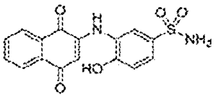 | O=C1C(NC2=C(O)C=CC(S( N)(=O)=O)=C2)=CC(C3=CC= CC=C31)=O | C16H12N2O5S | 344.34 |
| 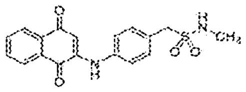 | O=C1C=C(NC2=CC=C(CS( NC)(=O)=O)C=C2)C(C3=CC= CC=C31)=O | C18H16N2O4S | 356.4 |

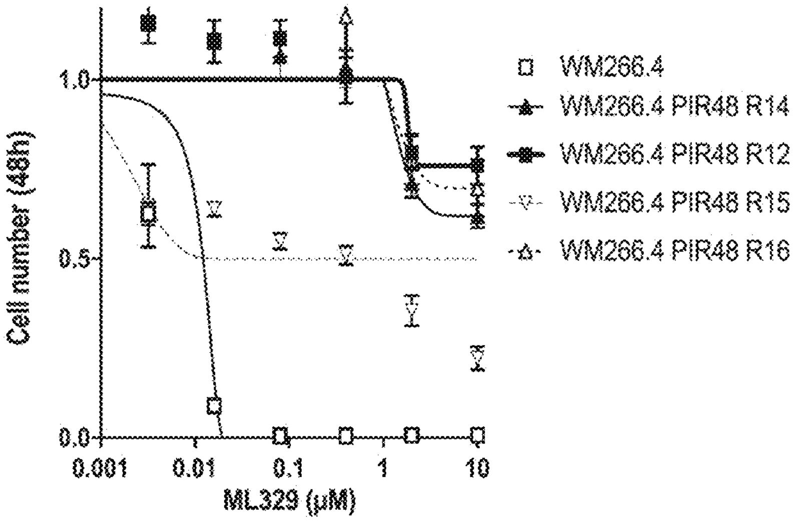
FIG. 32G
FIG. 32H
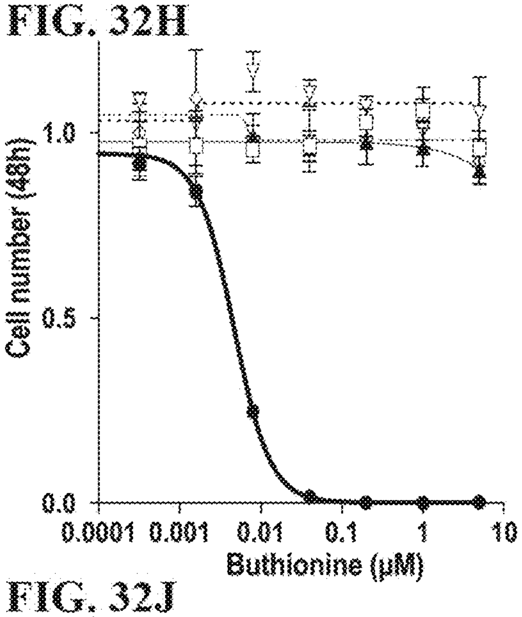
FIG. 32I
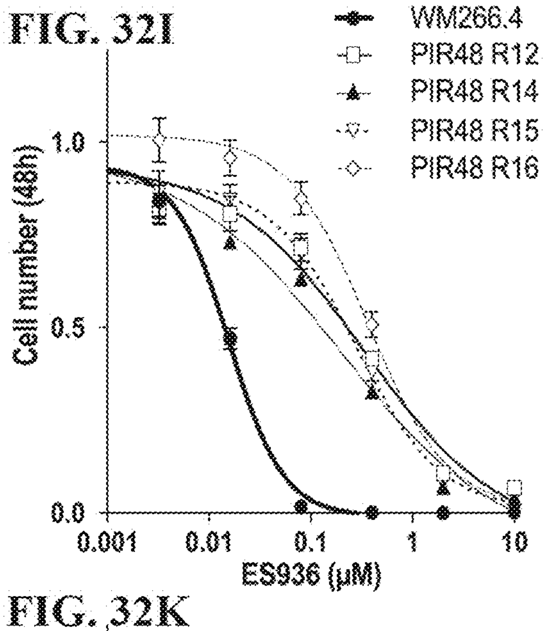
FIG. 32J
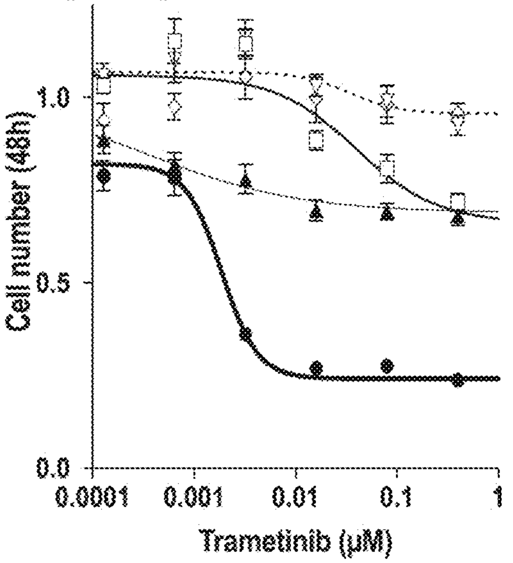
FIG. 32K
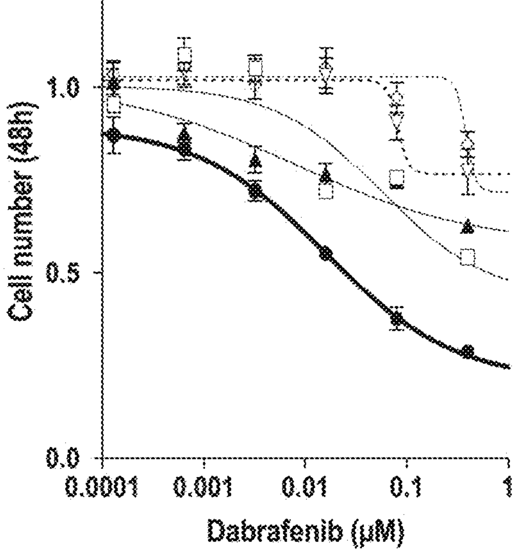

BIOMARKERS PREDICTIVE OF CANCER CELL RESPONSE TO ML329 OR A DERIVATIVE THEREOF

CROSS-REFERENCE TO RELATED APPLICATIONS

This application is the U.S. national phase of International Patent Application No. PCT/US2019/063072, filed on 25 Nov. 2019, which claims the benefit of priority to U.S. Provisional Application Ser. No. 62/771,429, filed on 26 Nov. 2018; U.S. Provisional Application Ser. No. 62/775,181, filed on 4 Dec. 2018; and U.S. Provisional Application Ser. No. 62/935,386, filed on 14 Nov. 2019; the entire contents of each of said applications are incorporated herein in their entirety by this reference.

STATEMENT OF RIGHTS

This invention was made with government support under grant number HG005031 awarded by The National Institutes of Health. The government has certain rights in the invention.

BACKGROUND OF THE INVENTION

ML329 (4-[(1,4-dioxo-1,4-dihydronapthalen-2-yl)amino]benzenesulfonamide) is a small molecule that was initially identified as an inhibitor of microphthalmia-associated transcription factor (MITF) (Faloon et al. (2012) *Probe Reports from the NIH Molecular Libraries Program* [Internet]. Bethesda (Md.). National Center for Biotechnoogy Information (US); 2010-2012 Dec. 13 [Updated 2014 Sep. 18]). However, the mechanism of action of ML329 is unknown such that, for example, biomarker(s) useful for selecting subjects responsive to ML329 are unknown. Accordingly, there is a great need to identify the mechanism of action of ML329 in cancers in order to develop improved diagnostic, prognostic, and therapeutic strategies.

SUMMARY OF THE INVENTION

The present invention is based, at least in part, on the discovery of the mechanism of action by which ML329 and derivatives thereof selectively inhibit the hyperproliferation of cancer cells (e.g., kills cancer cells) by being selectively converted in certain cancer cells into an active form. In particular, it is described herein that ML329 and derivatives thereof are bioreduced by an enzyme, NAD(P)H quinone dehydrogenase 1 (NQO1), which is preferentially expressed in some cancer types. The bioreduction is required to convert ML329 and derivatives thereof into an active form. ML329 associates with the protein kinase, casein kinase II (CK2), which is an essential kinase and its reduction/inhibition is lethal (Litchfield et al. (2003) *Biochem. J.* 369:1-15). NQO1 is necessary and sufficient for the activation of ML329 and derivatives thereof, thus enabling selective targeting of the essential kinase, CK2, to desired cancer cells with high NQO1 expression and/or avoiding effects on undesired cells (e.g., cells other than desired target cancer cells of interest, such as non-cancerous normal cells). It is further described that NQO1 is highly expressed in the context of inactivating mutations in kelch-like ECH-associated protein 1 (KEAP1). The KEAP1/NRF2 pathway is commonly mutated in many tumor types, including lung and renal cell carcinomas, but not melanoma. Moreover, it is determined herein that ML329 binds to CK2alpha and CK2alpha prime (two subunits of the CK2 holoenzyme) in vitro and inhibits CK2 activity in an ATP-competitive manner. Thus, ML329 is an ATP-competitive inhibitor of the pan-essential kinase CK2, but requires metabolic activation that preferentially occurs in cells with activated NRF2 signaling. Collectively, the description provided herein establishes the basis for the development of ML329 or its derivatives as an approach to target a clinically relevant pathway in cancer, such as melanoma, and further identifies the KEAP/NRF2 pathway as being activated in most melanomas via a non-genomic mechanism. Based on the results described herein, it is believed that NRF2-dysregulated tumors, including melanoma, are targets for therapeutic, diagnostic, and prognostic purposes with ML329.

Accordingly, biomarkers (e.g., NQO1, NRF2 and/or inhibiting mutations thereof, and/or KEAP1 and/or inhibiting mutations thereof) are provided that predict responsiveness to treatment with ML329 or a derivative thereof, in cancer cells. Also provided are methods for stratifying subjects who are predicted to be responsive to ML329 or a derivative thereof based upon a determination and analysis of such biomarkers according to amount (e.g., copy number or level of expression) and/or activity, such as loss or gain of function, relative to a control. Such analyses can be used to perform a number of diagnostic and prognostic assays described herein, either alone or in combination with useful therapeutic regimens (e.g., based on predictions of clinical response, subject survival or relapse, timing of adjuvant or neoadjuvant treatment, etc.). The biomarker amount and/or activity can be absolute, such as a determination of a value, or relative, such as by a relative increase in NRF2 subcellularly localized nuclear amounts relative to cytoplasmic amounts.

In one aspect, a method of identifying the likelihood of reducing hyperproliferation of a cancer cell contacted with ML329 or a derivative thereof, the method comprising: a) obtaining or providing a sample comprising cancer cell; b) measuring the presence, copy number, amount, and/or activity of i) at least one biomarker listed in Table 1A and/or ii) at least one biomarker listed in Table 1B in the sample; and c) comparing the presence, copy number, amount, and/or activity of i) the at least one biomarker listed in Table 1A and/or ii) the at least one biomarker listed in Table 1B in a control, wherein the absence of or a significantly decreased amount or activity of the at least one biomarker listed in Table 1A in the sample and/or the presence of or a significantly increased amount or activity of the at least one biomarker listed in Table 1B thereof in the sample relative to the control sample identifies the cancer cell as being less likely to be responsive to ML329 or a derivative thereof; or wherein the presence of or a significantly increased amount or activity of the at least one biomarker listed in Table 1A in the subject sample and/or the absence of or a decreased amount or activity of the at least one biomarker listed in Table 1B in the sample relative to the control sample identifies the cancer cell as being more likely to be responsive to ML329 or a derivative thereof, is provided.

Numerous embodiments are further provided that can be applied to any aspect of the present invention described herein. For example, in one embodiment, the methods described herein further comprise contacting the cancer cell with ML329 or the derivative thereof if the cancer cell is determined likely to be responsive to ML329 or the derivative thereof or contacting the cancer cell with an anti-cancer therapy other than ML329 or the derivative thereof as a single agent if the cancer cell is determined to be less likely to be responsive to ML329 or the derivative thereof. In another embodiment, the anti-cancer therapy other than ML329 or the derivative thereof as a single agent comprises ML329 or the derivative thereof. In still another embodiment, the anti-cancer therapy is selected from the group consisting of targeted therapy, chemotherapy, radiation therapy, and/or hormonal therapy. In yet another embodiment, the anti-cancer therapy contacts the cancer cell in combination with ML329 or the derivative thereof, optionally wherein the anti-cancer therapy contacts the cancer cell before, after, or concurrently with ML329 or the derivative thereof. In another embodiment, the targeted therapy is an immunotherapy. In still another embodiment, the immunotherapy is cell-based. In yet another embodiment, the immunotherapy comprises a cancer vaccine and/or virus. In another embodiment, the immunotherapy inhibits an immune checkpoint. In still another embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR. In yet another embodiment, the immune checkpoint is PD-1, PD-L1, or CTLA-4. In another embodiment, the contacting occurs in vivo, ex vivo, or in vitro. In still another embodiment, the cancer cell has a KEAP1 loss-of-function mutation. In yet another embodiment, the KEAP1 loss-of-function mutation is a coding region mutation, or a mutation at the corresponding amino acid in the human KEAP1 protein or ortholog thereof. In another embodiment, the cancer is selected from the group consisting of melanoma, lung cancer, head and neck squamous cell carcinomas, kidney cancer, pancreas cancer, prostate cancer, bladder cancer, uterine cancer, head and neck cancer, and esophagus cancer. In still another embodiment, the sample is from a subject afflicted with cancer. In yet another embodiment, the control is determined from a cancerous or non-cancerous sample from a subject. In another embodiment, the control is determined from a cancerous or non-cancerous sample from a member of the same species to which the subject belongs. In still another embodiment, the control is a reference value. In yet another embodiment, the control comprises cells, optionally wherein the cells are cancer cells. In another embodiment, the control sample comprises cancer cells that are responsive to ML329 or the derivative thereof.

In another aspect, a method of assessing the efficacy of ML329 or a derivative thereof for treating a cancer in a subject or prognosing progression of a cancer in a subject, the method comprising: a) detecting in a subject sample comprising cancer cells at a first point in time the presence, copy number, amount, and/or activity of i) at least one biomarker listed in Table 1A and/or ii) at least one biomarker listed in Table 1B; b) repeating step a) during at least one subsequent point in time after administration of ML329 or the derivative thereof; and c) comparing the presence, copy number, amount, and/or activity of i) the at least one biomarker listed in Table 1A and/or ii) the at least one biomarker listed in Table 1B from steps a) and b), wherein the absence of or a significantly decreased amount or activity of i) the at least one biomarker listed in Table 1A and/or ii) the at least one biomarker listed in Table 1B in the cancer cells of the subsequent sample, relative to the sample at the first point in time, indicates that ML329 or the derivative thereof does not treat the cancer in the subject; and wherein the presence of or a significantly increased amount or activity of i) the at least one biomarker listed in Table 1A and/or ii) the at least one biomarker listed in Table 1B in the subsequent sample, relative to the sample at the first point in time, indicates that ML329 or the derivative thereof treats the cancer in the subject, is provided.

As described above, embodiments are applicable to any method described herein. For example, in one embodiment, between the first point in time and the subsequent point in time, the subject has undergone treatment, completed treatment, and/or is in remission for the cancer. In another embodiment, the first and/or at least one subsequent sample is selected from the group consisting of ex vivo and in vivo samples. In still another embodiment, the first and/or at least one subsequent sample is obtained from an animal model of the cancer. In yet another embodiment, the first and/or at least one subsequent sample is a portion of a single sample or pooled samples obtained from the subject. In another embodiment, the sample comprises cells, cell lines, histological slides, paraffin embedded tissue, fresh frozen tissue, fresh tissue, biopsies, blood, plasma, serum, buccal scrape, saliva, cerebrospinal fluid, urine, stool, mucus, bone marrow, peritumoral tissue, and/or intratumoral tissue obtained from the subject. In still another embodiment, the methods described herein further comprise determining responsiveness to ML329 or the derivative thereof by measuring at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In yet another embodiment, the methods described herein further comprise recommending, prescribing, or administering ML329 or the derivative thereof to the subject if ML329 or the derivative thereof is determined to treat the cancer in the subject. In another embodiment, the methods described herein further comprise recommending, prescribing, or administering a therapy other than ML329 or the derivative thereof as a single agent to the subject if ML329 or the derivative thereof is determined not to treat the cancer in the subject.

In still another aspect, a cell-based assay for screening for anti-CK2 agents that have a selective cytotoxic or cytostatic effect on cancer cells expressing i) at least one biomarker listed in Table 1A and/or ii) at least one biomarker listed in Table 1B comprising contacting the cancer cells with an anti-CK2 test agent, and determining the ability of the test agent to reduce the viability or proliferation of the cancer cells relative to control cancer cells that express reduced or none of i) the at least one biomarker listed in Table 1A and/or ii) the at least one biomarker listed in Table 1B, is provided.

As described above, certain embodiments are applicable to any method described herein. For example, in one embodiment, the control is determined from a cancerous or non-cancerous sample from a subject or a member of the same species to which the subject belongs.

In another embodiment, the control is a reference value. In still another embodiment, the control sample comprises cancer cells lacking functional NQO1 (e.g., NQO1-deleted cells) and/or cancer cells that are not responsive to ML329 or a derivative thereof. In yet another embodiment, the cancer cell is isolated from an animal model of cancer, or a human patient afflicted with cancer. In another embodiment, the step of contacting occurs in vivo, ex vivo, or in vitro. In still another embodiment, the agent is administered in a pharmaceutically acceptable formulation. In yet another embodiment, the cancer or the cancer cell has a KEAP1 loss-of-function mutation. In another embodiment, the KEAP1 loss-of-function mutation is a coding region mutation, or a mutation at the corresponding amino acid in the human KEAP1 protein or ortholog thereof. In still another embodiment, the cancer is selected from the group consisting of melanoma, lung cancer, head and neck squamous cell carcinomas, kidney cancer, pancreas cancer, prostate cancer, bladder cancer, uterine cancer, head and neck cancer, and esophagus cancer. In yet another embodiment, the ML329 derivative has a Formula:

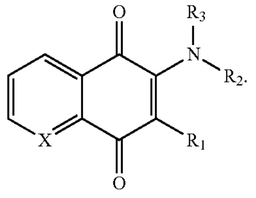

wherein: (i) X is CH; $R_1$ is hydrogen, halogen, optionally substituted heterocycloalkyl, optionally substituted heteroaryl, optionally substituted aryl, optionally substituted alkoxy, optionally substituted lower alkyl, amino, optionally substituted alkylamino, optionally substituted dialkylamino, —$NHCH_2CH{=}CH_2$, or $CH_2CH{=}CH_2$; $R_2$ is optionally substituted lower alkyl, optionally substituted aryl or heteroaryl, optionally substituted benzyl, —C(O)—$R_4$, —$S(O)_2$ —$R_4$, or —$CH(R_5)R_4$, or —$CH_2CH{=}CH_2$; $R_3$ is hydrogen, optionally substituted lower alkyl, or acyl; $R_4$ is optionally substituted aryl or heteroaryl; $R_5$ is hydrogen or lower alkyl; and pharmaceutically acceptable salts thereof, provided that compound is not 4-((1,4-dioxo-1,4-dihydronaphthalen-2-yl)amino)benzensulfonamide; or (ii) X is N; $R_1$ is hydrogen, halogen, optionally substituted heterocycloalkyl, optionally substituted heteroaryl, optionally substituted aryl, optionally substituted alkoxy, optionally substituted lower alkyl, amino, optionally substituted alkylamino, optionally substituted dialkylamino, or —$NHCH_2CH{=}CH_2$; $R_2$ is hydrogen, optionally substituted lower alkyl, optionally substituted aryl or heteroaryl, optionally substituted benzyl, —C(O)—$R_4$, —$S(O)_2$—$R_4$, or —$CH(R_5)$—$R_4$, or —$CH_2CH{=}CH_2$; $R_3$ is hydrogen, optionally substituted lower alkyl, or acyl; $R_4$ is optionally substituted aryl or heteroaryl; $R_5$ is hydrogen or lower alkyl; and pharmaceutically acceptable salts thereof. In another embodiment, X is CH; $R_1$ is hydrogen, halogen, a 5- or 6-membered heterocycloalkyl or heteroaryl (each optionally substituted with lower alkyl or phenyl), alkoxy, phenyl, lower alkyl (optionally substituted with phenyl), —$N(CH_2CH_3)_2$), —$NHCH_2CH{=}CH_2$, $NH_2$, or —$CH_2CH{=}CH_2$; $R_2$ is lower alkyl, phenyl (optionally mono- or di-substituted independently with halogen, lower alkyl, —$S(O)_2NH_2$ or alkoxy), —$CH_2$-phenyl (said phenyl optionally substituted with halogen), C(O)-phenyl (said phenyl optionally substituted with halogen), $S(O)_2$-phenyl (said phenyl optionally substituted with halogen), $S(O)_2$-thiophenyl (said thiophenyl optionally substituted with halogen), thiophenyl, or —$CH_2CH{=}CH_2$; and $R_3$ is hydrogen, lower alkyl, or acetyl. In still another embodiment, $R_1$ is hydrogen, chlorine, methyl, methoxy, phenyl, piperazinyl, methylpiperazinyl, piperidinyl, morpholinyl, thiomorpholinyl, phenylpiperazinyl, ethyl-piperazinyl, —$NHCH_2CH{=}CH_2$, —$CH_2CH{=}CH_2$, —$NH_2$, tert-butyl-piperazinyl, pyrrolidinyl, —$NHCH_2CH_2CH_2N(CH_2CH_3)_2$, —$CH_2CH_2CH_2N(CH_2CH_3)_2$, or —$CH(CH_3)$phenyl. In yet another embodiment, $R_2$ is methyl, —$CH_2CH{=}CH_2$, phenyl, —$CH_2$-chlorophenyl, chlorophenyl, acetyl, —C(O)-phenyl, —C(O)-bromophenyl, —$S(O)_2$-phenyl, —$S(O)_2$-bromophenyl, —$S(O)_2$-thiazolyl, —$S(O)_2$-bromothiazolyl, difluorophenyl, methoxyphenyl or -phenyl-$S(O)_2NH_2$. In another embodiment, $R_3$ is hydrogen, methyl or acetyl. In still another embodiment, X is CH; $R_1$ is a 5- or 6-membered heterocycloalkyl (optionally substituted with lower alkyl), or a lower alkyl (optionally substituted with —$N(CH_2CH_3)_2$); $R_2$ is methyl; and $R_3$ is acetyl. In yet another embodiment, X is CH; $R_1$ is a 5- or 6-membered heterocycloalkyl (optionally substituted with lower alkyl or phenyl), or $NH_2$; $R_2$ is —$C(O)R_4$; $R_3$ is H; and $R_4$ is a phenyl, optionally substituted with a halogen. In another embodiment, X is CH; $R_1$ is a hydrogen, alkoxy, $NH_2$, or a 5- or 6-membered heterocycloalkyl (optionally substituted with lower alkyl); $R_2$ is —$S(O)_2$—$R_4$; $R_3$ is H; and $R_4$ is a phenyl or thiophenyl, each of which can be optionally substituted with halogen. In still another embodiment, X is CH; $R_1$ is a 5- or 6-membered heterocycloalkyl (optionally substituted with lower alkyl or phenyl); $R_2$ is a phenyl, optionally substituted with one or two independently selected substituents from the group consisting of halogen and alkoxy; and $R_3$ is H. In yet another embodiment, X is N; $R_1$ is hydrogen, halogen, a 5- or 6-membered heterocycloalkyl or heteroaryl (optionally substituted with lower alkyl or phenyl), alkoxy, lower alkyl (optionally substituted with phenyl or —$N(CH_2CH_3)_2$), or $NH_2$; $R_2$ is lower alkyl, phenyl (optionally mono-or di-substituted independently with halogen, lower alkyl, —$S(O)_2$ $NH_2$ or alkoxy), $CH_2$-phenyl (said phenyl optionally substituted with halogen, C (O)-phenyl (said phenyl optionally substituted with halogen), $S(O)_2$-phenyl (said phenyl optionally substituted with halogen), $S(O)_2$-thiophenyl (said thiophenyl optionally substituted with halogen), or thiophenyl; and pharmaceutically acceptable salts thereof. In another embodiment, the compound is selected from the group consisting of:

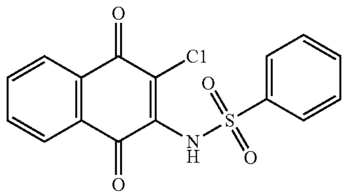,

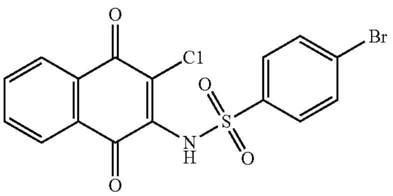

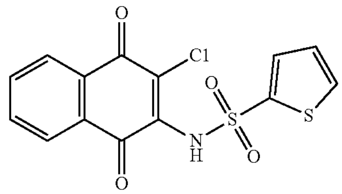,

-continued
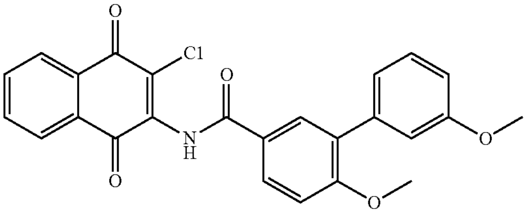
,
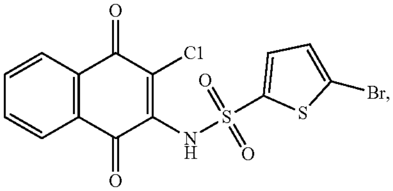
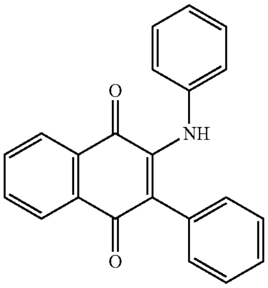
,
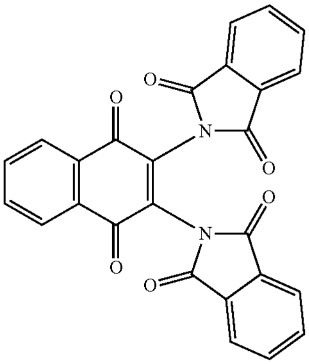
,
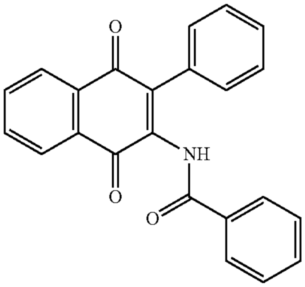
,
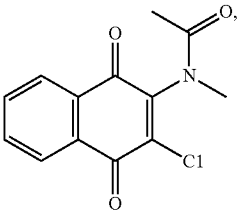
-continued
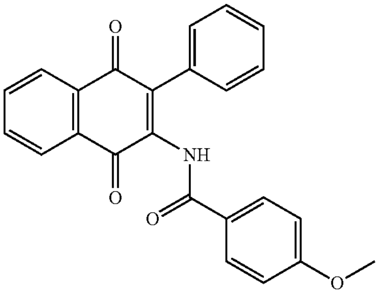
,
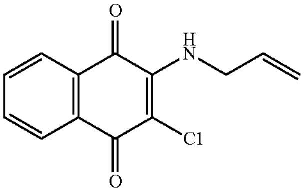
,
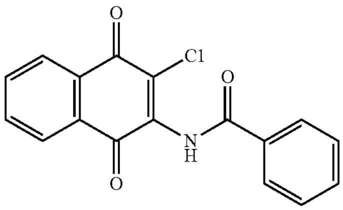
,
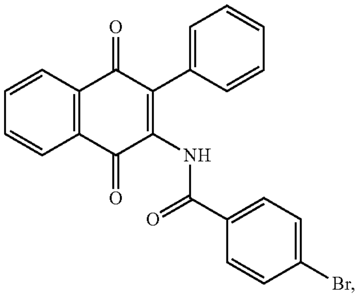
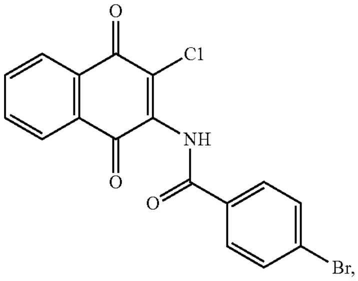
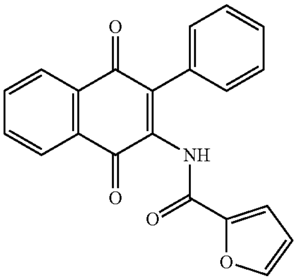
, -continued
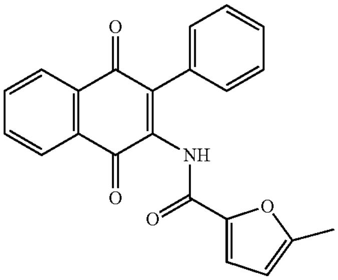
,
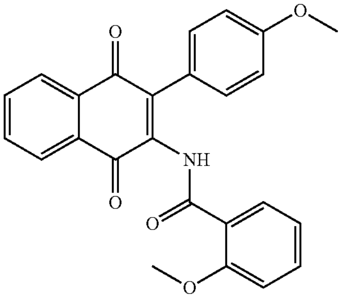
,
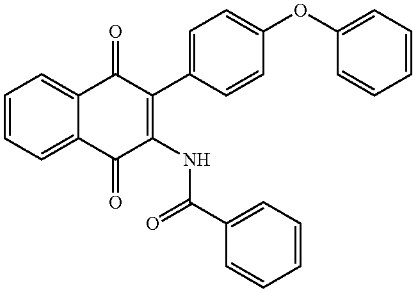
,
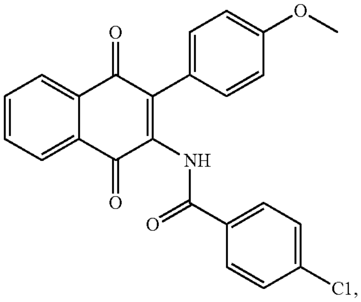
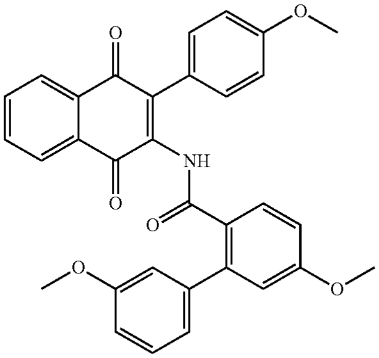
,
-continued
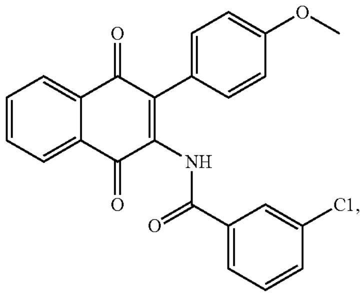
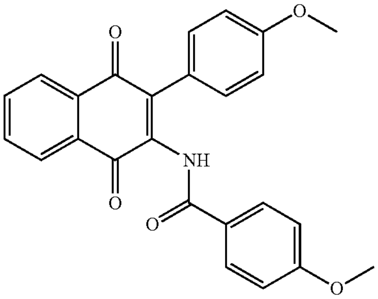
,
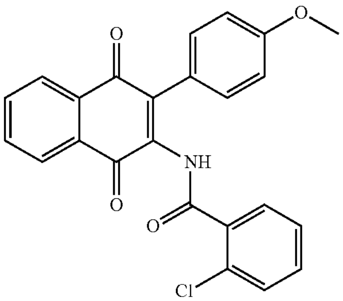
,
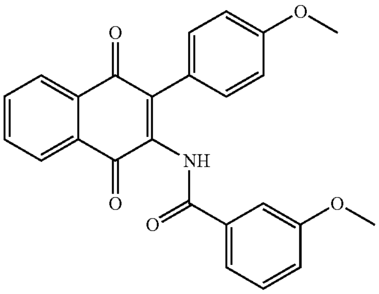
,
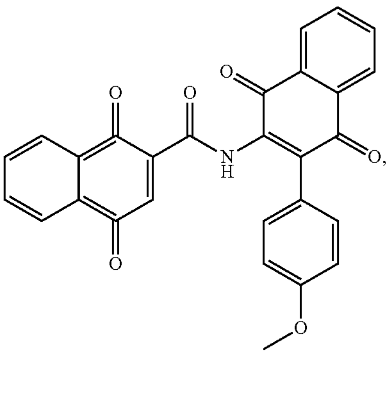

-continued
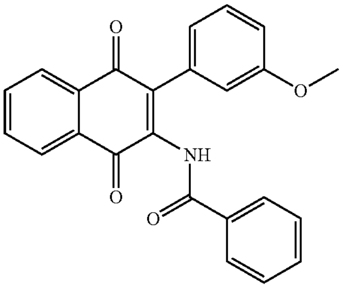
,
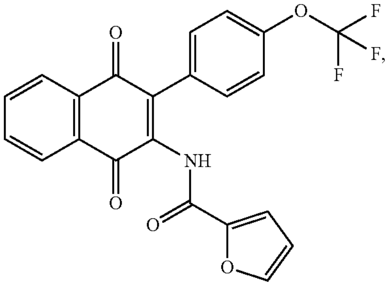
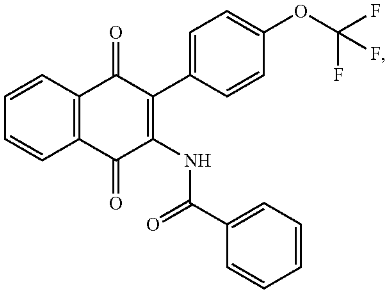
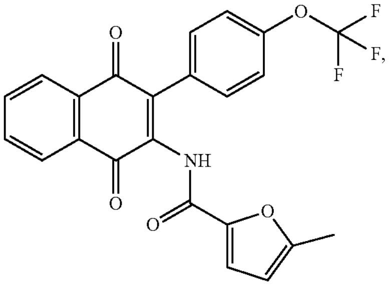
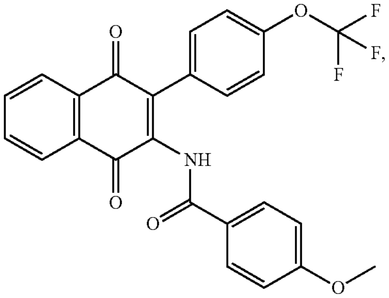
-continued
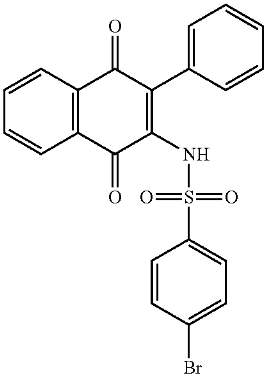
,
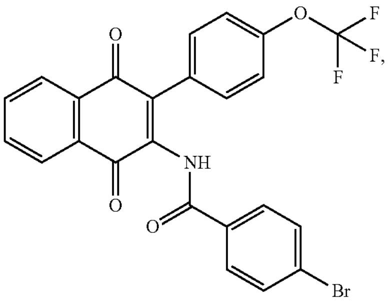
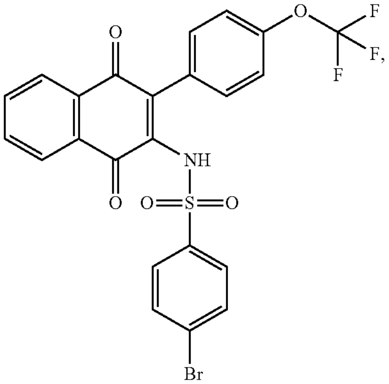
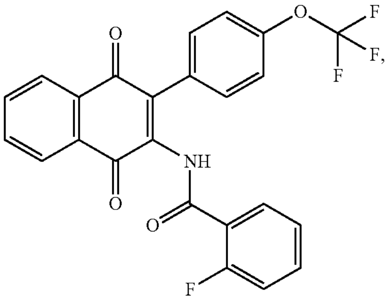
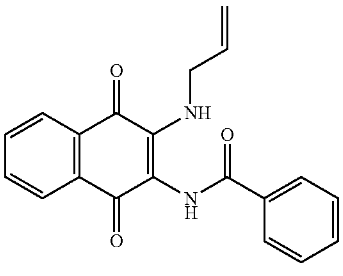
, -continued
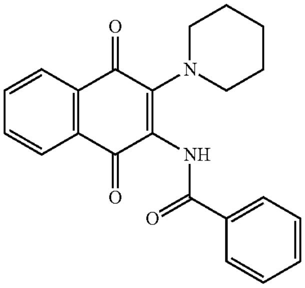
,
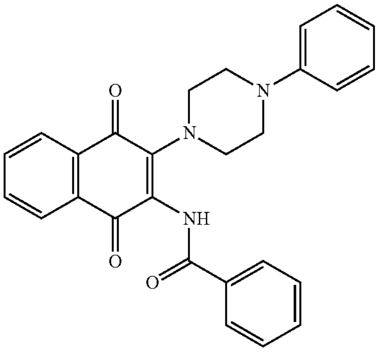
,
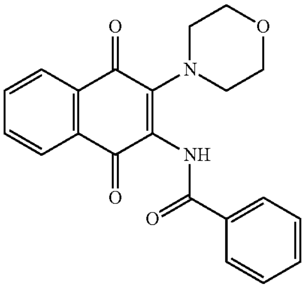
,
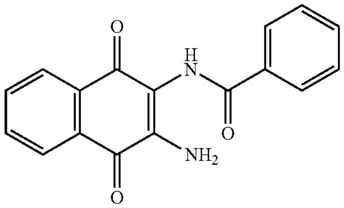
,
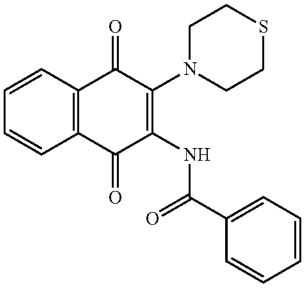
,
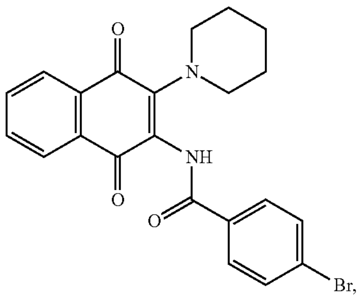
-continued
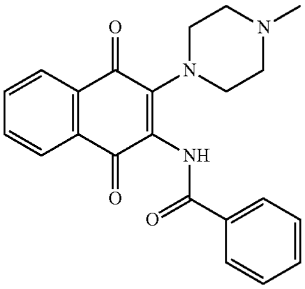
,
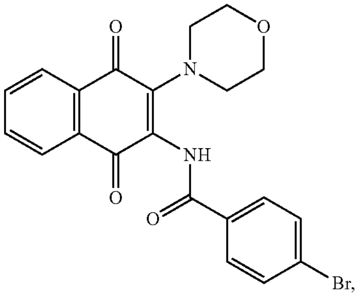
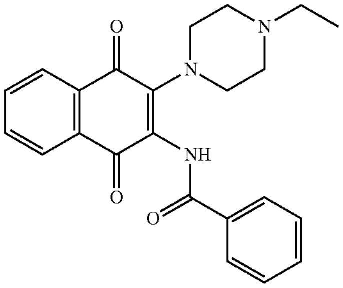
,
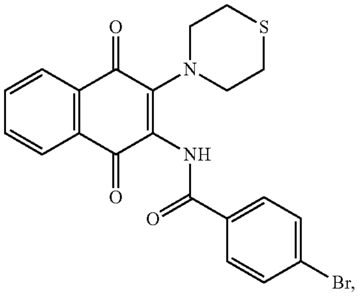
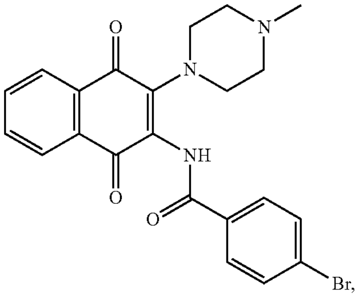
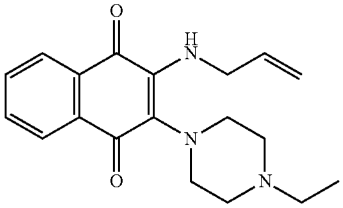
, -continued
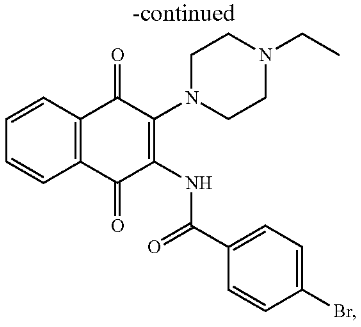
,
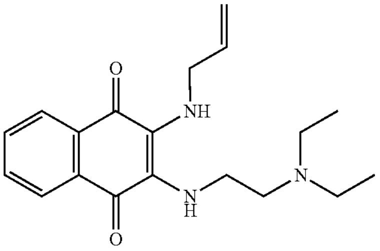
,
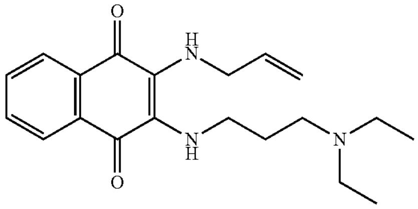
,
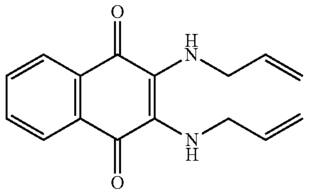
,
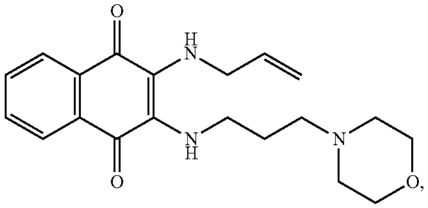
,
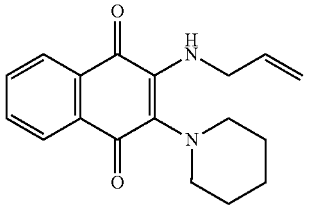
,
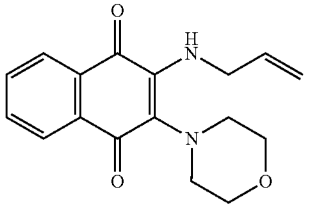
,
-continued
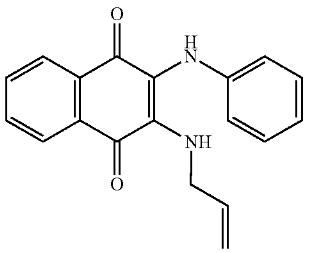
,
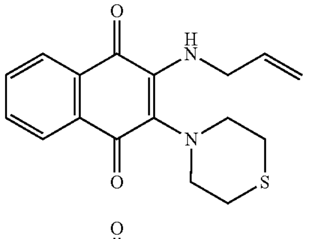
,
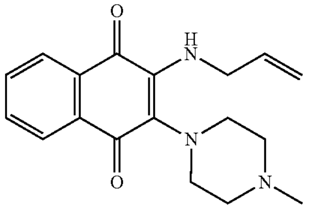
,
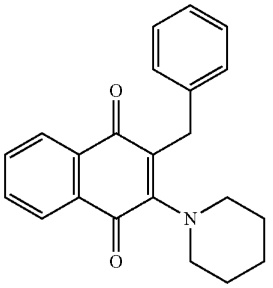
,
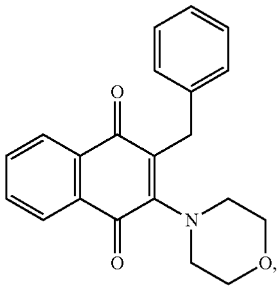
,
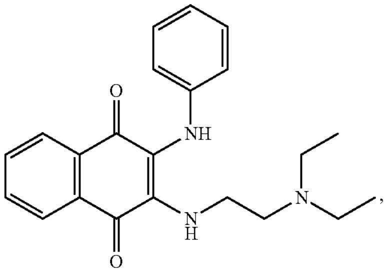
, -continued
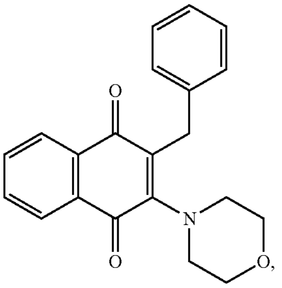
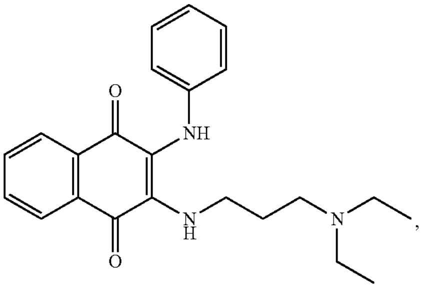
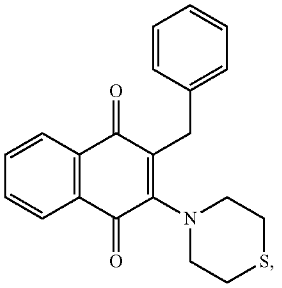
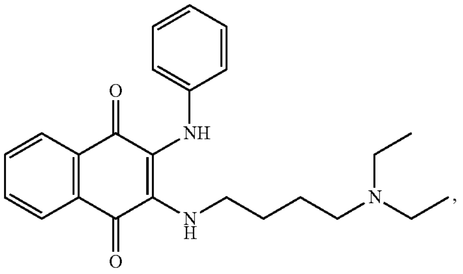
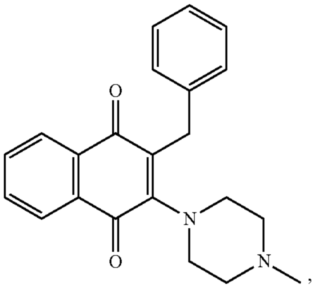
-continued
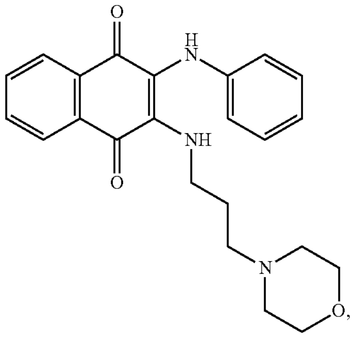
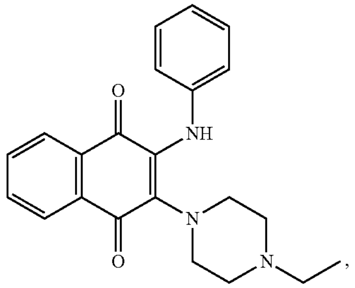
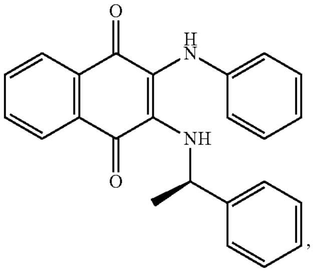
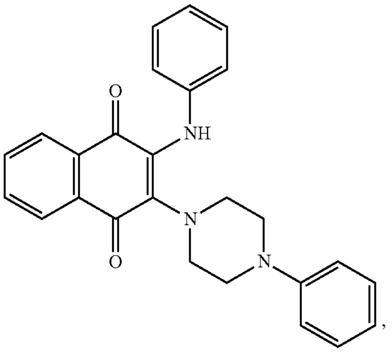
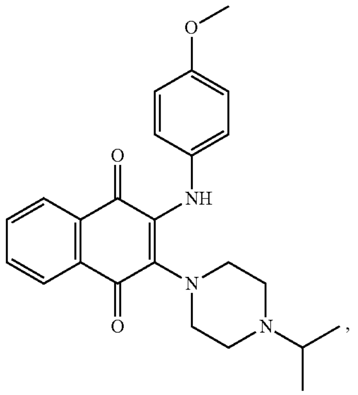

-continued
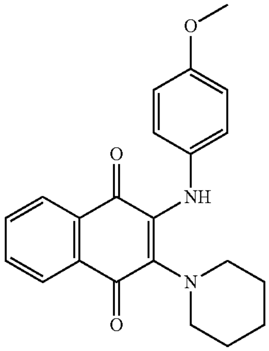
,
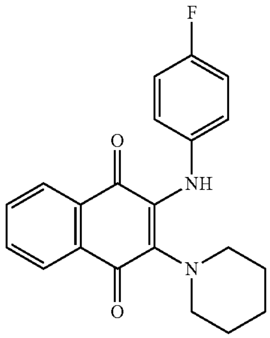
,
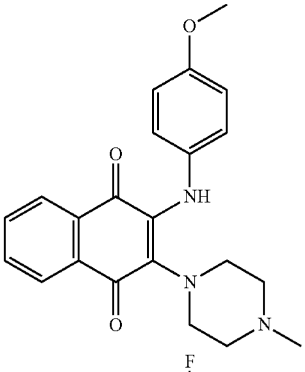
,
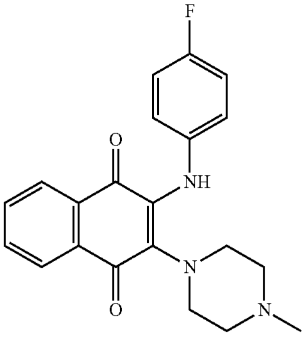
,
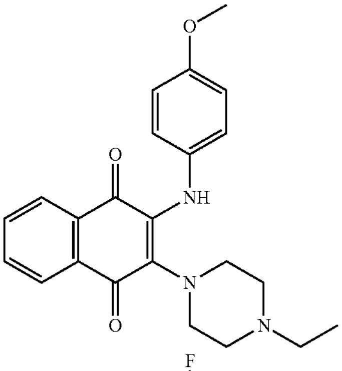
,
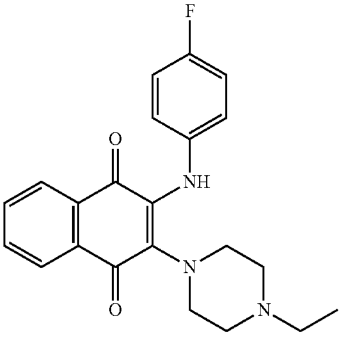
,
-continued
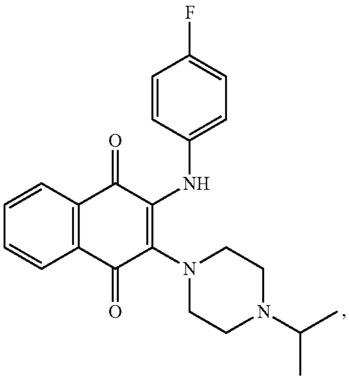
,
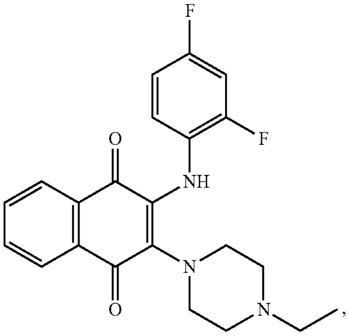
,
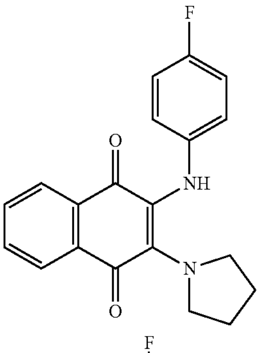
,
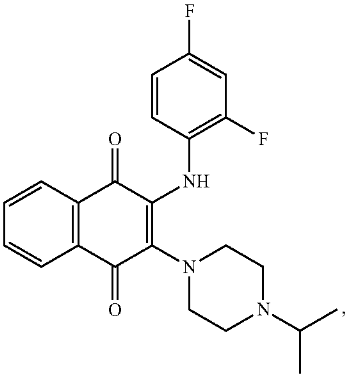
, -continued
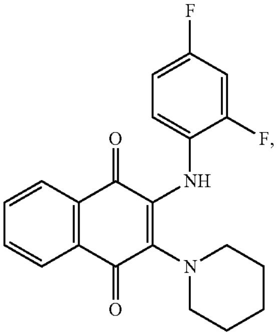
,
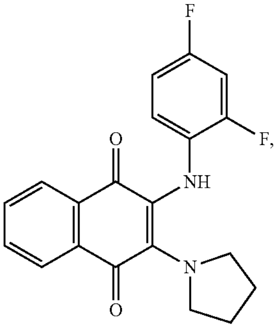
,
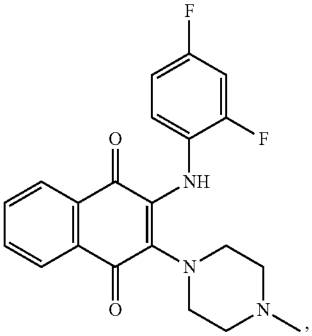
,
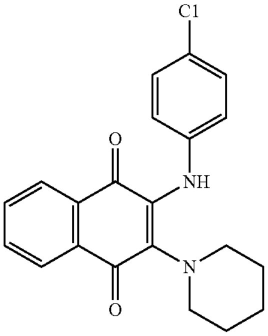
,
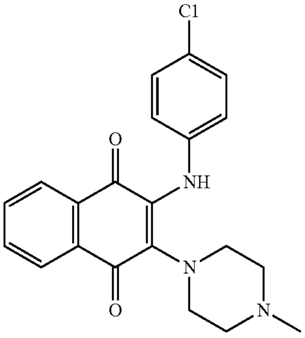
,
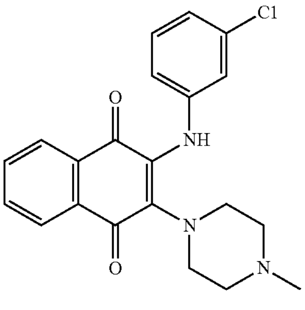
-continued
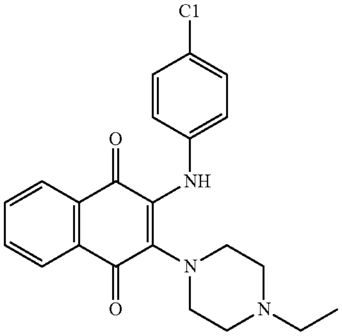
,
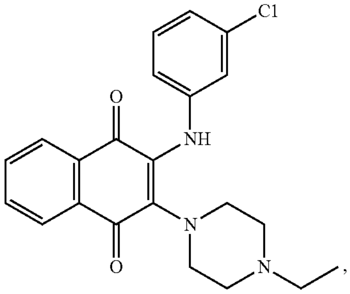
,
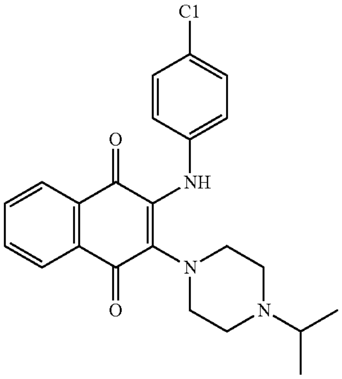
,
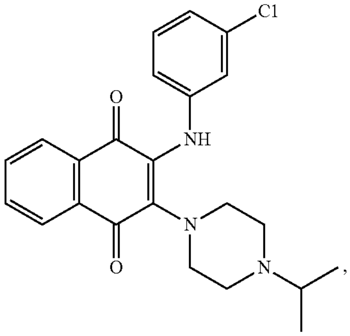
,
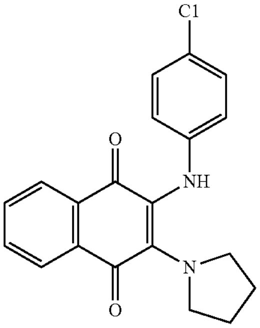
,
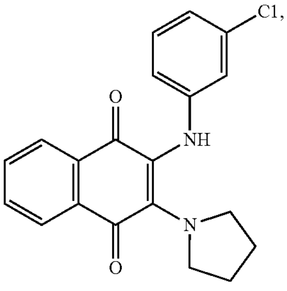
, -continued
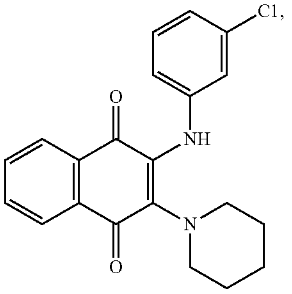
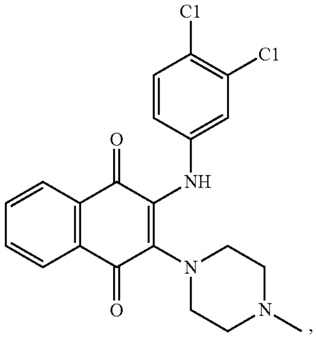
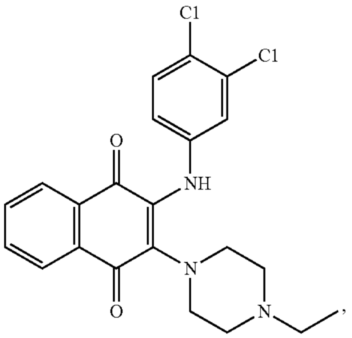
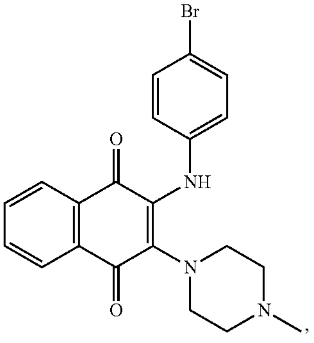
-continued
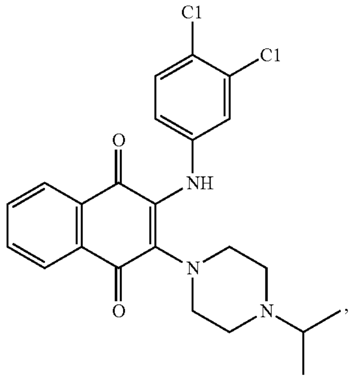
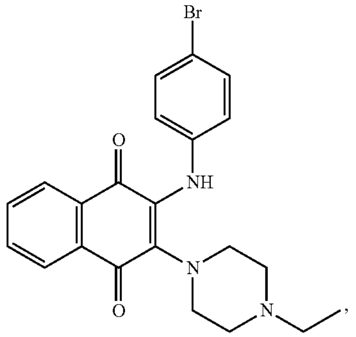
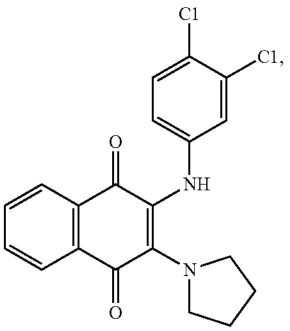
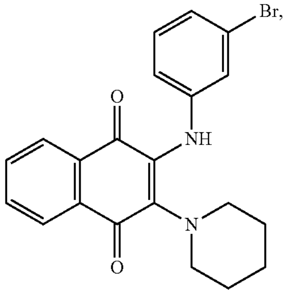
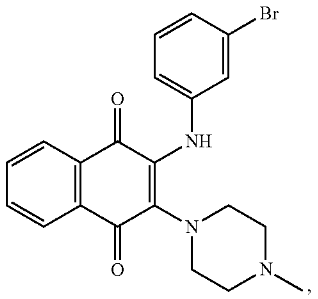

-continued
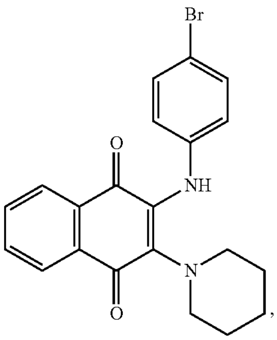
,
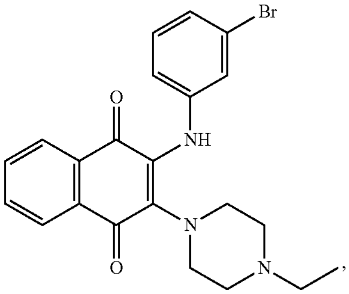
,
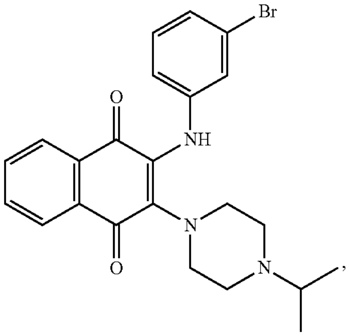
,
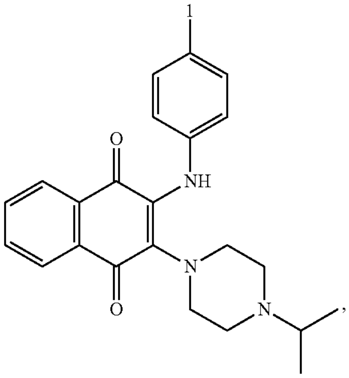
,
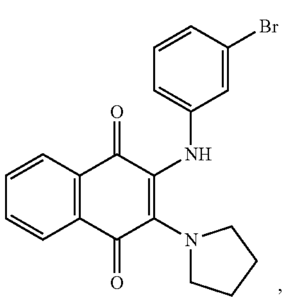
,
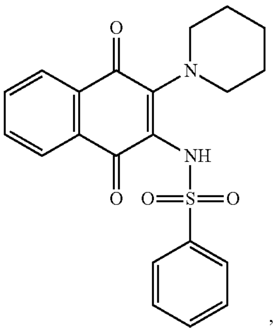
,
-continued
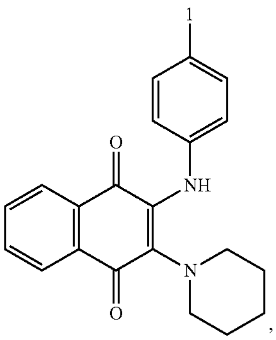
,
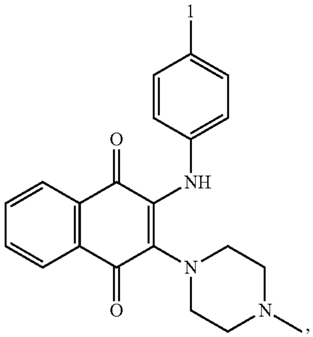
,
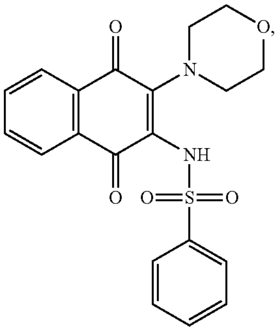
,
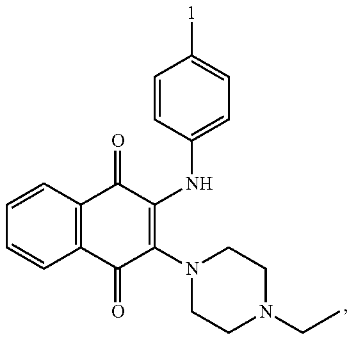
,
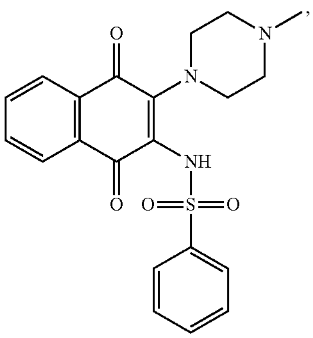
, -continued
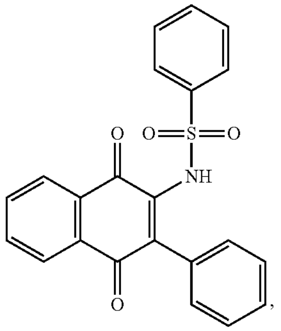
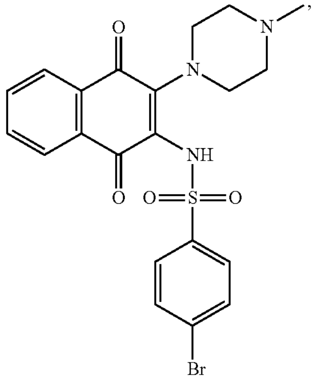
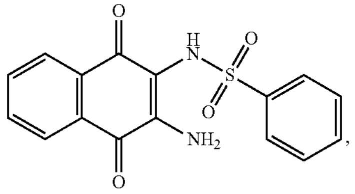
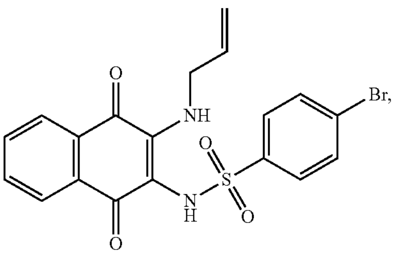
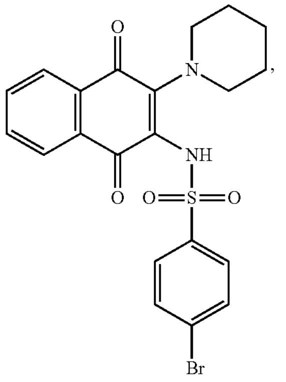
-continued
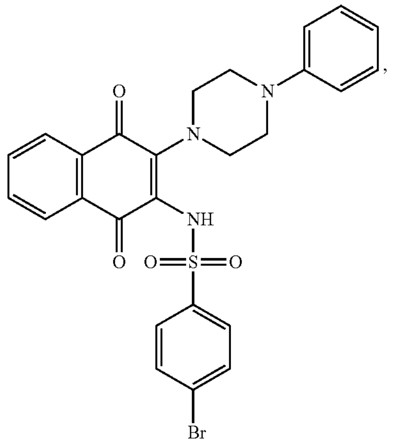
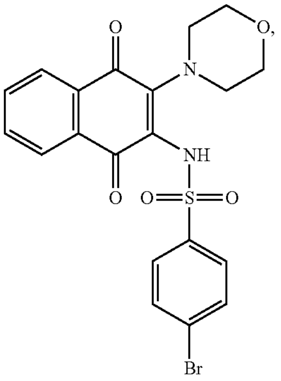
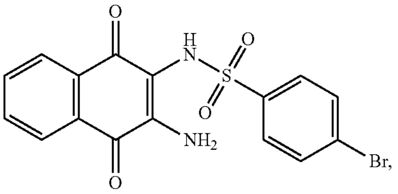
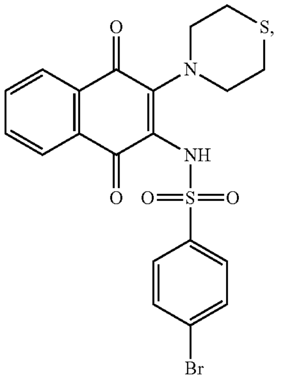
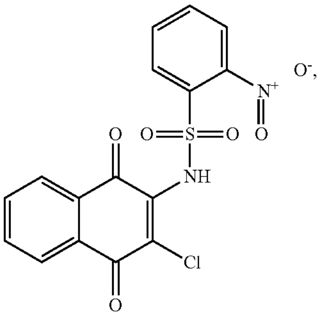

-continued
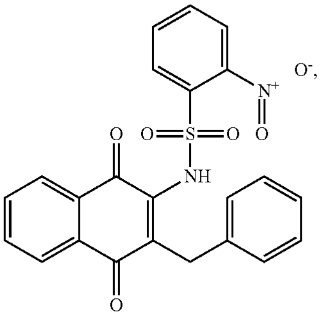
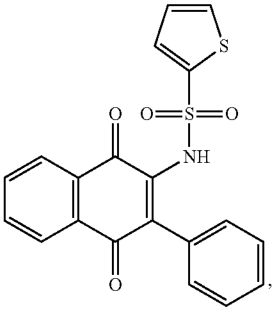
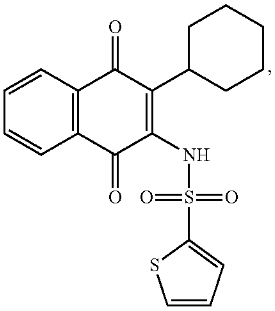
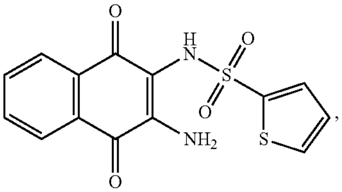
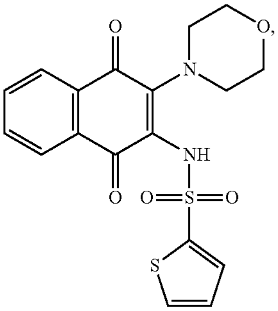
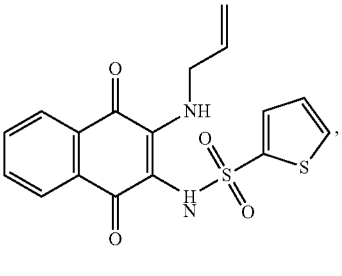
-continued
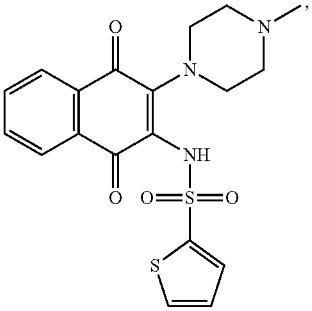
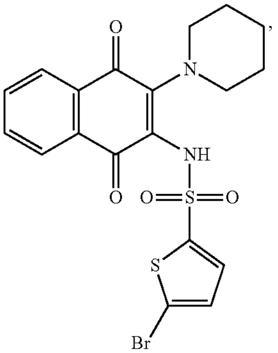
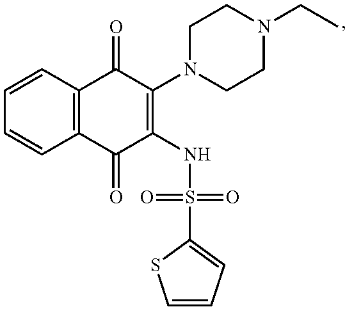
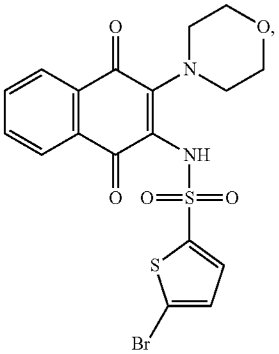
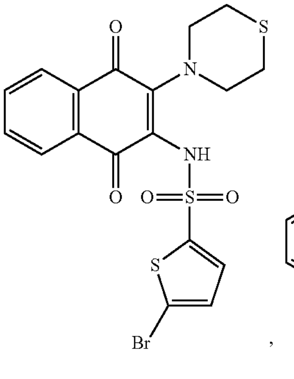
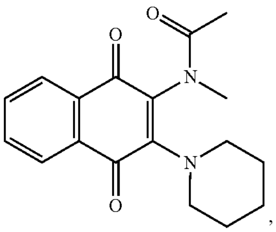

-continued
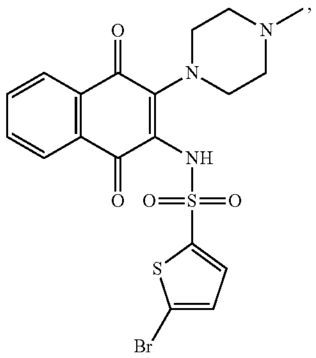
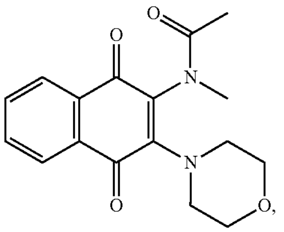
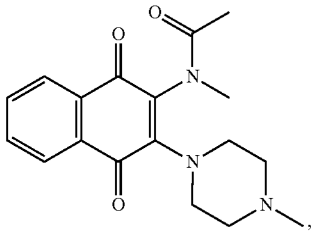
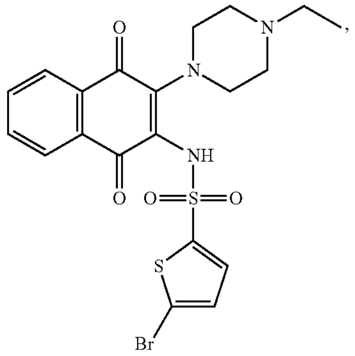
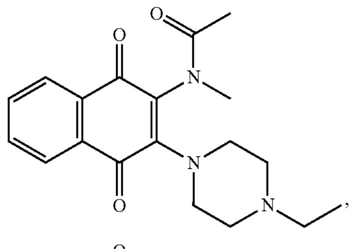
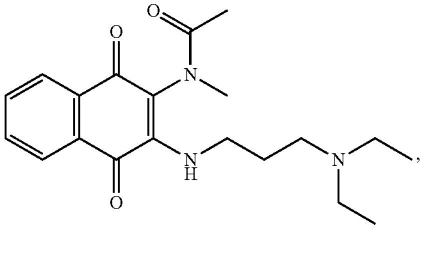
-continued
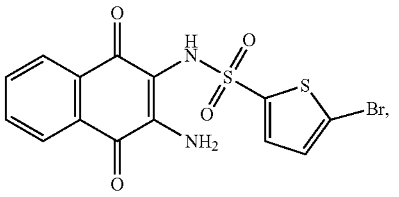
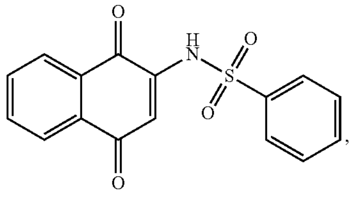
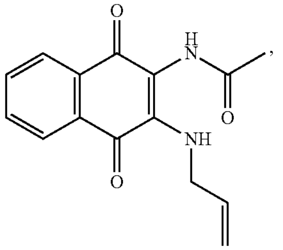
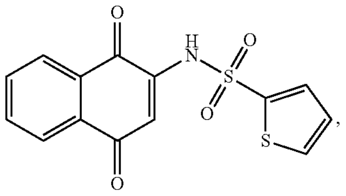
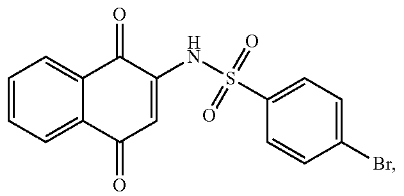
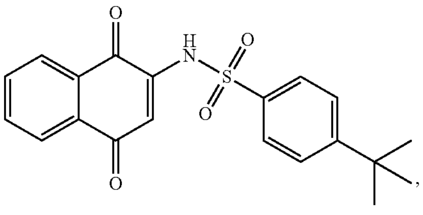
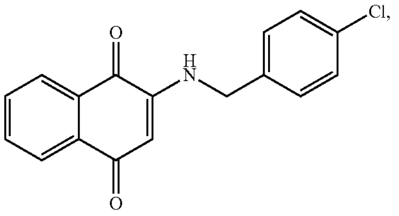
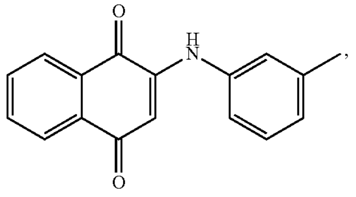

-continued
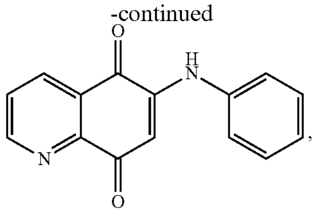
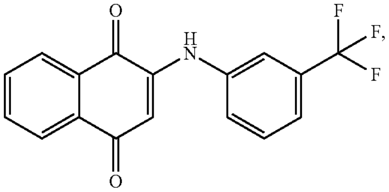
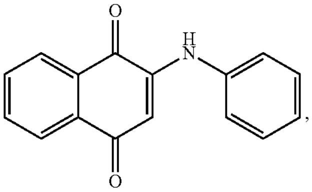
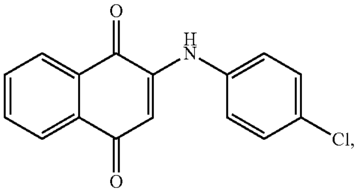
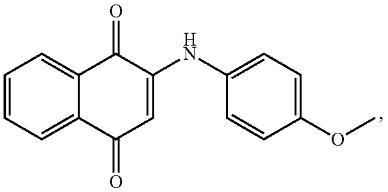
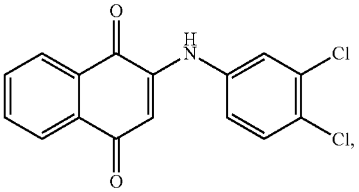
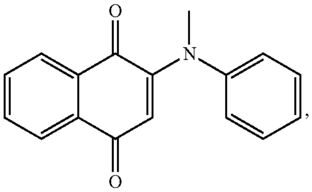
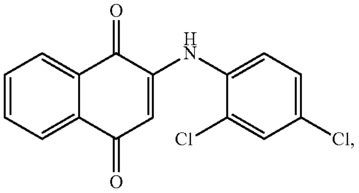
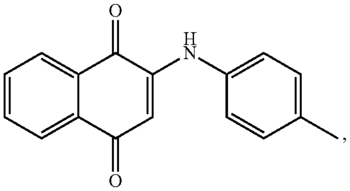
-continued
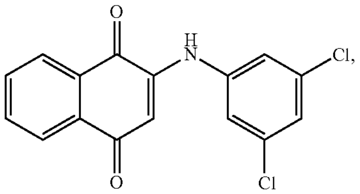
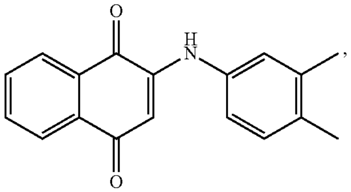
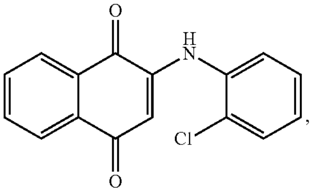
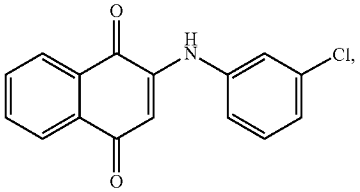
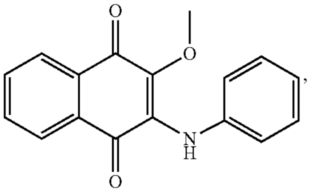
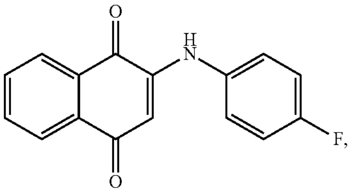
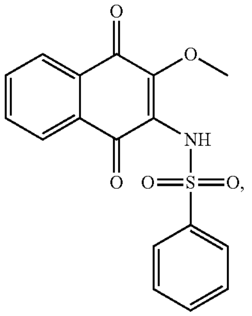

-continued

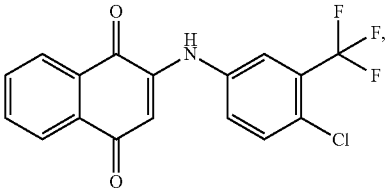

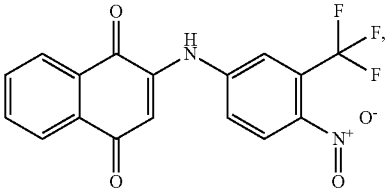

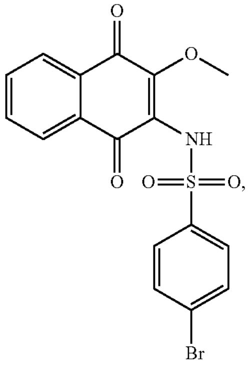

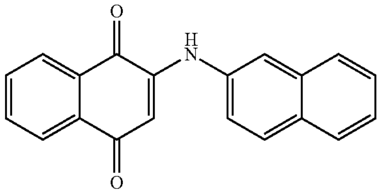
,

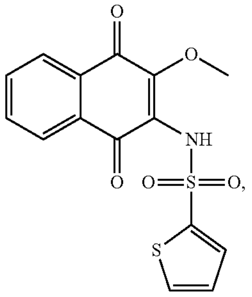

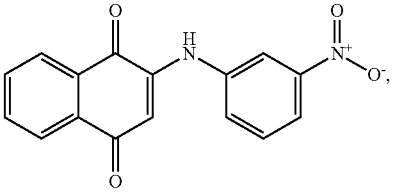

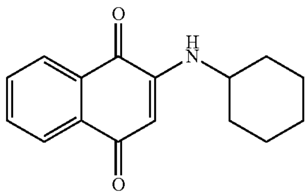
,
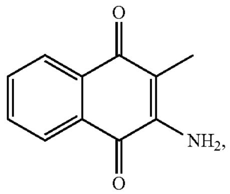

-continued

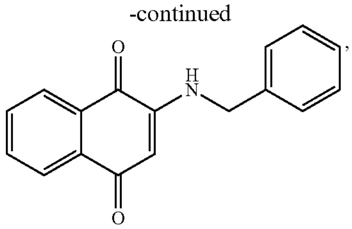
,

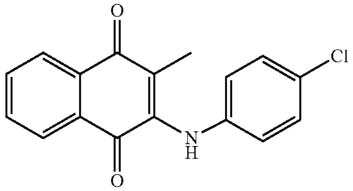
and

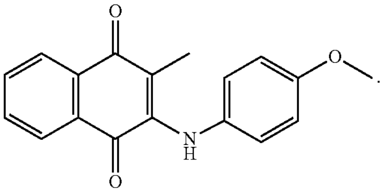

In still another embodiment, ML329 or a derivative thereof is ML329, CX4945, SCAP105461, or SCAP105463. In yet another embodiment, the subject is an animal model of cancer. In another embodiment, the animal model is a rodent model. In still another embodiment, the subject is a mammal. In yet another embodiment, the mammal is a mouse or a human. In another embodiment, the mammal is a human.

BRIEF DESCRIPTION OF FIGURES

FIG. 1 is adapted from Craig and Stitzel (2003) *Modern Pharmacology With Clinical Applications, Sixth Edition* (ISBN-13:978-0781737623).

FIGS. 2A and 2B are adapted from Kaelin (2005) *Nat. Rev. Cancer* 5:689-698. FIG. 2A shows that for a target is present uniquely in a cancer cell, target specific agent modulators can be used to selectively kill the cancer cell, such as BRAF (V600E)-specific inhibitors of this mutated form of BRAF. FIG. 2B shows that for a target that is present in both a cancer cell and a normal cell, a general requirement is that the target is enhanced in the cancer cell for target agent modulators to kill the cancer cell in a content-driven therapeutic manner. This is the mechanism by which most anti-cancer drugs, including chemotherapy, act.:

FIG. 7A and FIG. 7B show the identification of molecular targets of ML329.

FIGS. 9A and 9B are adapted from Battistutta (2009) *Cell Mol. Life Sci.* 66:1868-

1889. FIG. 9B shows that V66A/174A CK2a mutants are unable to bind to many ATP-competitive inhibitors of CK2 in vitro. V66A/174A CK2A mutants have normal kinase activity in vitro.

FIG. 11B shows common essential genes in the curve centered on the dotted vertical line, which are genes identified in a large, pan-cancer screen that rank in the top X most depleting genes in at least 90% of cell lines. X is chosen empirically using the minimum of the distribution of gene ranks in their $90^{th}$ percentile least depleting lines.

FIG. 22A shows the effect of ML329 on melanoma cell lines (red) and non-melanoma cell lines. FIG. 22B shows the effect of ML329 on MITF and MITF target genes. *, $p<0.000001$.

FIG. 23A show that a mass spectrometry approach identified CK2 as a target of ML329. FIG. 23B shows the effect of ML320 and the ATP-competitive inhibitor CX-4945 on CK2 signaling in melanoma and non-melanoma cells. FIG. 23C shows the results of pan-kinome screening profiling for ML329.

FIG. 24A shows that screening of 489 cell lines identified NQO1 as a biomarker of ML329 cytotoxicity. FIG. 24B and FIG. 24C show that ML329 is necessary and sufficient for ML329 activity. FIG. 24D shows that ML329 is a direct substrate of Nqo1 in vitro. FIG. 24E shows that Nqo1 is required for ML329 inhibition of CK2 in vitro. FIG. 24F shows that Nqo1 is not required for inhibition of CK2 in vitro by CX-4945.

FIG. 26A shows an overall scheme of a small molecule screen to identify regulators of MITF. SK-MEL-5 cells stably expressing the TRPM1 promoter fused to the luciferase gene were screened with 331,578 compounds. Secondary screens of putative hits including evaluating cytotoxicity in 2 MITF-dependent cell lines (SK-MEL-5, MALME) and 1 MITF-independent cell line (A375M) and evaluation the effect of candidate hits on the mRNA of MITF and target genes. Prioritized hits suppressed the growth of MITF-dependent cell lines at <10 μM, were inactive in A375M cells, and suppressed MITF at <10 μM. BRD-K45681478 was the lead hit, which was modified by structure-function analysis to generate the compound ML329. FIG. 26B show cell number after 48 h treatment of melanoma cell lines (red) compared to non-melanoma cell lines (black) with ML329. FIG. 26C shows a proportion of Annexin V-positive cells after treatment with ML329 (24 h). MITF-dependent cell lines are depicted in green, whereas the MITF-independent cell line is depicted in red. FIG. 26D shows levels of M-MITF and transcriptional targets after treatment with ML329 (1 μM, 24 h). FIG. 26E shows levels of M-MITF and TPRM1 in WM266.4 cells with or without M-MITF expression. FIG. 26F shows cell number after 48 h treatment with ML329 in WM266.4 cells with and without M-MITF overexpression. FIG. 26G shows levels of MITF, NQO1, phospho-ERK, or total ERK protein in established (black) and early passage (colored) melanoma cell lines. FIG. 26H shows cell number after 48 h treatment of established (black) and early passage (colored) melanoma cell lines with ML329.

FIG. 27A shows quantification of hydrogen peroxide levels in the absence of DTT. FIG. 27B shows quantification of hydrogen peroxide levels in the presence of DTT. FIG. 27C shows quantification of hydrogen peroxide levels with added exogenous hydrogen peroxide. FIG. 27D shows quantification of hydrogen peroxide levels with DA3003 (a compound capable of redox cycling), without added DTT. FIG. 27E shows quantification of hydrogen peroxide levels with added DA3003 and DTT. FIG. 27F shows quantification of hydrogen peroxide levels with ML329, without added DTT. FIG. 27G shows quantification of hydrogen peroxide with ML329 with added DTT.

FIG. 28A shows an approach for identification of targets of ML329 by mass spectrometry. Whole protein lysates were generated from SK-MEL-5 melanoma cells and mixed with either KUC114363 (a derivative of ML329 conjugated to agarose beads) or KUC114363 along with competing amounts of soluble ML329. Mass spectrometry was used to identify proteins that bound KUC114363 whose binding was diminished upon treatment with ML329.

28H shows quantification of MITF and MITF target TRPM1 following overexpression of CK2α' (CSNK2A2) in WM266.4 cells. FIG. 28O shows cell number after 48 h ML329 treatment of WM266.4 cells stably expressing wild-type or drug-resistant (I174A) mutant CK2a (CSNK2A1).

FIG. 29A shows chemical synthesis of KUC114361, KUC114362, and KUC114363. FIG. 29F shows a summary of $IC_{50}$ of ML329 and derivatives in melanoma and non-melanoma cell lines. FIG. 29V shows structure and chemical characteristics of ML329 derivatives. FIG. 29Z shows area-under-the-curve (AUC) for CX4945, ML329 or its derivatives in indicated SK-MEL5 cell line. The fold change in AUC between vector and drug-resistant CSNK2A1 expressing cell lines is indicated.

FIG. 30A shows cell number of 489 cancer cell lines of indicated lineage following treatment with 0.3125 μM ML329. FIG. 30B shows correlation of ML329 cytotoxicity with gene expression in 489 cell lines using PRISM (PMID: 26928769). Negative odds are associated with sensitivity to ML329 whereas positive odds are associated with insensitivity to ML329. FIG. 30C shows association of MITF mRNA and ML329 cytotoxicity (AUC) across all cell lines (n=489; grey) or melanoma cell lines (red). FIG. 30D shows association of TRPM1 mRNA and ML329 cytotoxicity (AUC) across all cell lines (n=489; grey) or melanoma cell lines (red). FIG. 30E shows top KEGG gene-set correlated with sensitivity to ML329 across all cell lines. FIG. 30F shows association of G6PD protein on ML329 sensitivity across all cell lines (grey) or melanoma cell lines (red). FIG. 30G shows association of NADP metabolite on ML329 sensitivity across all cell lines (grey) or melanoma cell lines (red). FIG. 30H shows association of dependence of melanoma cell lines to MITF depletion by CRISPR to ML329 sensitivity.

FIG. 31A shows distribution of barcodes for each cell line in PRISM assay. Strictly Standardized Mean Difference (SSMD) was determined for each cell line. Cell lines with SSMD<2 were filtered out. All cell lines tested had SSMD>2. FIG. 31B shows correlation of viability of ML329 at indicated doses across 489 cell lines. FIG. 31C shows viability of 489 cell lines at each ML329 dose tested (dotted line=50% viability). FIG. 31D shows sensitivity of A375, SKMEL-5 and MALME cell lines to ML329 from PRISM assay. FIG. 31E shows area under the curve for ML329 treatment of 489 cell lines with indicated lineage.

FIG. 32A-FIG. 32K shows that melanoma-specific NQO1 expression leads to lineage specific cytotoxicity. FIG. 32A shows expression of NQO1 mRNA across lineages, highlighting the skin/melanocyte lineage in red. FIG. 32B shows expression of NFE2L2 mRNA (encoding NRF2) across lineages, highlighting the skin/melanocyte lineage in red. FIG. 32C shows protein levels of NQO1 in SKMEL-5 cells following their CRISPR deletion. FIG. 32D shows protein levels of NQO1 in WM266.4 cells following their CRISPR deletion. FIG. 32E shows protein levels of NRF2 in SKMEL-5 cells following their CRISPR deletion. FIG. 32F shows protein levels of NRF2 in WM266.4 cells following their CRISPR deletion. FIG. 32G-FIG. 32K show cell number of individual ML329-resistant clones after 48 h treatment with ML329 (FIG. 32G), buthionine (FIG. 32H), ES936 (FIG. 32I), trametinib (FIG. 32J), or dabrafenib (FIG. 32K).

FIG. 34A shows serum levels of ML329 after single dose of ML329 (10 mg/kg) delivered intraperitoneally. FIG. 34B shows serum levels of ML329 after single dose of ML329 (10 mg/kg) delivered by intravenous injection.

FIG. 35A shows expression of NQO1 mRNA in wild-type and KEAP1-mutant lung cancer cell lines. FIG. 35B shows sensitivity of wild-type and KEAP1-mutated lung cancer cell lines to ML329. 'Sensitive' cell lines had IC50<10 μM, whereas 'insensitive' cell lines had $IC_{50}$>10 μM. FIG. 35C shows colony formation assay measuring effect of ML329 in HCC-44 or A549 cell lines with or without KEAP1 re-expression. FIG. 35D shows cell number of HCC-44 cells expressing KEAP1 or control vector after 24 h treatment with ML329.

Figure 1:
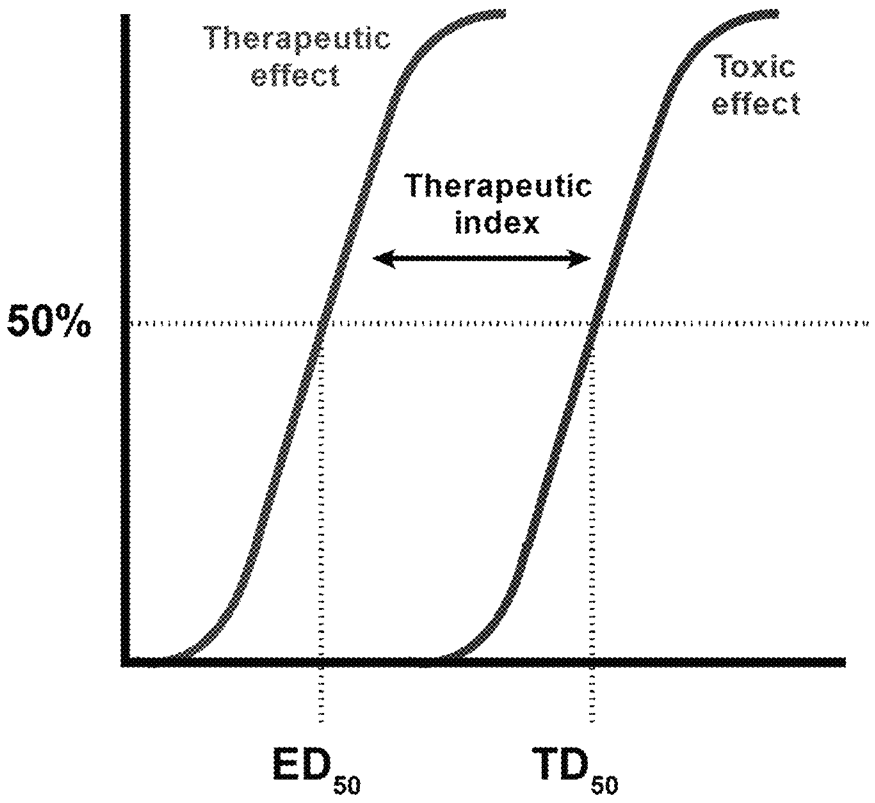
FIG. 1 illustrates the "Achilles' heal" of cancer therapeutics.
Figure 2A:
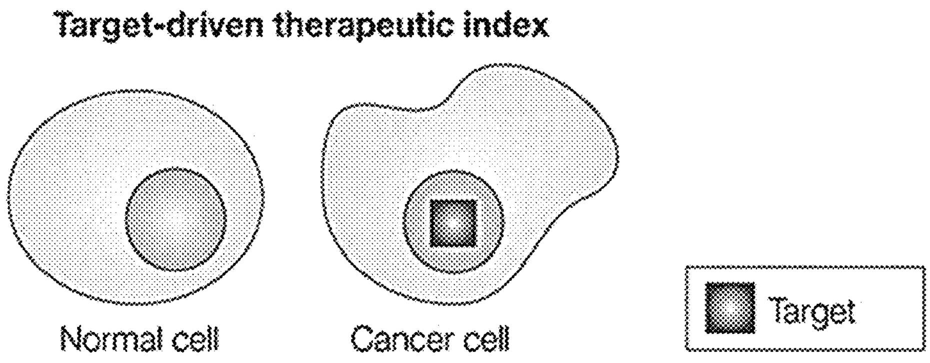
FIG. 2A and FIG. 2B show approaches to maximizing therapeutic index.
Figure 2B:
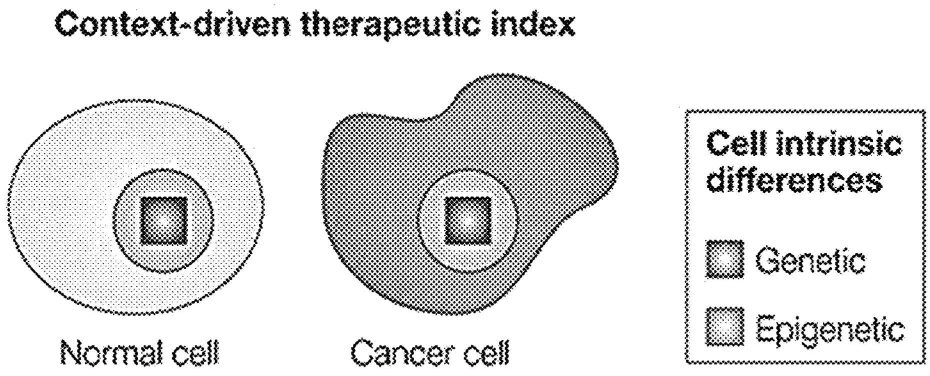
Figure 3:
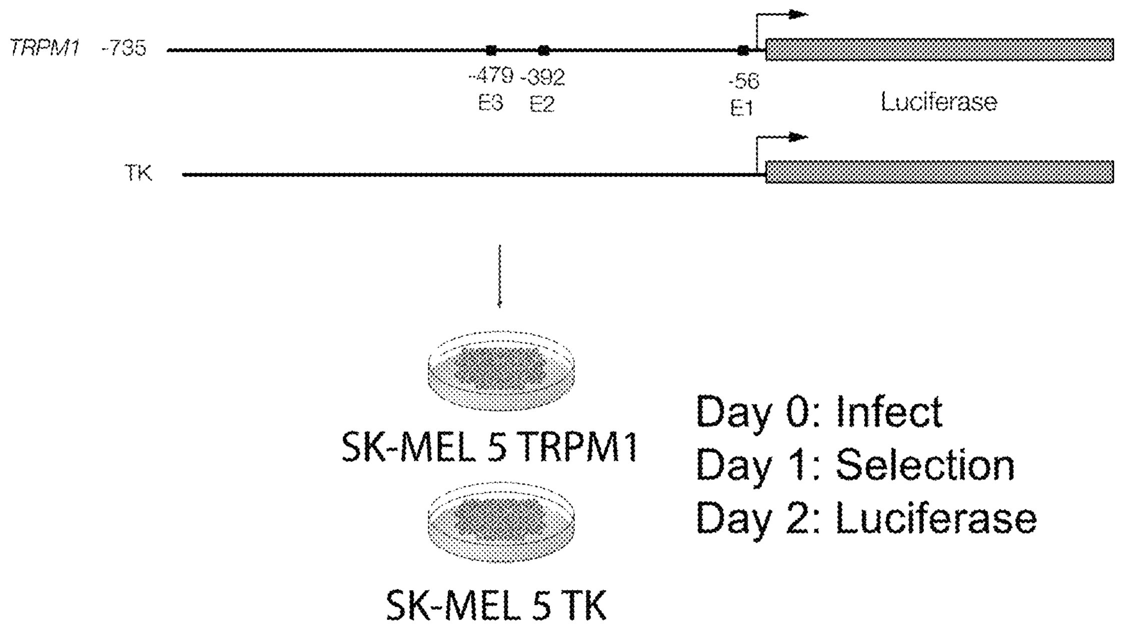
FIG. 3 shows as schematic of a small molecule screen to identify essential regulators of M-MITF activity.
Figure 4:
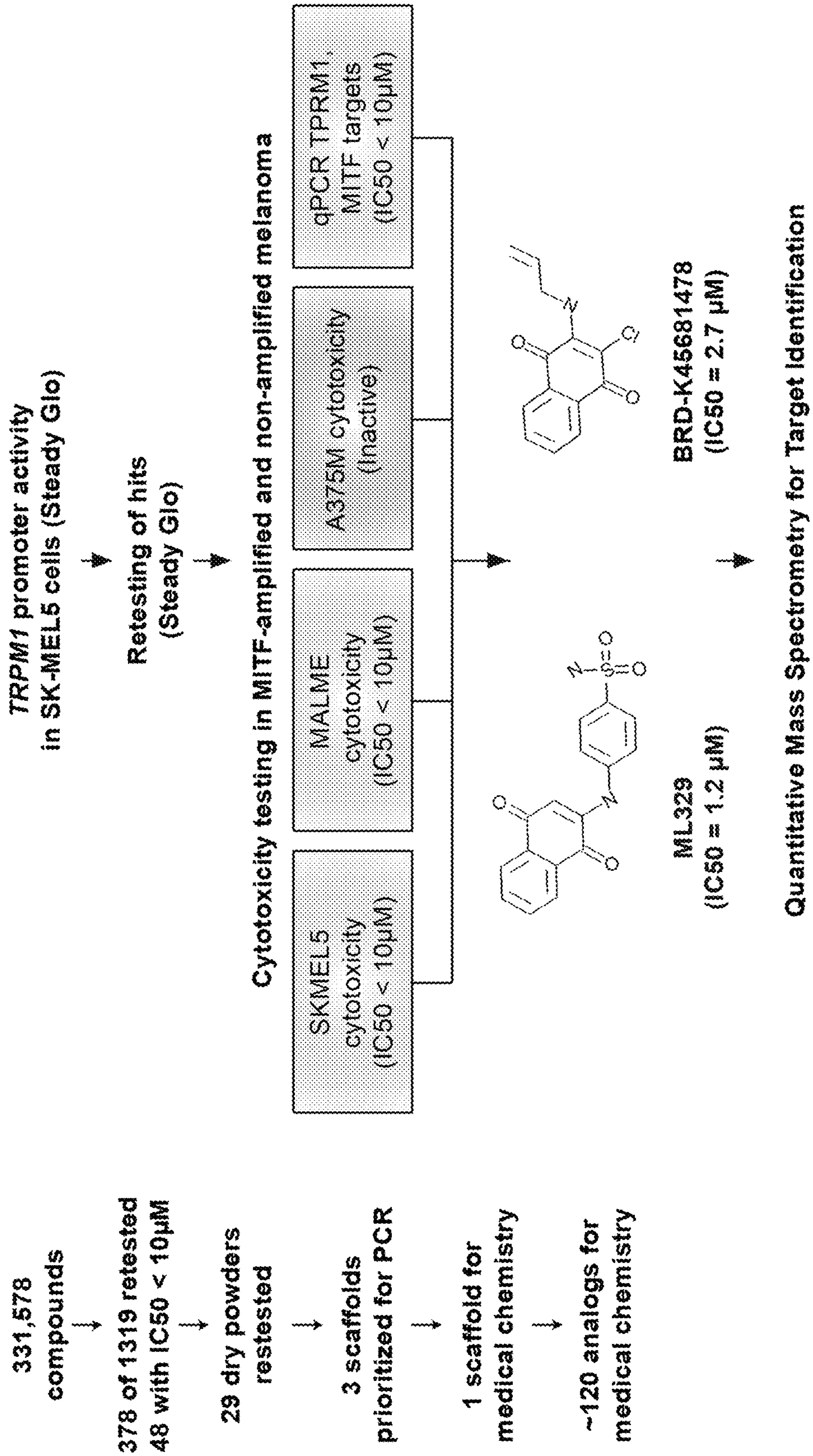
FIG. 4 shows the results of an MITF inhibitor small molecule screen that identified ML329.
Figure 5A:
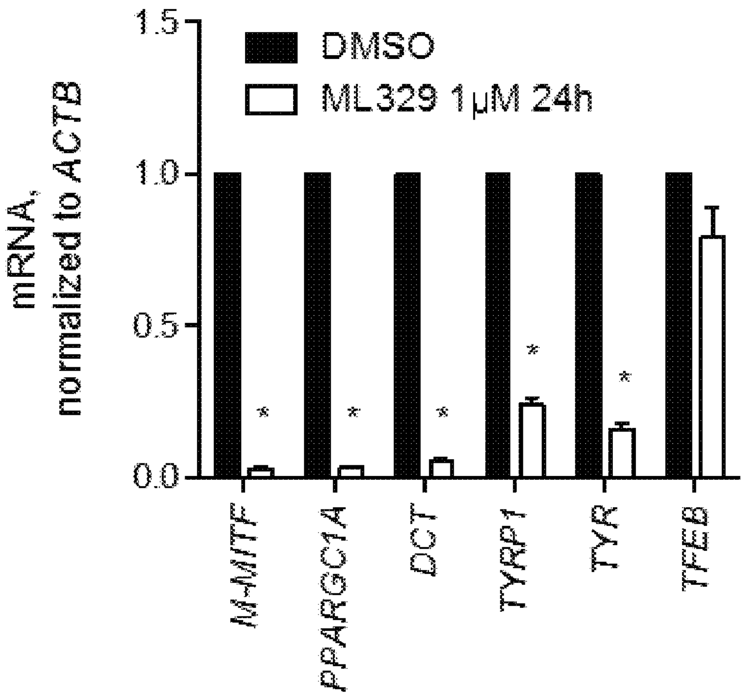
FIG. 5A and FIG. 5B show the selectivity of ML329 to the melanocyte lineage. MITF overexpression was demonstrated to lead to partial resistance to ML329.
Figure 5B:
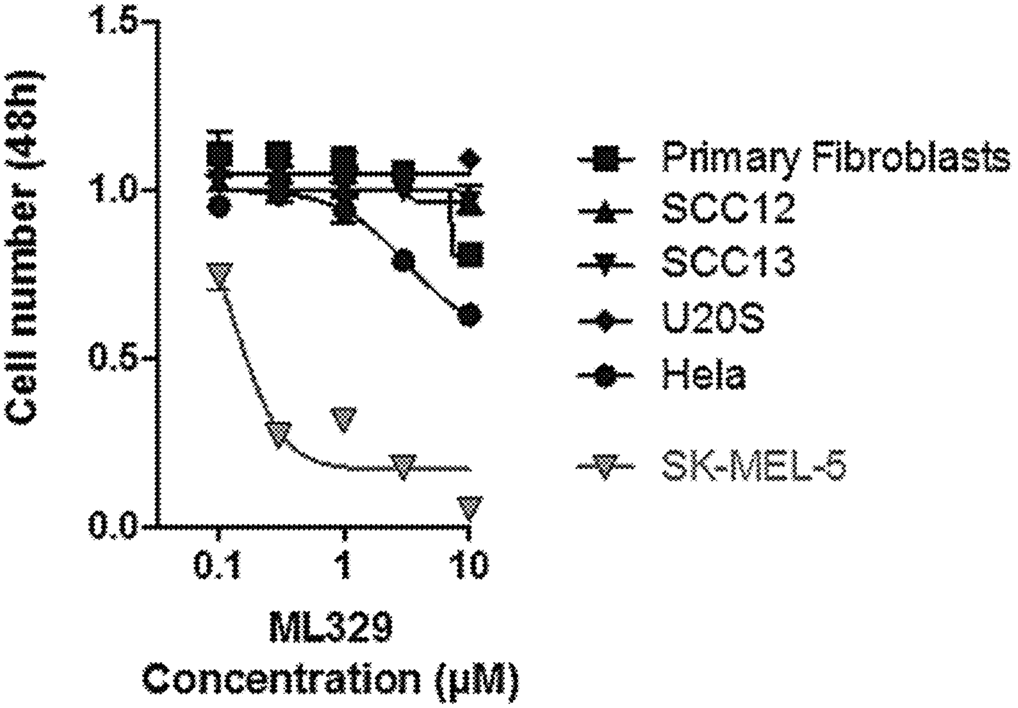
Figures 6A, 6B:
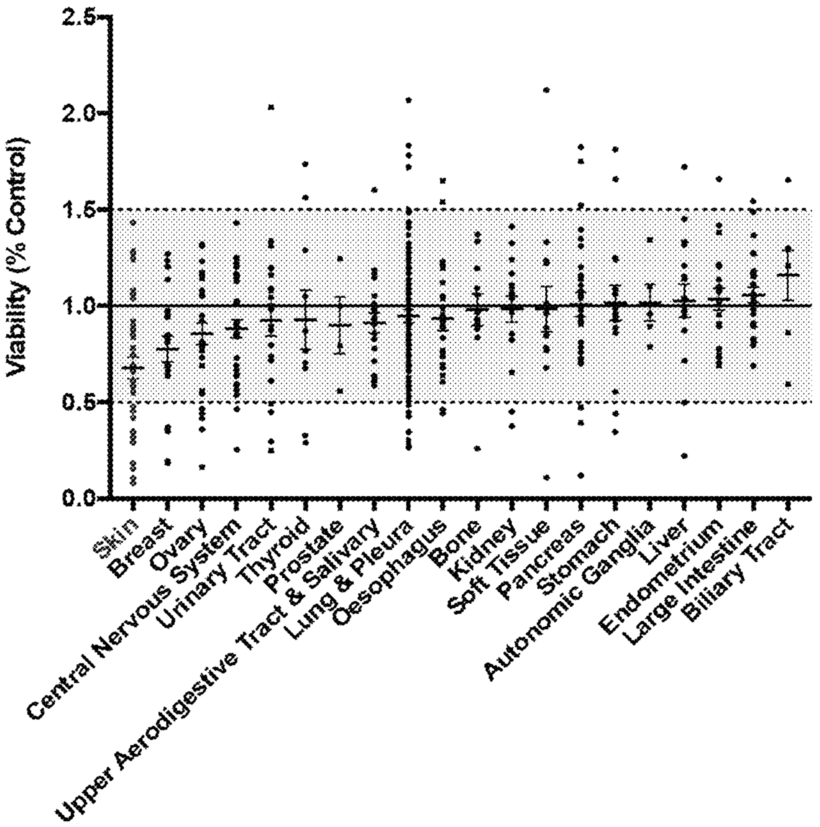
FIG. 6A and FIG. 6B show the results of screening of ~500 cell lines for determinants of ML329 sensitivity.
Figure 7A:
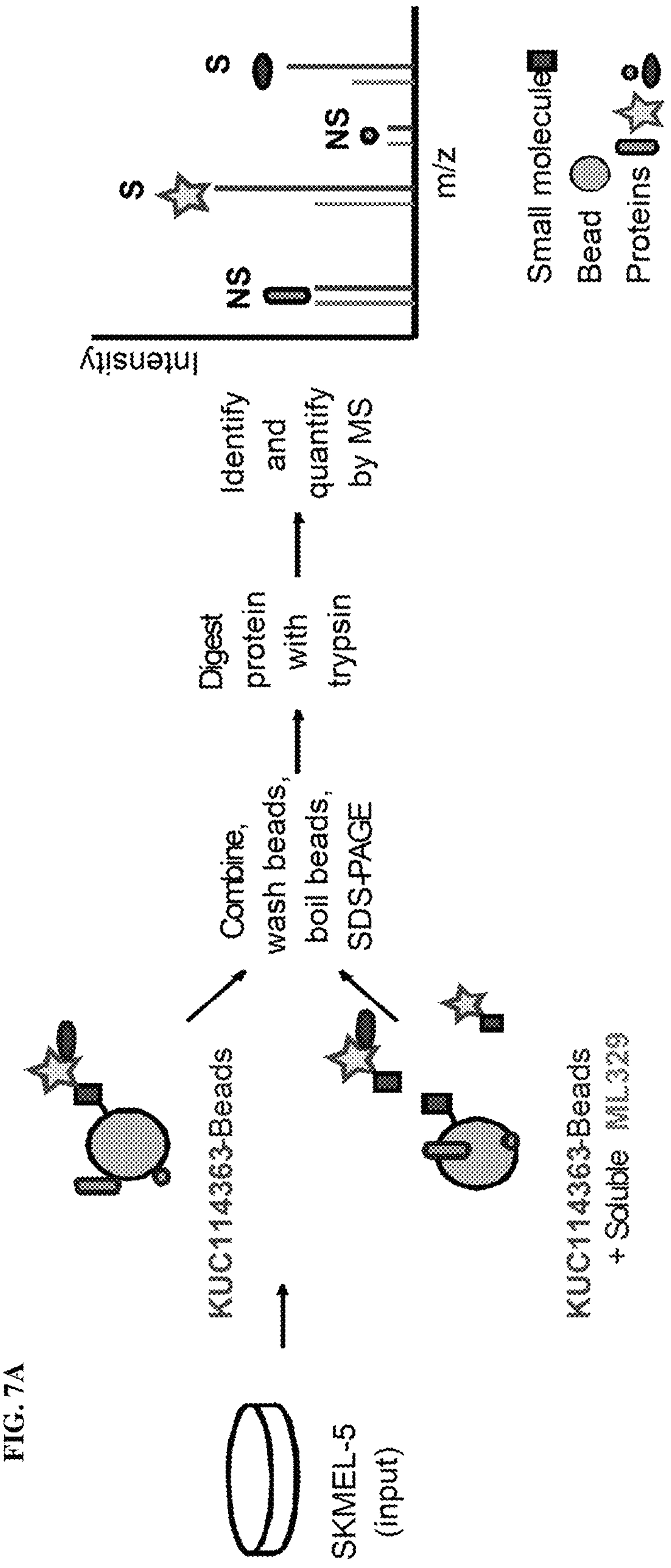
Figure 8:
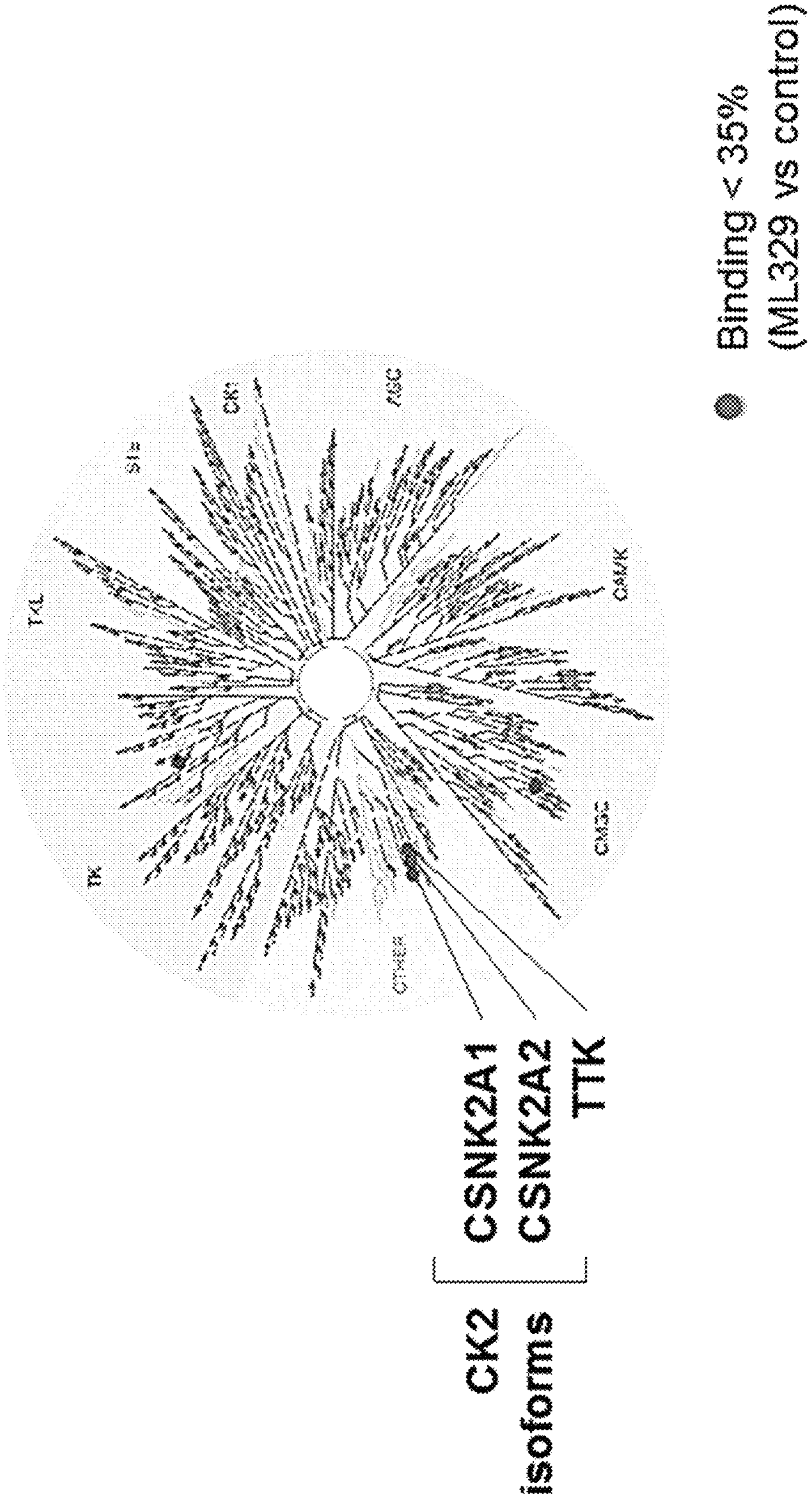
FIG. 8 shows the interaction of ML329 with the kinome.
Figures 9A, 9B:
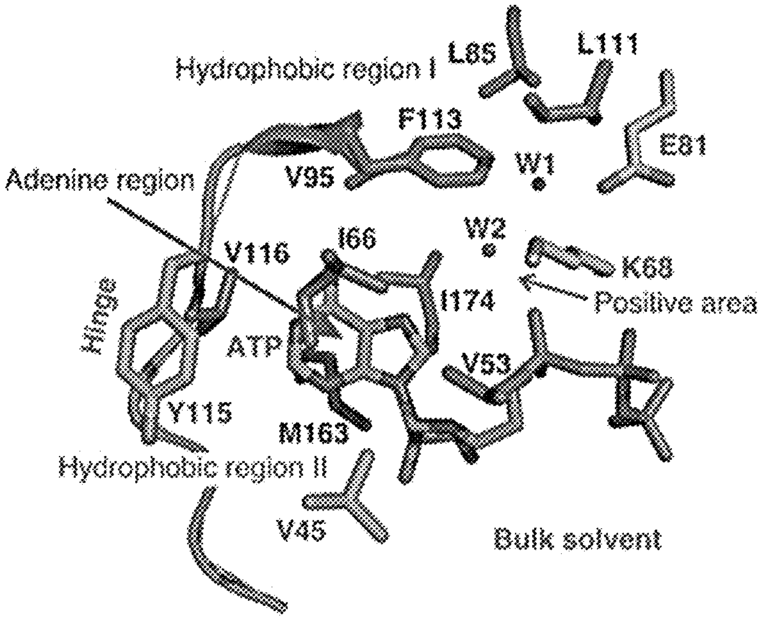
FIG. 9A and FIG. 9B show drug-resistant mutants for casein kinase II (CK2) inhibitors.
Figure 10:
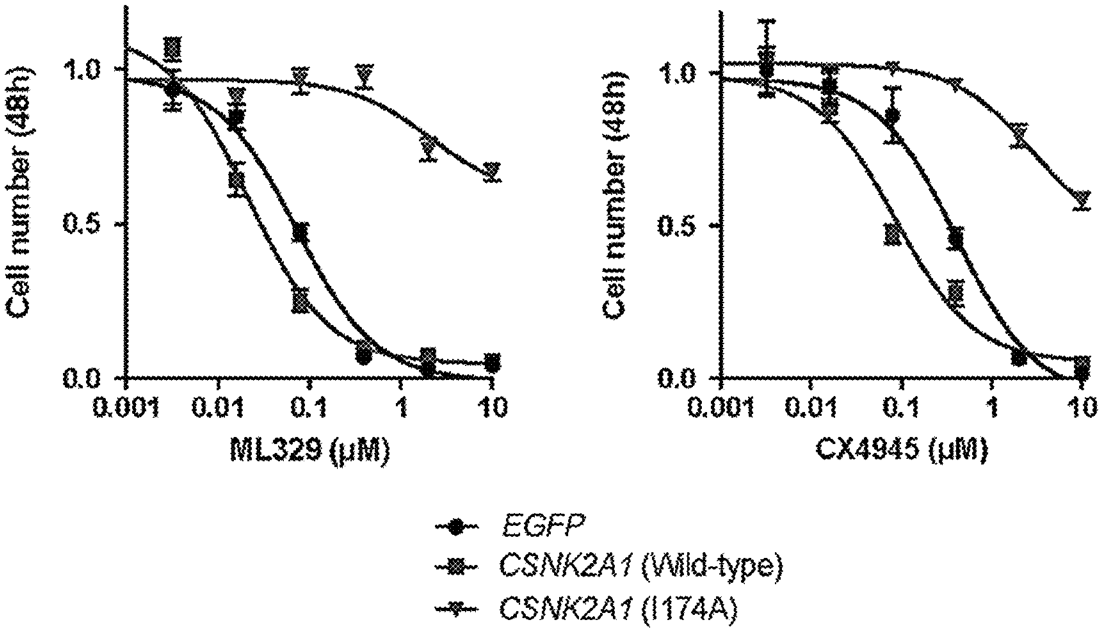
FIG. 10 shows that ML329 cytotoxicity is dependent on CK2.

For any figure showing a bar histogram, curve, or other data associated with a legend, the bars, curve, or other data presented from left to right for each indication correspond directly and in order to the boxes from top to bottom, or from left to right, of the legend.

DETAILED DESCRIPTION OF THE INVENTION

The present invention is based, at least in part, on the discovery of biomarkers (e.g., NQO1, NRF2, and/or activating mutations thereof, and/or KEAP1 and/or inhibiting mutations thereof) of selective inhibition of hyperproliferation of cancer cells (e.g., kills cancer cells) of interest by ML329 and derivatives thereof. The present invention provides methods for stratifying subjects who are predicted to be responsive to ML329 or a derivative thereof based upon a determination and analysis of such biomarkers according to amount (e.g., copy number or level of expression) and/or activity, such as loss- or gain-of-function, relative to a control. Such analyses can be used to perform a number of diagnostic and prognostic assays described herein, either alone or in combination with useful therapeutic regimens (e.g., based on predictions of clinical response, subject survival or relapse, timing of adjuvant or neoadjuvant treatment, etc.).

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples.

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies encompassed by the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies encompassed by the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined.

In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the "predictive score."

The term "biomarker" refers to a measurable entity encompassed by the present invention that has been determined to be predictive of responsiveness to ML329 or a derivative thereof in a cancer. Biomarkers can include, without limitation, nucleic acids (e.g., genomic nucleic acids and/or transcribed nucleic acids) and proteins, including those shown in Table 1, the Examples, and the Figures. Many biomarkers listed in Table 1 are also useful as therapeutic targets. In one embodiment, such targets are NQO1, NRF2 and/or KEAP1 members shown in Table 1.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term “body fluid” refers to fluids that are excreted or secreted from the body as well as fluids that are normally not (e.g. amniotic fluid, aqueous humor, bile, blood and blood plasma, cerebrospinal fluid, cerumen and earwax, cowper’s fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms “cancer” or “tumor” or “hyperproliferative” refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. As used herein, the term “cancer” includes premalignant as well as malignant cancers. As used herein, the term “cancer” includes premalignant as well as malignant cancers. Cancers include, but are not limited to, B cell cancer, e.g., multiple myeloma, Waldenström’s macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing’s tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms’ tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin’s disease and non-Hodgkin’s disease), multiple myeloma, Waldenstrom’s macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In certain embodiments, the cancer whose phenotype is determined by the method encompassed by the present invention is an epithelial cancer such as, but not limited to, bladder cancer, breast cancer, cervical cancer, colon cancer, colorectal cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In some embodiments, the present invention is used in the treatment, diagnosis, and/or prognosis of melanoma and its subtypes.

In some embodiments, the cancer is melanoma. The term “melanoma” generally refers to cancers derived from melanocytes. Although melanocytes are predominantly located in skin, they are also found in other parts of the body, including the eye and bowel. Although cutaneous melanoma is most common, melanoma can originate from any melanocyte in the body. Though melanoma is less than five percent of the skin cancers, it is the seventh most common malignancy in the U.S. and is responsible for most of the skin cancer related deaths. The incidence has increased dramatically in the last several decades due to altered sun exposure habits of the population. Several hereditary risk factors are also known. Other important risk factors are the number of pigment nevi, the number dysplastic nevi, and skin type. An increased risk is coupled to many nevi, both benign and dysplastic, and fair skin. Familial history of malignant melanomas is a risk factor, and approximately 8-12% of malignant melanoma cases are familial. Additional details are well known, such as described in US Pat. Publs. 2012-0269764 and 2013-0237445.

Malignant melanomas are clinically recognized based on the ABCD(E) system, where A stands for asymmetry, B for border irregularity, C for color variation, D for diameter >5 mm, and E for evolving. Further, an excision biopsy can be performed in order to corroborate a diagnosis using microscopic evaluation. Infiltrative malignant melanoma is traditionally divided into four principal histopathological subgroups: superficial spreading melanoma (SSM), nodular malignant melanoma (NMM), lentigo maligna melanoma (LMM), and acral lentiginous melanoma (ALM). Other rare types also exists, such as desmoplastic malignant melanoma. A substantial subset of malignant melanomas appear to arise from melanocytic nevi and features of dysplastic nevi are often found in the vicinity of infiltrative melanomas. Melanoma is thought to arise through stages of progression from normal melanocytes or nevus cells through a dysplastic nevus stage and further to an in situ stage before becoming invasive. Some of the subtypes evolve through different phases of tumor progression, which are called radial growth phase (RGP) and vertical growth phase (VGP).

Malignant melanomas are staged according to the American Joint Committee on Cancer (AJCC) TNM-classification system, where Clark level is considered in T-classification. The T stage describes the local extent of the primary tumor, i.e., how far the tumor has invaded and imposed growth into surrounding tissues, whereas the N stage and M stage describe how the tumor has developed metastases, with the N stage describing spread of tumor to lymph nodes and the M stage describing growth of tumor in other distant organs. Early stages include: T0-1, N0, M0, representing localized tumors with negative lymph nodes. More advanced stages include: T2-4, N0, M0, localized tumors with more widespread growth and T1-4, N1-3, M0, tumors that have metastasized to lymph nodes and T1-4, N1-3, M1, tumors with a metastasis detected in a distant organ.

Stages I and II represent no metastatic disease and for stage I (T1a/b-2a,N0,M0) prognosis is very good. The 5-year survival for stage I disease is 90-95%, for stage II (T2b-4-b,N0,M0) the corresponding survival rate ranges from 80 to 45%. Stages III (T1a-4-b,N1a-3,M0) and IV (T(aII), N(aII), M1a-c) represent spread disease, and for these stages 5-year survival rates range from 70 to 24%, and from 19 to 7%, respectively. "Clark's level" is a measure of the layers of skin involved in a melanoma and is a melanoma prognostic factor. For example, level I involves the epidermis. Level II involves the epidermis and upper dermis. Level III involves the epidermis, upper dermis, and lower dermis. Level IV involves the epidermis, upper dermis, lower dermis, and subcutis. When the primary tumor has a thickness of >1 mm, ulceration, or Clark level IV-V, sentinel node biopsy (SNB) is typically performed. SNB is performed by identifying the first draining lymph node/s (i.e., the SN) from the tumour. This is normally done by injection of radiolabelled colloid particles in the area around the tumour, followed by injection of Vital Blue dye. Rather than dissection of all regional lymph nodes, which was the earlier standard procedure, only the sentinel nodes are generally removed and carefully examined. Following complete lymph node dissection is only performed in confirmed positive cases.

In addition to staging and diagnosis, factors like T-stage, Clark level, SNB status, Breslow's depth, ulceration, and the like can be used as endpoints and/or surrogates for analyses according to the present invention. For example, patients who are diagnosed at an advanced stage with metastases generally have a poor prognosis. For patients diagnosed with a localized disease, the thickness of the tumor measured in mm (Breslow) and ulceration can be endpoints for prognosis. Breslow's depth is determined by using an ocular micrometer at a right angle to the skin. The depth from the granular layer of the epidermis to the deepest point of invasion to which tumor cells have invaded the skin is directly measured. Clark level is important for thin lesions (<1 mm). Other prognostic factors include age, anatomic site of the primary tumor and gender. The sentinel node (SN) status can also be a prognostic factor, especially since the 5-year survival of SN-negative patients has been shown to be as high as 90%. Similarly, overall survival (OS) can be used as a standard primary endpoint. OS takes in to account time to death, irrespective of cause, e.g. if the death is due to cancer or not. Loss to follow-up is censored and regional recurrence, distant metastases, second primary malignant melanomas and second other primary cancers are ignored. Other surrogate endpoints for survival can be used, as described further herein, such as disease-free survival (DFS), which includes time to any event related to the same cancer, i.e. all cancer recurrences and deaths from the same cancer are events.

In addition to endpoints, certain diagnostic and prognostic markers can be analyzed in conjunction with the methods described herein. For example, lactate dehydrogenase (LDH) can be measured as a marker for disease progression. Patients with distant metastases and elevated LDH levels belong to stage IV M1c. Another serum biomarker of interest is S100B. High S100B levels are associated with disease progression, and a decrease in the S100B level is an indicator of treatment response. Melanoma-inhibiting activity (MIA) is yet another serum biomarker that has been evaluated regarding its prognostic value. Studies have shown that elevated MIA levels are rare in stage I and II disease, whereas in stage III or IV, elevation in MIA levels can be seen in 60-100% of cases. Additional useful biomarkers include RGS1 (associated with reduced relapse-free survival (RFS)), osteopontin (associated with both reduced RFS and disease-specific survival (DSS), and predictive of SLN metastases), HER3 (associated with reduced survival), and NCOA3 (associated with poor RFS and DSS, and predictive of SLN metastases). In addition, HM1B-45, Ki-67 (MIB1), MITF and MART-1/Melan-A or combinations of any described marker may be used for staining (Ivan & Prieto, 2010, Future Oncol. 6(7), 1163-1175; Linos et al., 2011, Biomarkers Med. 5(3) 333-360). In a literature review Rothberg et al. report that melanoma cell adhesion molecule (MCAM)/MUC18, matrix metalloproteinase-2, Ki-67, proliferating cell nuclear antigen (PCNA) and p16/INK4A are predictive of either all-cause mortality or melanoma specific mortality (Rothberg et al., 2009 J. Nat. Canc. Inst. 101(7) 452-474).

Currently, the typical primary treatment of malignant melanoma is radical surgery. Even though survival rates are high after excision of the primary tumour, melanomas tend to metastasize relatively early, and for patients with metastatic melanoma the prognosis is poor, with a 5-year survival rate of less than 10%. Radical removal of distant metastases with surgery can be an option and systemic chemotherapy can be applied, but response rates are normally low (in most cases less than 20%), and most treatment regiments fail to prolong overall survival. The first FDA-approved chemotherapeutic agent for treatment of metastatic melanoma was dacarbazine (DTIC), which can give response rates of approximately 20%, but where less than 5% may be complete responses. Temozolamid is an analog of DTIC that has the advantage of oral administration, and which have been shown to give a similar response as DTIC. Other chemotherapeutic agents, for example different nitrosureas, cisplatin, carboplatin, and vinca alkaloids, have been used, but without any increase in response rates. Since chemotherapy is an inefficient treatment method, immunotherapy agents have also been proposed. Most studied are interferon-alpha and interleukin-2. As single agents they have not been shown to give a better response than conventional treatment, but in combination with chemotherapeutic agents higher response rates have been reported. For patients with resected stage IIB or III melanoma, some studies have shown that adjuvant interferon alfa has led to longer disease free survival. For first- or second-line stage III and IV melanoma systemic treatments include: carboplatin, cisplatin, dacarbazine, interferon alfa, high-dose interleukin-2, paclitaxel, temozolomide, vinblastine or combinations thereof (NCCN Guidelines, ME-D, MS-9-13). Recently, the FDA approved Zelboraf™ (vemurafenib, also known as INN, PLX4032, RG7204 or $R_{05185426}$) for unresectable or metastatic melanoma with the BRAF V600E mutation (Bollag et al. (2010) *Nature* 467:596-599 and Chapman et al. (2011) *New Eng. J. Med.* 364:2507-2516). Another recently approved drug for unresectable or metastatic melanoma is Yervoy® (ipilimumab) an antibody which binds to cytotoxic T-lymphocyte-associated antigen 4 (CTLA-4) (Hodi et al. (2010) *New Eng. J. Med.* 363:711-723). Others recently reported that patients with KIT receptor activating mutations or over-expression responded to Gleevac® (imatinib mesylate) (Carvajal et al. (2011) *JAMA* 305:2327-2334). In addition, radiation treatment may be given as an adjuvant after removal of lymphatic metastases, but malignant melanomas are relatively radioresistant. Radiation treatment might also be used as palliative treatment. Melanoma oncologists have also noted that BRAF mutations are common in both primary and metastatic melanomas and that these mutations are reported to be present in 50-70% of all melanomas. This has led to an interest in B-raf inhibitors, such as sorafenib, as therapeutic agents.

In certain embodiments, the cancer is lung cancer or head and neck squamous cell carcinoma. KEAP1 mutations are common in lung cancers and head and neck squamous cell carcinomas. It has been determined herein that KEAP1 mutations associated with high NQO1 expression are found in approximately 25% of lung cancers. In some embodiments, the cancer is kidney cancer, pancreas cancer, or prostate cancer, such as where KEAP1 loss of function has been detected. In some embodiments, the cancer is bladder cancer, uterine cancer, head and neck cancer, lung cancer or esophagus cancer, such as where NRF2 mutations are observed. The cancer encompassed by the present invention is not limited to the cancer types listed above, as KEAP1/NRF2 mutations exist in virtually all cancer types at lower frequencies.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods encompassed by the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods encompassed by the present invention are not limited to use of a specific cut-off point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene (i.e., the wild type biomarker is diploid). The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide immunotherapy that generally increases immune responses against the cancer. Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code encompassed by the present invention to determine the presence or absence of a cancer or subtype thereof in an individual. The term also includes methods, systems, and code for assessing the level of disease activity in an individual.

The term "NQO1" refers to NAD(P)H quinone dehydrogenase 1 as well as the NQO1 gene (also known as DTD, QR1, DHQU, DIA4, NMOR1, and NMORI), depending on the context. NQO1 is a member of the NAD(P)H dehydrogenase (quinone) family and encodes a cytoplasmic 2-electron reductase. This FAD-binding protein forms homodimers and reduces quinones to hydroquinones. NQO1's enzymatic activity prevents the one electron reduction of quinones that results in the production of radical species. Mutations in NQO1 have been associated with tardive dyskinesia (TD), an increased risk of hematotoxicity after exposure to benzene, and susceptibility to various forms of cancer. Altered expression of NQO1 has been seen in many tumors and is also associated with Alzheimer's disease (AD). Multiple transcript variants encoding different isoforms, and orthologues in different species can been found, and are exemplified herein, without limitation, in Table 1.

Human NQO1 nucleic acid (NM_000903.2, NM_001025433.1, NM_001025434.1, and NM_001286137.1) and amino acid (NP_000894.1, NP_001020604.1, NP_001020605.1, and NP_001273066.1) sequences are publicly available on the GenBank database maintained by the U.S. National Center for Biotechnology Information. Nucleic acid and polypeptide sequences of NQO1 orthologs in species other than humans are also well known and include, for example, mouse NQO1 (NM_008706.5 and NP_032732.3), chimpanzee NQO1 (XM_016930091.1 and XP_016785580.1, XM_523404.6 and XP_523404.4, and XM_016930090.1 and XP_016785579.1), monkey NQO1 (NM_001260998.1 and NP_001247927.1), dog NQO1 (XM_848524.5 and XP_853617.3), cattle NQO1 (NM_001034535.1 and NP_001029707.1), rat NQO1 (NM_017000.3 and NP_058696.2), and chicken NQO1 (NM_001277619.1 and NP_001264548.1, NM_001277620.1 and NP_001264549.1, and NM_001277621.1 and NP_001264550.1). Representative sequences of NQO1 orthologs are presented below in Table 1.

Anti-NQO1 antibodies suitable for detecting NQO1 protein are well-known in the art and include, for example, antibodies AM06702SU-N and AM06703SU-N(Origene), antibodies NB200-209, NBP1-85223, and NB100-1005 (Novus Biologicals, Littleton, CO), antibodies ab28947, ab80588, and ab239896 (AbCam, Cambridge, MA), etc. In addition, reagents are well-known for detecting NQO1. Moreover, multiple siRNA, shRNA, CRISPR constructs for reducing NQO1 expression can be found in the commercial product lists of the above-referenced companies, such as siRNA products #sc-37139 and sc-37140 and CRISPR product #sc-400190-KO-2 from Santa Cruz Biotechnology, RNAi products TF311109 and TL311109, and CRISPR products KN200620 and KN311189 (Origene), and multiple CRISPR products from GenScript (Piscataway, NJ). It is to be noted that the term can further be used to refer to any combination of features described herein regarding NQO1 molecules. For example, any combination of sequence composition, percentage identify, sequence length, domain structure, functional activity, etc. can be used to describe an NQO1 molecule encompassed by the present invention.

The term "NRF2" refers to Nuclear Factor, Erythroid 2 Like 2 as well as the NRF2 gene (also known as NRF2, HEBP1, and IMDDHH), depending on the context. NRF2 is a transcription factor which is a member of a small family of basic leucine zipper (bZIP) proteins. The encoded transcription factor regulates genes which contain antioxidant response elements (ARE) in their promoters; many of these genes encode proteins involved in response to injury and inflammation which includes the production of free radicals. Multiple transcript variants encoding different isoforms, and orthologues of NRF2 in different species can been found, and are exemplified herein, without limitation, in Table 1. NRF2 is a transcription activator that binds to antioxidant response (ARE) elements in the promoter regions of target genes. NRF2 is important for the coordinated up-regulation of genes in response to oxidative stress. It can be involved in the transcriptional activation of genes of the beta-globin cluster by mediating enhancer activity of hypersensitive site 2 of the beta-globin locus control region.

Human NRF2 nucleic acid (NM_006164.4, NM_001145412.3, NM_001145413.3, NM_001313900.1, NM_001313901.1, NM_001313902.1, NM_001313903.1 and NM_001313904.1) and amino acid (NP_006155.2, NP_001138884.1, NP_001300829.1, NP_001300830.1, NP_001138885.1, NP_001300831.1, NP 001300832.1 and NP_001300833.1) sequences are publicly available on the GenBank database maintained by the U.S. National Center for Biotechnology Information. Nucleic acid and polypeptide sequences of NRF2 orthologs in species other than humans are also well known and include, for example, mouse NRF2 (NM_010902.4 and NP_035032.1, and NR_132727.1), chimpanzee NRF2 (XM_001145876.5 and XP_001145876.3, XM_009443801.3 and XP_009442076.2, XM_003309327.4 and XP_003309375.2, and XM_009443802.3 and XP_009442077.2), dog NRF2 (XM_022414833.1 and XP_022270541.1, XM_005640352.3 and XP_005640409.1, and XM_014110726.1 and XP_013966201.1), cattle NRF2 (NM_001011678.2 and NP_001011678.2), rat NRF2 (NM_031789.2 and NP_113977.1), and chicken NRF2 (NM_205117.1 and NP_990448.1). Representative sequences of NRF2 orthologs are presented below in Table 1.

Anti-NRF2 antibodies suitable for detecting NRF2 protein are well-known in the art and include, for example, antibodies AP13999PU-N and AP14000PU-N(Origene), antibodies NBP1-32822, MAB3925, and NBP2-67465 (Novus Biologicals, Littleton, CO), antibodies ab62352, ab76026, and ab180845 (AbCam, Cambridge, MA), etc. In addition, reagents are well-known for detecting NRF2. Moreover, multiple siRNA, shRNA, CRISPR constructs for reducing NRF2 expression can be found in the commercial product lists of the above-referenced companies, such as siRNA products #sc-37030 and sc-44332 and CRISPR product #sc-400017 from Santa Cruz Biotechnology, RNAi products TG311194 and TL311194, and CRISPR products KN204140 and KN310937 (Origene), and multiple CRISPR products from GenScript (Piscataway, NJ). It is to be noted that the term can further be used to refer to any combination of features described herein regarding NRF2 molecules. For example, any combination of sequence composition, percentage identify, sequence length, domain structure, functional activity, etc. can be used to describe an NRF2 molecule encompassed by the present invention.

The term "KEAP1" refers to Kelch Like ECH Associated Protein 1 as well as the KEAP1 gene (also known as INrf2 and KLHL19), depending on the context. KEAP1 is a protein containing KELCH-1 like domains, as well as a BTB/POZ domain. Kelch-like ECH-associated protein 1 interacts with NF-E2-related factor 2 in a redox-sensitive manner and the dissociation of the proteins in the cytoplasm is followed by transportation of NF-E2-related factor 2 to the nucleus. This interaction results in the expression of the catalytic subunit of gamma-glutamylcysteine synthetase. KEAP1 acts as a substrate adapter protein for the E3 ubiquitin ligase complex formed by CUL3 and RBX1 and targets NFE2L2/NRF2 for ubiquitination and degradation by the proteasome, thus resulting in the suppression of its transcriptional activity and the repression of antioxidant response element-mediated detoxifying enzyme gene expression. KEAP1 retains NFE2L2/NRF2 and can also retain BPTF in the cytosol. It also targets PGAM5 for ubiquitination and degradation by the proteasome. Multiple transcript variants encoding different isoforms, and orthologues in different species can been found, and are exemplified herein, without limitation, in Table 1.

Human KEAP1 nucleic acid (NM_012289.3 and NM_203500.1) and amino acid (NP_036421.2 and NP_987096.1) sequences are publicly available on the GenBank database maintained by the U.S. National Center for Biotechnology Information. Nucleic acid and polypeptide sequences of KEAP1 orthologs in species other than humans are also well known and include, for example, mouse KEAP1 (NM_001110305.1 and NP_001103775.1, NM_001110306.1 and NP_001103776.1, NM_001110307.1 and NP_001103777.1, and NM_016679.4 and NP_057888.1), chimpanzee KEAP1 (NM_001279961.1 and NP_001266890.1), dog KEAP1 (XM_005632897.3 and XP_005632954.1, and XM_533917.6 and XP_533917.2), frog KEAP1 (NM_001008023.1 and NP_001008024.1), cattle KEAP1 (NM_001101142.1 and NP_001094612.1), and rat KEAP1 (NM_057152.2 and NP_476493.2). Representative sequences of KEAP1 orthologs are presented below in Table 1.

Anti-KEAP1 antibodies suitable for detecting KEAP1 protein are well-known in the art and include, for example, antibodies AP32137PU-N and AP52328PU-N(Origene), antibodies NBP2-03319, MAB3024, and NBP1-83106 (Novus Biologicals, Littleton, CO), antibody ab119403 (AbCam, Cambridge, MA), etc. In addition, reagents are well-known for detecting KEAP1. Moreover, multiple siRNA, shRNA, CRISPR constructs for reducing KEAP1 expression can be found in the commercial product lists of the above-referenced companies, such as siRNA products #sc-156042 and sc-43878 and CRISPR product #sc-400190-KO-2 from Santa Cruz Biotechnology, RNAi products TF303778 and TL303778, and CRISPR products KN202189 and KN308748 (Origene), and multiple CRISPR products from GenScript (Piscataway, NJ). It is to be noted that the term can further be used to refer to any combination of features described herein regarding KEAP1 molecules. For example, any combination of sequence composition, percentage identify, sequence length, domain structure, functional activity, etc. can be used to describe an KEAP1 molecule encompassed by the present invention.

The term "inhibiting mutation" for a biomarker, such as NQO1, NRF2 or KEAP1, refers to any mutation in the biomarker, such as a mutation in a biomarker nucleic acid or protein, that results in reduced biomarker protein amounts and/or function. Inhibiting mutations that substantially eliminate biomarker protein amounts and/or function are referred to as "loss-of-function mutations." By contrast, "gain-of-function" mutations refer to mutations that result in increased biomarker protein amounts and/or function. In certain embodiments, the term "gain-of-function" can simply refer to the presence of a biomarker of interest (e.g., nucleic acid and/or protein, such as wild-type) without a requirement for a mutation. Representative, non-limiting nucleic acid mutations include single-base substitutions, multi-base substitutions, insertion mutations, deletion mutations, frameshift mutations, missesnse mutations, nonsense mutations, splice-site mutations, epigenetic modifications (e.g., methylation, phosphorylation, acetylation, ubiquitylation, sumoylation, histone acetylation, histone deacetylation, and the like), and combinations thereof. In some embodiments, the mutation is a "nonsynonymous mutation," meaning that the mutation alters the amino acid sequence of the biomarker. Such mutations reduce or eliminate biomarker protein amounts and/or function by eliminating proper coding sequences required for proper biomarker protein translation and/or coding for biomarker proteins that are non-functional or have reduced function (e.g., deletion of enzymatic and/or structural domains, reduction in protein stability, alteration of sub-cellular localization, and the like). Such mutations are well-known in the art. In addition, a representative list describing a wide variety of structural mutations correlated with the functional result of reduced or eliminated biomarker protein amounts and/or function is described in the Tables and the Examples.

KEAP mutations are widely distributed in the KEAP1 gene and are found in virtually all domains of the protein. Somatic mutations in the KEAP1 gene, similar to those in the NRF2 gene, affect protein-protein interactions, i.e., the binding of NRF2 to KEAP1 (Taguchi and Yamamoto (2017) *Frontiers in Oncology* 7:1-11). Representative, non-limiting loss of function mutations of KEAP1 include, but are not limited to, the following and the present invention encompasses mutations at corresponding positions in orthologs of the listed nucleic acid positions or amino acid positions, which can be readily determined by the ordinarily skilled artisan using well-known bioinformatics methods and genetic sequences described herein:

| Positio | CDS Mutation | AA Mutation | Mutationn | Count | Type |
|---|---|---|---|---|---|
| 1 | c.1_1875del1875 | p.0 | 6196673 | 1 | Whole gene deletion |
| 4 | c.10G > C | p.D4H | 4410364 | 1 | Substitution - Missense |
| 6 | c.16A > T | p.R6W | 6949317 | 1 | Substitution - Missense |
| 8 | c.24C > G | p.S8R | 5021994 | 1 | Substitution - Missense |
| 9 | c.25G > A | p.G9R | 2812662 | 1 | Substitution - Missense |
| 11 | c.31G > A | p.G11R | 5554506 | 1 | Substitution - Missense |
| 12 | c.34G > T | p.A12S | 6395578 | 2 | Substitution - Missense |
| 13 | c.38G > A | p.C13Y | 6191663 | 1 | Substitution - Missense |
| 15 | c.44G > A | p.R15Q | 6975298 | 1 | Substitution - Missense |
| 15 | c.44G > T | p.R15L | 710185 | 1 | Substitution - Missense |
| 15 | c.43C > T | p.R15* | 5952474 | 1 | Substitution - Nonsense |
| 20 | c.60G > T | p.Q20H | 4986189 | 1 | Substitution - Missense |
| 20 | c.58C > T | p.Q20* | 4073875 | 1 | Substitution - Nonsense |
| 21 | c.62C > A | p.S21* | 6942529 | 1 | Substitution - Nonsense |
| 23 | c.68G > A | p.C23Y | 32539 | 1 | Substitution - Missense |
| 24 | c.70_83 > A | p.P24fs*4 | 6865904 | 1 | Complex - frameshift |
| 25 | c.73G > A | p.E25K | 417774 | 2 | Substitution - Missense |
| 25 | c.73G > C | p.E25Q | 6917556 | 1 | Substitution - Missense |
| 29 | c.85G > A | p.D29N | 6371459 | 2 | Substitution - Missense |
| 30 | c.88G > A | p.A30T | 2812660 | 3 | Substitution - Missense |
| 33 | c.97T > C | p.Y33H | 7340467 | 1 | Substitution - Missense |
| 33 | c.98A > G | p.Y33C | 2812658 | 1 | Substitution - Missense |
| 34 | c.100G > A | p.A34T | 4073874 | 1 | Substitution - Missense |
| 34 | c.101C > T | p.A34V | 7201842 | 1 | Substitution - Missense |
| 35 | c.103_104TC > AT | p.S35I | 1285709 | 1 | Substitution - Missense |
| 36 | c.106A > G | p.T36A | 6953664 | 1 | Substitution - Missense |
| 40 | c.119C > T | p.A40V | 2812655 | 1 | Substitution - Missense |
| 42 | c.125T > C | p.V42A | 6196572 | 1 | Substitution - Missense |
| 42 | c.125T > G | p.V42G | 6492182 | 1 | Substitution - Missense |
| 43 | c.127_129ACG > T | p.T43fs*35 | 6959134 | 1 | Complex - frameshift |
| 43 | c.128C > T | p.T43M | 6191664 | 2 | Substitution - Missense |
| 45 | c.134C > A | p.S45Y | 3959488 | 1 | Substitution - Missense |
| 45 | c.134C > T | p.S45F | 4073873 | 6 | Substitution - Missense |
| 46 | c.136C > T | p.Q46* | 6083856 | 1 | Substitution - Nonsense |
| 47 | c.140A > G | p.H47R | 3718031 | 2 | Substitution - Missense |
| 48 | c.143G > A | p.G48D | 5476019 | 2 | Substitution - Missense |
| 50 | c.149G > A | p.R50H | 990609 | 2 | Substitution - Missense |
| 51 | c.152C > G | p.T51S | 6969651 | 1 | Substitution - Missense |
| 52 | c.156C > A | p.F52L | 6975842 | 1 | Substitution - Missense |
| 53 | c.158G > T | p.S53I | 5791857 | 1 | Substitution - Missense |
| 54 | c.160T > G | p.Y54D | 1136093 | 1 | Substitution - Missense |
| 54 | c.161A > G | p.Y54C | 94575 | 1 | Substitution - Missense |
| 56 | c.166delC | p.L56fs*12 | 6984131 | 1 | Deletion - Frameshift |
| 57 | c.169G > T | p.E57* | 6927769 | 1 | Substitution - Nonsense |
| 59 | c.175C > T | p.H59Y | 5794003 | 1 | Substitution - Missense |
| 61 | c.182delA | p.K61fs*7 | 7340616 | 1 | Deletion - Frameshift |
| 63 | c.187G > A | p.A63T | 1611495 | 2 | Substitution - Missense |
| 63 | c.188C > A | p.A63D | 6968181 | 1 | Substitution - Missense |
| 63 | c.188C > T | p.A63V | 6951358 | 1 | Substitution - Missense |
| 67 | c.201G > T | p.M67I | 6925190 | 1 | Substitution - Missense |
| 68 | c.203A > G | p.N68S | 6438153 | 3 | Substitution - Missense |
| 69 | c.205G > T | p.E69* | 6955934 | 1 | Substitution - Nonsense |
| 71 | c.212G > A | p.R71Q | 4951265 | 1 | Substitution - Missense |
| 71 | c.212G > T | p.R71L | 378705 | 3 | Substitution - Missense |
| 73 | c.218G > A | p.S73N | 6454273 | 1 | Substitution - Missense |
| 73 | c.218G > T | p.S73I | 3959487 | 2 | Substitution - Missense |
| 75 | c.223C > T | p.Q75* | 710186 | 1 | Substitution - Nonsense |
| 78 | c.232G > A | p.D78N | 6557467 | 1 | Substitution - Missense |
| 79 | c.235G > T | p.V79F | 6524628 | 1 | Substitution - Missense |

-continued

| Positio | CDS Mutation | AA Mutation | Mutationn | Count | Type |
|---|---|---|---|---|---|
| 82 | c.245A > C | p.Q82P | 6919698 | 1 | Substitution - Missense |
| 82 | c.246G > T | p.Q82H | 6196628 | 1 | Substitution - Missense |
| 82 | c.244C > T | p.Q82* | 6913062 | 1 | Substitution - Nonsense |
| 83 | c.247G > A | p.V83I | 4987166 | 1 | Substitution - Missense |
| 83 | c.247G > T | p.V83F | 6524627 | 2 | Substitution - Missense |
| 91 | c.271G > A | p.A91T | 2812647 | 2 | Substitution - Missense |
| 91 | c.271G > T | p.A91S | 3378602 | 3 | Substitution - Missense |
| 94 | c.282G > T | p.M94I | 6524626 | 1 | Substitution - Missense |
| 95 | c.283delG | p.A95fs*62 | 6971184 | 1 | Deletion - Frameshift |
| 95 | c.283G > A | p.A95T | 990608 | 3 | Substitution - Missense |
| 95 | c.283G > T | p.A95S | 6524625 | 1 | Substitution - Missense |
| 95 | c.284C > T | p.A95V | 5550782 | 1 | Substitution - Missense |
| 96 | c.287A > G | p.H96R | 6925008 | 1 | Substitution - Missense |
| 96 | c.287A > T | p.H96L | 398498 | 1 | Substitution - Missense |
| 96 | c.288C > G | p.H96Q | 5614595 | 1 | Substitution - Missense |
| 97 | c.291G > T | p.K97N | 6149742 | 1 | Substitution - Missense |
| 97 | c.289A > T | p.K97* | 2812646 | 1 | Substitution - Nonsense |
| 98 | c.293T > G | p.V98G | 6915445 | 1 | Substitution - Missense |
| 99 | c.295G > A | p.V99M | 6910166 | 1 | Substitution - Missense |
| 99 | c.295G > T | p.V99L | 6083857 | 1 | Substitution - Missense |
| 100 | c.299T > C | p.L100P | 6149743 | 1 | Substitution - Missense |
| 102 | c.305C > T | p.S102L | 6149744 | 4 | Substitution - Missense |
| 103 | c.308C > T | p.S103F | 6958217 | 1 | Substitution - Missense |
| 104 | c.312C > A | p.S104R | 4922491 | 1 | Substitution - Missense |
| 105 | c.314delC | p.P105fs*52 | 328699 | 1 | Deletion - Frameshift |
| 105 | c.313C > T | p.P105S | 7226843 | 1 | Substitution - Missense |
| 107 | c.319T > C | p.F107L | 6196642 | 1 | Substitution - Missense |
| 108 | c.323delA | p.K108fs*49 | 6934671 | 1 | Deletion - Frameshift |
| 110 | c.328A > C | p.M110L | 6579953 | 2 | Substitution - Missense |
| 110 | c.328A > G | p.M110V | 6083858 | 3 | Substitution - Missense |
| 110 | c.330G > A | p.M110I | 337518 | 1 | Substitution - Missense |
| 110 | c.330G > T | p.M110I | 6948781 | 2 | Substitution - Missense |
| 112 | c.334A > T | p.T112S | 6948780 | 1 | Substitution - Missense |
| 114 | c.340G > T | p.G114W | 1725916 | 2 | Substitution - Missense |
| 116 | c.346C > T | p.R116W | 1524051 | 1 | Substitution - Missense |
| 116 | c.347G > C | p.R116P | 3796565 | 3 | Substitution - Missense |
| 117 | c.349G > A | p.E117K | 6149745 | 1 | Substitution - Missense |
| 117 | c.351G > T | p.E117D | 6917923 | 3 | Substitution - Missense |
| 117 | c.349G > T | p.E117* | 6982240 | 2 | Substitution - Nonsense |
| 121 | c.361G > T | p.E121* | 6967929 | 1 | Substitution - Nonsense |
| 123 | c.367G > A | p.V123M | 7329043 | 1 | Substitution - Missense |
| 123 | c.367G > T | p.V123L | 6083859 | 2 | Substitution - Missense |
| 125 | c.373A > G | p.I125V | 269429 | 1 | Substitution - Missense |
| 125 | c.373A > T | p.I125F | 6964902 | 1 | Substitution - Missense |
| 127 | c.380G > A | p.G127D | 6438115 | 3 | Substitution - Missense |
| 127 | c.380G > C | p.G127A | 6978486 | 1 | Substitution - Missense |
| 130 | c.388C > A | p.P130T | 6970908 | 1 | Substitution - Missense |
| 130 | c.389C > T | p.P130L | 3528285 | 3 | Substitution - Missense |
| 132 | c.395T > G | p.V132G | 6944122 | 1 | Substitution - Missense |
| 133 | c.398T > G | p.M133R | 6933024 | 1 | Substitution - Missense |
| 133 | c.399G > A | p.M133I | 4653017 | 1 | Substitution - Missense |
| 134 | c.399_400insA | p.E134fs*5 | 6944731 | 1 | Insertion - Frameshift |
| 135 | c.403C > T | p.R135C | 4433833 | 3 | Substitution - Missense |
| 135 | c.404G > T | p.R135L | 2812643 | 1 | Substitution - Missense |
| 137 | c.411_423 > GG | p.I137fs*33 | 6912430 | 1 | Complex - frameshift |
| 137 | c.410T > C | p.I137T | 4941180 | 1 | Substitution - Missense |
| 138 | c.413A > C | p.E138A | 1172563 | 1 | Substitution - Missense |
| 138 | c.412G > T | p.E138* | 6980073 | 1 | Substitution - Nonsense |
| 139 | c.417C > A | p.F139L | 6083860 | 1 | Substitution - Missense |
| 141 | c.422A > G | p.Y141C | 94574 | 1 | Substitution - Missense |
| 141 | c.422A > T | p.Y141F | 380449 | 1 | Substitution - Missense |
| 142 | c.424A > G | p.T142A | 6980310 | 1 | Substitution - Missense |
| 142 | c.425C > T | p.T142M | 564829 | 3 | Substitution - Missense |
| 144 | c.431C > A | p.S144Y | 6909985 | 1 | Substitution - Missense |
| 144 | c.431C > T | p.S144F | 6083861 | 1 | Substitution - Missense |
| 145 | c.435C > G | p.I145M | 6492287 | 1 | Substitution - Missense |
| 147 | c.441_445GGGCG > TGGCT | p.M147_E149 > IG* | 6921846 | 1 | Complex - compound |
| 149 | c.445G > A | p.E149K | 6006187 | 3 | Substitution - Missense |
| 149 | c.445G > C | p.E149Q | 6975181 | 1 | Substitution - Missense |
| 151 | c.452G > A | p.C151Y | 5634314 | 4 | Substitution - Missense |
| 152 | c.454_455delGT | p.V152fs*21 | 6936833 | 1 | Deletion - Frameshift |
| 152 | c.454_455GT > AA | p.V152N | 4456087 | 1 | Substitution - Missense |
| 153 | c.460_461insTCC | p.L153_H154insL | 6933778 | 1 | Insertion - In frame |
| 153 | c.457C > T | p.L153F | 4590889 | 4 | Substitution - Missense |
| 155 | c.463G > T | p.V155F | 710187 | 5 | Substitution - Missense |
| 155 | c.464T > C | p.V155A | 6083862 | 1 | Substitution - Missense |
| 156 | c.466A > T | p.M156L | 3959486 | 2 | Substitution - Missense |

-continued

| Positio | CDS Mutation | AA Mutation | Mutationn | Count | Type |
|---|---|---|---|---|---|
| 156 | c.467T > C | p.M156T | 6920373 | 1 | Substitution - Missense |
| 157 | c.471C > A | p.N157K | 6945157 | 1 | Substitution - Missense |
| 158 | c.472G > A | p.G158S | 5575724 | 1 | Substitution - Missense |
| 158 | c.472G > C | p.G158R | 6565397 | 1 | Substitution - Missense |
| 159 | c.474_475TG > CT | p.A159S | 5967497 | 1 | Substitution - Missense |
| 159 | c.475G > A | p.A159T | 6196644 | 1 | Substitution - Missense |
| 159 | c.475G > C | p.A159P | 6149746 | 1 | Substitution - Missense |
| 161 | c.481A > G | p.M161V | 6924346 | 1 | Substitution - Missense |
| 161 | c.483G > A | p.M161I | 1630692 | 1 | Substitution - Missense |
| 161 | c.483G > T | p.M161I | 6524624 | 3 | Substitution - Missense |
| 165 | c.493G > A | p.D165N | 1390137 | 3 | Substitution - Missense |
| 167 | c.499delG | p.V167fs*63 | 6917727 | 1 | Deletion - Frameshift |
| 167 | c.499G > T | p.V167F | 710188 | 3 | Substitution - Missense |
| 168 | c.502G > T | p.V168F | 6928790 | 1 | Substitution - Missense |
| 169 | c.505C > T | p.R169C | 990606 | 2 | Substitution - Missense |
| 171 | c.512G > T | p.C171F | 6524623 | 2 | Substitution - Missense |
| 173 | c.518A > G | p.D173G | 6490765 | 1 | Substitution - Missense |
| 175 | c.523delC | p.L175fs*55 | 1727613 | 2 | Deletion - Frameshift |
| 178 | c.532C > T | p.Q178* | 3989651 | 1 | Substitution - Nonsense |
| 182 | c.543_544insC | p.S182fs*11 | 6196654 | 1 | Insertion - Frameshift |
| 183 | c.547A > C | p.N183H | 6981097 | 1 | Substitution - Missense |
| 183 | c.548A > G | p.N183S | 6196637 | 1 | Substitution - Missense |
| 184 | c.550G > A | p.A184T | 6963593 | 1 | Substitution - Missense |
| 185 | c.554T > A | p.I185N | 1189874 | 1 | Substitution - Missense |
| 185 | c.554T > C | p.I185T | 990605 | 1 | Substitution - Missense |
| 186 | c.556G > A | p.G186S | 2812636 | 1 | Substitution - Missense |
| 186 | c.556G > C | p.G186R | 6438143 | 2 | Substitution - Missense |
| 186 | c.556G > T | p.G186C | 6916727 | 2 | Substitution - Missense |
| 186 | c.556_557GG > TT | p.G186F | 6974025 | 1 | Substitution - Missense |
| 186 | c.557G > T | p.G186V | 4434025 | 2 | Substitution - Missense |
| 187 | c.560T > A | p.I187N | 6921950 | 1 | Substitution - Missense |
| 188 | c.563C > T | p.A188V | 6196645 | 1 | Substitution - Missense |
| 189 | c.567C > G | p.N189K | 116773 | 1 | Substitution - Missense |
| 191 | c.571G > A | p.A191T | 6149747 | 1 | Substitution - Missense |
| 191 | c.571G > C | p.A191P | 6980450 | 1 | Substitution - Missense |
| 191 | c.572C > A | p.A191D | 1211810 | 1 | Substitution - Missense |
| 192 | c.574G > A | p.E192K | 6914997 | 3 | Substitution - Missense |
| 192 | c.574G > T | p.E192* | 6955519 | 1 | Substitution - Nonsense |
| 193 | c.579G > C | p.Q193H | 1196320 | 2 | Substitution - Missense |
| 195 | c.583G > C | p.G195R | 6923882 | 1 | Substitution - Missense |
| 195 | c.584G > T | p.G195V | 6149748 | 1 | Substitution - Missense |
| 196 | c.587G > T | p.C196F | 5681736 | 2 | Substitution - Missense |
| 198 | c.592G > T | p.E198* | 6911504 | 1 | Substitution - Nonsense |
| 200 | c.599A > C | p.H200P | 6196676 | 1 | Substitution - Missense |
| 204 | c.610C > G | p.R204G | 6975696 | 1 | Substitution - Missense |
| 204 | c.611G > C | p.R204P | 6083863 | 2 | Substitution - Missense |
| 205 | c.614A > T | p.E205V | 6959682 | 1 | Substitution - Missense |
| 205 | c.613G > T | p.E205* | 6524622 | 1 | Substitution - Nonsense |
| 206 | c.618C > A | p.Y206* | 6339857 | 1 | Substitution - Nonsense |
| 207 | c.619_621delATC | p.I207delI | 6287472 | 1 | Deletion - In frame |
| 207 | c.620T > A | p.I207N | 7340468 | 1 | Substitution - Missense |
| 207 | c.620T > G | p.I207S | 6975695 | 1 | Substitution - Missense |
| 211 | c.631T > A | p.F211I | 6985375 | 1 | Substitution - Missense |
| 211 | c.633T > G | p.F211L | 6931108 | 1 | Substitution - Missense |
| 212 | c.635G > A | p.G212E | 6982849 | 1 | Substitution - Missense |
| 213 | c.637G > T | p.E213* | 6920181 | 1 | Substitution - Nonsense |
| 214 | c.640G > A | p.V214M | 4073869 | 1 | Substitution - Missense |
| 216 | c.646A > T | p.K216* | 6923373 | 1 | Substitution - Nonsense |
| 217 | c.649C > T | p.Q217* | 7339889 | 1 | Substitution - Nonsense |
| 218 | c.652G > A | p.E218K | 6989080 | 1 | Substitution - Missense |
| 218 | c.652G > C | p.E218Q | 96325 | 4 | Substitution - Missense |
| 218 | c.653A > T | p.E218V | 1524056 | 3 | Substitution - Missense |
| 219 | c.655G > A | p.E219K | 6911905 | 2 | Substitution - Missense |
| 219 | c.655G > C | p.E219Q | 2812630 | 2 | Substitution - Missense |
| 219 | c.655_656GA > TC | p.E219S | 6965928 | 1 | Substitution - Missense |
| 220 | c.660C > G | p.F220L | 7239656 | 1 | Substitution - Missense |
| 224 | c.670_677delTCCCACTG | p.S224fs*123 | 6916717 | 1 | Deletion - Frameshift |
| 224 | c.671C > A | p.S224Y | 710189 | 1 | Substitution - Missense |
| 224 | c.671C > T | p.S224F | 6929636 | 1 | Substitution - Missense |
| 228 | c.683T > C | p.L228P | 6438142 | 2 | Substitution - Missense |
| 231 | c.691C > A | p.L231I | 6692797 | 1 | Substitution - Missense |
| 231 | c.691C > G | p.L231V | 710190 | 1 | Substitution - Missense |
| 233 | c.698G > A | p.S233N | 6196629 | 1 | Substitution - Missense |
| 234 | c.700C > T | p.R234W | 4855177 | 3 | Substitution - Missense |
| 234 | c.701G > C | p.R234P | 5669062 | 2 | Substitution - Missense |
| 235 | c.704A > C | p.D235A | 6539041 | 1 | Substitution - Missense |
| 236 | c.706G > A | p.D236N | 1524057 | 5 | Substitution - Missense |

-continued

| Positio | CDS Mutation | AA Mutation | Mutationn | Count | Type |
|---|---|---|---|---|---|
| 236 | c.706G > C | p.D236H | 1196953 | 3 | Substitution - Missense |
| 236 | c.706G > T | p.D236Y | 6196635 | 3 | Substitution - Missense |
| 236 | c.707A > T | p.D236V | 6919940 | 2 | Substitution - Missense |
| 237 | c.709_709delC | p.L237fs*1 | 6196724 | 1 | Deletion - Frameshift |
| 237 | c.709C > A | p.L237M | 3937823 | 2 | Substitution - Missense |
| 237 | c.710T > A | p.L237Q | 6491268 | 1 | Substitution - Missense |
| 238 | c.713_731del19 | p.N238fs*33 | 6945769 | 1 | Deletion - Frameshift |
| 238 | c.712A > G | p.N238D | 6975251 | 1 | Substitution - Missense |
| 239 | c.715G > A | p.V239M | 5712866 | 1 | Substitution - Missense |
| 241 | c.721T > C | p.C241R | 5821024 | 1 | Substitution - Missense |
| 241 | c.722G > A | p.C241Y | 1611494 | 2 | Substitution - Missense |
| 242 | c.724G > A | p.E242K | 6196570 | 2 | Substitution - Missense |
| 242 | c.725A > C | p.E242A | 6586340 | 1 | Substitution - Missense |
| 243 | c.728C > G | p.S243C | 710191 | 1 | Substitution - Missense |
| 244 | c.730G > A | p.E244K | 1303939 | 2 | Substitution - Missense |
| 244 | c.730G > C | p.E244Q | 6986830 | 1 | Substitution - Missense |
| 246 | c.738C > G | p.F246L | 6083864 | 1 | Substitution - Missense |
| 248 | c.742G > A | p.A248T | 3718030 | 3 | Substitution - Missense |
| 249 | c.747delC | p.C249fs*1 | 3665412 | 1 | Deletion - Frameshift |
| 249 | c.746G > A | p.C249Y | 4073868 | 2 | Substitution - Missense |
| 252 | c.755G > T | p.W252L | 6922265 | 2 | Substitution - Missense |
| 252 | c.756G > T | p.W252C | 1524058 | 3 | Substitution - Missense |
| 253 | c.757_758insG | p.V253fs*97 | 6196763 | 1 | Insertion - Frameshift |
| 254 | c.761A > C | p.K254T | 1659425 | 1 | Substitution - Missense |
| 254 | c.761A > G | p.K254R | 6924835 | 1 | Substitution - Missense |
| 256 | c.767A > G | p.D256G | 6196640 | 1 | Substitution - Missense |
| 257 | c.770G > A | p.C257Y | 6911916 | 1 | Substitution - Missense |
| 258 | c.772G > T | p.E258* | 6915065 | 2 | Substitution - Nonsense |
| 260 | c.779G > A | p.R260Q | 710192 | 4 | Substitution - Missense |
| 260 | c.779G > T | p.R260L | 335836 | 3 | Substitution - Missense |
| 260 | c.778C > T | p.R260* | 96324 | 2 | Substitution - Nonsense |
| 261 | c.781C > T | p.R261W | 6924861 | 2 | Substitution - Missense |
| 261 | c.782G > A | p.R261Q | 6692801 | 1 | Substitution - Missense |
| 261 | c.782G > C | p.R261P | 6083865 | 1 | Substitution - Missense |
| 262 | c.786C > A | p.F262L | 6692803 | 1 | Substitution - Missense |
| 263 | c.788_790delACG | p.Y263_V264 > F | 6972164 | 1 | Complex - deletion |
| 264 | c.791T > C | p.V264A | 7276333 | 1 | Substitution - Missense |
| 265 | c.793C > T | p.Q265* | 1680643 | 2 | Substitution - Nonsense |
| 266 | c.797C > T | p.A266V | 6692802 | 1 | Substitution - Missense |
| 268 | c.803T > C | p.L268P | 6083866 | 1 | Substitution - Missense |
| 269 | c.805delC | p.R269fs*8 | 4450725 | 1 | Deletion - Frameshift |
| 269 | c.805C > T | p.R269W | 1726253 | 6 | Substitution - Missense |
| 269 | c.806G > T | p.R269L | 6920660 | 1 | Substitution - Missense |
| 271 | c.811G > A | p.V271M | 1524059 | 3 | Substitution - Missense |
| 271 | c.811G > T | p.V271L | 4925833 | 3 | Substitution - Missense |
| 272 | c.815_816delGC | p.R272fs*77 | 6936381 | 1 | Deletion - Frameshift |
| 272 | c.814C > T | p.R272C | 6196679 | 3 | Substitution - Missense |
| 272 | c.815G > A | p.R272H | 379170 | 2 | Substitution - Missense |
| 272 | c.815G > C | p.R272P | 368093 | 2 | Substitution - Missense |
| 272 | c.815G > T | p.R272L | 2812623 | 1 | Substitution - Missense |
| 273 | c.818G > C | p.C273S | 6924709 | 1 | Substitution - Missense |
| 274 | c.821A > G | p.H274R | 5816784 | 2 | Substitution - Missense |
| 274 | c.821A > T | p.H274L | 6973404 | 1 | Substitution - Missense |
| 274 | c.822C > A | p.H274Q | 6191662 | 1 | Substitution - Missense |
| 275 | c.824C > T | p.S275L | 6938629 | 1 | Substitution - Missense |
| 277 | c.830C > T | p.T277M | 4889408 | 2 | Substitution - Missense |
| 278 | c.832C > T | p.P278S | 6149749 | 2 | Substitution - Missense |
| 278 | c.833C > A | p.P278Q | 2812621 | 1 | Substitution - Missense |
| 278 | c.833C > G | p.P278R | 377897 | 1 | Substitution - Missense |
| 278 | c.833C > T | p.P278L | 4924669 | 1 | Substitution - Missense |
| 280 | c.838T > C | p.F280L | 6196627 | 1 | Substitution - Missense |
| 280 | c.839T > A | p.F280Y | 6149750 | 1 | Substitution - Missense |
| 281 | c.841C > A | p.L281M | 6978384 | 1 | Substitution - Missense |
| 281 | c.842T > C | p.L281P | 6196631 | 1 | Substitution - Missense |
| 282 | c.845A > C | p.Q282P | 6334528 | 2 | Substitution - Missense |
| 283 | c.847A > C | p.M283L | 4653016 | 1 | Substitution - Missense |
| 284 | c.851A > T | p.Q284L | 6083867 | 3 | Substitution - Missense |
| 284 | c.850C > T | p.Q284* | 372918 | 1 | Substitution - Nonsense |
| 287 | c.859A > T | p.K287* | 6083868 | 1 | Substitution - Nonsense |
| 288 | c.862T > C | p.C288R | 4073867 | 1 | Substitution - Missense |
| 288 | c.863G > A | p.C288Y | 6196630 | 1 | Substitution - Missense |
| 288 | c.863G > T | p.C288F | 5944191 | 1 | Substitution - Missense |
| 291 | c.871delC | p.L291fs*26 | 6919625 | 1 | Deletion - Frameshift |
| 291 | c.871C > A | p.L291M | 6959248 | 1 | Substitution - Missense |
| 294 | c.880G > T | p.D294Y | 2812618 | 3 | Substitution - Missense |
| 294 | c.881A > T | p.D294V | 6971354 | 1 | Substitution - Missense |
| 295 | c.883T > C | p.S295P | 5621093 | 1 | Substitution - Missense |

-continued

| Positio | CDS Mutation | AA Mutation | Mutationn | Count | Type |
|---|---|---|---|---|---|
| 296 | c.886_958 > GCT | p.R296fs*9 | 6956905 | 1 | Complex - frameshift |
| 296 | c.886delC | p.R296fs*21 | 6970387 | 1 | Deletion - Frameshift |
| 296 | c.887_891delGCTGC | p.R296fs*52 | 6980361 | 1 | Deletion - Frameshift |
| 296 | c.886C > T | p.R296C | 6950413 | 2 | Substitution - Missense |
| 300 | c.899A > G | p.Y300C | 5572552 | 3 | Substitution - Missense |
| 302 | c.904_905insG | p.V302fs*48 | 1167868 | 1 | Insertion - Frameshift |
| 304 | c.911T > A | p.I304N | 6964179 | 1 | Substitution - Missense |
| 304 | c.912C > G | p.I304M | 3959485 | 2 | Substitution - Missense |
| 305 | c.915C > G | p.F305L | 6493173 | 1 | Substitution - Missense |
| 307 | c.919G > T | p.E307* | 6970742 | 1 | Substitution - Nonsense |
| 310 | c.929T > C | p.L310P | 710193 | 1 | Substitution - Missense |
| 311 | c.931C > T | p.H311Y | 6958948 | 1 | Substitution - Missense |
| 311 | c.932A > C | p.H311P | 3959484 | 1 | Substitution - Missense |
| 311 | c.932A > G | p.H311R | 4073866 | 2 | Substitution - Missense |
| 311 | c.932A > T | p.H311L | 7240720 | 1 | Substitution - Missense |
| 313 | c.937C > G | p.P313A | 6909586 | 1 | Substitution - Missense |
| 314 | c.939delC | p.T314fs*3 | 392221 | 1 | Deletion - Frameshift |
| 314 | c.941_967del27 | p.T314_P322delTQVMPC | 6968535 | 1 | Deletion - In frame |
| 314 | c.941C > T | p.T314M | 2812615 | 1 | Substitution - Missense |
| 316 | c.946_951delGTGATG | p.V316_M317delVM | 404900 | 1 | Deletion - In frame |
| 317 | c.951G > T | p.M317I | 6240506 | 1 | Substitution - Missense |
| 318 | c.953C > T | p.P318L | 710194 | 2 | Substitution - Missense |
| 320 | c.958_959CG > TA | p.R320 > ? | 383936 | 1 | Complex |
| 320 | c.958C > T | p.R320W | 1524062 | 5 | Substitution - Missense |
| 320 | c.959G > A | p.R320Q | 710195 | 3 | Substitution - Missense |
| 320 | c.959G > C | p.R320P | 346494 | 1 | Substitution - Missense |
| 320 | c.959G > T | p.R320L | 2812614 | 4 | Substitution - Missense |
| 321 | c.961_964GCGC > CCGT | p.A321_P322 > PS | 6930042 | 1 | Complex - compound |
| 321 | c.961G > A | p.A321T | 6913724 | 1 | Substitution - Missense |
| 321 | c.962C > T | p.A321V | 6216277 | 2 | Substitution - Missense |
| 322 | c.965C > T | p.P322L | 6196718 | 2 | Substitution - Missense |
| 323 | c.966delC | p.K323fs*5 | 6960614 | 1 | Deletion - Frameshift |
| 323 | c.968delA | p.K323fs*5 | 5669306 | 1 | Deletion - Frameshift |
| 324 | c.970G > A | p.V324M | 1255509 | 1 | Substitution - Missense |
| 325 | c.974G > A | p.G325D | 7274085 | 1 | Substitution - Missense |
| 326 | c.976C > T | p.R326C | 5513458 | 2 | Substitution - Missense |
| 326 | c.977G > A | p.R326H | 990604 | 1 | Substitution - Missense |
| 330 | c.989C > T | p.T330I | 6196632 | 2 | Substitution - Missense |
| 331 | c.991_1008 > AAGG | p.A331fs*14 | 6962898 | 1 | Complex - frameshift |
| 331 | c.991G > C | p.A331P | 6964791 | 1 | Substitution - Missense |
| 332 | c.995_1007del13 | p.G332fs*64 | 6968449 | 1 | Deletion - Frameshift |
| 332 | c.995delG | p.G332fs*68 | 6957225 | 1 | Deletion - Frameshift |
| 332 | c.994G > A | p.G332S | 6877357 | 2 | Substitution - Missense |
| 332 | c.994G > T | p.G332C | 5264513 | 5 | Substitution - Missense |
| 332 | c.995G > T | p.G332V | 6524621 | 1 | Substitution - Missense |
| 333 | c.996_996delC | p.G333fs*67 | 6196653 | 1 | Deletion - Frameshift |
| 333 | c.996_997delCG | p.G333fs*16 | 6967536 | 1 | Deletion - Frameshift |
| 333 | c.997G > A | p.G333S | 6083869 | 2 | Substitution - Missense |
| 333 | c.997G > T | p.G333C | 1193323 | 7 | Substitution - Missense |
| 333 | c.997_998GG > TT | p.G333F | 6926691 | 1 | Substitution - Missense |
| 334 | c.1003_1004insACT | p.Y334_F335insY | 6945770 | 1 | Insertion - In frame |
| 334 | c.1000T > C | p.Y334H | 94573 | 1 | Substitution - Missense |
| 335 | c.1003T > G | p.F335V | 6956782 | 1 | Substitution - Missense |
| 336 | c.1007G > A | p.R336Q | 6196638 | 2 | Substitution - Missense |
| 336 | c.1006C > T | p.R336* | 95621 | 3 | Substitution - Nonsense |
| 337 | c.1009C > T | p.Q337* | 6191668 | 1 | Substitution - Nonsense |
| 338 | c.1013C > T | p.S338L | 6196652 | 2 | Substitution - Missense |
| 338 | c.1013_1014CG > TT | p.S338F | 6922441 | 1 | Substitution - Missense |
| 339 | c.1015C > T | p.L339F | 6955518 | 1 | Substitution - Missense |
| 342 | c.1024C > A | p.L342M | 6196636 | 1 | Substitution - Missense |
| 350 | c.1048G > A | p.G350S | 2812611 | 4 | Substitution - Missense |
| 350 | c.1048_1049GG > AA | p.G350N | 5611323 | 1 | Substitution - Missense |
| 352 | c.1056G > A | p.W352* | 6968407 | 1 | Substitution - Nonsense |
| 353 | c.1058T > C | p.L353P | 6982443 | 1 | Substitution - Missense |
| 354 | c.1061G > T | p.R354L | 3783169 | 1 | Substitution - Missense |
| 356 | c.1067_1077del11 | p.A356fs*55 | 6937363 | 1 | Deletion - Frameshift |
| 356 | c.1066G > A | p.A356T | 6191665 | 1 | Substitution - Missense |
| 357 | c.1069G > A | p.D357N | 6196639 | 1 | Substitution - Missense |
| 359 | c.1076_1097del22 | p.Q359fs*34 | 6196720 | 1 | Deletion - Frameshift |
| 359 | c.1075C > T | p.Q359* | 6196634 | 1 | Substitution - Nonsense |
| 361 | c.1082C > T | p.P361L | 6524620 | 5 | Substitution - Missense |
| 362 | c.1084_1095del12 | p.R362_L365del | 6834756 | 1 | Deletion - In frame |
| 362 | c.1084C > T | p.R362W | 7213602 | 1 | Substitution - Missense |
| 362 | c.1085G > A | p.R362Q | 94572 | 6 | Substitution - Missense |
| 362 | c.1085G > C | p.R362P | 6914731 | 1 | Substitution - Missense |
| 364 | c.1090G > A | p.G364S | 1189873 | 1 | Substitution - Missense |
| 364 | c.1090G > T | p.G364C | 395069 | 7 | Substitution - Missense |

-continued

| Positio | CDS Mutation | AA Mutation | Mutationn | Count | Type |
|---|---|---|---|---|---|
| 364 | c.1090_1091GG > TT | p.G364F | 6985044 | 1 | Substitution - Missense |
| 364 | c.1091G > A | p.G364D | 6557466 | 1 | Substitution - Missense |
| 364 | c.? | p.G364C | 6196680 | 1 | Substitution - Missense |
| 367 | c.1100G > A | p.G367D | 6191669 | 1 | Substitution - Missense |
| 368 | c.1103G > A | p.C368Y | 3701407 | 2 | Substitution - Missense |
| 368 | c.1103G > T | p.C368F | 6912426 | 1 | Substitution - Missense |
| 369 | c.1105G > A | p.V369M | 7230096 | 1 | Substitution - Missense |
| 369 | c.1105G > C | p.V369L | 710196 | 1 | Substitution - Missense |
| 369 | c.1106T > C | p.V369A | 6196717 | 2 | Substitution - Missense |
| 371 | c.1110_1111delGG | p.G371fs*43 | 6196722 | 1 | Deletion - Frameshift |
| 375 | c.1123T > C | p.Y375H | 6539040 | 1 | Substitution - Missense |
| 378 | c.1132G > T | p.G378C | 6930456 | 2 | Substitution - Missense |
| 379 | c.1136G > A | p.G379D | 4951275 | 3 | Substitution - Missense |
| 379 | c.1136G > T | p.G379V | 4930153 | 1 | Substitution - Missense |
| 380 | c.1139G > C | p.R380T | 6539039 | 1 | Substitution - Missense |
| 380 | c.1140G > T | p.R380S | 6339856 | 1 | Substitution - Missense |
| 382 | c.1146C > G | p.N382K | 6909585 | 1 | Substitution - Missense |
| 384 | c.1151C > T | p.P384L | 6191667 | 1 | Substitution - Missense |
| 389 | c.1165G > T | p.D389Y | 398736 | 2 | Substitution - Missense |
| 389 | c.1166A > G | p.D389G | 6936437 | 1 | Substitution - Missense |
| 391 | c.1170delC | p.S391fs*9 | 6917983 | 1 | Deletion - Frameshift |
| 392 | c.1174delG | p.A392fs*8 | 5364723 | 1 | Deletion - Frameshift |
| 392 | c.1174G > A | p.A392T | 7275434 | 1 | Substitution - Missense |
| 392 | c.1174G > C | p.A392P | 6920516 | 1 | Substitution - Missense |
| 396 | c.1186_1187insC | p.Y396fs*19 | 4950717 | 1 | Insertion - Frameshift |
| 396 | c.1187_1188insA | p.Y396fs*1 | 6938265 | 2 | Insertion - Frameshift |
| 396 | c.1188C > G | p.Y396* | 6969855 | 1 | Substitution - Nonsense |
| 397 | c.1189_1191delAAC | p.N397delN | 392394 | 1 | Deletion - In frame |
| 399 | c.1197G > A | p.M399I | 6946018 | 2 | Substitution - Missense |
| 402 | c.1204C > T | p.Q402* | 6966284 | 2 | Substitution - Nonsense |
| 403 | c.1208G > T | p.W403L | 6962573 | 1 | Substitution - Missense |
| 403 | c.1209G > T | p.W403C | 6920783 | 2 | Substitution - Missense |
| 403 | c.1208G > A | p.W403* | 6954854 | 1 | Substitution - Nonsense |
| 407 | c.1220C > T | p.A407V | 1130008 | 1 | Substitution - Missense |
| 409 | c.1224delC | p.M409fs*l | 6916353 | 3 | Deletion - Frameshift |
| 409 | c.1226T > C | p.M409T | 474128 | 1 | Substitution - Missense |
| 412 | c.1234C > T | p.P412S | 6196641 | 2 | Substitution - Missense |
| 413 | c.1237delC | p.R413fs*45 | 6923454 | 1 | Deletion - Frameshift |
| 413 | c.1238G > A | p.R413H | 6438114 | 3 | Substitution - Missense |
| 413 | c.1238G > T | p.R413L | 2812610 | 3 | Substitution - Missense |
| 414 | c.1241A > T | p.N414I | 6955906 | 1 | Substitution - Missense |
| 415 | c.1243C > G | p.R415G | 6196677 | 1 | Substitution - Missense |
| 415 | c.1243C > T | p.R415C | 6083870 | 2 | Substitution - Missense |
| 416 | c.1246A > T | p.I416F | 6938327 | 1 | Substitution - Missense |
| 417 | c.1249G > A | p.G417R | 6083871 | 1 | Substitution - Missense |
| 417 | c.1250G > A | p.G417E | 6083872 | 1 | Substitution - Missense |
| 417 | c.1250G > T | p.G417V | 4604203 | 3 | Substitution - Missense |
| 418 | c.1252G > A | p.V418M | 94571 | 1 | Substitution - Missense |
| 418 | c.1252G > T | p.V418L | 710197 | 1 | Substitution - Missense |
| 419 | c.1255G > T | p.G419W | 349505 | 3 | Substitution - Missense |
| 419 | c.1256G > T | p.G419V | 6974281 | 1 | Substitution - Missense |
| 420 | c.1258delG | p.V420fs*38 | 6948680 | 2 | Deletion - Frameshift |
| 420 | c.1253_1254insT | p.V420fs*25 | 6961096 | 1 | Insertion - Frameshift |
| 422 | c.1264G > A | p.D422N | 710198 | 7 | Substitution - Missense |
| 422 | c.1264G > C | p.D422H | 6972089 | 1 | Substitution - Missense |
| 422 | c.1264G > T | p.D422Y | 6918704 | 2 | Substitution - Missense |
| 423 | c.1268G > T | p.G423V | 564843 | 1 | Substitution - Missense |
| 424 | c.1272_1288del17 | p.H424fs*15 | 6921113 | 1 | Deletion - Frameshift |
| 424 | c.1271A > G | p.H424R | 6191666 | 1 | Substitution - Missense |
| 425 | c.1275C > G | p.I425M | 6908697 | 1 | Substitution - Missense |
| 427 | c.1280C > A | p.A427D | 6933104 | 1 | Substitution - Missense |
| 427 | c.? | p.A427V | 6196675 | 1 | Substitution - Missense |
| 430 | c.1288G > A | p.G430S | 6557464 | 2 | Substitution - Missense |
| 430 | c.1288G > T | p.G430C | 2812606 | 5 | Substitution - Missense |
| 431 | c.1292C > T | p.S431F | 6950034 | 2 | Substitution - Missense |
| 433 | c.1298delG | p.G433fs*25 | 6947323 | 1 | Deletion - Frameshift |
| 433 | c.1297G > A | p.G433S | 6938026 | 2 | Substitution - Missense |
| 436 | c.1306C > A | p.H436N | 5614594 | 1 | Substitution - Missense |
| 441 | c.1321G > T | p.E441* | 6524619 | 3 | Substitution - Nonsense |
| 444 | c.1330G > T | p.E444* | 1662411 | 3 | Substitution - Nonsense |
| 446 | c.1336G > T | p.E446* | 6979735 | 1 | Substitution - Nonsense |
| 447 | c.1339C > T | p.R447W | 6932612 | 1 | Substitution - Missense |
| 448 | c.1343A > G | p.D448G | 6965732 | 1 | Substitution - Missense |
| 449 | c.1345G > T | p.E449* | 564844 | 3 | Substitution - Nonsense |
| 450 | c.1348T > C | p.W450R | 6942474 | 1 | Substitution - Missense |
| 452 | c.1353delC | p.L452fs*6 | 438484 | 1 | Deletion - Frameshift |
| 453 | c.1356_1357insA | p.V453fs*27 | 438483 | 1 | Insertion - Frameshift |

-continued

| Positio | CDS Mutation | AA Mutation | Mutationn | Count | Type |
|---|---|---|---|---|---|
| 456 | c.1367T > A | p.M456K | 6939576 | 1 | Substitution - Missense |
| 457 | c.1369_1369delC | p.L457fs*1 | 6196723 | 1 | Deletion - Frameshift |
| 459 | c.1376G > A | p.R459Q | 1711813 | 1 | Substitution - Missense |
| 460 | c.1378A > G | p.R460G | 6083873 | 1 | Substitution - Missense |
| 460 | c.1379G > T | p.R460M | 3742714 | 1 | Substitution - Missense |
| 460 | c.1380G > T | p.R460S | 1195038 | 2 | Substitution - Missense |
| 461 | c.1381A > G | p.I461V | 6149751 | 1 | Substitution - Missense |
| 461 | c.1381A > T | p.I461F | 6941471 | 1 | Substitution - Missense |
| 461 | c.1383C > G | p.I461M | 6932471 | 1 | Substitution - Missense |
| 462 | c.1384G > T | p.G462W | 2812605 | 1 | Substitution - Missense |
| 464 | c.1391G > T | p.G464V | 6956863 | 1 | Substitution - Missense |
| 466 | c.1396G > C | p.A466P | 6196716 | 1 | Substitution - Missense |
| 467 | c.1400T > C | p.V467A | 6854657 | 2 | Substitution - Missense |
| 470 | c.1408C > A | p.R470S | 564846 | 2 | Substitution - Missense |
| 470 | c.1408C > T | p.R470C | 564847 | 13 | Substitution - Missense |
| 470 | c.1409G > A | p.R470H | 1524064 | 6 | Substitution - Missense |
| 474 | c.1421C > T | p.A474V | 6956987 | 1 | Substitution - Missense |
| 475 | c.1423G > C | p.V475L | 1711812 | 1 | Substitution - Missense |
| 476 | c.1426_1427GG > AA | p.G476K | 6951405 | 1 | Substitution - Missense |
| 476 | c.? | p.G476R | 6196678 | 1 | Substitution - Missense |
| 477 | c.1429G > A | p.G477S | 3371136 | 1 | Substitution - Missense |
| 478 | c.1431delC | p.F478fs*22 | 6954284 | 1 | Deletion - Frameshift |
| 479 | c.1435G > C | p.D479H | 6851663 | 2 | Substitution - Missense |
| 479 | c.1435G > T | p.D479Y | 6937447 | 1 | Substitution - Missense |
| 479 | c.1436A > G | p.D479G | 6083874 | 1 | Substitution - Missense |
| 480 | c.1438G > T | p.G480W | 710199 | 7 | Substitution - Missense |
| 480 | c.1439G > A | p.G480E | 5609244 | 1 | Substitution - Missense |
| 480 | c.1439G > T | p.G480V | 6960710 | 1 | Substitution - Missense |
| 483 | c.1447C > A | p.R483S | 3959483 | 3 | Substitution - Missense |
| 483 | c.1447C > T | p.R483C | 6083875 | 1 | Substitution - Missense |
| 483 | c.1448G > A | p.R483H | 6191687 | 3 | Substitution - Missense |
| 485 | c.1454A > G | p.N485S | 3937822 | 1 | Substitution - Missense |
| 487 | c.1460C > A | p.A487D | 5816316 | 1 | Substitution - Missense |
| 488 | c.1462G > A | p.E488K | 6928034 | 2 | Substitution - Missense |
| 488 | c.1463A > T | p.E488V | 6926408 | 1 | Substitution - Missense |
| 488 | c.1464G > T | p.E488D | 990603 | 1 | Substitution - Missense |
| 491 | c.1473C > A | p.Y491* | 6916540 | 1 | Substitution - Nonsense |
| 492 | c.1474C > T | p.P492S | 6920595 | 1 | Substitution - Missense |
| 493 | c.1477G > A | p.E493K | 6967239 | 1 | Substitution - Missense |
| 493 | c.1477G > C | p.E493Q | 6191686 | 2 | Substitution - Missense |
| 493 | c.1478A > C | p.E493A | 6916358 | 1 | Substitution - Missense |
| 493 | c.1479G > C | p.E493D | 710200 | 1 | Substitution - Missense |
| 493 | c.1477G > T | p.E493* | 6465525 | 1 | Substitution - Nonsense |
| 496 | c.1486G > A | p.E496K | 6984631 | 1 | Substitution - Missense |
| 496 | c.1486G > T | p.E496* | 6910328 | 1 | Substitution - Nonsense |
| 497 | c.1490G > T | p.W497L | 6149752 | 1 | Substitution - Missense |
| 497 | c.1491G > A | p.W497* | 6493585 | 1 | Substitution - Nonsense |
| 500 | c.1500_1503delCACA | p.I500fs*3 | 6969851 | 1 | Deletion - Frameshift |
| 503 | c.1508T > A | p.M503K | 6083876 | 1 | Substitution - Missense |
| 504 | c.1511A > G | p.N504S | 6908811 | 1 | Substitution - Missense |
| 506 | c.1516A > G | p.I506V | 710201 | 1 | Substitution - Missense |
| 507 | c.1519_1519delC | p.R507fs*25 | 6196817 | 3 | Deletion - Frameshift |
| 507 | c.1520_1520delG | p.R507fs*25 | 6196818 | 1 | Deletion - Frameshift |
| 507 | c.1520G > A | p.R507Q | 6191661 | 1 | Substitution - Missense |
| 507 | c.1520G > T | p.R507L | 6947893 | 1 | Substitution - Missense |
| 507 | c.1519C > T | p.R507* | 2812600 | 1 | Substitution - Nonsense |
| 509 | c.1525G > T | p.G509W | 6083877 | 1 | Substitution - Missense |
| 509 | c.1526G > A | p.G509E | 6928841 | 1 | Substitution - Missense |
| 509 | c.1526G > C | p.G509A | 6979339 | 1 | Substitution - Missense |
| 510 | c.1529C > T | p.A510V | 6967956 | 1 | Substitution - Missense |
| 511 | c.1531G > A | p.G511S | 2812599 | 1 | Substitution - Missense |
| 511 | c.1531G > T | p.G511C | 6965797 | 1 | Substitution - Missense |
| 513 | c.1537T > A | p.C513S | 4140210 | 1 | Substitution - Missense |
| 518 | c.1552_1560TGTATCTAT > GGTGT | p.C518_Y520 > GV* | 6966627 | 1 | Complex - compound |
| 518 | c.1553_1554delGT | p.C518fs*8 | 7340785 | 1 | Deletion - Frameshift |
| 519 | c.1554_1555insT | p.I519fs*8 | 990602 | 1 | Insertion - Frameshift |
| 522 | c.1565C > T | p.A522V | 32809 | 1 | Substitution - Missense |
| 523 | c.1568G > T | p.G523V | 6944569 | 2 | Substitution - Missense |
| 524 | c.1570G > T | p.G524C | 94570 | 2 | Substitution - Missense |
| 525 | c.1574A > G | p.Y525C | 4913158 | 1 | Substitution - Missense |
| 527 | c.1579_1580GG > TT | p.G527F | 6083878 | 1 | Substitution - Missense |
| 528 | c.1583A > C | p.Q528P | 6939152 | 1 | Substitution - Missense |
| 529 | c.1584_1585delGG | p.D529fs*44 | 6933647 | 1 | Deletion - Frameshift |
| 530 | c.1588C > T | p.Q530* | 6914164 | 2 | Substitution - Nonsense |
| 535 | c.1603G > C | p.E535Q | 7318248 | 1 | Substitution - Missense |
| 535 | c.1603G > T | p.E535* | 6910554 | 1 | Substitution - Nonsense |
| 536 | c.1607G > A | p.R536H | 180623 | 1 | Substitution - Missense |

-continued

| Positio | CDS Mutation | AA Mutation | Mutationn | Count | Type |
|---|---|---|---|---|---|
| 537 | c.1607_1608insTG | p.Y537fs*12 | 7087422 | 1 | Insertion - Frameshift |
| 537 | c.1609T > C | p.Y537H | 4073865 | 1 | Substitution - Missense |
| 537 | c.1611C > A | p.Y537* | 6196564 | 1 | Substitution - Nonsense |
| 541 | c.1622C > T | p.T541I | 4073864 | 1 | Substitution - Missense |
| 542 | c.1626_1627delGA | p.E542fs*31 | 4949875 | 2 | Deletion - Frameshift |
| 542 | c.1624_1626GAG > AAC | p.E542N | 6909627 | 1 | Substitution - Missense |
| 542 | c.1625A > T | p.E542V | 6420384 | 2 | Substitution - Missense |
| 542 | c.1624G > T | p.E542* | 6967522 | 1 | Substitution - Nonsense |
| 543 | c.1628C > T | p.T543M | 4695085 | 2 | Substitution - Missense |
| 544 | c.1630T > C | p.W544R | 474127 | 1 | Substitution - Missense |
| 544 | c.1632G > T | p.W544C | 710202 | 1 | Substitution - Missense |
| 546 | c.1638delC | p.F546fs*2 | 6912761 | 1 | Deletion - Frameshift |
| 546 | c.1637_1638TC > AA | p.F546* | 6982284 | 1 | Substitution - Nonsense |
| 547 | c.1637_1638insT | p.V547fs*27 | 6975294 | 1 | Insertion - Frameshift |
| 549 | c.? | p.P549L | 6437997 | 1 | Substitution - Missense |
| 550 | c.1647delC | p.M550fs*1 | 6961533 | 2 | Deletion - Frameshift |
| 550 | c.1649_1650insA | p.M550fs*24 | 6978527 | 1 | Insertion - Frameshift |
| 550 | c.1650G > A | p.M550I | 3388547 | 2 | Substitution - Missense |
| 551 | c.1653G > T | p.K551N | 6370970 | 2 | Substitution - Missense |
| 552 | c.1654C > A | p.H552N | 6253398 | 1 | Substitution - Missense |
| 554 | c.1661G > A | p.R554Q | 1524066 | 3 | Substitution - Missense |
| 555 | c.1663_1680del18 | p.S555_T560del | 6196776 | 2 | Deletion - In frame |
| 555 | c.1663A > T | p.S555C | 1189872 | 2 | Substitution - Missense |
| 556 | c.1666G > A | p.A556T | 2812594 | 1 | Substitution - Missense |
| 556 | c.1666G > T | p.A556S | 96323 | 1 | Substitution - Missense |
| 556 | c.1667C > T | p.A556V | 6438117 | 1 | Substitution - Missense |
| 558 | c.1672G > A | p.G558R | 6954866 | 2 | Substitution - Missense |
| 561 | c.1681G > A | p.V561I | 6692799 | 1 | Substitution - Missense |
| 563 | c.1687C > G | p.Q563E | 94569 | 1 | Substitution - Missense |
| 563 | c.1688A > G | p.Q563R | 6930455 | 1 | Substitution - Missense |
| 564 | c.1691G > A | p.G564E | 6441008 | 1 | Substitution - Missense |
| 565 | c.1692_1693insT | p.R565fs*1 | 6930460 | 1 | Insertion - Frameshift |
| 566 | c.1697_1700delTCTA | p.I566fs*28 | 6907100 | 2 | Deletion - Frameshift |
| 567 | c.1701C > A | p.Y567* | 6977109 | 1 | Substitution - Nonsense |
| 568 | c.1702G > T | p.V568F | 2812593 | 1 | Substitution - Missense |
| 570 | c.1709G > T | p.G570V | 6191685 | 1 | Substitution - Missense |
| 570 | c.1708G > T | p.G570* | 6933814 | 2 | Substitution - Nonsense |
| 571 | c.1711G > C | p.G571R | 6924949 | 1 | Substitution - Missense |
| 571 | c.1712G > C | p.G571A | 2812591 | 1 | Substitution - Missense |
| 572 | c.1715A > G | p.Y572C | 94568 | 3 | Substitution - Missense |
| 579 | c.1735G > A | p.D579N | 6976698 | 1 | Substitution - Missense |
| 579 | c.1735G > T | p.D579Y | 1662410 | 1 | Substitution - Missense |
| 582 | c.1744G > A | p.E582K | 5042226 | 1 | Substitution - Missense |
| 584 | c.1752delC | p.Y584fs*1 | 1659324 | 1 | Deletion - Frameshift |
| 584 | c.1750_1751insA | p.Y584fs*1 | 6201646 | 1 | Insertion - Frameshift |
| 584 | c.1751_1752insA | p.Y584fs*1 | 6958829 | 1 | Insertion - Frameshift |
| 584 | c.1751A > G | p.Y584C | 3718029 | 3 | Substitution - Missense |
| 585 | c.1753G > A | p.D585N | 4878962 | 2 | Substitution - Missense |
| 587 | c.1760A > G | p.D587G | 4773549 | 1 | Substitution - Missense |
| 588 | c.1761_1762insT | p.T588fs*31 | 392053 | 1 | Insertion - Frameshift |
| 589 | c.1764_1765insA | p.D589fs*30 | 6921527 | 1 | Insertion - Frameshift |
| 591 | c.1772G > T | p.W591L | 6196571 | 3 | Substitution - Missense |
| 591 | c.1773G > A | p.W591* | 6967481 | 1 | Substitution - Nonsense |
| 592 | c.1776C > G | p.S592R | 6493646 | 1 | Substitution - Missense |
| 593 | c.1777G > A | p.E593K | 4531303 | 1 | Substitution - Missense |
| 596 | c.1787G > A | p.R596Q | 6952384 | 1 | Substitution - Missense |
| 596 | c.1786C > T | p.R596* | 6980280 | 1 | Substitution - Nonsense |
| 601 | c.1801_1802CG > T | p.R601fs*1 | 6927312 | 1 | Complex - frameshift |
| 601 | c.1800delC | p.R601fs* > 24 | 7003166 | 1 | Deletion - Frameshift |
| 601 | c.1801C > T | p.R601W | 400196 | 2 | Substitution - Missense |
| 601 | c.1802G > T | p.R601L | 6923276 | 4 | Substitution - Missense |
| 603 | c.1807G > T | p.G603W | 368688 | 4 | Substitution - Missense |
| 603 | c.1808G > T | p.G603V | 6913357 | 3 | Substitution - Missense |
| 605 | c.1813G > C | p.G605R | 6965262 | 1 | Substitution - Missense |
| 606 | c.1816G > A | p.V606M | 6196633 | 2 | Substitution - Missense |
| 610 | c.1830G > A | p.M610I | 6961136 | 1 | Substitution - Missense |
| 611 | c.1831G > A | p.E611K | 6196643 | 1 | Substitution - Missense |
| 611 | c.1833G > C | p.E611D | 384772 | 1 | Substitution - Missense |
| 613 | c.1837T > C | p.C613R | 4991203 | 1 | Substitution - Missense |
| 613 | c.1838G > T | p.C613F | 6576393 | 2 | Substitution - Missense |
| 615 | c.1843A > T | p.K615* | 5967496 | 1 | Substitution - Nonsense |
| 620 | c.? | p.Q620del | 7335648 | 1 | Deletion - In frame |
| 620 | c.1860G > T | p.Q620H | 7281533 | 1 | Substitution - Missense |
|  | c.1698_1708+22del33 | p.? | 6945766 | 1 | Unknown |
|  | c.1708_1708+1GG > TT | p.? | 6927565 | 1 | Unknown |
|  | c.1326-1G > A | p.? | 6923432 | 1 | Unknown |
|  | c.1326-2A > T | p.? | 4949871 | 1 | Unknown |

-continued

| Positio | CDS Mutation | AA Mutation | Mutationn | Count | Type |
|---|---|---|---|---|---|
| | c.1326-9C > A | p.? | 7243412 | 1 | Unknown |
| | c.1531+1G > T | p.? | 6956065 | 1 | Unknown |
| | c.1532-1G > T | p.? | 6969960 | 1 | Unknown |
| | c.1532-2A > G | p.? | 381459 | 2 | Unknown |
| | c.1532-6_1533delCTTTAGGC | p.? | 6959276 | 1 | Unknown |
| | c.1708+2T > A | p.? | 6149754 | 1 | Unknown |
| | c.1709-2A > G | p.? | 7088100 | 1 | Unknown |
| | c.1709-5C > T | p.? | 6279866 | 1 | Unknown |
| | c.640-12delC | p.? | 6196719 | 1 | Unknown |
| | c.640-1G > A | p.? | 6972470 | 1 | Unknown |
| | c.640-4G > A | p.? | 5458701 | 1 | Unknown |
| | c.? | p.? | 6196674 | 4 | Unknown |
| | c.?_?del? | p.? | 6904523 | 1 | Unknown |

The KEAP1 mutations listed above are based on the reference sequence of the human KEAP1 transcript variant 1 (coding sequence nucleotides 164 to 2038 of NM_203500.2, which represents a coding cDNA having a length of 1,875 nucleotides) which encodes the human KEAP1 isoform 1 (NP_987096.1). The sequences of the human KEAP1 transcript variant 1 (NM_203500.2) and the human KEAP1 isoform 1 (NP_987096.1) are included in the Table 1B below.

The term "expression signature" or "signature" refers to a group of two or more coordinately expressed biomarkers. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune checkpoint" refers to a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, TLT-2, ILT-4, TIGIT, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein.

The term "immune checkpoint inhibitor" or "immune checkpoint therapy" refers to the use of agents that inhibit immune checkpoint nucleic acids and/or proteins. Inhibition of one or more immune checkpoints can block or otherwise neutralize inhibitory signaling to promote immunomodulation. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof, as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. Similarly, a biological function, such as the function of a protein and/or binding of one protein to another, is inhibited if it is decreased as compared to a reference state, such as a control like a wild-type state or a state in the absence of an applied agent. For example, the binding of a protein to one or more of its binding partners, such as the binding of KEAP1 and NRF2, and/or resulting effect, such as KEAP1/NRF2 signaling and/or NQO1 expression, is inhibited or deficient if the binding, signaling, and other effects like NQO1 expression are decreased due to contact with an agent, such as ML329 or a derivative thereof, in comparison to when the protein and/or binding partner is not contacted with the agent. Such inhibition or deficiency can be induced, such as by application of agent at a particular time and/or place, or can be constitutive, such as by continual administration. Such inhibition or deficiency can also be partial or complete (e.g., essentially no measurable activity in comparison to a reference state, such as a control like a wild-type state). Essentially complete inhibition or deficiency is referred to as blocked. In some embodiments, inhibition that is incomplete, such as partial blocking, is determined to have at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 2×, 3×, 4×, 5×, 6×, 7×, 8×, 9×, 10×, 15×, 20×, 25×, 30×, 35×, 40×, 45×, 50×, 55×, 60×, 65×, 70×, 75×, 80×, 85×, 90×, 95×, 100×, 105×, 110×, 120×, 125×, 150×, 200×, 250×, 300×, 350×, 400×, 450×, 500×, 600×, 700×, 800×, 900×, 1000×, or greater, or any range in between, inclusive, less binding, signaling, immune effect, etc. in the experimental state, such as the presence of ML329 or a derivative thereof, as compared to a reference state, such as the absence of ML320 or the derivative thereof. Such percentage changes apply equally well to other relevant metrics, such as ML320 relative to a derivative thereof of interest, competition assay kinetic metrics, binding affinity metrics, and the like. Similarly, such percentage changes apply equally well when comparing among hosts, such as mouse versus mouse or human versus human proteins and/or cells, or when comparing between hosts, such as human antibody against mouse proteins, human antibody against mouse proteins having human epitopes, and the like.

Similarly, a biological function, such as the function of a protein, is inhibited if it is decreased as compared to a reference state, such as a control like a wild-type state. For example, activity of a mutant KEAP1 and/or wild type KEAP1 that is contacted with an inhibitor is inhibited or deficient if the activity is decreased due to the mutation and/or contact with the inhibitor, in comparison to the wild-type KEAP1 and/or KEAP1 not contacted with the inhibitor. Such inhibition or deficiency can be induced, such as by application of agent at a particular time and/or place, or can be constitutive, such as by a heritable mutation. Such inhibition or deficiency can also be partial or complete (e.g., essentially no measurable activity in comparison to a reference state, such as a control like a wild-type state). Essentially complete inhibition or deficiency is referred to as blocked.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker encompassed by the present invention. The kit may be promoted, distributed, or sold as a unit for performing the methods encompassed by the present invention. The kit may comprise one or more reagents necessary to express a composition useful in the methods encompassed by the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression of a biomarker is the level of expression of the biomarker in cells of a subject, e.g., a human patient, not afflicted with a cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as ML329 or a derivative thereof, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of a housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to ML329 or a derivative thereof. Such predictive use of the biomarker may be confirmed by, e.g., (1) increased or decreased copy number (e.g., by FISH, FISH plus SKY, single-molecule sequencing, e.g., as described in the art at least at Augustin et al. (2001) *J. Biotechnol.,* 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to ML329 or a derivative thereof treatment or non-ML329 or a derivative thereof treatment or those developing resistance thereto).

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia. In one embodiment, a metaplasia is a pre-malignant lesion.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer, development of one or more clinical factors, or recovery from the disease.

The term "response to anti-cancer therapy" relates to any response of the hyperproliferative disorder (e.g., cancer) to an anti-cancer agent, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy is able to produce a significant decrease in tumor volume at a level of statistical significance (e.g., $p<0.05$) when compared to tumor volume of untreated tumor in the circumstance where the primary cancer alone is unable to produce a statistically significant decrease in tumor volume compared to tumor volume of untreated tumor. This generally applies to tumor volume measurements made at a time when the untreated tumor is growing log rhythmically. In some embodiments, the combination allows for a dose defined as a "sub-cytotoxic dose" of one or more of the agents of the combination. A "sub-cytotoxic dose" is a dose that does not necessarily induce cell death (CD) but still has a negative effect on cell growth.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene encompassed by the present invention, or a fragment thereof, short interfering RNA (siRNA), and small molecules which interfere with or inhibit expression of a target biomarker nucleic acid by RNA interference (RNAi).

"RNA interference (RNAi)" is an evolutionally conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G et al. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

In addition to RNAi, genome editing can be used to modulate the copy number or genetic sequence of a biomarker of interest, such as constitutive or induced knockout or mutation of a biomarker of interest, such as KEAP1 or an KEAP1 pathway component like NRF2 and/or NQO1. For example, the CRISPR-Cas system can be used for precise editing of genomic nucleic acids (e.g., for creating non-functional or null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well-known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326:1509-1512; Moscou and Bogdanove (2009) *Science* 326:1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47). Such genetic strategies can use constitutive expression systems or inducible expression systems according to well-known methods in the art.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method encompassed by the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., chemotherapeutic, and/or radiation therapy). In some embodiments, normal cells are not affected to an extent that causes the normal cells to be unduly injured by the ML329 or a derivative thereof or non-ML329 or a derivative thereof treatment. An increased sensitivity or a reduced sensitivity to a therapeutic treatment is measured according to a known method in the art for the particular treatment and methods described herein below, including, but not limited to, cell proliferative assays (Tanigawa, N et al. (9821) *Cancer Res* 42: 2159-2164), cell death assays (Weisenthal, L et al. (1984) *Cancer Res* 94: 161-173; Weisenthal, L et al. (1985) *Cancer Treat Rep* 69: 615-632; Weisenthal, L et al. Harwood Academic Publishers, 1993: 415-432; Weisenthal, L (1994) *Contrib Gynecol Obstet* 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "subject" refers to any healthy animal, mammal or human, or any animal, mammal or human afflicted with a cancer. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods encompassed by the present invention may be administered in a sufficient amount to produce a reasonable benefit/risk ratio applicable to such treatment.

The terms "therapeutically-effective amount" and "effective amount" as used herein means that amount of a compound, material, or composition comprising a compound encompassed by the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

In one embodiment, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

The term "SCAP105461" has the following chemical structure and properties, although the purity listed represents the purity used in the working examples described herein and the purity can vary depending upon the intended use according to well-known methods of chemical formulation preparation:

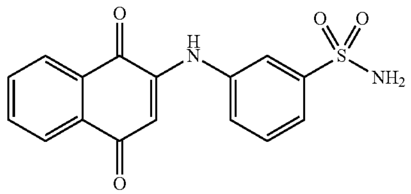 [SMILES: NS(=O)(=O)c1cccc(NC2=CC(=O)c3ccccc3C2=O)c1]

| SMILES | Assay Provider Vial Barcode Number | Purity (%) | Molecular Formula (including salts) | Molecular Weight |
|---|---|---|---|---|
| O=C1C(NC2=CC=CC(S(N)(=O)=O)=C2)=CC(C3=CC=CC=C31)=O | SCAP105461 | 95% | C16H12N2O4S | 328.34 |

tion induced by a heterologous promoter under the control of the 5' IL-2 gene enhancer or by a multimer of the AP1 sequence that can be found within the enhancer (Kang et al. (1992) *Science* 257:1134).

As used herein, the term "unresponsiveness" includes refractivity of cancer cells to therapy or refractivity of therapeutic cells, such as immune cells, to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T The term "SCAP105463" has the following chemical structure and properties, although the purity listed represents the purity used in the working examples described herein and the purity can vary depending upon the intended use according to well-known methods of chemical formulation preparation:

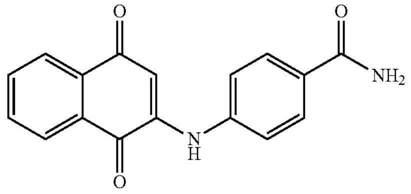 [SMILES: NC(=O)c1ccc(NC2=CC(=O)c3ccccc3C2=O)cc1]

| SMILES | Assay Provider Vial Barcode Number | Purity (%) | Molecular Formula (including salts) | Molecular Weight |
|---|---|---|---|---|
| O=C1C=C(NC2=CC=C(C(N)=O)C=C2)C(C3=CC=CC=C31)=O | SCAP105463 | 97% | C17H12N2O3 | 292.29 |

The term "CX4945" or "Silmitasertib" refers to 5-[(3-Chlorophenyl)amino]benzo[c]-2,6-naphthyridine-8-carboxylic acid (Molecule Weight: 349.8; Formula: $C_{19}H_{12}C_1N_3O_2$, SMILES code: C1=CC(=CC(=C1)Cl)NC2=C3C=CN=CC3=C4C=CC(=CC4=N2)C(=O)O). It is a potent and selective orally bioavailable small molecule inhibitor of CK2 that inhibits human umbilical vein endothelial cell migration, tube formation, and blocks CK2-dependent hypoxia-induced factor 1 alpha (HIF-1α) transcription in cancer cells (Ampofo et al. (2015) *Biochim. Biophys. Acta Mol. Basis Dis.* 1852:2123-2136; Ribeiro et al. (2017) *Leukemia* 31:1603-1610; Gandin et al. (2016) *Nat. Commun.* 7:11127; Ampofo et al. (2016) *Eur. Surg. Res.* 57:111-124). CX4945 has the following chemical structure:

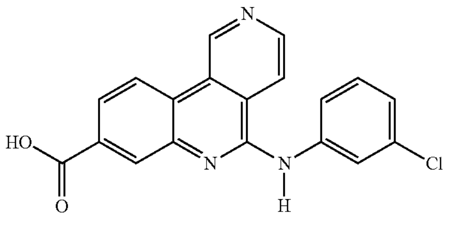 [SMILES: O=C(O)c1ccc2c(c1)nc(Nc1cccc(Cl)c1)c1ccncc12]

The term "ML329" refers to (4-[(1,4-dioxo-1,4-dihydronapthalen-2-yl)amino]benzenesulfonamide) and has the following chemical structure:

ML329

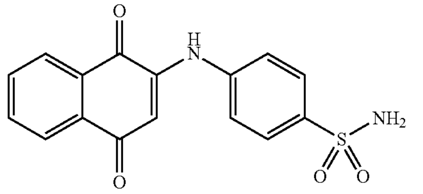

ML329 and derivatives thereof useful according to the present invention are well-known in the art (see, for example, U.S. Pat. Publ. 2017/0334842). In one embodiment, ML329 or a derivative thereof are compounds of Formula (IV):

(IV)

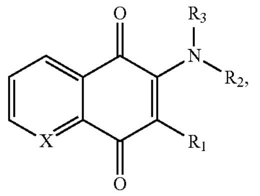

wherein:

X is CH or N;

$R_1$ is hydrogen, halogen, optionally substituted heterocycloalkyl, optionally substituted heteroaryl, optionally substituted aryl, optionally substituted alkoxy, optionally substituted lower alkyl, amino, optionally substituted alkylamino, optionally substituted dialkylamino;

$R_2$ is hydrogen, optionally substituted lower alkyl, optionally substituted aryl or heteroaryl, optionally substituted benzyl, —C(O)—$R_4$, —$S(O)_2$—$R_4$, or —CH($R_5$)—$R_4$;

$R_3$ is hydrogen, optionally substituted lower alkyl, or acyl;

$R_4$ is optionally substituted aryl or heteroaryl;

$R_5$ is hydrogen or lower alkyl; and pharmaceutically acceptable salts thereof.

In various embodiments of compounds of Formula (IV), $R_1$ can be selected from the group consisting of hydrogen; halogen; a 5- or 6-membered heterocyclyl or heteroaryl, said heterocyclyl or heteroaryl optionally substituted with lower alkyl or phenyl; alkoxy; phenyl; lower alkyl, optionally substituted with phenyl, alkylamino or dialkylamino; and amino.

In some embodiments of the various aspects disclosed herein, $R_1$ can be selected from the group consisting of hydrogen, chlorine, methyl, methoxy, phenyl, piperazinyl, methylpiperazinyl, ethylpiperzinyl, piperidinyl, morpholinyl, thiomorpholinyl, phenyl-piperazinyl, ethyl-piperazinyl, —$NHCH_2CH{=}CH_2$, $NH_2$, tert-butyl-piperazinyl, pyrrolidinyl, —$NHCH_2CH_2CH_2N(CH_2CH_3)_2$ and —$NHCH(CH_3)$ phenyl.

In some embodiments, X is CH and $R_1$ is selected from selected from the group consisting of hydrogen; halogen; a 5- or 6-membered heterocyclyl or heteroaryl, said heterocyclyl or heteroaryl optionally substituted with lower alkyl or phenyl; alkoxy; phenyl; lower alkyl, optionally substituted with phenyl, alkylamino or dialkylamino; and amino.

In various compounds of Formula (IV), X can be CH and $R_1$ can be hydrogen, chlorine, methyl, methoxy, phenyl, piperazinyl, methylpiperazinyl, ethylpiperzinyl, piperidinyl, morpholinyl, thiomorpholinyl, phenyl-piperazinyl, ethyl-piperazinyl, —$NHCH_2CH{=}CH_2$, —$NH_2$, tert-butyl-piperazinyl, pyrrolidinyl, —$NHCH_2CH_2CH_2N(CH_2CH_3)_2$ and —$NHCH(CH_3)$phenyl.

In some compounds of Formula (IV), X is CH and $R_1$ can be selected from hydrogen, chlorine, methyl, methoxy, phenyl, piperazinyl, methylpiperazinyl, piperidinyl, morpholinyl, thiomorpholinyl, phenyl-piperazinyl, ethyl-piperazinyl, —$CH_2CH{=}CH_2$, $NH_2$, tert-butyl-piperazinyl, pyrrolidinyl, —$CH_2CH_2CH_2N(CH_2CH_3)_2$ or —$CH(CH_3)$phenyl.

In various embodiments, $R_2$ can be selected from hydrogen; lower alkyl; phenyl, optionally mono- or bi-substituted independently with halogen, lower alkyl, —$S(O)_2NH_2$ or alkoxy; optionally substituted benzyl; C(O)-phenyl, said phenyl unsubstituted or substituted with halogen; $S(O)_2$-phenyl, said phenyl unsubstituted or substituted with halogen; $(O)_2$-thiophenyl, said thiophenyl unsubstituted or substituted with halogen; and thiophenyl.

In some embodiments of the various aspects disclosed herein, $R_2$ can be selected from the group consisting of methyl, hydrogen, —$CH_2CH{=}CH_2$, phenyl, —$CH_2$-chlorophenyl, chlorophenyl, acetyl, —C(O)-phenyl, —C(O)-bromophenyl, —$S(O)_2$-phenyl, —$S(O)_2$-bromophenyl, —$S(O)_2$-thiazolyl, —$S(O)_2$-bromothiazolyl, difluorophenyl, methoxyphenyl, and -phenyl-$S(O)_2NH_2$.

In some embodiments, X is CH and $R_2$ can be selected from the group consisting of hydrogen; lower alkyl; phenyl, optionally mono- or bi-substituted independently with halogen, lower alkyl, —$S(O)_2NH_2$ or alkoxy; optionally substituted benzyl; C(O)-phenyl, said phenyl unsubstituted or substituted with halogen; $S(O)_2$-phenyl, said phenyl unsubstituted or substituted with halogen; $S(O)_2$-thiophenyl, said thiophenyl unsubstituted or substituted with halogen; and thiophenyl. In some compounds of Formula (IV), X is CH and $R_2$ is selected from methyl, hydrogen, —$CH_2CH{=}CH_2$, phenyl, —$CH_2$-chlorophenyl, chlorophenyl, acetyl, —C(O)-phenyl, —C(O)-bromophenyl, —$S(O)_2$-phenyl, —$S(O)_2$-bromophenyl, —$S(O)_2$-thiazolyl, —$S(O)_2$-bromothiazolyl, difluorophenyl, methoxyphenyl, and -phenyl-$S(O)_2NH_2$.

In some compounds of Formula (IV), $R_2$ is selected from methyl, hydrogen, $CH_2CH{=}CH_2$, phenyl, $CH_2$-chlorophenyl, chlorophenyl, acetyl, —C(O)-phenyl, —C(O)-bromophenyl, $S(O)_2$-phenyl, —$S(O)_2$-bromophenyl, —$S(O)_2$- thiazolyl, —$S(O)_2$-bromothiazolyl, difluorophenyl, methoxyphenyl, and -phenyl-$S(O)_2NH_2$; and $R_1$ is selected form the group consisting of hydrogen, chlorine, methyl, methoxy, phenyl, piperazinyl, methylpiperazinyl, ethylpiperzinyl, piperidinyl, morpholinyl, thiomorpholinyl, phenyl-piperazinyl, ethyl-piperazinyl, —$NHCH_2CH{=}CH_2$, —$NH_2$, tert-butyl-piperazinyl, pyrrolidinyl, —$NHCH_2CH_2CH_2N(CH_2CH_3)_2$ and —$NHCH(CH_3)$phenyl.

In various embodiments of compounds of Formula (IV), $R_3$ can be selected from hydrogen, methyl, or acetyl.

In some embodiments, X is CH and $R_3$ is hydrogen, lower alkyl or acyl. In some embodiments, X is CH and $R_3$ is hydrogen, methyl or acetyl.

In some compounds, $R_3$ is hydrogen, lower alkyl or acyl and $R_1$ is a 5- or 6-membered heteroacycloalkyl (optionally substituted with lower alkyl or phenyl), lower alkyl (optionally substituted with diethylamino (—$N(CH_2CH_3)_2$)), or amino. In one embodiment, $R_3$ is acetyl and $R_1$ is a 5- or 6-membered heteroacycloalkyl (optionally substituted with lower alkyl) or lower alkyl (optionally substituted with diethylamino). In other embodiments, $R_3$ is hydrogen and $R_1$ is a 5- or 6-membered heteroacycloalkyl (optionally substituted with lower alkyl or phenyl).

In some embodiments, $R_3$ is hydrogen, lower alkyl or acyl and $R_2$ is selected from the group consisting of hydrogen; lower alkyl; phenyl, optionally mono- or bi-substituted independently with halogen, lower alkyl, —$S(O)_2NH_2$ or alkoxy; optionally substituted benzyl; C(O)-phenyl, said phenyl unsubstituted or substituted with halogen; $S(O)_2$-phenyl, said phenyl unsubstituted or substituted with halogen; $S(O)_2$-thiophenyl, said thiophenyl unsubstituted or substituted with halogen; and thiophenyl.

In some embodiments, $R_3$ is hydrogen, methyl or acetyl and $R_2$ is methyl, hydrogen, $CH_2CH{=}CH_2$, phenyl, $CH_2$-chlorophenyl, chlorophenyl, acetyl, —C(O)-phenyl, C(O)-bromophenyl, —$S(O)_2$-phenyl, —$S(O)_2$-bromophenyl, —$S(O)_2$-thiazolyl, —$S(O)_2$-bromothiazolyl, difluorophenyl, methoxyphenyl, and -phenyl-$S(O)_2NH_2$; and $R_1$ is selected form the group consisting of hydrogen, chlorine, methyl, methoxy, phenyl, piperazinyl, methylpiperazinyl, ethylpiperzinyl, piperidinyl, morpholinyl, thiomorpholinyl, phenyl-piperazinyl, ethyl-piperazinyl, —$NHCH_2CH{=}CH_2$, —$NH_2$, tert-butyl-piperazinyl, pyrrolidinyl, —$NHCH_2CH_2CH_2N(CH_2CH_3)_2$ or —$NHCH(CH_3)$phenyl In various embodiments of compounds of Formula (IV), $R_4$ can be an optionally substituted phenyl or thiophenyl. In some embodiments, $R_4$ is a phenyl or thiophenyl, wherein the phenyl or thiophenyl is optionally substituted with halogen.

In some embodiments of compounds of Formula (IV), $R_5$ can be hydrogen or methyl. In some embodiments, a compound of Formula (IV) is a compound of Formula (I):

(I)

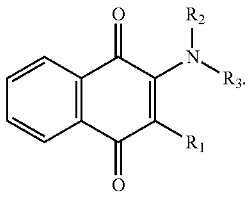

wherein $R_1$ is hydrogen, halogen, a 5- or 6-membered heterocycloalkyl or heteroaryl (optionally substituted with lower alkyl or phenyl), alkoxy, phenyl, lower alkyl (optionally substituted with phenyl or $N(CH_2CH_3)_2$), or $NH_2$; $R_2$ is hydrogen, lower alkyl, phenyl (optionally mono- or di-substituted independently with halogen, lower alkyl, —$S(O)_2NH_2$ or alkoxy), $CH_2$-phenyl (said phenyl optionally substituted with halogen, C(O)-phenyl (said phenyl optionally substituted with halogen), $S(O)_2$-phenyl (said phenyl optionally substituted with halogen), $S(O)_2$-thiophenyl (said thiophenyl optionally substituted with halogen), or thiophenyl; $R_3$ is hydrogen, lower alkyl, or acetyl; and pharmaceutically acceptable salts thereof.

In some embodiments of the various aspects disclosed herein, provided is a compound of formula (I), wherein $R_1$ is hydrogen, chlorine, methyl, methoxy, phenyl, piperazinyl, methylpiperazinyl, piperidinyl, morpholinyl, thiomorpholinyl, phenyl-piperazinyl, ethyl-piperazinyl, —$NHCH_2CH{=}CH_2$, —$CH_2CH{=}CH_2$, —$NH_2$, tert-butyl-piperazinyl, pyrrolidinyl, —$CH_2CH_2CH_2N(CH_2CH_3)_2$ or —$CH(CH_3)$phenyl.

In another embodiment of the invention, provided is a compound of formula (I), wherein $R_2$ is methyl, hydrogen, —$CH_2CH{=}CH_2$, phenyl, —$CH_2$-chlorophenyl, chlorophenyl, acetyl, —C(O)— phenyl, —C(O)-bromophenyl, —$S(O)_2$-phenyl, —$S(O)_2$-bromophenyl, —$S(O)_2$-thiazolyl, —$S(O)_2$-bromothiazolyl, difluorophenyl, methoxyphenyl or -phenyl-$S(O)_2NH_2$.

In another embodiment of the invention, provided is a compound of formula (I), wherein $R_3$ is hydrogen, methyl or acetyl.

In various compounds of Formula (IV), a compound of Formula (IV) is a compound of Formula (Ia):

(Ia)

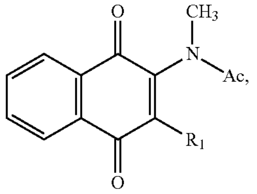

wherein $R_1$ is a 5- or 6-membered heterocycloalkyl (optionally substituted with lower alkyl) or a lower alkyl (optionally substituted with diethylamino); and pharmaceutically acceptable salts thereof.

In another embodiment encompassed by the present invention, a ring carbon in the benzo-ring of the naphthoquinone of the compound of Formula (I) can be replaced with a nitrogen atom.

In some other embodiments, a compound of Formula (IV) is a compound of Formula (Ib):

(Ib)

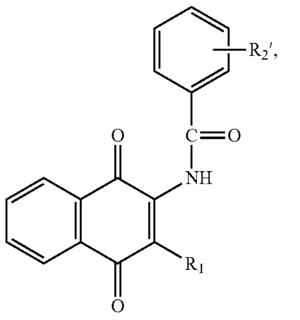

wherein $R_1$ is a 5- or 6-membered heterocycloalkyl (unsubstituted or substituted with lower alkyl or phenyl) or $NH_2$; $R_2$ is hydrogen or halogen; and pharmaceutically acceptable salts thereof.

In yet some other embodiments, a compound of Formula (IV) is a compound of Formula (Ic):

(Ic)

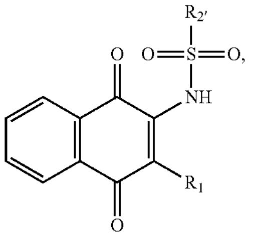

wherein $R_1$ is a 5- or 6-membered heterocycloalkyl (optionally substituted with lower alkyl), hydrogen, alkoxy, or $NH_2$; $R_{2'}$ is a phenyl (optionally substituted with halogen) or a thiophenyl (optionally substituted with halogen); and pharmaceutically acceptable salts thereof.

In still some other embodiments, a compound of Formula (IV) is a compound of Formula (Id):

(Id)

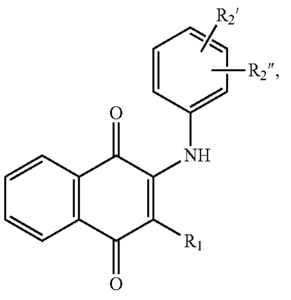

wherein $R_1$ is a 5- or 6-membered heterocycloalkyl (optionally substituted with lower alkyl or phenyl); $R_{2'}$ and $R_{2''}$ are independently or each other hydrogen, halogen or alkoxy; and pharmaceutically acceptable salts thereof.

In some embodiments, X is N and $R_1$ is selected from selected from the group consisting of hydrogen; halogen; a 5- or 6-membered heterocyclyl or heteroaryl, said heterocyclyl or heteroaryl optionally substituted with lower alkyl or phenyl; alkoxy; phenyl; lower alkyl, optionally substituted with phenyl, alkylamino or dialkylamino; and amino. In various compounds of Formula (IV), X can be N and $R_1$ can be hydrogen, chlorine, methyl, methoxy, phenyl, piperazinyl, methylpiperazinyl, ethylpiperzinyl, piperidinyl, morpholinyl, thiomorpholinyl, phenyl-piperazinyl, ethyl-piperazinyl, —$NHCH_2CH{=}CH_2$, —$NH_2$, tert-butyl-piperazinyl, pyrrolidinyl, $NHCH_2CH_2CH_2N(CH_2CH_3)_2$ and NHCH($CH_3$)phenyl.

In some compounds of Formula (IV), X is N and $R_1$ can be selected from hydrogen, chlorine, methyl, methoxy, phenyl, piperazinyl, methylpiperazinyl, piperidinyl, morpholinyl, thiomorpholinyl, phenyl-piperazinyl, ethyl-piperazinyl, $CH_2CH{=}CH_2$, $NH_2$, tert-butyl-piperazinyl, pyrrolidinyl, $CH_2CH_2CH_2N(CH_2CH_3)_2$ or $CH(CH_3)$phenyl. In one embodiment, X is N and $R_1$ is phenyl.

In some embodiments, X is N and $R_2$ can be selected from the group consisting of hydrogen; lower alkyl; phenyl, optionally mono- or bi-substituted independently with halogen, lower alkyl, —$S(O)_2NH_2$ or alkoxy; optionally substituted benzyl; C(O)-phenyl, said phenyl unsubstituted or substituted with halogen; $S(O)_2$-phenyl, said phenyl unsubstituted or substituted with halogen; $S(O)_2$-thiophenyl, said thiophenyl unsubstituted or substituted with halogen; and thiophenyl. In some compounds of Formula (IV), X is N and $R_2$ is selected from methyl, hydrogen, —$CH_2CH{=}CH_2$, phenyl, —$CH_2$-chlorophenyl, chlorophenyl, acetyl, —C(O)-phenyl, —C(O)-bromophenyl, —$S(O)_2$-phenyl, —$S(O)_2$-bromophenyl, —$S(O)_2$-thiazolyl, —$S(O)_2$-bromothiazolyl, difluorophenyl, methoxyphenyl, and -phenyl-$S(O)_2NH_2$. In one embodiment, X is N and $R_2$ is H.

In some embodiments, X is N and $R_3$ is hydrogen, lower alkyl or acyl. In some embodiments, X is N and $R_3$ is hydrogen, methyl or acetyl. In one embodiment, X is N and $R_3$ is hydrogen.

In some embodiments, a compound of Formula (IV) is a compound of Formula (III):

(III)

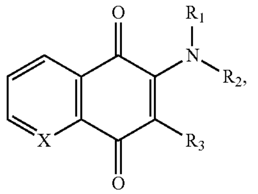

wherein X is nitrogen; $R_3$ is hydrogen, halogen, a 5- or 6-membered heterocycloalkyl or heteroaryl (optionally substituted with lower alkyl or phenyl), alkoxy, lower alkyl (optionally substituted with phenyl or —$N(CH_2CH_3)_2$), or $NH_2$; $R_2$ is hydrogen, lower alkyl, phenyl (optionally mono- or di-substituted independently with halogen, lower alkyl, —$S(O)_2NH_2$ or alkoxy), $CH_2$-phenyl (said phenyl optionally substituted with halogen, C(O)-phenyl (said phenyl optionally substituted with halogen), $S(O)_2$-phenyl (said phenyl optionally substituted with halogen), $S(O)_2$-thiophenyl (said thiophenyl optionally substituted with halogen), or thiophenyl; and $R_1$ is hydrogen, lower alkyl, or acetyl.

In some embodiments, a compound of Formula (IV) is a compound selected from the group of compounds shown in Tables 2-7. In one embodiment, the compound of Formula (IV) is 4-((1,4-dioxo-1,4-dihydronaphthalen-2-yl)amino) benzenesulfonamide (ML329).

TABLE 2
Round 1 SAR and Anilino-substituted Naphthoquinone Compounds
| | | Structure<br>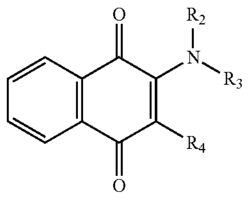 | | | | Target Potency IC50 (μM) | | | | | Antitarget Potency IC50 (μM) | | Fold Selectivity A375/ |
|---|---|---|---|---|---|---|---|---|---|---|---|---|---|
| Entry | * | R1 | R2 | R3 | n | TRPM1 | n | SKMEL5 | n | MALME-3M | n | A375 | TRPM1 |
| 1 | S | —Cl | 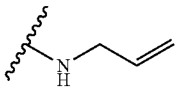 [SMILES: *NCC=C] | —H | 1 | 2.7 | 1 | 9.5 | 1 | 7.9 | 1 | 62.3 | 23 |
| | | Purity (UPLC): 100% | | | | | | | | | | | |
| 2 | S | 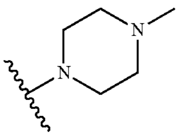 [SMILES: *N1CCN(C)CC1] | —Ph | —H | 1 | 6.1 | 1 | 23.9 | 1 | 16.4 | 1 | 45.7 | 7 |
| | | Purity (UPLC): 95% | | | | | | | | | | | |
| 3 | S | 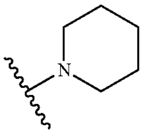 [SMILES: *N1CCCCC1] | —Ph | —H | 1 | 6.3 | 1 | 17.4 | 1 | 5.8 | 1 | 44.3 | 7 |
| | | Purity (UPLC): 92% | | | | | | | | | | | |
| 4 | S | —H | —Ph | —H | 1 | 4.7 | 1 | 2.8 | 1 | 3.4 | 1 | 59.3 | 13 |
| | | Purity (UPLC): 99% | | | | | | | | | | | |
| 5 | S | —OMe | —Ph | —H | 1 | 6.3 | 1 | 3.2 | 1 | 8.2 | 1 | 59.0 | 9 |
| | | Purity (UPLC): 91% | | | | | | | | | | | |
| 6 | S | 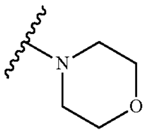 | —Ph | —H | 1 | 6.4 | 1 | 17.2 | 1 | 24.9 | 1 | 68.9 | 11 |
| | | Purity (UPLC): 96% | | | | | | | | | | | |
| 7 | S | 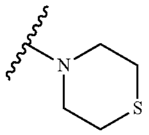 [SMILES: *N1CCSCC1] | —Ph | —H | 1 | 9.8 | 1 | 62.4 | 1 | 70.0 | 1 | 69.8 | 7 |

TABLE 2-continued

Round 1 SAR and Anilino-substituted Naphthoquinone Compounds

| | | Structure | | | | Target Potency IC50 (μM) | | | | | Antitarget Potency IC50 (μM) | | Fold Selectivity A375/ |
|---|---|---|---|---|---|---|---|---|---|---|---|---|---|
| | | 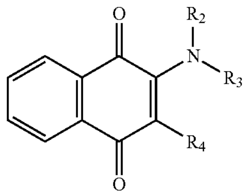 | | | | | | | | | | | |
| Entry | * | R1 | R2 | R3 | n | TRPM1 | n | SKMEL5 | n | MALME-3M | n | A375 | TRPM1 |
| | | Purity (UPLC): 93% | | | | | | | | | | | |
| 8 | S | 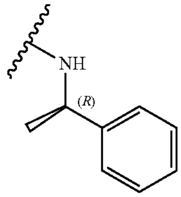 | —Ph | —H | 1 | 10.8 | 1 | 70.0 | 1 | 70.0 | 1 | 64.6 | 6 |
| | | Purity (UPLC): 95% | | | | | | | | | | | |
| 9 | S | 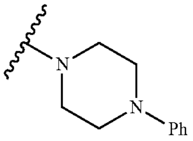 [SMILES: *N1CCN(c2ccccc2)CC1] | —Ph | —H | 1 | 20.8 | 1 | 70.0 | 1 | 70.0 | 1 | 70.0 | 3 |
| | | Purity (UPLC): 95% | | | | | | | | | | | |
| 10 | S | —Ph | —Ph | —H | 1 | 11.3 | 1 | 30.0 | 1 | 41.9 | 1 | 70.0 | 6 |
| | | Purity (UPLC): 100% | | | | | | | | | | | |
| 11 | S | —H | —Ph | —Me | 1 | 16.2 | 1 | 2.3 | 1 | ND | 1 | 70.0 | 4 |
| | | Purity (UPLC): 94% | | | | | | | | | | | |
| 12 | S | —H | —Me | —H | 1 | 12.6 | 1 | 61.8 | 1 | 44.9 | 1 | 70.0 | 6 |
| | | Purity (UPLC): 96% | | | | | | | | | | | |
| 13 | S | —H | —H | —H | 1 | 3.2 | 1 | 8.5 | 1 | 7.3 | 1 | 64.0 | 20 |
| | | Purity (UPLC): 92% | | | | | | | | | | | |
| 14 | S | —H | 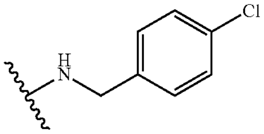 [SMILES: *NCc1ccc(Cl)cc1] | —H | 1 | 70.0 | 1 | 53.3 | 1 | ND | 1 | 70.0 | 1 |
| | | Purity (UPLC): 94% | | | | | | | | | | | |
| 15 | S | —Me | 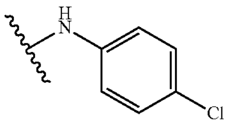 [SMILES: *Nc1ccc(Cl)cc1] | —H | 1 | 40.7 | 1 | 0.8 | 1 | ND | 1 | 70.0 | 2 |
| | | Purity (UPLC): 100% | | | | | | | | | | | |

*P = purchased; S = synthesized

TABLE 3
Round 1 SAR and N-methylacetamide-substituted Naphthoquinone Compounds
| | | Structure 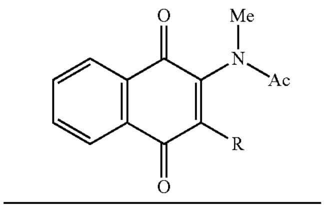 | Target Potency IC50 (μM) | | | | | | Antitarget Potency IC50 (μM) | | Fold Selectivity A375/ |
|---|---|---|---|---|---|---|---|---|---|---|---|
| Entry | * | R | n | TRPM1 | n | SKMELS | n | MALME-3M | n | A375 | TRPM1 |
| 1 | S | 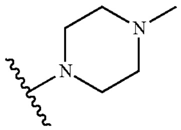 [SMILES: *N1CCN(C)CC1] Purity (UPLC): 100% | 1 | 0.4 | 1 | 4.4 | 1 | 2.0 | 1 | 14.4 | 36 |
| 2 | S | 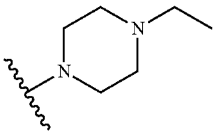 [SMILES: *N1CCN(CC)CC1] Purity (UPLC): 100% | 1 | 0.4 | 1 | 4.9 | 1 | 2.5 | 1 | 11.3 | 27 |
| 3 | S | 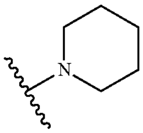 [SMILES: *N1CCCCC1] Purity (UPLC): 99% | 1 | 0.7 | 1 | 4.6 | 1 | 4.9 | 1 | 29.0 | 40 |
| 4 | S | 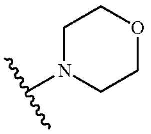 [SMILES: *N1CCOCC1] Purity (UPLC): 99% | 1 | 2.1 | 1 | 7.8 | 1 | 7.4 | 1 | 26.3 | 12 |
| 5 | S | 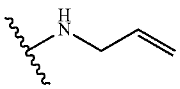 [SMILES: *NCC=C] Purity (UPLC): 92% | 1 | 0.1 | 1 | 0.6 | 1 | 0.7 | 1 | 11.0 | 119 |
| 6 | S | 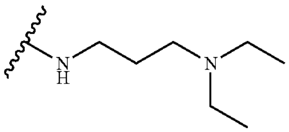 [SMILES: *NCCCN(CC)CC] Purity (UPLC): 100% | 1 | 0.4 | 1 | 4.4 | 1 | 3.1 | 1 | 4.8 | 11 |
*P = purchased; S = synthesized

TABLE 4

Round 1 SAR and Benzoyl-substituted Naphthoquinone compounds

| | | | | | | | | | | | | |
|---|---|---|---|---|---|---|---|---|---|---|---|---|
| 3 | S | —H | 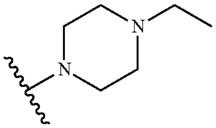 [SMILES: *N1CCN(CC)CC1] Purity (UPLC): 100% | 1 | 0.9 | 1 | 7.2 | 1 | 3.8 | 1 | 23.6 | 25 |
| 4 | S | —H | —NH2 Purity (UPLC): 100% | 1 | 6.6 | 1 | 11.7 | 1 | 12.2 | 1 | 67.2 | 10 |
| 5 | S | —H | 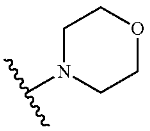 [SMILES: *N1CCOCC1] Purity (UPLC): 97% | 1 | 7.8 | 1 | 28.2 | 1 | 18.6 | 1 | 40.2 | 5 |
| 6 | S | —H | 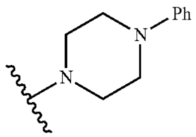 [SMILES: *N1CCN(c2ccccc2)CC1] Purity (UPLC): 98% | 1 | 41.7 | 1 | 70.0 | 1 | 64.0 | 1 | 70.0 | 2 |

*P = purchased; S = synthesized

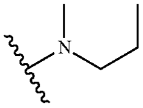 [SMILES: *N(C)CCC]

Purity (UPLC): 99%

TABLE 5

Round 1 SAR Benzene- and Thiopene-substituted Naphthoquinone Compounds

| | | 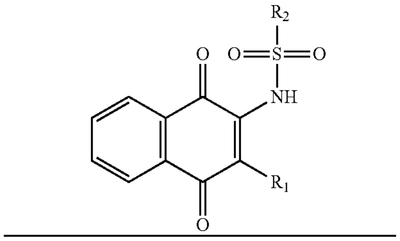 | | Target Potency IC50 (nM) | | | | | | Antitarget Potency IC50 (nM) | | Fold Selectivity A375/ |
|---|---|---|---|---|---|---|---|---|---|---|---|---|
| Entry | * | R1 | R2 | n | TRPM1 | n | SKMELS | n | MALME-3M | n | A375 | TRPM1 |
| 1 | S | 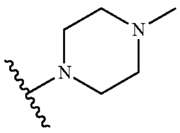 [SMILES: *N1CCN(C)CC1] Purity (UPLC): 98% | —Ph | 1 | 0.9 | 1 | 14.6 | 1 | 7.3 | 1 | 37.5 | 42 |
| 2 | S | 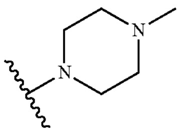 [SMILES: *N1CCN(C)CC1] Purity (UPLC): 96% | 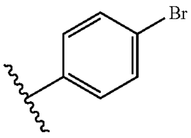 [SMILES: *c1ccc(Br)cc1] | 1 | 3.4 | 1 | 45.1 | 1 | 70.0 | 1 | 60.5 | 18 |

TABLE 5-continued
Round 1 SAR Benzene- and Thiopene-substituted Naphthoquinone Compounds
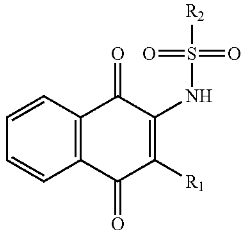
| Entry | * | R1 | R2 | Target Potency IC50 (nM) n | TRPM1 | n | SKMELS | n | MALME-3M | Antitarget Potency IC50 (nM) n | A375 | Fold Selectivity A375/ TRPM1 |
|---|---|---|---|---|---|---|---|---|---|---|---|---|
| 3 | S | 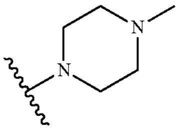 [SMILES: *N1CCN(C)CC1] | 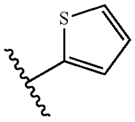 [SMILES: *c1cccs1] | 1 | 2.6 | 1 | 42.2 | 1 | 11.7 | 1 | 55.8 | 25 |
| | | Purity (UPLC): 96% | | | | | | | | | | |
| 4 | S | 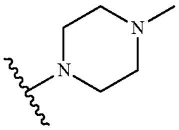 [SMILES: *N1CCN(C)CC1] | 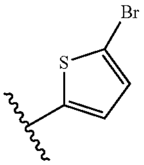 [SMILES: *c1ccc(Br)s1] | 1 | 3.0 | 1 | 28.7 | 1 | 9.8 | 1 | 59.8 | 20 |
| | | Purity (UPLC): 99% | | | | | | | | | | |
| 5 | S | —H | —Ph | 1 | 7.1 | 1 | 8.9 | 1 | 13.6 | 1 | 70.0 | 10 |
| | | Purity (UPLC): 99% | | | | | | | | | | |
| 6 | S | —H | 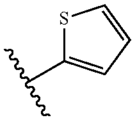 [SMILES: *c1cccs1] | 1 | 6.5 | 1 | 12.8 | 1 | 27.8 | 1 | 70.0 | 11 |
| | | Purity (UPLC): 99% | | | | | | | | | | |
| 7 | S | 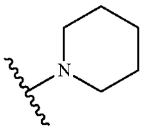 [SMILES: *N1CCCCC1] | 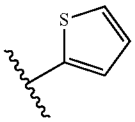 [SMILES: *c1cccs1] | 1 | 21.8 | 1 | 50.3 | 1 | 48.8 | 1 | 70.0 | 3 |
| | | Purity (UPLC): 96% | | | | | | | | | | |
| 8 | S | —NH2 | —Ph | 1 | 7.2 | 1 | 15.4 | 1 | 15.5 | 1 | 66.2 | 9 |
| | | Purity (UPLC): 100% | | | | | | | | | | |
| 9 | S | 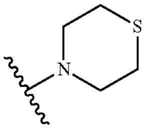 [SMILES: *N1CCSCC1] | 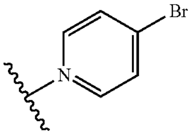 | 1 | 25.3 | 1 | 55.5 | 1 | 51.7 | 1 | 70.0 | 3 |
| | | Purity (UPLC): 97% | | | | | | | | | | |
| 10 | S | —OMe | —Ph | | 7.7 | | 14.1 | | 18.6 | | 70.0 | 9 |
| | | Purity (UPLC): 98% | | | | | | | | | | |
*P = purchased; S = synthesized TABLE 6
Round 2 SAR and Anilio- and Nitrogen-heterocycle-substituted Naphthoquinone Compounds
Structure
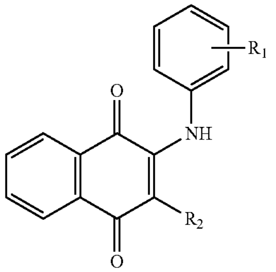
| Entry | Previous Entry | * | R1 | R2 | Target Potency IC50 (nM) n | TRPM1 | n | SKMELS | n | MALME-3M | Antitarget Potency IC50 (nM) n | A375 | Fold Selectivity A375/ TRPM1 |
|---|---|---|---|---|---|---|---|---|---|---|---|---|---|
| 1 | Table3/Entry 2 | S | —H | 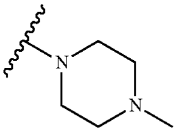 [SMILES: *N1CCN(C)CC1] | 1 | 6.1 | 1 | 23.9 | 1 | 16.4 | 1 | 45.7 | 7 |
| | Purity (UPLC): 95% | | | | | | | | | | | | |
| 2 | — | S | 2,4-diF | 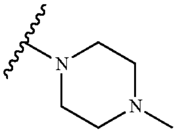 [SMILES: *N1CCN(C)CC1] | 1 | 11.4 | 1 | 9.9 | 1 | 25.4 | 1 | 70.0 | 6 |
| | Purity (UPLC): 97% | | | | | | | | | | | | |
| 3 | — | S | 2,4-diF | 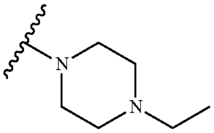 [SMILES: *N1CCN(CC)CC1] | 1 | 7.4 | 1 | 9.0 | 1 | 26.3 | 1 | 70.0 | 9 |
| | Purity (UPLC): 100% | | | | | | | | | | | | |
| 4 | — | S | 2,4-diF | 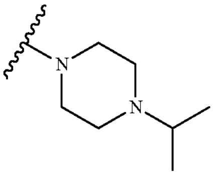 [SMILES: *N1CCN(C(C)C)CC1] | 1 | 6.0 | 1 | 8.7 | 1 | 25.4 | 1 | 70.0 | 12 |
| | Purity (UPLC): 100% | | | | | | | | | | | | |
| 5 | — | S | 4-OMe | 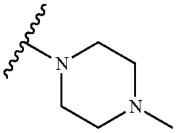 [SMILES: *N1CCN(C)CC1] | 1 | 24.9 | 1 | 16.4 | 1 | ND | 1 | 70.0 | 3 |
| | Purity (UPLC): 94% | | | | | | | | | | | | |
| 6 | — | S | 4-OMe | 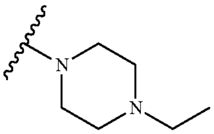 [SMILES: *N1CCN(CC)CC1] | 1 | 6.9 | 1 | 12.2 | 1 | ND | 1 | 70.0 | 10 |
| | Purity (UPLC): 95% | | | | | | | | | | | | |

TABLE 6-continued
Round 2 SAR and Anilio- and Nitrogen-heterocycle-substituted Naphthoquinone Compounds
Structure
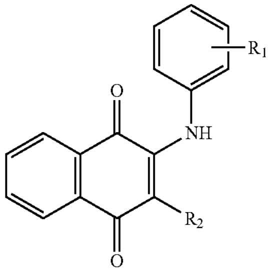
| | | | | | Target Potency IC50 (nM) | | | | | | Antitarget Potency IC50 (nM) | | Fold Selectivity A375/ |
|---|---|---|---|---|---|---|---|---|---|---|---|---|---|
| Entry | Previous Entry | * | R1 | R2 | n | TRPM1 | n | SKMELS | n | MALME-3M | n | A375 | TRPM1 |
| 7 | — | S | 4-OMe | 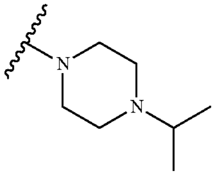 [SMILES: *N1CCN(C(C)C)CC1] | 1 | 3.3 | 1 | 16.6 | 1 | ND | 1 | 45.1 | 14 |
| 8 | Table 3/Entry 2 | S | —H | 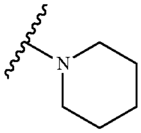 [SMILES: *N1CCCCC1] | 1 | 6.3 | 1 | 17.4 | 1 | 5.8 | 1 | 44.3 | 7 |
| | Purity (UPLC): 92% | | | | | | | | | | | | |
| 9 | — | S | 2,4-diF | 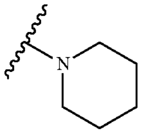 [SMILES: *N1CCCCC1] | 1 | 0.9 | 1 | 3.6 | 1 | ND | 1 | 21.8 | 23 |
| | Purity (UPLC): 96% | | | | | | | | | | | | |
| 10 | — | S | 2,4-diF | 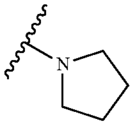 [SMILES: *N1CCCC1] | 1 | 0.7 | 1 | 2.3 | 1 | ND | 1 | 8.1 | 12 |
| | Purity (UPLC): 95% | | | | | | | | | | | | |
| 11 | — | S | 4-OMe | 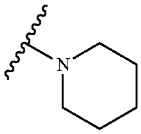 [SMILES: *N1CCCCC1] | 1 | 7.2 | 1 | 3.7 | 1 | 11.2 | 1 | 56.2 | 8 |
| | Purity (UPLC): 95% | | | | | | | | | | | | |
| 12 | Table 3/Entry 6 | S | —H | 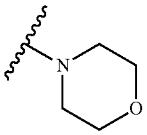 [SMILES: *N1CCOCC1] | 1 | 6.4 | 1 | 37.2 | 1 | 24.9 | 1 | 68.9 | 11 |
| | Purity (UPLC): 96% | | | | | | | | | | | | |

TABLE 6-continued

Round 2 SAR and Anilio- and Nitrogen-heterocycle-substituted Naphthoquinone Compounds Structure

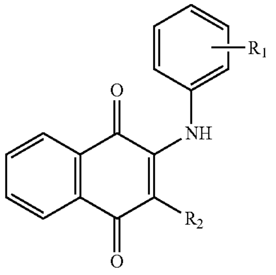

| Entry | Previous Entry | * | R1 | R2 | Target Potency IC50 (nM) n | TRPM1 | n | SKMELS | n | MALME-3M | Antitarget Potency IC50 (nM) n | A375 | Fold Selectivity A375/ TRPM1 |
|---|---|---|---|---|---|---|---|---|---|---|---|---|---|
| 13 | Table 3/Entry 7 | S | —H | 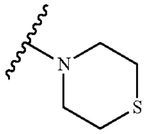 [SMILES: *N1CCSCC1] | 1 | 9.8 | 1 | 62.4 | 1 | 70.0 | 1 | 69.8 | 7 |
| | Purity (UPLC): 93% | | | | | | | | | | | | |
| 14 | Table 3/Entry 9 | S | —H | 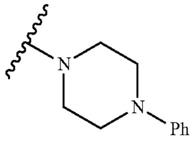 [SMILES: *N1CCN(c2ccccc2)CC1] | 1 | 20.8 | 1 | 70.0 | 1 | 70.0 | 1 | 70.0 | 3 |
| | Purity (UPLC): 95% | | | | | | | | | | | | |

*P = purchased; S = synthesized

TABLE 7

Round 2 SAR and Hydrogen-substituted Naphthoquinone compounds

Structure

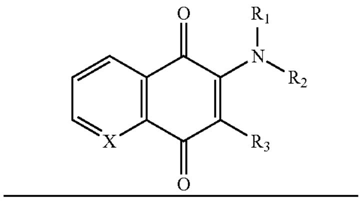

| Entry | Previous Entry | * | R1 | R2 | R3 | X | Target Potency IC50 (nM) n | TRPM1 | n | SKMELS | n | MALME-3M | Anti-target Po-tency IC50 (nM) n | A375 | Fold Select-ivity A375/ TRPM1 |
|---|---|---|---|---|---|---|---|---|---|---|---|---|---|---|---|
| 1 | Table 3/ Entry 13 | S | —H Purity (UPLC): 92% | —H | —H | CH | 1 | 3.2 | 1 | 8.5 | 1 | 7.6 | 1 | 64.0 | 20 |
| 2 | Table 3/ Entry 12 | S | —Me Purity (UPLC): 96% | —H | —H | CH | 1 | 12.6 | 1 | 61.8 | 1 | 44.9 | 1 | 70.0 | 6 |
| 3 | Table 3/ Entry 4 | S | —Ph Purity (UPLC): 99% | —H | —H | CH | 1 | 4.7 | 1 | 2.8 | 1 | 3.4 | 1 | 59.3 | 13 |
| 4 | — | P | —Ph Purity (UPLC): 100% | —H | —H | N | 1 | 0.4 | 1 | 0.2 | 1 | ND | 1 | '6.2 | 39 |
| 5 | Table 3/ Entry 11 | S | —Ph Purity (UPLC): 94% | —Me | —H | CH | 1 | 16.2 | 1 | 2.3 | 1 | ND | 1 | 70.0 | 4 |

TABLE 7-continued

Round 2 SAR and Hydrogen-substituted Naphthoquinone compounds

| Entry | Previous Entry | * | Structure<br>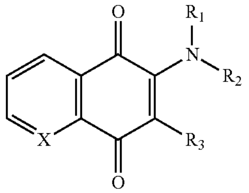<br>R1 | R2 | R3 | X | n | Target Potency IC50 (nM)<br>TRPM1 | n | SKMELS | n | MALME-3M | n | Anti-target Potency IC50 (nM)<br>A375 | Fold Selectivity<br>A375/TRPM1 |
|---|---|---|---|---|---|---|---|---|---|---|---|---|---|---|---|
| 6 | — | S | 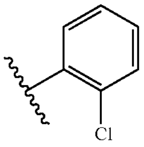 [SMILES: *c1ccccc1Cl]<br>Purity (UPLC): 95% | —H | —H | CH | 1 | 5.4 | 1 | 0.2 | 1 | ND | 1 | 70.0 | 13 |
| 7 | — | S | 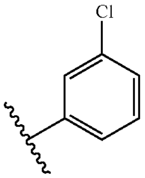 [SMILES: *c1cccc(Cl)c1]<br>Purity (UPLC): 97% | —H | —H | CH | 1 | 23.9 | 1 | 0.7 | 1 | ND | 1 | 22.3 | 1 |
| 8 | Table 3/ Entry 15 | S | 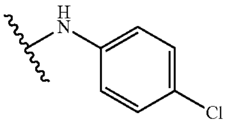 [SMILES: *Nc1ccc(Cl)cc1]<br>Purity (UPLC): 100% | —H | —Me | CH | 1 | 40.7 | | 0.8 | 1 | ND | 1 | 70.0 | 2 |
| 9 | — | S | 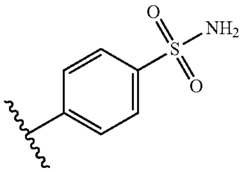 [SMILES: *c1ccc(S(N)(=O)=O)cc1]<br>Purity (UPLC): 100% | —H | —H | CH | 1 | 1.2 | 1 | 0.1 | 1 | 0.7 | 1 | 70.0 | 58 |
| 10 | — | S | 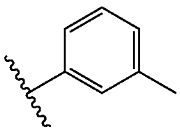 [SMILES: *c1cccc(C)c1]<br>Purity (UPLC): 98% | —H | —H | CH | 1 | 18.9 | 1 | 0.7 | 1 | ND | 1 | 70.0 | 4 |
| 11 | — | S | 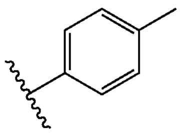 [SMILES: *c1ccc(C)cc1]<br>Purity (UPLC): 95% | —H | —H | CH | 1 | 6.6 | 1 | 1.2 | 1 | 13.5 | 1 | 70.0 | 11 |

TABLE 7-continued

Round 2 SAR and Hydrogen-substituted Naphthoquinone compounds

Structure

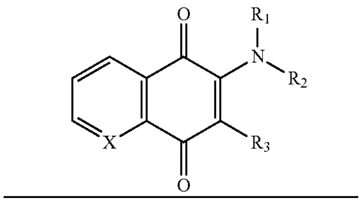

| Entry | Previous Entry | * | R1 | R2 | R3 | X | n | Target Potency IC50 (nM) TRPM1 | n | SKMELS | n | MALME-3M | n | Anti-target Potency IC50 (nM) A375 | Fold Selectivity A375/TRPM1 |
|---|---|---|---|---|---|---|---|---|---|---|---|---|---|---|---|
| 12 | Table 3/ Entry 14 | S | 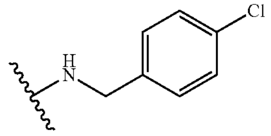 [SMILES: *NCc1ccc(Cl)cc1] Purity (UPLC): 94% | —H | —H | CH | 1 | 20.0 | 1 | 53.3 | 1 | ND | 1 | 70.0 | 1 |
| 13 | — | S | 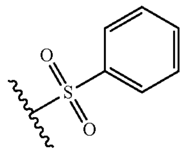 [SMILES: *S(=O)(=O)c1ccccc1] Purity (UPLC): 99% | —H | —H | CH | 1 | 7.1 | 1 | 8.9 | 1 | 13.6 | 1 | 70.0 | 10 |
| 14 | Table 6/ Entry 6 | S | 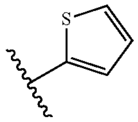 Purity (UPLC): 99% | —H | —H | CH | 1 | 6.5 | 1 | 12.8 | 1 | 27.8 | 1 | 70.0 | 11 |

*P = purchased; S = synthesized

It will be appreciated that the compounds of general Formula (IV) can be. derivatized at functional groups to provide derivatives which are capable of conversion back to the parent compound in vivo. Physiologically acceptable and metabolically labile derivatives, which are capable of producing the parent compounds of general Formula IV in vivo are also within the scope of this invention. Thus, the disclosure also provides derivates, analogues, prodrugs, and pharmaceutically acceptable salts of the compounds of Formula (IV).

Compounds disclosed herein can be prepared beginning with commercially available starting materials and utilizing general synthetic techniques and procedures known to those skilled in the art. Chemicals may be purchased from companies such as for example Sigma-Aldrich, VWR and Alfa Aesar. Chromatography supplies and equipment may be purchased from such companies as for example Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Mettler Toledo Instrument Newark, Del. Biotage, ISCO and Analogix columns are pre-packed silica gel columns used in standard chromatography. Exemplary synthesis of various compounds of Formula (IV) is described in the Examples section. Ordinarily skilled artisans can easily adapt the methods described in the Examples sections for preparing any one of the compounds of Formula (IV).

For example, compounds of Formula (I) can be prepared according to the following schemes:

Scheme 1. Synthesis of 4-((1,4-dioxo-1,4-dihydronaphthalen-2-yl)amino)benzenesulfonamide

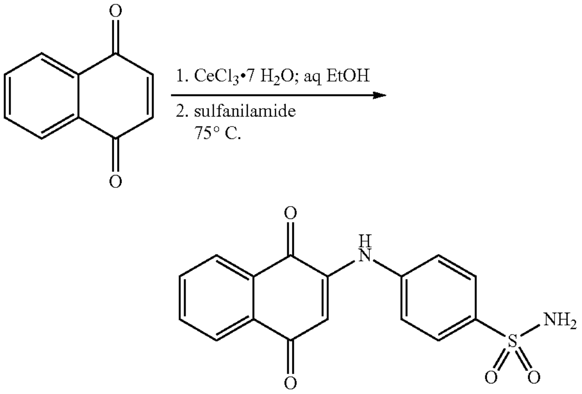

Compound 4-((1,4-dioxo-1,4-dihydronaphthalen-2-yl)amino)-benzenesulfonamide of Example 1 can be synthesized in one step from commercially available 1,4-naphthoquinone and sulfanilamide using cerium(III) chloride heptahydrate as a Lewis acid catalyst as shown in Scheme 1. The reaction was allowed to stir at 75° C. for three days (unoptimized) then dilute citric acid was added to the reaction suspension and the insoluble material was collected by filtration. The filter cake was washed with water, dried, then purified by preparative RPLC.

Exemplary embodiments of the various aspects disclosed herein can be described by one or more of the following paragraphs:

1. A compound of Formula (IV):

(IV)

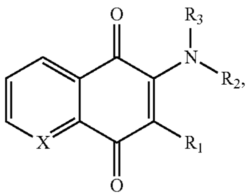

wherein:

X is CH or N;

R1 is hydrogen, halogen, optionally substituted heterocycloalkyl, optionally substituted heteroaryl, optionally substituted aryl, optionally substituted alkoxy, optionally substituted lower alkyl, amino, optionally substituted alkylamino, optionally substituted dialkylamino;

R2 is hydrogen, optionally substituted lower alkyl, optionally substituted aryl or heteroaryl, optionally substituted benzyl, —C(O)—R4, —S(O)2-R4, or —CH(R5)-R4;

R3 is hydrogen, optionally substituted lower alkyl, or acyl;

R4 is optionally substituted aryl or heteroaryl;

R5 is hydrogen or lower alkyl; and pharmaceutically acceptable salts thereof.

2. The compound of paragraph 1, wherein the compound is of Formula (I):

(I)

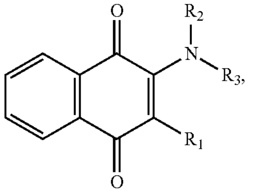

wherein:

R1 is hydrogen, halogen, a 5- or 6-membered heterocycloalkyl or heteroaryl (optionally substituted with lower alkyl or phenyl), alkoxy, phenyl, lower alkyl (optionally substituted with phenyl or —N(CH2CH3)2), or $NH_2$;

R2 is hydrogen, lower alkyl, phenyl (optionally mono- or di-substituted independently with halogen, lower alkyl, —S(O)2NH2 or alkoxy), —CH2-phenyl (said phenyl optionally substituted with halogen, C(O)-phenyl (said phenyl optionally substituted with halogen), S(O)2-phenyl (said phenyl optionally substituted with halogen), S(O)2-thiophenyl (said thiophenyl optionally substituted with halogen), or thiophenyl;

R3 is hydrogen, lower alkyl, or acetyl; and pharmaceutically acceptable salts thereof.

3. The compound of paragraph 1 or 2, wherein R1 is hydrogen, chlorine, methyl, methoxy, phenyl, piperazinyl, methylpiperazinyl, piperidinyl, morpholinyl, thiomorpholinyl, phenyl-piperazinyl, ethyl-piperazinyl, —NHCH2CH═CH2, —CH2CH═CH2, —NH2, tert-butyl-piperazinyl, pyrrolidinyl, —NCH2CH2CH2N(CH2CH3)2, —CH2CH2CH2N(CH2CH3)2, or —CH(CH3)phenyl.

4. The compound of any of paragraphs 1-3, wherein R2 is methyl, hydrogen, —CH2CH═CH2, phenyl, CH2-chlorophenyl, chlorophenyl, acetyl, —C(O)-phenyl, —C(O)-bromophenyl, —S(O)2-phenyl, —S(O)2-bromophenyl, —S(O)2-thiazolyl, —S(O)2-bromothiazolyl, difluorophenyl, methoxyphenyl or -phenyl-S(O)2NH2.

5. The compound of any of paragraphs 1-4, wherein R3 is hydrogen, methyl or acetyl.

6. The compound of any of paragraphs 1-5, wherein the compound is of Formula (Ia):

(Ia)

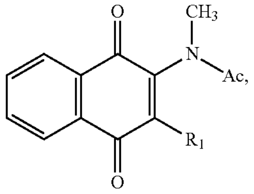

wherein:

R1 is a 5- or 6-membered heterocycloalkyl (optionally substituted with lower alkyl), or a lower alkyl (optionally substituted with —N(CH2CH3)2); and Pharmaceutically acceptable salts thereof.

7. The compound of any of paragraphs 1-6, wherein the compound is of Formula (Ib):

(Ib)

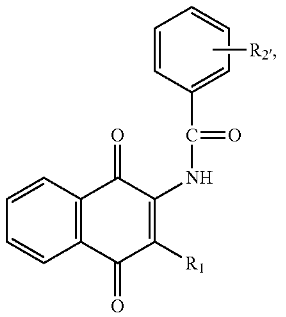

wherein:

R1 is a 5- or 6-membered heterocycloalkyl (optionally substituted with lower alkyl or phenyl), or $NH_2$;

R2' is hydrogen or halogen; and pharmaceutically acceptable salts thereof.

8. The compound of any of paragraphs 1-7, wherein the compound is of Formula (Ic):

(Ic)

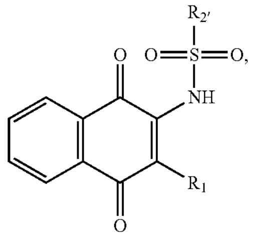

wherein:

R1 is a hydrogen, alkoxy, NH2, or a 5- or 6-membered heterocycloalkyl (optionally substituted with lower alkyl);

R2' is a phenyl or thiophenyl, each can be optionally substituted with halogen; and pharmaceutically acceptable salts thereof.

9. The compound of any of paragraphs 1-8, wherein the compound is of Formula (Id):

(Id)

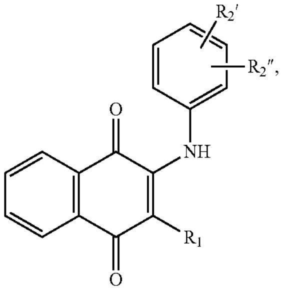

wherein:

R1 is a 5- or 6-membered heterocycloalkyl (optionally substituted with lower alkyl or phenyl);

R2' and R2" are independently or each other hydrogen, halogen, or alkoxy; and pharmaceutically acceptable salts thereof.

10. The compound of any of paragraphs 1-9, wherein the compound is of Formula (III):

(III)

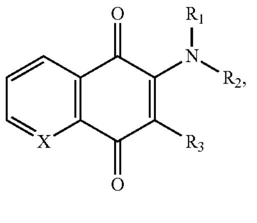

wherein:

X is nitrogen;

R1 is hydrogen, lower alkyl, or acetyl;

R2 is hydrogen, lower alkyl, phenyl (optionally mono- or di-substituted independently with halogen, lower alkyl, —S(O)2NH2 or alkoxy), CH2-phenyl (said phenyl optionally substituted with halogen, C(O)-phenyl (said phenyl optionally substituted with halogen), S(O)2-phenyl (said phenyl optionally substituted with halogen), S(O)2-thiophenyl (said thiophenyl optionally substituted with halogen), or thiophenyl;

R3 is hydrogen, halogen, a 5- or 6-membered heterocycloalkyl or heteroaryl (optionally substituted with lower alkyl or phenyl), alkoxy, lower alkyl (optionally substituted with phenyl or —N(CH2CH3)2), or NH2; and pharmaceutically acceptable salts thereof.

11. The compound of any of paragraphs 1-10, wherein the compound is selected from the group consisting of compounds shown in Tables 2-7.

12. The compound of any of paragraphs 1-11, wherein the compound is 4-((1,4-dioxo-1,4-dihydronaphthalen-2-yl)amino)benzenesulfonamide.

13. A pharmaceutical composition, comprising a therapeutically effective amount of a compound of any of paragraphs 1-12 and a pharmaceutically acceptable carrier.

As used herein, the term “alkyl”, alone or in combination with other groups, refers to a branched or straight-chain monovalent saturated aliphatic hydrocarbon radical of one to twenty carbon atoms, preferably one to sixteen carbon atoms, more preferably one to ten carbon atoms.

As used herein, the term “alkenyl”, alone or in combination with other groups, refers to a straight-chain or branched hydrocarbon residue having an olefinic bond.

The term “cycloalkyl” refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbomyl, adamantyl, indanyl and the like. In a preferred embodiment, the “cycloalkyl” moieties can optionally be substituted with one, two, three or four substituents. Each substituent can independently be, alkyl, alkoxy, halogen, amino, hydroxyl or oxygen unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term “heterocycloalkyl” denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate. For example, the term “heterocyclyl” can refer to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

The terms "bicyclic" and "tricyclic" refers to fused, bridged, or joined by a single bond polycyclic ring assemblies.

The term "lower alkyl", alone or in combination with other groups, refers to a branched or straight-chain alkyl radical of one to nine carbon atoms, preferably one to six carbon atoms, more preferably one to four carbon atoms. This term is further exemplified by radicals such as methyl, ethyl, n-propyl, isopropyl, n-butyl, s-butyl, isobutyl, tert-butyl, n-pentyl, 3-methylbutyl, n-hexyl, 2-ethylbutyl and the like.

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. The term "aryl" includes aromatic mono- or polycarbocyclic radicals of 6 to 12 carbon atoms having at least one aromatic ring. Exemplary aryl groups include, but are not limited to, 1,2,3,4-tetrahydronaphthalene, 1,2-dihydronaphthalene, indanyl, 1H-indenyl, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The alkyl, lower alkyl and aryl groups can be substituted or unsubstituted. When substituted, there will generally be, for example, 1 to 4 substituents present. These substituents may optionally form a ring with the alkyl, lower alkyl or aryl group with which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, three, or four ring heteroatoms selected from N, O, and S, with the remaining ring atoms being C. One or two ring carbon atoms of the heteroaryl group can be replaced with a carbonyl group. For example, the term "heteroaryl" can refer to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. $C_x$ heteroaryl and $C_x$-$C_y$heteroaryl are typically used where X and Y indicate the number of carbon atoms in the ring system. Heteroaryls include, but are not limited to, those derived from benzo[b]furan, benzo[b]thiophene, benzimidazole, imidazo[4,5-c]pyridine, quinazoline, thieno[2, 3-c]pyridine, thieno[3,2-b]pyridine, thieno[2, 3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The heterocycloalkyl and heteroaryl groups described above can be substituted independently with one, two, or three substituents. Substituents can include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazoyl and carbolinyl).

As used herein, the term “alkoxy” means alkyl-O—; and “alkoyl” means alkyl-CO—. Alkoxy substituent groups or alkoxy-containing substituent groups may be substituted by, for example, one or more alkyl groups.

As used herein, the term “halogen” means a fluorine, chlorine, bromine or iodine radical, preferably a fluorine, chlorine or bromine radical, and more preferably a bromine or chlorine radical. The term “cyano” means the radical —CN.

The term, “heteroatom” refers to an atom that is not a carbon atom. Particular examples of heteroatoms include, but are not limited to nitrogen, oxygen, sulfur and halogens. A “heteroatom moiety” includes a moiety where the atom by which the moiety is attached is not a carbon. Examples of heteroatom moieties include —N═, —$NR^N$—, —$N^+(O^-)$═, —O—, —S— or —$S(O)_2$, —$OS(O)_2$—, and —SS—, wherein $R^N$ is H or a further substituent.

The term “hydroxy” means the radical OH.

The term “imine derivative” means a derivative comprising the moiety —C(NR)—, wherein R comprises a hydrogen or carbon atom alpha to the nitrogen.

The term “nitro” means the radical —$NO_2$.

An “oxaaliphatic,” “oxaalicyclic”, or “oxaaromatic” mean an aliphatic, alicyclic, or aromatic, as defined herein, except where one or more oxygen atoms (—O—) are positioned between carbon atoms of the aliphatic, alicyclic, or aromatic respectively.

An “oxoaliphatic,” “oxoalicyclic”, or “oxoaromatic” means an aliphatic, alicyclic, or aromatic, as defined herein, substituted with a carbonyl group. The carbonyl group can be an aldehyde, ketone, ester, amide, acid, or acid halide As used herein, the term “amino” means —$NH_2$. The term “alkylamino” means a nitrogen moiety having at least one straight or branched unsaturated aliphatic, cyclyl, or heterocyclyl radicals attached to the nitrogen. For example, representative amino groups include —$NH_2$, —$NHCH_3$, —$N(CH_3)_2$, —$NH(C_1\text{-}C_{10}alkyl)$, —$N(C_1\text{-}C_{10}alkyl)_2$, and the like. The term “alkylamino” includes “alkenylamino,” “alkynylamino,” “cyclylamino,” and “heterocyclylamino.” The term “arylamino” means a nitrogen moiety having at least one aryl radical attached to the nitrogen. For example —NHaryl, and —$N(aryl)_2$. The term “heteroarylamino” means a nitrogen moiety having at least one heteroaryl radical attached to the nitrogen. For example —NHheteroaryl, and —$N(heteroaryl)_2$. Optionally, two substituents together with the nitrogen can also form a ring. Unless indicated otherwise, the compounds described herein containing amino moieties can include protected derivatives thereof. Suitable protecting groups for amino moieties include acetyl, tert-butoxycarbonyl, benzyloxycarbonyl, and the like.

The term “aralkyl”, as used herein, refers to an alkyl group substituted with an aryl group (e.g., an aromatic or heteroaromatic group).

The term “alkylthio” refers to an alkyl group, as defined above, having a sulfur radical attached thereto. In preferred embodiments, the “alkylthio” moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —$SO_2$—. It is noted that the sulfonyl radical can be further substituted with a variety of substituents to form different sulfonyl groups including sulfonic acids (—$SO_3H$), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —$OCH_2CH_2OCH_3$, and the like.

The term "alkoxycarbonyl" means —C(O)O-(alkyl), such as —C(═O)$OCH_3$, —C(═O)$OCH_2CH_3$, and the like.

The term "alkoxyalkyl" means -(alkyl)-O-(alkyl), such as —$CH_2OCH_3$, —$CH_2OCH_2CH_3$, and the like.

The term "aryloxy" means —O-(aryl), such as —O-phenyl, —O-pyridinyl, and the like.

The term "arylalkyl" means -(alkyl)-(aryl), such as benzyl (i.e., —$CH_2$phenyl), —$CH_2$ pyrindinyl, and the like.

The term "arylalkyloxy" means —O-(alkyl)-(aryl), such as —O-benzyl, —O—$CH_2$-pyridinyl, and the like.

The term "cycloalkyloxy" means —O-(cycloalkyl), such as —O-cyclohexyl, and the like.

The term "cycloalkylalkyloxy" means —O-(alkyl)-(cycloalkyl, such as —$OCH_2$cyclohexyl, and the like.

The term "aminoalkoxy" means —O-(alkyl)-$NH_2$, such as —$OCH_2NH_2$, —$OCH_2CH_2NH_2$, and the like.

The term "mono- or di-alkylamino" means —NH(alkyl) or —N(alkyl)(alkyl), respectively, such as —$NHCH_3$, —$N(CH_3)_2$, and the like.

The term "mono- or di-alkylaminoalkoxy" means —O-(alkyl)-NH(alkyl) or —O-(alkyl)-N(alkyl)(alkyl), respectively, such as —$OCH_2NHCH_3$, —$OCH_2CH_2N(CH_3)_2$, and the like.

The term "arylamino" means —NH(aryl), such as —NH-phenyl, —NH-pyridinyl, and the like.

The term "arylalkylamino" means —NH-(alkyl)-(aryl), such as —NH-benzyl, —$NHCH_2$ pyridinyl, and the like.

The term "cycloalkylamino" means —NH-(cycloalkyl), such as —NH-cyclohexyl, and the like.

The term "cycloalkylalkylamino" —NH-(alkyl)-(cycloalkyl), such as —$NHCH_2$-cyclohexyl, and the like.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —$CH_3$) as well as —$CR_aR_bR_c$ where $R_a$, $R_b$, and $R_c$ can each independently be hydrogen or any other substituent where the atom alpha to the carbon is a heteroatom or cyano. Hence, $CF_3$, $CH_2OH$ and $CH_2CN$ are all $C_1$ alkyls.

The term "optionally substituted" means that the specified group or moiety is unsubstituted or is substituted with one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted.

The term "substituent" refers to a group "substituted" on the substituted entity at any atom of that entity. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring. In some embodiments, the substituent group is selected from alkyl, ester, amide, monocarbonyl, dicarbonyl, ketones, aldehydes, and the like. As used herein, the term, "aromatic" means a moiety wherein the constituent atoms make up an unsaturated ring system, all atoms in the ring system are $sp^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

Compounds of formula I can have one or more asymmetric carbon or sulfur atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms. The invention encompasses the compounds as individual isomers substantially free of other isomers and alternatively, as mixtures of various isomers, e.g., racemic mixtures of enantiomers.

Certain compounds, as described herein can have one or more double bonds that can exist as either a Z or E isomer, unless otherwise indicated. The compounds disclosed herein can also have axial chirality. As used herein, the term "axial chirality", refers to chirality in which a molecule, or a portion thereof, does not possess a stereogenic center but has an axis of chirality about which a set of substituents is held in a spatial arrangement that is not superimposable on its minor image. Axial chirality may be observed, for example, in atropisomeric biaryl compounds where the rotation about the aryl-aryl bond is restricted. It will be appreciated that a compound encompassed by the present invention may possess axial chirality whether or not other stereogenic centers are present elsewhere in the molecule.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane polarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R and S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+) and (−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); 65 (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction $F_{(+)}$ and $F_{(-)}$ (where the sum of $F_{(+)}$ and $F_{(-)}=1$). The enantiomeric excess is defined as $*F_{(+)}-F_{(-)}*$ and the percent enantiomeric excess by $100x*F_{(+)}-F_{(-)}*$. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereopreferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A nonselective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

In some embodiments, the compounds disclosed herein are pure isomers or enantiomers.

The term "analog" as used herein refers to a compound that results from substitution, replacement or deletion of various organic groups or hydrogen atoms from a parent compound. As such, some monoterpenoids can be considered to be analogs of monoterpenes, or in some cases, analogs of other monoterpenoids, including derivatives of monoterpenes. An analog is structurally similar to the parent compound, but can differ by even a single element of the same valence and group of the periodic table as the element it replaces.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper (1962) *Prog. Drug. Res.* 4:221-294; Morozowich et al (1977) *Design of Biopharmaceutical Properties through Prodrugs and Analogs* 40; Roche (1987) *Bioreversible Carriers in Drug in Drug Design, Theory and Application*; Bundgaard (1985) *Design of Prodrugs*; Wang et al. (1999) *Curr. Pharm. Design.* 5:265-287; Pauletti et al. (1997) *Adv. Drug. Delivery Rev.* 27:235-256; Mizen et al. (1998) *Pharm. Biotech. ll:* 345-365; Gaignault et al. (1996) *Pract. Med. Chem.* 671-696; Asgharnejad (2000) *Transport Processes in Pharmaceutical Systems* 185-218; Balant et al. (1990) *Eur. J. Drug Metab. Pharmacokinet.* 15:143-53; Balimane and Sinko (1999) *Adv. Drug Delivery Rev.* 39:183-209; Browne (1997) *Clin. Neuropharmacol.* 20: 1-12; Bundgaard (1979) *Arch. Pharm. Chemi* 86:1-39; Bundgaard (1987) *Controlled Drug Delivery* 17:179-196; Bundgaard (1992) Arfv. *Drug Delivery Rev.* 8:1-38; Fleisher et al. (1996) *Arfv. Drug Delivery Rev.* 19:115-130; Fleisher et al. (1985) *Methods Enzymol.* 112:360-381; Farquhar et al. (1983) *Pharm. Sci.,* 72: 324-325; Freeman et al. (1991) *Chem. Soc., Chem. Commun.,* 875-877; Friis and Bundgaard (1996) *Eur. J. Pharm. Sci.* 4:49-59; Gangwar et al. (1977) *Des. Biopharm. Prop. Prodrugs Analogs,* [*Symp.*] Meeting Date 1976, 409-421; Nathwani and Wood (1993) *Drugs* 45:866-894; Sinhababu and Thakker (1996) *Adv. Drug Delivery Rev.* 19:241-273; Stella et al. (1985) *Drugs* 29:455-473; Tan et al. (1999) *Adv. Drug Delivery Rev.* 39:117-151; Taylor (1996) *Adv. Drug Delivery Rev.* 19:131-148; Valentino and Borchardt (1997) *Drug Discovery Today* 2:148-155; Wiebe and Knaus (1999) *Adv. Drug Delivery Rev.:* 39:63-80; Waller et al. (1989) *Br. J. Clin. Pharmac.* 28:497-507, content of all of which is herein incorporated by reference in its entirety.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers encompassed by the present invention (e.g., biomarkers listed in Table 1) are well known in the art and readily available on publicly available databases, such as the National Center for Biotechnology Information (NCBI). For example, exemplary nucleic acid and amino acid sequences derived from publicly available sequence databases are provided below. It is to be noted that the terms described above can further be used to refer to any combination of features described herein regarding the biomarkers. For example, any combination of sequence composition, percentage identify, sequence length, domain structure, functional activity, etc. can be used to describe a biomarker encompassed by the present invention.

TABLE 1A

| Inhibiting mutations of KEAP1, including loss-of-function mutations of KEAP1 NQO1 NRF2 |
|---|
| SEQ ID NO: 1 *Homo sapiens* NQO1 cDNA, transcript variant 1 (NM_000903.2; CDS: 192-1016) |
| 1 ccgcccttgt aggctgtcca cctcaaacgg gccggacagg atatataaga gagaatgcac |
| 61 cgtgcactac acacgcgact cccacaaggt tgcagccgga gccgcccagc tcaccgagag |
| 121 cctagttccg gccagggtcg ccccggcaac cacgagccca gccaatcagc gccccggact |
| 181 gcaccagagc catggtcggc agaagagcac tgatcgtact ggctcactca gagaggacgt |
| 241 ccttcaacta tgccatgaag gaggctgctg cagcggcttt gaagaagaaa ggatgggagg |
| 301 tggtggagtc ggacctctat gccatgaact tcaatcccat catttccaga aaggacatca |
| 361 caggtaaact gaaggaccct gcgaactttc agtatcctgc cgagtctgtt ctggcttata |
| 421 aagaaggcca tctgagccca gatattgtgg ctgaacaaaa gaagctggaa gccgcagacc |
| 481 ttgtgatatt ccagttcccc ctgcagtggt ttggagtccc tgccattctg aaaggctggt |
| 541 ttgagcgagt gttcatagga gagtttgctt acacttacgc tgccatgtat gacaaaggac |
| 601 ccttccggag taagaaggca gtgctttcca tcaccactgg tggcagtggc tccatgtact |
| 661 ctctgcaagg gatccacggg gacatgaatg tcattctctg gccaattcag agtggcattc |
| 721 tgcatttctg tggcttccaa gtcttagaac ctcaactgac atatagcatt gggcacactc |
| 781 cagcagacgc ccgaattcaa atcctggaag gatggaagaa acgcctggag aatatttggg |
| 841 atgagacacc actgtatttt gctccaagca gcctctttga cctaaacttc caggcaggat |
| 901 tcttaatgaa aaaagaggta caggatgagg agaaaaacaa gaaatttggc ctttctgtgg |
| 961 gccatcactt gggcaagtcc atcccaactg acaaccagat caaagctaga aaatgagatt |
| 1021 ccttagcctg gatttccttc taacatgtta tcaaatctgg gtatctttcc aggcttccct |
| 1081 gacttgcttt agtttttaag atttgtgttt ttcttttttcc acaaggaata aatgagaggg |
| 1141 aatcgactgt attcgtgcat tttggatca tttttaactg attcttatga ttactatcat |
| 1201 ggcatataac caaaatccga ctgggctcaa gaggccactt agggaaagat gtagaaagat |
| 1261 gctagaaaaa tgttctttaa aggcatctac acaatttaat tcctcttttt agggctaaag |
| 1321 ttttagggta cagtttggct aggtatcatt caactctcca atgttctatt aatcacctct |
| 1381 ctgtagttta tggcagaagg gaattgctca gagaaggaaa agactgaatc tacctgccct |
| 1441 aagggactta acttgtttgg tagttagcca tctaatgctt gtttatgata tttcttgctt |
| 1501 tcaattacaa agcagttact aatatgccta gcacaagtac cactcttggt cagcttttgt |
| 1561 tgtttatata cagtacacag ataccttgaa aggaagagct aataaatctc ttctttgctg |
| 1621 cagtcatcta cttttttttt aattaaaaaa aatttttttt tgaagcagtc ttgctctgtt |
| 1681 acccaggctg gagtgcagtg gtgtgatctc ggctcactgc aacctctgcc tcccaggttc |
| 1741 cagcaattct cctgcctcag cctccctagt agctgggatg acaggcgcct gccatcatgc |
| 1801 ctgactaatt tttgtatttt tagtagagac ggcgtttcac catgttggcc aggctggtct |
| 1861 caaactcctg acctcaggtg atccgcctac ctcagcctcc caaagtgctg ggattacagg |
| 1921 cgtgatccac cacacctggc ccttgcaatc ttctacttta aggtttgcag agataaacca |
| 1981 ataaatccac accgtacatc tgcaatatga attcaagaaa ggaaatagta ccttcaatac |
| 2041 ttaaaaatag tcttccacaa aaaatacttt atttctgatc tatacaaatt ttcagaaggt |
| 2101 tattttcttt atcattgcta aactgatgac ttactatggg atggggtcca gtcccatgac |
| 2161 cttggggtac aattgtaaac ctagagtttt atcaactttg gtgaacagtt ttggcataat |
| 2221 agtcaatttc tacttctgga agtcatctca ttccactgtt ggtattatat aattcaagga |
| 2281 gaatatgata aaacactgcc ctcttgtggt gcattgaaag aagagatgag aaatgatgaa |
| 2341 aaggttgcct gaaaaatggg agacagcctc ttacttgcca agaaaatgaa gggattggac |
| 2401 cgagctggaa aacctccttt accagatgct gactggcact ggtggttttt gctctcgaca |
| 2461 gtatccacaa tagctgacgg ctgggtgttt cagtttgaaa atattttgtt gccttcatct |
| 2521 tcactgcaat tttgtgtaaa tttctcaaag atctgaatta aataaataaa attcatttct |
| 2581 acagacccac aaaaaaaaaa a |
| SEQ ID NO: 2 *Homo sapiens* NQO1 cDNA, transcript variant 2 (NM_001025433.1; CDS: 192-914) |
| 1 ccgcccttgt aggctgtcca cctcaaacgg gccggacagg atatataaga gagaatgcac |
| 61 cgtgcactac acacgcgact cccacaaggt tgcagccgga gccgcccagc tcaccgagag |
| 121 cctagttccg gccagggtcg ccccggcaac cacgagccca gccaatcagc gccccggact |
| 181 gcaccagagc catggtcggc agaagagcac tgatcgtact ggctcactca gagaggacgt |
| 241 ccttcaacta tgccatgaag gaggctgctg cagcggcttt gaagaagaaa ggatgggagg |
| 301 tggtggagtc ggacctctat gccatgaact tcaatcccat catttccaga aaggacatca |
| 361 caggtaaact gaaggaccct gcgaactttc agtatcctgc cgagtctgtt ctggcttata |
| 421 aagaaggcca tctgagccca gatattgtgg ctgaacaaaa gaagctggaa gccgcagacc |
| 481 ttgtgatatt ccagttcccc ctgcagtggt ttggagtccc tgccattctg aaaggctggt |
| 541 ttgagcgagt gttcatagga gagtttgctt acacttacgc tgccatgtat gacaaaggac |
| 601 ccttccggag tggcattctg catttctgtg gcttccaagt cttagaacct caactgacat |
| 661 atagcattgg gcacactcca gcagacgccc gaattcaaat cctggaagga tggaagaaac |
| 721 gcctggagaa tatttgggat gagacaccac tgtattttgc tccaagcagc ctctttgacc |
| 781 taaacttcca ggcaggattc ttaatgaaaa aagaggtaca ggatgaggag aaaaacaaga |
| 841 aatttggcct ttctgtgggc catcacttgg gcaagtccat cccaactgac aaccagatca |
| 901 aagctagaaa atgagattcc ttagcctgga tttccttcta acatgttatc aaatctgggt |
| 961 atctttccag gcttccctga cttgctttag tttttaagat ttgtgttttt ctttttccac |
| 1021 aaggaataaa tgagagggaa tcgactgtat tcgtgcattt ttggatcatt tttaactgat |
| 1081 tcttatgatt actatcatgg catataacca aaatccgact gggctcaaga ggccacttag |
| 1141 ggaaagatgt agaaagatgc tagaaaaatg ttctttaaag gcatctacac aatttaattc |
| 1201 ctctttttag ggctaaagtt ttagggtaca gtttggctag gtatcattca actctccaat |
| 1261 gttctattaa tcacctctct gtagtttatg gcagaaggga attgctcaga gaaggaaaag |
| 1321 actgaatcta cctgccctaa gggacttaac ttgtttggta gttagccatc taatgcttgt |
| 1381 ttatgatatt tcttgctttc aattacaaag cagttactaa tatgcctagc acaagtacca |
| 1441 ctcttggtca gcttttgttg tttatataca gtacacagat accttgaaag gaagagctaa |
| 1501 taaatctctt ctttgctgca gtcatctact ttttttttaa ttaaaaaaaa tttttttttg |
| 1561 aagcagtctt gctctgttac ccaggctgga gtgcagtggt gtgatctcgg ctcactgcaa |
| 1621 cctctgcctc ccaggttcca gcaattctcc tgcctcagcc tccctagtag ctgggatgac |

TABLE 1A -continued

Inhibiting mutations of KEAP1, including loss-of-function mutations of KEAP1 NQO1 NRF2

```
1681 aggcgcctgc catcatgcct gactaatttt tgtattttta gtagagacgg cgtttcacca
1741 tgttggccag gctggtctca aactcctgac ctcaggtgat ccgcctacct cagcctccca
1801 aagtgctggg attacaggcg tgatccacca cacctggccc ttgcaatctt ctactttaag
1861 gtttgcagag ataaaccaat aaatccacac cgtacatctg caatatgaat tcaagaaagg
1921 aaatagtacc ttcaatactt aaaaatagtc ttccacaaaa aatactttat ttctgatcta
1981 tacaaatttt cagaaggtta ttttctttat cattgctaaa ctgatgactt actatgggat
2041 ggggtccagt cccatgacct tggggtacaa ttgtaaacct agagttttat caactttggt
2101 gaacagtttt ggcataatag tcaatttcta cttctggaag tcatctcatt ccactgttgg
2161 tattatataa ttcaaggaga atatgataaa acactgccct cttgtggtgc attgaaagaa
2221 gagatgagaa atgatgaaaa ggttgcctga aaaatgggag acagcctctt acttgccaag
2281 aaaatgaagg gattggaccg agctggaaaa cctcctttac cagatgctga ctggcactgg
2341 tggtttttgc tctcgacagt atccacaata gctgacggct gggtgtttca gtttgaaaat
2401 attttgttgc cttcatcttc actgcaattt tgtgtaaatt tctcaaagat ctgaattaaa
2461 taaataaaat tcatttctac agacccacaa aaaaaaaaa
```

SEQ ID NO: 3 *Homo sapiens* P01901 cDNA, transcript variant 3
(NM_001025434.1; CDS:192-902)

```
   1 ccgcccttgt aggctgtcca cctcaaacgg gccggacagg atatataaga gagaatgcac
  61 cgtgcactac acacgcgact cccacaaggt tgcagccgga gccgcccagc tcaccgagag
 121 cctagttccg gccagggtcg ccccggcaac cacgagccca gccaatcagc gccccggact
 181 gcaccagagc catggtcggc agaagagcac tgatcgtact ggctcactca gagaggacgt
 241 ccttcaacta tgccatgaag gaggctgctg cagcggcttt gaagaagaaa ggatgggagg
 301 tggtggagtc ggacctctat gccatgaact tcaatcccat catttccaga aaggacatca
 361 caggtaaact gaaggaccct gcgaactttc agtatcctgc cgagtctgtt ctggcttata
 421 aagaaggcca tctgagccca gatattgtgg ctgaacaaaa gaagctggaa gccgcagacc
 481 ttgtgatatt ccagagtaag aaggcagtgc tttccatcac cactggtggc agtggctcca
 541 tgtactctct gcaagggatc cacggggaca tgaatgtcat tctctggcca attcagagtg
 601 gcattctgca tttctgtggc ttccaagtct tagaacctca actgacatat agcattgggc
 661 acactccagc agacgcccga attcaaatcc tggaaggatg gaagaaacgc ctggagaata
 721 tttgggatga gacaccactg tattttgctc caagcagcct ctttgaccta aacttccagg
 781 caggattctt aatgaaaaaa gaggtacagg atgaggagaa aaacaagaaa tttggccttt
 841 ctgtgggcca tcacttgggc aagtccatcc caactgacaa ccagatcaaa gctagaaaat
 901 gagattcctt agcctggatt tccttctaac atgttatcaa atctgggtat ctttccaggc
 961 ttccctgact tgctttagtt tttaagattt gtgtttttct ttttccacaa ggaataaatg
1021 agagggaatc gactgtattc gtgcattttt ggatcatttt taactgattc ttatgattac
1081 tatcatggca tataaccaaa atccgactgg gctcaagagg ccacttaggg aaagatgtag
1141 aaagatgcta gaaaaatgtt ctttaaaggc atctacacaa tttaattcct ctttttaggg
1201 ctaaagtttt agggtacagt ttggctaggt atcattcaac tctccaatgt tctattaatc
1261 acctctctgt agtttatggc agaagggaat tgctcagaga aggaaaagac tgaatctacc
1321 tgccctaagg gacttaactt gtttggtagt tagccatcta atgcttgttt atgatatttc
1381 ttgctttcaa ttacaaagca gttactaata tgcctagcac aagtaccact cttggtcagc
1441 ttttgttgtt tatatacagt acacagatac cttgaaagga agagctaata aatctcttct
1501 ttgctgcagt catctacttt ttttttaatt aaaaaaaatt ttttttgaa gcagtcttgc
1561 tctgttaccc aggctggagt gcagtggtgt gatctcggct cactgcaacc tctgcctccc
1621 aggttccagc aattctcctg cctcagcctc cctagtagct gggatgacag gcgcctgcca
1681 tcatgcctga ctaatttttg tatttttagt agagacggcg tttcaccatg ttggccaggc
1741 tggtctcaaa ctcctgacct caggtgatcc gcctacctca gcctcccaaa gtgctgggat
1801 tacaggcgtg atccaccaca cctggccctt gcaatcttct actttaaggt ttgcagagat
1861 aaaccaataa atccacaccg tacatctgca atatgaattc aagaaaggaa atagtacctt
1921 caatacttaa aaatagtctt ccacaaaaaa tactttattt ctgatctata caaattttca
1981 gaaggttatt ttctttatca ttgctaaact gatgacttac tatgggatgg ggtccagtcc
2041 catgaccttg gggtacaatt gtaaacctag agttttatca actttggtga acagttttgg
2101 cataatagtc aatttctact tctggaagtc atctcattcc actgttggta ttatataatt
2161 caaggagaat atgataaaac actgccctct tgtggtgcat tgaaagaaga gatgagaaat
2221 gatgaaaagg ttgcctgaaa aatgggagac agcctcttac ttgccaagaa aatgaaggga
2281 ttggaccgag ctggaaaacc tcctttacca gatgctgact ggcactggtg gtttttgctc
2341 tcgacagtat ccacaatagc tgacggctgg gtgtttcagt ttgaaaatat tttgttgcct
2401 tcatcttcac tgcaattttg tgtaaatttc tcaaagatct gaattaaata aataaaattc
2461 atttctacag acccacaaaa aaaaaaa
```

SEQ ID NO: 4 *Homo sapiens* NO01 cDNA, transcript variant 4
(NM_001286137.1; CDS: 230-838)

```
   1 atcctccgcc cagcacccca ggattcaggc gttgggtccc gcccttgtag gctgtccacc
  61 tcaaacgggc cggacaggat atataagaga gaatgcaccg tgcactacac acgcgactcc
 121 cacaaggttg cagccggagc cgcccagctc accgagagcc tagttccggc cagggtcgcc
 181 ccggcaacca cgagcccagc caatcagcgc cccggactgc accagagcca tggtcggcag
 241 aagagcactg atcgtactgg ctcactcaga gaggacgtcc ttcaactatg ccatgaagga
 301 ggctgctgca gcggctttga agaagaaagg atgggaggtg gtggagtcgg acctctatgc
 361 catgaacttc aatcccatca tttccagaaa ggacatcaca ggtaaactga aggaccctgc
 421 gaactttcag tatcctgccg agtctgttct ggcttataaa gaaggccatc tgagcccaga
 481 tattgtggct gaacaaaaga agctggaagc cgcagacctt gtgatattcc agagtggcat
 541 tctgcatttc tgtggcttcc aagtcttaga acctcaactg acatatagca ttgggcacac
 601 tccagcagac gcccgaattc aaatcctgga aggatggaag aaacgcctgg agaatatttg
 661 ggatgagaca ccactgtatt ttgctccaag cagcctcttt gacctaaact tccaggcagg
 721 attcttaatg aaaaaagagg tacaggatga ggagaaaaac aagaaatttg gcctttctgt
 781 gggccatcac ttgggcaagt ccatcccaac tgacaaccag atcaaagcta gaaaatgaga
 841 ttccttagcc tggatttcct tctaacatgt tatcaaatct gggtatcttt ccaggcttcc
```

TABLE 1A -continued

Inhibiting mutations of KEAP1, including loss-of-function mutations of KEAP1 NQO1 NRF2

901 ctgacttgct ttagttttta agatttgtgt ttttcttttt ccacaaggaa taaatgagag
961 ggaatcgact gtattcgtgc atttttggat catttttaac tgattcttat gattactatc
1021 atggcatata accaaaatcc gactgggctc aagaggccac ttagggaaag atgtagaaag
1081 atgctagaaa aatgttcttt aaaggcatct acacaattta attcctcttt ttagggctaa
1141 agttttaggg tacagtttgg ctaggtatca ttcaactctc caatgttcta ttaatcacct
1201 ctctgtagtt tatggcagaa gggaattgct cagagaagga aaagactgaa tctacctgcc
1261 ctaagggact taacttgttt ggtagttagc catctaatgc ttgtttatga tatttcttgc
1321 tttcaattac aaagcagtta ctaatatgcc tagcacaagt accactcttg gtcagctttt
1381 gttgtttata tacagtacac agataccttg aaaggaagag ctaataaatc tcttctttgc
1441 tgcagtcatc tacttttttt ttaattaaaa aaaatttttt tttgaagcag tcttgctctg
1501 ttacccaggc tggagtgcag tggtgtgatc tcggctcact gcaacctctg cctcccaggt
1561 tccagcaatt ctcctgcctc agcctcccta gtagctggga tgacaggcgc ctgccatcat
1621 gcctgactaa tttttgtatt tttagtagag acggcgtttc accatgttgg ccaggctggt
1681 ctcaaactcc tgacctcagg tgatccgcct acctcagcct cccaaagtgc tgggattaca
1741 ggcgtgatcc accacacctg gcccttgcaa tcttctactt taaggtttgc agagataaac
1801 caataaatcc acaccgtaca tctgcaatat gaattcaaga aaggaaatag taccttcaat
1861 acttaaaaat agtcttccac aaaaaatact ttatttctga tctatacaaa ttttcagaag
1921 gttattttct ttatcattgc taaactgatg acttactatg ggatggggtc cagtcccatg
1981 accttggggt acaattgtaa acctagagtt ttatcaactt tggtgaacag ttttggcata
2041 atagtcaatt tctacttctg gaagtcatct cattccactg ttggtattat ataattcaag
2101 gagaatatga taaaacactg ccctcttgtg gtgcattgaa agaagagatg agaaatgatg
2161 aaaaggttgc ctgaaaaatg ggagacagcc tcttacttgc caagaaaatg aagggattgg
2221 accgagctgg aaaacctcct ttaccagatg ctgactggca ctggtggttt ttgctctcga
2281 cagtatccac aatagctgac ggctgggtgt ttcagtttga aaatattttg ttgccttcat
2341 cttcactgca attttgtgta aatttctcaa agatctgaat taaataaata aaattcattt
2401 ctacagaccc acaaaaaaaa aaa SEQ ID NO: 5 *Homo sapiens* NQO1 amino acid sequence, isoform 1
(NP_000894.1)
1 mvgrralivl ahsertsfny amkeaaaaal kkkgwevves dlyamnfnpi isrkditgkl
61 kdpanfqypa esvlaykegh lspdivaeqk kleaadlvif qfplqwfgvp ailkgwfery
121 figefaytya amydkgpfrs kkavlsittg gsgsmyslqg ihgdmnvilw pigsgilhfc
181 gfqvlepqlt ysightpada riqilegwkk rlenlwdetp lyfapsslfd lnfgagflmk
241 kevqdeeknk kfglsvghhl gksiptdnqi kark SEQ ID NO: 6 *Homo sapiens* NQO1 amino acid sequence, isoform 2
(NP_001020604.1)
1 mvgrralivl ahsertsfny amkeaaaaal kkkgwevves dlyamnfnpi isrkditgkl
61 kdpanfqypa esvlaykegh lspdivaeqk kleaadlvif qfplqwfgvp ailkgwfery
121 figefaytya amydkgpfrs gilhfcgfqv lepqltysig htpadarigi legwkkrlen
181 iwdetplyfa psslfdlnfq agflmkkevq deeknkkfgl svghhlgksi ptdnqikark SEQ ID NO: 7 *Homo sapiens* NQO1 amino acid sequence, isoform 3
(NP_001020605.1)
1 mvgrralivl ahsertsfny amkeaaaaal kkkgwevves dlyamnfnpi isrkditgkl
61 kdpanfqypa esvlaykegh lspdivaeqk kleaadlvif gskkavlsit tggsgsmysl
121 ggihgdmnvi lwpiqsgilh fcgfqvlepq ltysightpa darigilegw kkrlenlwde
181 tplyfapssl fdlnfgagfl mkkevqdeek nkkfglsvgh hlgksiptdn qikark SEQ ID NO: 8 *Homo sapiens* NQO1 amino acid sequence, isoform 4
(NP_001273066.1)
1 mvgrralivl ahsertsfny amkeaaaaal kkkgwevves dlyamnfnpi isrkditgkl
61 kdpanfqypa esvlaykegh lspdivaeqk kleaadlvif qsgilhfcgf qvlepqltys
121 ightpadari qllegwkkrl enlwdetply fapsslfdln fgagflmkke vqdeeknkkf
181 glsvghhlgk siptdnqika rk SEQ ID NO: 9 *Mus musculus* NQO1 cDNA (NM_008706.5; CDS: 134-958)
1 aggctcagct cttactagcc tagcctgtag ccagccctaa ggatctctcc gaagagcttt
61 agggtcgtct tggcaaccag ctgctcagcc aatcagcgtt cggtattacg atcctccctc
121 aacatctgga gccatggcgg cgagaagagc cctgattgta ctggcccatt cagagaagac
181 atcattcaac tacgccatga aggaggctgc tgtagaggct ctgaagaaga gaggatggga
241 ggtactcgaa tctgacctct atgctatgaa cttcaacccc atcatttcca gaaatgacat
301 cacaggtgag ctgaaggact cgaagaactt tcagtatcct tccgagtcat ctctagcata
361 taaggaagga cgcctgagcc cagatattgt ggccgaacac aagaagctgg aagctgcaga
421 cctggtgata tttcagttcc cattgcagtg gtttggggtg ccagccattc tgaaaggctg
481 gtttgagaga gtgctcgtag caggatttgc ctacacatat gctgccatgt acgacaacgg
541 tcctttccag aataagaaga ccttgctttc tatcaccact gggggtagcg gctccatgta
601 ctctcttcag ggtgtccacg gggacatgaa cgtcattctc tggccgattc agagtggcat
661 cctgcgtttc tgtggcttcc aggtcttaga acctcaactg gtttacagca ttggccacac
721 tccaccagat gcccgcatgc agatcctgga aggatggaag aaacgtctgg aaaccgtctg
781 ggaggagacc ccactctatt ttgctccaag cagcctgttt gacctaaact ttcaggcagg
841 attcttaatg aaaaaggaag ttcaagagga gcagaagaag aacaagtttg gcctctctgt
901 gggccatcac ctgggcaagt ccattccagc tgacaaccag atcaaagcta gaaaataagg
961 attttttcc taacatatag ttagacgcag ctttcttttt ccccagcttg tctgacttgc
1021 tttcattttt ttcctttgct ccacgaggat gggaaaagga gtaagtttgc ttcatgcttt
1081 tttttttttt ttgatagttc tgccataaca acaaaatgaa tgaagtcaga ttaggagcct
1141 cagggcaagg tgcagaagcg agctggaaat actcttctag gtcatttatg caatattcgc TABLE 1A -continued

| Inhibiting mutations of KEAP1, including loss-of-function mutations of KEAP1 NQO1 NRF2 |
|---|
| 1201 cattttcttc ggctagtcc cagttagatg gcatccagtc ctccatcaag attcgttgtc |
| 1261 tataattacc tctctgtggt ttagggcaga agggaattgc tcaaagtaaa caatggccga |
| 1321 gggactaact tgtttagcag ttagcagtta gctaaagcct gtttatgata catcctggtt |
| 1381 tcaattactg tgcagtgact gacatggcgc ccagggggtt ggctctccag ctcttttctg |
| 1441 tcttgtacac agcacaccca ggtcctggga aaggaatttt aaaacagatc tccgtctcat |
| 1501 tctttctatt tcttttttt tttaatcgaa ataaatgaat acatcacaca to |
| |
| SEQ ID NO: 10 *Mus musculus* NQO1 amino acid sequence (NP_032732.3) |
| 1 maarralivl ahsektsfny amkeaaveal kkrgwevles dlyamnfnpl isrnditgel |
| 61 kdsknfqyps esslaykegr lspdivaehk kleaadlvif qfplqwfgvp ailkgwfery |
| 121 lvagfaytya amydngpfqn kktllsittg gsgsmyslqg vhgdmnvilw pigsgilrfc |
| 181 gfqvlepqlv ysightppda rmqilegwkk rletvweetp lyfapsslfd lnfgagflmk |
| 241 kevqeeqkkn kfglsvghhl gksipadnqi kark |
| |
| SEQ ID NO: 11 *Homo sapiens* NRF2 cDNA, transcript variant 1 (NM_006164.4; CDS:556-2373) |
| 1 aaatcaggga ggcgcagctc ctacaccaac gcctttccgg ggctccgggt gtgtttgttc |
| 61 caactgttta aactgtttca aagcgtccga actccagcga ccttcgcaaa caactcttta |
| 121 tctcgcgggc gagagcgctg cccttatttg cgggggaggg caaactgaac gccggcaccg |
| 181 gggagctaac ggagacctcc tctaggtccc ccgcctgctg ggaccccagc tggcagtccc |
| 241 ttcccgcccc cggaccgcga gcttcttgcg tcagccccgg cgcgggtggg ggattttcgg |
| 301 aagctcagcc cgcgcggccg gcgggggaag gaagggcccg gactcttgcc ccgcccttgt |
| 361 ggggcgggag gcggagcggg gcaggggccc gccggcgtgt agccgattac cgagtgccgg |
| 421 ggagcccgga ggagccgccg acgcagccgc caccgccgcc gccgccgcca ccagagccgc |
| 481 cctgtccgcg ccgcgcctcg gcagccggaa cagggccgcc gtcggggagc cccaacacac |
| 541 ggtccacagc tcatcatgat ggacttggag ctgccgccgc cgggactccc gtcccagcag |
| 601 gacatggatt tgattgacat actttggagg caagatatag atcttggagt aagtcgagaa |
| 661 gtatttgact tcagtcagcg acggaaagag tatgagctgg aaaaacagaa aaaacttgaa |
| 721 aaggaaagac aagaacaact ccaaaaggag caagagaaag ccttttttcgc tcagttacaa |
| 781 ctagatgaag agacaggtga atttctccca attcagccag cccagcacat ccagtcagaa |
| 841 accagtggat ctgccaacta ctcccaggtt gcccacattc ccaaatcaga tgctttgtac |
| 901 tttgatgact gcatgcagct tttggcgcag acattcccgt ttgtagatga caatgaggtt |
| 961 tcttcggcta cgtttcagtc acttgttcct gatattcccg gtcacatcga gagcccagtc |
| 1021 ttcattgcta ctaatcaggc tcagtcacct gaaacttctg ttgctcaggt agcccctgtt |
| 1081 gatttagacg gtatgcaaca ggacattgag caagtttggg aggagctatt atccattcct |
| 1141 gagttacagt gtcttaatat tgaaaatgac aagctggttg agactaccat ggttccaagt |
| 1201 ccagaagcca aactgacaga agttgacaat tatcattttt actcatctat accctcaatg |
| 1261 gaaaaagaag taggtaactg tagtccacat tttcttaatg cttttgagga ttccttcagc |
| 1321 agcatcctct ccacagaaga ccccaaccag ttgacagtga actcattaaa ttcagatgcc |
| 1381 acagtcaaca cagattttgg tgatgaattt tattctgctt tcatagctga gcccagtatc |
| 1441 agcaacagca tgccctcacc tgctacttta agccattcac tctctgaact tctaaatggg |
| 1501 cccattgatg tttctgatct atcactttgc aaagctttca accaaaacca ccctgaaagc |
| 1561 acagcagaat tcaatgattc tgactccggc atttcactaa acacaagtcc cagtgtggca |
| 1621 tcaccagaac actcagtgga atcttccagc tatggagaca cactacttgg cctcagtgat |
| 1681 tctgaagtgg aagagctaga tagtgcccct ggaagtgtca aacagaatgg tcctaaaaca |
| 1741 ccagtacatt cttctgggga tatggtacaa cccttgtcac catctcaggg gcagagcact |
| 1801 cacgtgcatg atgcccaatg tgagaacaca ccagagaaag aattgcctgt aagtcctggt |
| 1861 catcggaaaa ccccattcac aaaagacaaa cattcaagcc gcttggaggc tcatctcaca |
| 1921 agagatgaac ttagggcaaa agctctccat atcccattcc ctgtagaaaa aatcattaac |
| 1981 ctccctgttg ttgacttcaa cgaaatgatg tccaaagagc agttcaatga agctcaactt |
| 2041 gcattaattc gggatatacg taggaggggt aagaataaag tggctgctca gaattgcaga |
| 2101 aaaagaaaac tggaaaatat agtagaacta gagcaagatt tagatcattt gaaagatgaa |
| 2161 aaagaaaaat tgctcaaaga aaaaggagaa aatgacaaaa gccttcacct actgaaaaaa |
| 2221 caactcagca ccttatatct cgaagttttc agcatgctac gtgatgaaga tggaaaacct |
| 2281 tattctccta gtgaatactc cctgcagcaa acaagagatg gcaatgtttt ccttgttccc |
| 2341 aaaagtaaga agccagatgt taagaaaaac tagatttagg aggatttgac cttttctgag |
| 2401 ctagtttttt tgtactatta tactaaaagc tcctactgtg atgtgaaatg ctcatacttt |
| 2461 ataagtaatt ctatgcaaaa tcatagccaa aactagtata gaaaataata cgaaacttta |
| 2521 aaaagcattg gagtgtcagt atgttgaatc agtagtttca ctttaactgt aaacaatttc |
| 2581 ttaggacacc atttgggcta gtttctgtgt aagtgtaaat actacaaaaa cttatttata |
| 2641 ctgttcttat gtcatttgtt atattcatag atttatatga tgatatgaca tctggctaaa |
| 2701 aagaaattat tgcaaaacta accactatgt actttttttat aaatactgta tggacaaaaa |
| 2761 atggcatttt ttatattaaa ttgtttagct ctggcaaaaa aaaaaaattt taagagctgg |
| 2821 tactaataaa ggattattat gactgttaaa ttattaaaa |
| |
| SEQ ID NO: 12 *Homo sapiens* NRF2 cDNA, transcript variant 2 (NM_001145412.3; CDS:733-2502) |
| 1 ggcccttccg gggctgcgcg gctcccccgc ctcggtgccg gcaaaaatgt gcctagtcac |
| 61 ggggccgctc tcggggggaac tgaggtcgcc ttcgggctgg gacccggagc cccttcgccg |
| 121 cgccccaaga cctccttgag tgcgggctgc gacgcgctca ccccgctggg ccgtctgtgg |
| 181 gcgcggcttt gcgaagtcat ccatctctcg gatcactctc tggcagcctt gagctctctt |
| 241 gaaagcccag ccccgggacg agggaggagc gccttaagtg cccagcgggc tcagaagccc |
| 301 cgacgtgtgg cggctgagcc gggccccgcg cactttctcg gccggggagg ggttcgggct |
| 361 cgggcacccg gagttggccc ctcgtaacgc cgcgggaaag tgcgggcgag ggcagtggac |
| 421 tctgaggccg gagtcggcgg cacccggggc ttctagttcg gacgcggtgc cccctggtgg |
| 481 cgctcaccgc gcgcgtggcc ttggcttccg tgacagcgct cggttggccg tcacagcagc |
| 541 cctcggttgg ccctttcctg ctttatagcg tgcaaacctc gccgcgccag ggccaaggga |

TABLE 1A -continued

Inhibiting mutations of KEAP1, including loss-of-function mutations of KEAP1 NQO1 NRF2

```
 601 caggttggag ctgttgatct gttgcgcaat tgctattttc cccagagcgg ctttgtcttt
 661 ggatttagcg tttcagaatt gcaattccaa aatgtgtaag acgggatatt ctcttctgtg
 721 ctgtcaaggg acatggattt gattgacata ctttggaggc aagatataga tcttggagta
 781 agtcgagaag tatttgactt cagtcagcga cggaaagagt atgagctgga aaaacagaaa
 841 aaacttgaaa aggaaagaca agaacaactc caaaaggagc aagagaaagc ctttttcgct
 901 cagttacaac tagatgaaga gacaggtgaa tttctcccaa ttcagccagc ccagcacatc
 961 cagtcagaaa ccagtggatc tgccaactac tcccaggttg cccacattcc caaatcagat
1021 gctttgtact ttgatgactg catgcagctt ttggcgcaga cattcccgtt tgtagatgac
1081 aatgaggttt cttcggctac gtttcagtca cttgttcctg atattcccgg tcacatcgag
1141 agcccagtct tcattgctac taatcaggct cagtcacctg aaacttctgt tgctcaggta
1201 gcccctgttg atttagacgg tatgcaacag gacattgagc aagtttggga ggagctatta
1261 tccattcctg agttacagtg tcttaatatt gaaaatgaca agctggttga gactaccatg
1321 gttccaagtc cagaagccaa actgacagaa gttgacaatt atcattttta ctcatctata
1381 ccctcaatgg aaaaagaagt aggtaactgt agtccacatt ttcttaatgc ttttgaggat
1441 tccttcagca gcatcctctc cacagaagac cccaaccagt tgacagtgaa ctcattaaat
1501 tcagatgcca cagtcaacac agattttggt gatgaatttt attctgcttt catagctgag
1561 cccagtatca gcaacagcat gccctcacct gctactttaa gccattcact ctctgaactt
1621 ctaaatgggc ccattgatgt ttctgatcta tcactttgca aagctttcaa ccaaaaccac
1681 cctgaaagca cagcagaatt caatgattct gactccggca tttcactaaa cacaagtccc
1741 agtgtggcat caccagaaca ctcagtggaa tcttccagct atggagacac actacttggc
1801 ctcagtgatt ctgaagtgga agagctagat agtgcccctg gaagtgtcaa acagaatggt
1861 cctaaaacac cagtacattc ttctggggat atggtacaac ccttgtcacc atctcagggg
1921 cagagcactc acgtgcatga tgcccaatgt gagaacacac cagagaaaga attgcctgta
1981 agtcctggtc atcggaaaac cccattcaca aaagacaaac attcaagccg cttggaggct
2041 catctcacaa gagatgaact tagggcaaaa gctctcccata tcccattccc tgtagaaaaa
2101 atcattaacc tccctgttgt tgacttcaac gaaatgatgt ccaaagagca gttcaatgaa
2161 gctcaacttg cattaattcg ggatatacgt aggaggggta agaataaagt ggctgctcag
2221 aattgcagaa aaagaaaact ggaaaatata gtagaactag agcaagattt agatcatttg
2281 aaagatgaaa aagaaaaatt gctcaaagaa aaaggagaaa atgacaaaag ccttcaccta
2341 ctgaaaaaac aactcagcac cttatatctc gaagttttca gcatgctacg tgatgaagat
2401 ggaaaacctt attctcctag tgaatactcc ctgcagcaaa caagagatgg caatgttttc
2461 cttgttccca aaagtaagaa gccagatgtt aagaaaaact agatttagga ggatttgacc
2521 ttttctgagc tagttttttt gtactattat actaaaagct cctactgtga tgtgaaatgc
2581 tcatacttta taagtaattc tatgcaaaat catagccaaa actagtatag aaaataatac
2641 gaaactttaa aaagcattgg agtgtcagta tgttgaatca gtagtttcac tttaactgta
2701 aacaatttct taggacacca tttgggctag tttctgtgta agtgtaaata ctacaaaaac
2761 ttatttatac tgttcttatg tcatttgtta tattcataga tttatatgat gatatgacat
2821 ctggctaaaa agaaattatt gcaaaactaa ccactatgta ctttttttata aatactgtat
2881 ggacaaaaaa tggcattttt tatattaaat tgtttagctc tggcaaaaaa aaaaaatttt
2941 aagagctggt actaataaag gattattatg actgttaaat tattaaaa
```

SEQ ID NO: 13 *Homo sapiens* NRF2 cDNA, transcript variant 3 (NM_001145413.3; CDS:733-2481

```
   1 ggcccttccg gggctgcgcg gctcccccgc ctcggtgccg gcaaaaatgt gcctagtcac
  61 ggggccgctc tcgggggaac tgaggtcgcc ttcgggctgg gacccggagc cccttcgccg
 121 cgccccaaga cctccttgag tgcgggctgc gacgcgctca ccccgctggg ccgtctgtgg
 181 gcgcggcttt gcgaagtcat ccatctctcg gatcactctc tggcagcctt gagctctctt
 241 gaaagcccag ccccgggacg agggaggagc gccttaagtg cccagcgggc tcagaagccc
 301 cgacgtgtgg cggctgagcc gggcccccgcg cactttctcg gccggggagg ggttcgggct
 361 cgggcacccg gagttggccc ctcgtaacgc cgcgggaaag tgcgggcgag ggcagtggac
 421 tctgaggccg gagtcggcgg caccccgggc ttctagttcg gacgcggtgc cccctggtgg
 481 cgctcaccgc gcgcgtggcc ttggcttccg tgacagcgct cggttggccg tcacagcagc
 541 cctcggttgg ccctttcctg ctttatagcg tgcaaacctc gccgcgccag ggccaaggga
 601 caggttggag ctgttgatct gttgcgcaat tgctattttc cccagagcgg ctttgtcttt
 661 ggatttagcg tttcagaatt gcaattccaa aatgtgtaag acgggatatt ctcttctgtg
 721 ctgtcaaggg acatggattt gattgacata ctttggaggc aagatataga tcttggagta
 781 agtcgagaag tatttgactt cagtcagcga cggaaagagt atgagctgga aaaacagaaa
 841 aaacttgaaa aggaaagaca agaacaactc caaaaggagc aagagaaagc ctttttcgct
 901 cagttacaac tagatgaaga gacaggtgaa tttctcccaa ttcagccagc ccagcacatc
 961 cagtcagaaa ccagtggatc tgccaactac tcccaggttg cccacattcc caaatcagat
1021 gctttgtact ttgatgactg catgcagctt ttggcgcaga cattcccgtt tgtagatgac
1081 aatgagtcac ttgttcctga tattcccggt cacatcgaga gcccagtctt cattgctact
1141 aatcaggctc agtcacctga aacttctgtt gctcaggtag cccctgttga tttagacggt
1201 atgcaacagg acattgagca agtttgggag gagctattat ccattcctga gttacagtgt
1261 cttaatattg aaaatgacaa gctggttgag actaccatgg ttccaagtcc agaagccaaa
1321 ctgacagaag ttgacaatta tcatttttac tcatctatac cctcaatgga aaaagaagta
1381 ggtaactgta gtccacattt tcttaatgct tttgaggatt ccttcagcag catcctctcc
1441 acagaagacc ccaaccagtt gacagtgaac tcattaaatt cagatgccac agtcaacaca
1501 gattttggtg atgaatttta ttctgctttc atagctgagc ccagtatcag caacagcatg
1561 ccctcacctg ctactttaag ccattcactc tctgaacttc taaatgggcc cattgatgtt
1621 tctgatctat cactttgcaa agctttcaac caaaaccacc ctgaaagcac agcagaattc
1681 aatgattctg actccggcat ttcactaaac acaagtccca gtgtggcatc accagaacac
1741 tcagtggaat cttccagcta tggagacaca ctacttggcc tcagtgattc tgaagtggaa
1801 gagctagata gtgcccctgg aagtgtcaaa cagaatggtc ctaaaacacc agtacattct
1861 tctggggata tggtacaacc cttgtcacca tctcaggggc agagcactca cgtgcatgat
1921 gcccaatgtg agaacacacc agagaaagaa ttgcctgtaa gtcctggtca tcggaaaacc
1981 ccattcacaa aagacaaaca ttcaagccgc ttggaggctc atctcacaag agatgaactt
```

TABLE 1A -continued

Inhibiting mutations of KEAP1, including loss-of-function mutations of KEAP1 NQO1 NRF2

2041 agggcaaaag ctctccatat cccattccct gtagaaaaaa tcattaacct ccctgttgtt
2101 gacttcaacg aaatgatgtc caaagagcag ttcaatgaag ctcaacttgc attaattcgg
2161 gatatacgta ggaggggtaa gaataaagtg gctgctcaga attgcagaaa aagaaaactg
2221 gaaaatatag tagaactaga gcaagattta gatcatttga aagatgaaaa agaaaaattg
2281 ctcaaagaaa aaggagaaaa tgacaaaagc cttcacctac tgaaaaaaca actcagcacc
2341 ttatatctcg aagttttcag catgctacgt gatgaagatg gaaaacctta ttctcctagt
2401 gaatactccc tgcagcaaac aagagatggc aatgttttcc ttgttcccaa aagtaagaag
2461 ccagatgtta agaaaaacta gatttaggag gatttgacct tttctgagct agtttttttg
2521 tactattata ctaaaagctc ctactgtgat gtgaaatgct catactttat aagtaattct
2581 atgcaaaatc atagccaaaa ctagtataga aaataatacg aaactttaaa aagcattgga
2641 gtgtcagtat gttgaatcag tagtttcact ttaactgtaa acaatttctt aggacaccat
2701 ttgggctagt ttctgtgtaa gtgtaaatac tacaaaaact tatttatact gttcttatgt
2761 catttgttat attcatagat ttatatgatg atatgacatc tggctaaaaa gaaattattg
2821 caaaactaac cactatgtac tttttttataa atactgtatg gacaaaaaat ggcatttttt
2881 atattaaatt gtttagctct ggcaaaaaaa aaaaatttta agagctggta ctaataaagg
2941 attattatga ctgttaaatt attaaaa SEQ ID NO: 14 *Homo sapiens* NRF2 cDNA, transcript variant 4 (NM_001313900.1; CDS:607-2376)

1 ggcccttccg ggctgcgcg gctcccccgc ctcggtgccg gcaaaaatgt gcctagtcac
61 ggggccgctc tcgggggaac tgaggtcgcc ttcgggctgg gacccggagc cccttcgccg
121 cgccccaaga cctccttgag tgcgggctgc gacgcgctca ccccgctggg ccgtctgtgg
181 gcgcggcttt gcgaagtcat ccatctctcg gatcactctc tggcagcctt gagctctctt
241 gaaagcccag ccccgggacg agggaggagc gccttaagtg cccagcgggc tcagaagccc
301 cgacgtgtgg cggctgagcc gggccccgcg cactttctcg gccggggagg ggttcgggct
361 cgggcacccg gagttggccc ctcgtaacgc cgcgggaaag tgcgggcgag ggcagtggac
421 tctgaggccg gagtcggcgg cacccggggc ttctagttcg gacgcggtgc cccctggtgg
481 cgctcaccgc gcgcgtggcc ttggcttccg tgacagcgct cggttggccg tcacagcagc
541 cctcggttgg ccctttcctg ctttatagcg tgcaaacctc gccgcgccag ggccaaggga
601 caggacatgg atttgattga catactttgg aggcaagata tagatcttgg agtaagtcga
661 gaagtatttg acttcagtca gcgacggaaa gagtatgagc tggaaaaaca gaaaaaactt
721 gaaaaggaaa gacaagaaca actccaaaag gagcaagaga aagccttttt cgctcagtta
781 caactagatg aagagacagg tgaatttctc ccaattcagc cagcccagca catccagtca
841 gaaaccagtg gatctgccaa ctactcccag gttgcccaca ttcccaaatc agatgctttg
901 tactttgatg actgcatgca gcttttggcg cagacattcc cgtttgtaga tgacaatgag
961 gtttcttcgg ctacgtttca gtcacttgtt cctgatattc ccggtcacat cgagagccca
1021 gtcttcattg ctactaatca ggctcagtca cctgaaactt ctgttgctca ggtagcccct
1081 gttgatttag acggtatgca acaggacatt gagcaagttt gggaggagct attatccatt
1141 cctgagttac agtgtcttaa tattgaaaat gacaagctgg ttgagactac catggttcca
1201 agtccagaag ccaaactgac agaagttgac aattatcatt tttactcatc tataccctca
1261 atggaaaaag aagtaggtaa ctgtagtcca cattttctta atgcttttga ggattccttc
1321 agcagcatcc tctccacaga agaccccaac cagttgacag tgaactcatt aaattcagat
1381 gccacagtca acacagattt tggtgatgaa ttttattctg ctttcatagc tgagcccagt
1441 atcagcaaca gcatgccctc acctgctact ttaagccatt cactctctga acttctaaat
1501 gggcccattg atgtttctga tctatcactt tgcaaagctt tcaaccaaaa ccaccctgaa
1561 agcacagcag aattcaatga ttctgactcc ggcatttcac taaacacaag tcccagtgtg
1621 gcatcaccag aacactcagt ggaatcttcc agctatggag acacactact tggcctcagt
1681 gattctgaag tggaagagct agatagtgcc cctggaagtg tcaaacagaa tggtcctaaa
1741 acaccagtac attcttctgg ggatatggta caacccttgt caccatctca ggggcagagc
1801 actcacgtgc atgatgccca atgtgagaac acaccagaga aagaattgcc tgtaagtcct
1861 ggtcatcgga aaaccccatt cacaaaagac aaacattcaa gccgcttgga ggctcatctc
1921 acaagagatg aacttagggc aaaagctctc catatcccat tccctgtaga aaaaatcatt
1981 aacctccctg ttgttgactt caacgaaatg atgtccaaag agcagttcaa tgaagctcaa
2041 cttgcattaa ttcgggatat acgtaggagg ggtaagaata aagtggctgc tcagaattgc
2101 agaaaaagaa aactggaaaa tatagtagaa ctagagcaag atttagatca tttgaaagat
2161 gaaaaagaaa aattgctcaa agaaaaagga gaaaatgaca aaagccttca cctactgaaa
2221 aaacaactca gcaccttata tctcgaagtt ttcagcatgc tacgtgatga agatggaaaa
2281 ccttattctc ctagtgaata ctccctgcag caaacaagag atggcaatgt tttccttgtt
2341 cccaaaagta agaagccaga tgttaagaaa aactagattt aggaggattt gaccttttct
2401 gagctagttt ttttgtacta ttatactaaa agctcctact gtgatgtgaa atgctcatac
2461 tttataagta attctatgca aaatcatagc caaaactagt atagaaaata atacgaaact
2521 ttaaaaagca ttggagtgtc agtatgttga atcagtagtt tcactttaac tgtaaacaat
2581 ttcttaggac accatttggg ctagtttctg tgtaagtgta aatactacaa aaacttattt
2641 atactgttct tatgtcattt gttatattca tagatttata tgatgatatg acatctggct
2701 aaaaagaaat tattgcaaaa ctaaccacta tgtacttttt tataaatact gtatggacaa
2761 aaaatggcat tttttatatt aaattgttta gctctggcaa aaaaaaaaaa ttttaagagc
2821 tggtactaat aaaggattat tatgactgtt aaattattaa aa SEQ ID NO: 15 *Homo sapiens* NRF2 cDNA, transcript variant 5 (NM_001313901.1; CDS:699-2468

1 ggcccttccg ggctgcgcg gctcccccgc ctcggtgccg gcaaaaatgt gcctagtcac
61 ggggccgctc tcgggggaac tgaggtcgcc ttcgggctgg gacccggagc cccttcgccg
121 cgccccaaga cctccttgag tgcgggctgc gacgcgctca ccccgctggg ccgtctgtgg
181 gcgcggcttt gcgaagtcat ccatctctcg gatcactctc tggcagcctt gagctctctt
241 gaaagcccag ccccgggacg agggaggagc gccttaagtg cccagcgggc tcagaagccc
301 cgacgtgtgg cggctgagcc gggccccgcg cactttctcg gccggggagg ggttcgggct
361 cgggcacccg gagttggccc ctcgtaacgc cgcgggaaag tgcgggcgag ggcagtggac TABLE 1A -continued Inhibiting mutations of KEAP1, including loss-of-function mutations of KEAP1 NQO1 NRF2

```
 421 tctgaggccg gagtcggcgg cacccggggc ttctagttcg gacgcggtgc cccctggtgg
 481 cgctcaccgc gcgcgtggcc ttggcttccg tgacagcgct cggttggccg tcacagcagc
 541 cctcggttgg ccctttcctg ctttatagcg tgcaaacctc gccgcgccag ggccaaggga
 601 caggttggag ctgttgatct gttgcgcaat tgctattttc cccagagcgg ctttgtcttt
 661 ggatttagcg tttcagaatt gcaattccaa aatgtgacat ggatttgatt gacatacttt
 721 ggaggcaaga tatagatctt ggagtaagtc gagaagtatt tgacttcagt cagcgacgga
 781 aagagtatga gctggaaaaa cagaaaaaac ttgaaaagga aagacaagaa caactccaaa
 841 aggagcaaga gaaagccttt ttcgctcagt tacaactaga tgaagagaca ggtgaatttc
 901 tcccaattca gccagcccag cacatccagt cagaaaccag tggatctgcc aactactccc
 961 aggttgccca cattcccaaa tcagatgctt tgtactttga tgactgcatg cagcttttgg
1021 cgcagacatt cccgtttgta gatgacaatg aggtttcttc ggctacgttt cagtcacttg
1081 ttcctgatat tcccggtcac atcgagagcc cagtcttcat tgctactaat caggctcagt
1141 cacctgaaac ttctgttgct caggtagccc ctgttgattt agacggtatg caacaggaca
1201 ttgagcaagt ttgggaggag ctattatcca ttcctgagtt acagtgtctt aatattgaaa
1261 atgacaagct ggttgagact accatggttc caagtccaga agccaaactg acagaagttg
1321 acaattatca tttttactca tctataccct caatggaaaa agaagtaggt aactgtagtc
1381 cacattttct taatgctttt gaggattcct tcagcagcat cctctccaca gaagacccca
1441 accagttgac agtgaactca ttaaattcag atgccacagt caacacagat tttggtgatg
1501 aattttattc tgctttcata gctgagccca gtatcagcaa cagcatgccc tcacctgcta
1561 ctttaagcca ttcactctct gaacttctaa atggggcccat tgatgtttct gatctatcac
1621 tttgcaaagc tttcaaccaa aaccaccctg aaagcacagc agaattcaat gattctgact
1681 ccggcatttc actaaacaca agtcccagtg tggcatcacc agaacactca gtggaatctt
1741 ccagctatgg agacacacta cttggcctca gtgattctga agtggaagag ctagatagtg
1801 cccctggaag tgtcaaacag aatggtccta aaacaccagt acattcttct ggggatatgg
1861 tacaaccctt gtcaccatct caggggcaga gcactcacgt gcatgatgcc caatgtgaga
1921 acacaccaga gaaagaattg cctgtaagtc ctggtcatcg gaaaacccca ttcacaaaag
1981 acaaacattc aagccgcttg gaggctcatc tcacaagaga tgaacttagg gcaaaagctc
2041 tccatatccc attccctgta gaaaaaatca ttaacctccc tgttgttgac ttcaacgaaa
2101 tgatgtccaa agagcagttc aatgaagctc aacttgcatt aattcgggat atacgtagga
2161 ggggtaagaa taaagtggct gctcagaatt gcagaaaaag aaaactggaa aatatagtag
2221 aactagagca agatttagat catttgaaag atgaaaaaga aaaattgctc aaagaaaaag
2281 gagaaaatga caaaagcctt cacctactga aaaaacaact cagcacctta tatctcgaag
2341 ttttcagcat gctacgtgat gaagatggaa aaccttattc tcctagtgaa tactccctgc
2401 agcaaacaag agatggcaat gttttccttg ttcccaaaag taagaagcca gatgttaaga
2461 aaaactagat ttaggaggat ttgacctttt ctgagctagt ttttttgtac tattatacta
2521 aaagctccta ctgtgatgtg aaatgctcat actttataag taattctatg caaaatcata
2581 gccaaaacta gtatagaaaa taatacgaaa ctttaaaaag cattggagtg tcagtatgtt
2641 gaatcagtag tttcacttta actgtaaaca atttcttagg acaccatttg ggctagtttc
2701 tgtgtaagtg taaatactac aaaaacttat ttatactgtt cttatgtcat ttgttatatt
2761 catagattta tatgatgata tgacatctgg ctaaaaagaa attattgcaa aactaaccac
2821 tatgtacttt tttataaata ctgtatggac aaaaaatggc atttttata ttaaattgtt
2881 tagctctggc aaaaaaaaaa aattttaaga gctggtacta ataaaggatt attatgactg
2941 ttaaattatt aaaa
```

SEQ ID NO: 16 *Homo sapiens* NRF2 cDNA, transcript variant 6 (NM_001313902.1; CDS: 556-2283

```
   1 aaatcaggga ggcgcagctc ctacaccaac gcctttccgg ggctccgggt gtgtttgttc
  61 caactgttta aactgtttca aagcgtccga actccagcga ccttcgcaaa caactcttta
 121 tctcgcgggc gagagcgctg cccttatttg cgggggaggg caaactgaac gccggcaccg
 181 gggagctaac ggagacctcc tctaggtccc ccgcctgctg ggaccccagc tggcagtccc
 241 ttcccgcccc cggaccgcga gcttcttgcg tcagcccccgg cgcgggtggg ggattttcgg
 301 aagctcagcc cgcgcggccg gcgggggaag gaagggcccg gactcttgcc ccgccccttgt
 361 ggggcgggag gcggagcggg gcaggggccc gccggcgtgt agccgattac cgagtgccgg
 421 ggagcccgga ggagccgccg acgcagccgc caccgccgcc gccgccgcca ccagagccgc
 481 cctgtccgcg ccgcgcctcg gcagccggaa cagggccgcc gtcggggagc cccaacacac
 541 ggtccacagc tcatcatgat ggacttggag ctgccgccgc cgggactccc gtcccagcag
 601 gacatggatt tgattgacat actttggagg caagatatag atcttggagt aagtcgagaa
 661 gtatttgact tcagtcagcg acggaaagag tatgagctgg aaaaacagaa aaaacttgaa
 721 aaggaaagac aagaacaact ccaaaaggag caagagaaag cctttttcgc tcagttacaa
 781 ctagatgaag agacaggtga atttctccca attcagccag cccagcacat ccagtcagaa
 841 accagtggat ctgccaacta ctcccaggtt tcttcggcta cgtttcagtc acttgttcct
 901 gatattcccg gtcacatcga gagcccagtc ttcattgcta ctaatcaggc tcagtcacct
 961 gaaacttctg ttgctcaggt agcccctgtt gatttagacg gtatgcaaca ggacattgag
1021 caagtttggg aggagctatt atccattcct gagttacagt gtcttaatat tgaaaatgac
1081 aagctggttg agactaccat ggttccaagt ccagaagcca aactgacaga agttgacaat
1141 tatcattttt actcatctat accctcaatg gaaaaagaag taggtaactg tagtccacat
1201 tttcttaatg cttttgagga ttccttcagc agcatcctct ccacagaaga ccccaaccag
1261 ttgacagtga actcattaaa ttcagatgcc acagtcaaca cagattttgg tgatgaattt
1321 tattctgctt tcatagctga gcccagtatc agcaacagca tgccctcacc tgctacttta
1381 agccattcac tctctgaact tctaaatggg cccattgatg tttctgatct atcactttgc
1441 aaagctttca accaaaacca ccctgaaagc acagcagaat tcaatgattc tgactccggc
1501 atttcactaa acacaagtcc cagtgtggca tcaccagaac actcagtgga atcttccagc
1561 tatggagaca cactacttgg cctcagtgat tctgaagtgg aagagctaga tagtgcccct
1621 ggaagtgtca aacagaatgg tcctaaaaca ccagtacatt cttctgggga tatggtacaa
1681 cccttgtcac catctcaggg gcagagcact cacgtgcatg atgcccaatg tgagaacaca
1741 ccagagaaag aattgcctgt aagtcctggt catcggaaaa ccccattcac aaaagacaaa
1801 cattcaagcc gcttggaggc tcatctcaca agagatgaac ttagggcaaa agctctccat
```

TABLE 1A -continued

Inhibiting mutations of KEAP1, including loss-of-function mutations of KEAP1 NQO1 NRF2

1861 atcccattcc ctgtagaaaa aatcattaac ctccctgttg ttgacttcaa cgaaatgatg
1921 tccaaagagc agttcaatga agctcaactt gcattaattc gggatatacg taggaggggt
1981 aagaataaag tggctgctca gaattgcaga aaaagaaaac tggaaaatat agtagaacta
2041 gagcaagatt tagatcattt gaaagatgaa aaagaaaaat tgctcaaaga aaaaggagaa
2101 aatgacaaaa gccttcacct actgaaaaaa caactcagca ccttatatct cgaagttttc
2161 agcatgctac gtgatgaaga tggaaaacct tattctccta gtgaatactc cctgcagcaa
2221 acaagagatg gcaatgtttt ccttgttccc aaaagtaaga agccagatgt taagaaaaac
2281 tagatttagg aggatttgac cttttctgag ctagtttttt tgtactatta tactaaaagc
2341 tcctactgtg atgtgaaatg ctcatacttt ataagtaatt ctatgcaaaa tcatagccaa
2401 aactagtata gaaaataata cgaaacttta aaaagcattg gagtgtcagt atgttgaatc
2461 agtagtttca ctttaactgt aaacaatttc ttaggacacc atttgggcta gtttctgtgt
2521 aagtgtaaat actacaaaaa cttatttata ctgttcttat gtcatttgtt atattcatag
2581 atttatatga tgatatgaca tctggctaaa aagaaattat tgcaaaacta accactatgt
2641 actttttttat aaatactgta tggacaaaaa atggcatttt ttatattaaa ttgtttagct
2701 ctggcaaaaa aaaaaaattt taagagctgg tactaataaa ggattattat gactgttaaa
2761 ttattaaaa SEQ ID NO: 17 *Homo sapiens* NRF2 cDNA, transcript variant 7 (NM_001313903.1; CDS:556-2154

1 aaatcaggga ggcgcagctc ctacaccaac gcctttccgg ggctccgggt gtgtttgttc
61 caactgttta aactgtttca aagcgtccga actccagcga ccttcgcaaa caactcttta
121 tctcgcgggc gagagcgctg cccttatttg cgggggaggg caaactgaac gccggcaccg
181 gggagctaac ggagacctcc tctaggtccc ccgcctgctg ggaccccagc tggcagtccc
241 ttcccgcccc cggaccgcga gcttcttgcg tcagcccccgg cgcgggtggg ggattttcgg
301 aagctcagcc cgcgcggccg gcgggggaag gaagggcccg gactcttgcc ccgcccttgt
361 ggggcgggag gcggagcggg gcaggggccc gccggcgtgt agccgattac cgagtgccgg
421 ggagcccgga ggagccgccg acgcagccgc caccgccgcc gccgccgcca ccagagccgc
481 cctgtccgcg ccgcgcctcg gcagccggaa cagggccgcc gtcggggagc cccaacacac
541 ggtccacagc tcatcatgat ggacttggag ctgccgccgc cgggactccc gtcccagcag
601 gacatggatt tgattgacat actttggagg caagatatag atcttggagt tgcccacatt
661 cccaaatcag atgctttgta ctttgatgac tgcatgcagc ttttggcgca gacattcccg
721 tttgtagatg acaatgaggt ttcttcggct acgtttcagt cacttgttcc tgatattccc
781 ggtcacatcg agagcccagt cttcattgct actaatcagg ctcagtcacc tgaaacttct
841 gttgctcagg tagcccctgt tgatttagac ggtatgcaac aggacattga gcaagtttgg
901 gaggagctat tatccattcc tgagttacag tgtcttaata ttgaaaatga caagctggtt
961 gagactacca tggttccaag tccagaagcc aaactgacag aagttgacaa ttatcatttt
1021 tactcatcta taccctcaat ggaaaaagaa gtaggtaact gtagtccaca ttttcttaat
1081 gcttttgagg attccttcag cagcatcctc tccacagaag accccaacca gttgacagtg
1141 aactcattaa attcagatgc cacagtcaac acagattttg gtgatgaatt ttattctgct
1201 ttcatagctg agcccagtat cagcaacagc atgccctcac ctgctacttt aagccattca
1261 ctctctgaac ttctaaatgg gcccattgat gtttctgatc tatcactttg caaagctttc
1321 aaccaaaacc accctgaaag cacagcagaa ttcaatgatt ctgactccgg catttcacta
1381 aacacaagtc ccagtgtggc atcaccagaa cactcagtgg aatcttccag ctatggagac
1441 acactacttg gcctcagtga ttctgaagtg gaagagctag atagtgcccc tggaagtgtc
1501 aaacagaatg gtcctaaaac accagtacat tcttctgggg atatggtaca acccttgtca
1561 ccatctcagg ggcagagcac tcacgtgcat gatgcccaat gtgagaacac accagagaaa
1621 gaattgcctg taagtcctgg tcatcggaaa accccattca caaaagacaa acattcaagc
1681 cgcttggagg ctcatctcac aagagatgaa cttagggcaa aagctctcca tatcccattc
1741 cctgtagaaa aaatcattaa cctccctgtt gttgacttca acgaaatgat gtccaaagag
1801 cagttcaatg aagctcaact tgcattaatt cgggatatac gtaggagggg taagaataaa
1861 gtggctgctc agaattgcag aaaaagaaaa ctggaaaata tagtagaact agagcaagat
1921 ttagatcatt tgaaagatga aaaagaaaaa ttgctcaaag aaaaaggaga aaatgacaaa
1981 agccttcacc tactgaaaaa acaactcagc accttatatc tcgaagtttt cagcatgcta
2041 cgtgatgaag atggaaaacc ttattctcct agtgaatact ccctgcagca aacaagagat
2101 ggcaatgttt tccttgttcc caaaagtaag aagccagatg ttaagaaaaa ctagatttag
2161 gaggatttga ccttttctga gctagttttt ttgtactatt atactaaaag ctcctactgt
2221 gatgtgaaat gctcatactt tataagtaat tctatgcaaa atcatagcca aaactagtat
2281 agaaaataat acgaaacttt aaaaagcatt ggagtgtcag tatgttgaat cagtagtttc
2341 actttaactg taaacaattt cttaggacac catttgggct agtttctgtg taagtgtaaa
2401 tactacaaaa acttatttat actgttctta tgtcatttgt tatattcata gatttatatg
2461 atgatatgac atctggctaa aaagaaatta ttgcaaaact aaccactatg tactttttta
2521 taaatactgt atggacaaaa aatggcattt tttatattaa attgtttagc tctggcaaaa
2581 aaaaaaaatt ttaagagctg gtactaataa aggattatta tgactgttaa attattaaaa SEQ ID NO: 18 *Homo sapiens* NRF2 cDNA, transcript variant 8 (NM_001313904.1; CDS:914-2431

1 ggcccttccg gggctgcgcg gctcccccgc ctcggtgccg gcaaaaatgt gcctagtcac
61 ggggccgctc tcgggggaac tgaggtcgcc ttcgggctgg gacccggagc cccttcgccg
121 cgccccaaga cctccttgag tgcgggctgc gacgcgctca ccccgctggg ccgtctgtgg
181 gcgcggcttt gcgaagtcat ccatctctcg gatcactctc tggcagcctt gagctctctt
241 gaaagcccag ccccgggacg agggaggagc gccttaagtg cccagcgggc tcagaagccc
301 cgacgtgtgg cggctgagcc gggccccgcg cactttctcg gccggggagg ggttcgggct
361 cgggcacccg gagttggccc ctcgtaacgc cgcgggaaag tgcgggcgag ggcagtggac
421 tctgaggccg gagtcggcgg caccccgggc ttctagttcg gacgcggtgc cccctggtgg
481 cgctcaccgc gcgcgtggcc ttggcttccg tgacagcgct cggttggccg tcacagcagc
541 cctcggttgg ccctttcctg ctttatagcg tgcaaacctc gccgcgccag ggccaaggga
601 caggttggag ctgttgatct gttgcgcaat tgctattttc cccagagcgg ctttgtcttt TABLE 1A -continued

| Inhibiting mutations of KEAP1, including loss-of-function mutations of KEAP1 NQO1 NRF2 |
|---|
| 661 ggatttagcg tttcagaatt gcaattccaa aatgtgtaag acgggatatt ctcttctgtg<br>721 ctgtcaaggg acatggattt gattgacata ctttggaggc aagatataga tcttggagta<br>781 agtcgagaag tatttgactt cagtcagcga cggaaagagt atgagctgga aaaacagaaa<br>841 aaacttgaaa aggaaagaca agaacaactc caaaaggagc aagagaaagc ctttttcgct<br>901 cagttacaac tagatgaaga gacaggttgc ccacattccc aaatcagatg ctttgtactt<br>961 tgatgactgc atgcagcttt tggcgcagac attcccgttt gtagatgaca atgaggtttc<br>1021 ttcggctacg tttcagtcac ttgttcctga tattcccggt cacatcgaga gcccagtctt<br>1081 cattgctact aatcaggctc agtcacctga aacttctgtt gctcaggtag cccctgttga<br>1141 tttagacggt atgcaacagg acattgagca agtttgggag gagctattat ccattcctga<br>1201 gttacagtgt cttaatattg aaaatgacaa gctggttgag actaccatgg ttccaagtcc<br>1261 agaagccaaa ctgacagaag ttgacaatta tcatttttac tcatctatac cctcaatgga<br>1321 aaaagaagta ggtaactgta gtccacattt tcttaatgct tttgaggatt ccttcagcag<br>1381 catcctctcc acagaagacc ccaaccagtt gacagtgaac tcattaaatt cagatgccac<br>1441 agtcaacaca gattttggtg atgaatttta ttctgctttc atagctgagc ccagtatcag<br>1501 caacagcatg ccctcacctg ctactttaag ccattcactc tctgaacttc taaatgggcc<br>1561 cattgatgtt tctgatctat cactttgcaa agctttcaac caaaaccacc ctgaaagcac<br>1621 agcagaattc aatgattctg actccggcat ttcactaaac acaagtccca gtgtggcatc<br>1681 accagaacac tcagtggaat cttccagcta tggagacaca ctacttggcc tcagtgattc<br>1741 tgaagtggaa gagctagata gtgcccctgg aagtgtcaaa cagaatggtc ctaaaacacc<br>1801 agtacattct tctggggata tggtacaacc cttgtcacca tctcaggggc agagcactca<br>1861 cgtgcatgat gcccaatgtg agaacacacc agagaaagaa ttgcctgtaa gtcctggtca<br>1921 tcggaaaacc ccattcacaa aagacaaaca ttcaagccgc ttggaggctc atctcacaag<br>1981 agatgaactt agggcaaaag ctctccatat cccattccct gtagaaaaaa tcattaacct<br>2041 ccctgttgtt gacttcaacg aaatgatgtc caaagagcag ttcaatgaag ctcaacttgc<br>2101 attaattcgg gatatacgta ggaggggtaa gaataaagtg gctgctcaga attgcagaaa<br>2161 aagaaaactg gaaaatatag tagaactaga gcaagattta gatcatttga aagatgaaaa<br>2221 agaaaaattg ctcaaagaaa aaggagaaaa tgacaaaagc cttcacctac tgaaaaaaca<br>2281 actcagcacc ttatatctcg aagttttcag catgctacgt gatgaagatg gaaaacctta<br>2341 ttctcctagt gaatactccc tgcagcaaac aagagatggc aatgttttcc ttgttcccaa<br>2401 aagtaagaag ccagatgtta agaaaaacta gatttaggag gatttgacct tttctgagct<br>2461 agtttttttg tactattata ctaaaagctc ctactgtgat gtgaaatgct catactttat<br>2521 aagtaattct atgcaaaatc atagccaaaa ctagtataga aaataatacg aaactttaaa<br>2581 aagcattgga gtgtcagtat gttgaatcag tagtttcact ttaactgtaa acaatttctt<br>2641 aggacaccat ttgggctagt ttctgtgtaa gtgtaaatac tacaaaaact tatttatact<br>2701 gttcttatgt catttgttat attcatagat ttatatgatg atatgacatc tggctaaaaa<br>2761 gaaattattg caaaactaac cactatgtac ttttttataa atactgtatg gacaaaaaat<br>2821 ggcatttttt atattaaatt gtttagctct ggcaaaaaaa aaaaatttta agagctggta<br>2881 ctaataaagg attattatga ctgttaaatt attaaaa |
| SEQ ID NO: 19 *Homo sapiens* NRF2 amino acid sequence, isoform 1 (NP_006155.2)<br>1 mmdlelpppg lpsqqdmdli dilwrqdidl gvsrevfdfs qrrkeyelek qkklekerge<br>61 qlqkegekaf faqlqldeet geflpiqpaq hiqsetsgsa nysqvahipk sdalyfddcm<br>121 qllaqtfpfv ddnevssatf qslvpdipgh lespvflatn gagspetsva qvapvdldgm<br>181 qqdlegvwee llsipelqcl niendklvet tmvpspeakl tevdnyhfys sipsmekevg<br>241 ncsphflnaf edsfssilst edpnqltvns lnsdatvntd fgdefysafi aepsisnsmp<br>301 spatlshsls ellngpidvs dlslckafnq nhpestaefn dsdsgislnt spsvaspehs<br>361 vesssygdtl lglsdsevee ldsapgsvkq ngpktpvhss gdmvqplsps qgqsthvhda<br>421 qcentpekel pvspghrktp ftkdkhssrl eahltrdelr akalhipfpv eklinlpvvd<br>481 fnemmskeqf neaglalird irrrgknkva aqncrkrkle niveleqdld hlkdekekll<br>541 kekgendksl hllkkqlstl ylevfsmlrd edgkpyspse yslqqtrdgn vflvpkskkp<br>601 dvkkn |
| SEQ ID NO: 20 *Homo sapiens* NRF2 amino acid sequence, isoform 2 (NP_001138884.1, NP_001300829.1 and NP_001300830.1)<br>1 mdlidilwrq didlgvsrev fdfsqrrkey elekqkklek ergeglqkeq ekaffaqlql<br>61 deetgeflpi qpaghiqset sgsanysqva hipksdalyf ddcmqllaqt fpfvddnevs<br>121 satfqslvpd ipghlespvf latnqaqspe tsvaqvapvd ldgmqqdleg vweellsipe<br>181 lqclniendk lvettmvpsp eakltevdny hfyssipsme kevgnasphf lnafedsfss<br>241 ilstedpnql tvnslnsdat vntdfgdefy safiaepsis nsmpspatls hslsellngp<br>301 idvsdlslck afnqnhpest aefndsdsgi slntspsvas pehsvesssy gdtllglsds<br>361 eveeldsapg svkqngpktp vhssgdmvqp lspsqggsth vhdaqcentp ekelpvspgh<br>421 rktpftkdkh ssrleahltr delrakalhi pfpveklinl pvvdfnemms keqfneagla<br>481 lirdirrrgk nkvaaqncrk rklenivele qdldhlkdek ekllkekgen dkslhllkkg<br>541 lstlylevfs mlrdedgkpy spseyslqqt rdgnvflvpk skkpdvkkn |
| SEQ ID NO: 21 *Homo sapiens* NRF2 amino acid sequence, isoform 3 (NP_001138885.1)<br>1 mdlidilwrq didlgvsrev fdfsqrrkey elekqkklek ergeglqkeq ekaffaqlql<br>61 deetgeflpi qpaghiqset sgsanysqva hipksdalyf ddcmqllaqt fpfvddnesl<br>121 vpdipghles pvflatnqaq spetsvaqva pvdldgmqqd legvweells ipelqclnie<br>181 ndklvettmv pspeakltev dnyhfyssip smekevgncs phflnafeds fssilstedp<br>241 nqltvnslns datvntdfgd efysafiaep sisnsmpspa tlshslsell ngpidvsdls<br>301 lckafnqnhp estaefndsd sgislntsps vaspehsves ssygdtllgl sdseveelds<br>361 apgsvkqngp ktpvhssgdm vqplspsqgq sthvhdaqce ntpekelpvs pghrktpftk<br>421 dkhssrleah ltrdelraka lhipfpveki inlpvvdfne mmskeqfnea glalirdirr<br>481 rgknkvaagn crkrkleniv eleqdldhlk dekekllkek gendkslhll kkqlstlyle<br>541 vfsmlrdedg kpyspseysl qqtrdgnvfl vpkskkpdvk kn |

TABLE 1A -continued

Inhibiting mutations of KEAP1, including loss-of-function mutations of KEAP1 NQO1 NRF2

SEQ ID NO: 22 *Homo sapiens* NRF2 amino acid sequence, isoform 4
(NP_001300831.1)
```
  1 mmdlelpppg lpsqqdmdli dilwrqdidl gvsrevfdfs qrrkeyelek qkklekerge
 61 qlqkegekaf faqlqldeet geflpiqpaq hiqsetsgsa nysqvssatf qslvpdipgh
121 lespvflatn gagspetsva qvapvdldgm qqdlegvwee llsipelqcl niendklvet
181 tmvpspeakl tevdnyhfys sipsmekevg ncsphflnaf edsfssilst edpnciltvns
241 lnsdatvntd fgdefysafi aepsisnsmp spatlshsls ellngpidvs dlslckafnq
301 nhpestaefn dsdsgislnt spsvaspehs vesssygdtl lglsdsevee ldsapgsvkq
361 ngpktpvhss gdmvqplsps qgqsthvhda qcentpekel pvspghrktp ftkdkhssrl
421 eahltrdelr akalhipfpv eklinlpvvd fnemmskeqf neaglalird irrrgknkva
481 aqncrkrkle niveleqdld hlkdekekll kekgendksl hllkkqlstl ylevfsmlrd
541 edgkpyspse yslqqtrdgn vflvpkskkp dvkkn
```

SEQ ID NO: 23 *Homo sapiens* NRF2 amino acid sequence, isoform 5
(NP_001300832.1)
```
  1 mmdlelpppg lpsqqdmdli dilwrqdidl gvahipksda lyfddcmqll aqtfpfvddn
 61 evssatfqsl vpdipghies pvflatnqaq spetsvaqva pvdldgmqqd legvweells
121 ipelqclnie ndklvettmv pspeakltev dnyhfyssip smekevgncs phflnafeds
181 fssilstedp nqltvnslns datvntdfgd efysafiaep sisnsmpspa tlshslsell
241 ngpidvsdls lckafnqnhp estaefndsd sgislntsps vaspehsves ssygdtllgl
301 sdseveelds apgsvkqngp ktpvhssgdm vqplspsqgq sthvhdaqce ntpekelpvs
361 pghrktpftk dkhssrleah ltrdelraka lhipfpveki inlpvvdfne mmskeqfnea
421 glalirdirr rgknkvaagn crkrkleniv eleqdldhlk dekekllkek gendkslhll
481 kkqlstlyle vfsmlrdedg kpyspseysl qqtrdgnvfl vpkskkpdvk kn
```

SEQ ID NO: 24 *Homo sapiens* NRF2 amino acid sequence, isoform 6
(NP_001300833.1)
```
  1 mkrqvahipk sdalyfddcm qllaqtfpfv ddnevssatf qslvpdipgh lespvflatn
 61 gagspetsva qvapvdldgm qqdlegvwee llsipelqcl niendklvet tmvpspeakl
121 tevdnyhfys sipsmekevg ncsphflnaf edsfssilst edpnqltvns lnsdatvntd
181 fgdefysafi aepsisnsmp spatlshsls ellngpidvs dlslckafnq nhpestaefn
241 dsdsgislnt spsvaspehs vesssygdtl lglsdsevee ldsapgsvkq ngpktpvhss
301 gdmvqplsps qgqsthvhda qcentpekel pvspghrktp ftkdkhssrl eahltrdelr
361 akalhipfpv eklinlpvvd fnemmskeqf neaglalird irrrgknkva aqncrkrkle
421 niveleqdld hlkdekekll kekgendksl hllkkqlstl ylevfsmlrd edgkpyspse
481 yslqqtrdgn vflvpkskkp dvkkn
```

SEQ ID NO: 25 *Mus musculus* NRF2 cDNA, transcript variant 1 (NM_010902.4;
CDS: 256-2049)
```
   1 ctccatgccc ttgtcctgcc tctggccctt gcctcttgcc ctagcctttt ctccgcctct
  61 aagttcttgt cccgtcccta ggtccttgtt ccgccccccag ggggcggggg cggggcggac
 121 taaggctggc ctgccactcc agcgagcagg ctatctccta gttctccgct gctcggacta
 181 gccattgccg ccgcctcacc tctgctgcaa gtagcctcgc cgtcggggag ccctaccaca
 241 gcgtccgccc tcagcatgat ggacttggag ttgccaccgc caggactaca gtcccagcag
 301 gacatggatt tgattgacat cctttggagg caagacatag atcttggagt aagtcgagaa
 361 gtgtttgact ttagtcagcg acagaaggac tatgagctgg aaaaacagaa aaaactcgaa
 421 aaggaaagac aagagcaact ccagaaggaa caggagaagg ccttttttgc tcagtttcaa
 481 ctggatgaag aaacaggaga attcctccca attcagccgg cccagcacat ccagacagac
 541 accagtggat ccgccagcta ctcccaggtt gcccacattc ccaaacaaga tgccttgtac
 601 tttgaagact gtatgcagct tttggcagag acattcccat ttgtagatga ccatgagtcg
 661 cttgccctgg atatccccag ccacgctgaa agttcagtct tcactgcccc tcatcaggcc
 721 cagtccctca atagctctct ggaggcagcc atgactgatt taagcagcat agagcaggac
 781 atggagcaag tttggcagga gctattttcc attcccgaat tacagtgtct taataccgaa
 841 aacaagcagc tggctgatac taccgctgtt cccagcccag aagccacact gacagaaatg
 901 gacagcaatt accattttta ctcatcgatc tcctcgctgg aaaaagaagt gggcaactgt
 961 ggtccacatt tccttcatgg ttttgaggat tctttcagca gcatcctctc cactgatgat
1021 gccagccagc tgacctcctt agactcaaat cccaccttaa acacagattt tggcgatgaa
1081 ttttattctg ctttcatagc agagcccagt gacggtggca gcatgccttc ctccgctgcc
1141 atcagtcagt cactctctga actcctggac gggactattg aaggctgtga cctgtcactg
1201 tgtaaagctt tcaacccgaa gcacgctgaa ggcacaatgg aattcaatga ctctgactct
1261 ggcatttcac tgaacacgag tcccagccga gcgtccccag agcactccgt ggagtcttcc
1321 atttacggag acccaccgcc tgggttcagt gactcggaaa tggaggagct agatagtgcc
1381 cctggaagtg tcaaacagaa cggccctaaa gcacagccag cacattctcc tggagacaca
1441 gtacagcctc tgtcaccagc tcaagggcac agtgctccta tgcgtgaatc ccaatgtgaa
1501 aatacaacaa aaaaagaagt tcccgtgagt cctggtcatc aaaaagcccc attcacaaaa
1561 gacaaacatt caagccgctt agaggctcat ctcacacgag atgagcttag ggcaaaagct
1621 ctccatattc cattccctgt cgaaaaaatc attaacctcc ctgttgatga cttcaatgaa
1681 atgatgtcca aggagcaatt caatgaagct cagctcgcat tgatccgaga tatacgcagg
1741 agaggtaaga ataaagtcgc cgcccagaac tgtaggaaaa ggaagctgga gaacattgtc
1801 gagctggagc aagacttggg ccacttaaaa gacgagagag aaaaactact cagagaaaag
1861 ggagaaaacg acagaaacct ccatctactg aaaaggcggc tcagcacctt gtatcttgaa
1921 gtcttcagca tgttacgtga tgaggatgga aagccttact ctcccagtga atactctctg
1981 cagcaaacca gagatggcaa tgtgttcctt gttcccaaaa gcaagaagcc agatacaaag
2041 aaaaactagg ttcgggagga tggagccttt tctgagctag tgtttgtttt gtactgctaa
2101 aacttcctac tgtgatgtga aatgcagaaa cactttataa gtaactatgc agaattatag
2161 ccaaagctag tatagcaata atatgaaact ttacaaagca ttaaagtctc aatgttgaat
```

TABLE 1A -continued

Inhibiting mutations of KEAP1, including loss-of-function mutations of KEAP1 NQO1 NRF2

```
2221 cagtttcatt ttaactctca agttaatttc ttaggcacca tttgggagag tttctgttta
2281 agtgtaaata ctacagaact tatttatact gttctcactt gttacagtca tagacttata
2341 tgacatctgg ctaaaagcaa actattgaaa actaaccaga ccactatact tttttatata
2401 ctgtatgaac aggaaatgac atttttatat taaattgttt agctcataaa aattaaaagg
2461 agctagcact aataaaagaa tatcatgact taaacta
```

SEQ ID NO: 26 *Mus musculus* NRF2 transcript variant 2, non-coding RNA (NR 132727.1)

```
   1 ctccatgccc ttgtcctgcc tctggccctt gcctcttgcc ctagcctttt ctccgcctct
  61 aagttcttgt cccgtcccta ggtccttgtt ccgcccccag gggcggggg cggggcggac
 121 taaggctggc ctgccactcc agcgagcagg ctatctccta gttctccgct gctcggacta
 181 gccattgccg ccgcctcacc tctgctgcaa gtagcctcgc cgtcggggag ccctaccaca
 241 gcgtccgccc tcagcatgat ggacttggag ttgccaccgc caggactaca gtcccagcag
 301 agtgatggtt gcccacttgg tggattgctg tgcgtccaga cgaggcggta caagttttgg
 361 aaggaggttt ctgagcacgc agaaagtgtg tgatcagagg tggctgctct tgttgcagtg
 421 cagtgtctac tttatctgga cttagaccat ccccacgttg taaccttccg ttctcaaaac
 481 ccagtgtgac cagtgtctca cacaactcta tagtagattt ttaatctgct ttttatgtat
 541 atgggtgttt tgcctgtatg tatttctgtg taccatacat gtactcgatg ccttcagagt
 601 ccagaagaga gcatcagatt acagacagtt gtgagttgcc atataggttc catgaacaga
 661 tccagcttct gtgtaagagc agtgagtgct cttaaccact ggtttagcca tctctccagt
 721 ccctagtaat ccttttttata ggcccaaatt gcattgtagt agtcagcaac aatagtgagt
 781 accatgatgc actttcagat atatacatat gaaagtagtt gaaatataat ttctaagctc
 841 agggttaatt tatgtcttta ttgggaacac agagcccttt tacatgacgt gtttagtagc
 901 catggtaatc atctcatttg taaattatgc tattatggaa taatatgaaa aactattgag
 961 tttagtcatt aagagccctc tttgtgattc agattcacac cagctctttg gagtaattgc
1021 taatgatacc tagagtagtt tggaagggct aatgtccaca gttgtagcct cgggaagttg
1081 ttagccacac atttgcttag aggacacccg aggagggcat gggccatagt ggggaccgct
1141 gcagggctgc gctgtccacc accgcagcca ctagtcacct tgcagtctgg aaatgtgatg
1201 agtgacagaa accaagaggc tggagcttta gtgttaatga gcatgacatt tataaacagc
1261 agaaacgact tttctggtta ataagcctta ggtagtcctc tagctcagga ggaggctcgg
1321 ggctcctggt cctgcctttg tagggcagca ttgtgcgctg tcttgtgggt aagattattg
1381 tgctctgtca cctttaatat cacaacaata ctgttaacat gttaaaatgc tattggacca
1441 aattggatta aatacgttgt tcaaattaaa ttcactgtgt tgtttttgtt attgtgtctg
1501 agctgcaaac aatatcagtt acatatgtta ttcacattat atttcttatg aagttccttt
1561 agagcattct gtaatctaaa attagtgtgt atttttacat taaaatgaat tttcaattgt
1621 a
```

SEQ ID NO: 27 *Mus musculus* NRF2 amino acid sequence (NP_035032.1)

```
   1 mmdlelpppg lqsqqdmdll dllwrqdldl gvsrevfdfs qrqkdyelek qkklekerge
  61 qlqkegekaf faqfqldeet geflpiqpaq hlqtdtsgsa sysqvahlpk gdalyfedcm
 121 qllaetfpfv ddheslaldi pshaessvft aphgagslns sleaamtdls siegdmegvw
 181 gelfsipelq clntenkqla dttavpspea tltemdsnyh fyssisslek evgncgphfl
 241 hgfedsfssi lstddasqlt sldsnptlnt dfgdefysaf laepsdggsm pssaaisqsl
 301 selldgtieg cdlslckafn pkhaegtmef ndsdsgisln tspsraspeh svesslygdp
 361 ppgfsdseme eldsapgsvk qngpkaqpah spgdtvqpls pagghsapmr esqcenttkk
 421 evpvspghqk apftkdkhss rleahltrde lrakalhlpf pveklinlpv ddfnemmske
 481 gfneaglali rdirrrgknk vaagnorkrk lenivelegd lghlkderek llrekgendr
 541 nlhllkrrls tlylevfsml rdedgkpysp seyslggtrd gnvflvpksk kpdtkkn
```

* Included in Table 1A are RNA nucleic acid molecules (e.g., thymines replaced with uridines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1A, or a portion thereof Such nucleic acid molecules can have a function of the full-length nucleic acid as described further herein.
* Included in Table 1A are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1A, or a portion thereof. Such polypeptides can have a function of the full-length polypeptide as described further herein.
* Included in Table 1A are known NQO1, NRF2 and KEAP1 sequences, including those described herein and homologous sequences thereof, as well as KEAP1 null mutations, missense mutations, nonsense mutations, frameshift mutations, insertion mutation, deletion mutations, and rearrangement mutations.

TABLE 1B

KEAP1
Inhibiting mutations of NQO1, including loss-of-function mutations of NQO1
Inhibiting mutations of NRF2, including loss-of-function mutations of NRF2

SEQ ID NO: 28 *Homo sapiens* KEAP1 cDNA,transcriptvariant 1 (NM_203500.1; CDS:186-2060)

```
   1 ctttccgccc tctccccgcc tccttttcgg gcgtcccgag gccgctcccc aaccgacaac
  61 caagaccccg caggccacgc agccctggag ccgaggcccc ccgacggcgg aggcgcccgc
 121 gggtccccta cagccaaggt ccctgagtgc cagaggtggt ggtgttgctt atcttctgga
 181 accccatgca gccagatccc aggcctagcg gggctggggc ctgctgccga ttcctgcccc
 241 tgcagtcaca gtgccctgag gggcagggg acgcggtgat gtacgcctcc actgagtgca
```

TABLE 1B -continued

KEAP1
Inhibiting mutations of NQO1, including loss-of-function mutations of NQO1
Inhibiting mutations of NRF2, including loss-of-function mutations of NRF2

301 aggcggaggt gacgccctcc cagcatggca accgcacctt cagctacacc ctggaggatc
361 ataccaagca ggcctttggc atcatgaacg agctgcggct cagccagcag ctgtgtgacg
421 tcacactgca ggtcaagtac caggatgcac cggccgccca gttcatggcc cacaaggtgg
481 tgctggcctc atccagccct gtcttcaagg ccatgttcac caacgggctg cgggagcagg
541 gcatggaggt ggtgtccatt gagggtatcc accccaaggt catggagcgc ctcattgaat
601 tcgcctacac ggcctccatc tccatgggcg agaagtgtgt cctccacgtc atgaacggtg
661 ctgtcatgta ccagatcgac agcgttgtcc gtgcctgcag tgacttcctg gtgcagcagc
721 tggaccccag caatgccatc ggcatcgcca acttcgctga gcagattggc tgtgtggagt
781 tgcaccagcg tgcccgggag tacatctaca tgcattttgg ggaggtggcc aagcaagagg
841 agttcttcaa cctgtcccac tgccaactgg tgaccctcat cagccgggac gacctgaacg
901 tgcgctgcga gtccgaggtc ttccacgcct gcatcaactg ggtcaagtac gactgcgaac
961 agcgacggtt ctacgtccag gcgctgctgc gggccgtgcg ctgccactcg ttgacgccga
1021 acttcctgca gatgcagctg cagaagtgcg agatcctgca gtccgactcc cgctgcaagg
1081 actacctggt caagatcttc gaggagctca ccctgcacaa gcccacgcag gtgatgccct
1141 gccgggcgcc caaggtgggc cgcctgatct acaccgcggg cggctacttc cgacagtcgc
1201 tcagctacct ggaggcttac aaccccagtg acggcacctg gctccggttg gcggacctgc
1261 aggtgccgcg gagcggcctg gccggctgcg tggtgggcgg gctgttgtac gccgtgggcg
1321 gcaggaacaa ctcgcccgac ggcaacaccg actccagcgc cctggactgt tacaacccca
1381 tgaccaatca gtggtcgccc tgcgccccca tgagcgtgcc ccgtaaccgc atcggggtgg
1441 gggtcatcga tggccacatc tatgccgtcg gcggctccca cggctgcatc caccacaaca
1501 gtgtggagag gtatgagcca gagcgggatg agtggcactt ggtggcccca atgctgacac
1561 gaaggatcgg ggtgggcgtg gctgtcctca atcgtctcct ttatgccgtg gggggctttg
1621 acgggacaaa ccgccttaat tcagctgagt gttactaccc agagaggaac gagtggcgaa
1681 tgatcacagc aatgaacacc atccgaagcg gggcaggcgt ctgcgtcctg cacaactgta
1741 tctatgctgc tgggggctat gatggtcagg accagctgaa cagcgtggag cgctacgatg
1801 tggaaacaga gacgtggact ttcgtagccc ccatgaagca ccggcgaagt gccctgggga
1861 tcactgtcca ccaggggaga atctacgtcc ttggaggcta tgatggtcac acgttcctgg
1921 acagtgtgga gtgttacgac ccagatacag acacctggag cgaggtgacc cgaatgacat
1981 cgggccggag tggggtgggc gtggctgtca ccatggagcc ctgccggaag cagattgacc
2041 agcagaactg tacctgttga ggcacttttg tttcttgggc aaaaatacag tccaatgggg
2101 agtatcattg tttttgtaca aaaaccggga ctaaaagaaa agacagcact gcaaataacc
2161 catcttccgg gaagggaggc caggatgcct cagtgttaaa atgacatctc aaaagaagtc
2221 caaagcggga atcatgtgcc cctcagcgga gccccgggag tgtccaagac agcctggctg
2281 ggaaaggggg tgtggaaaga gcaggcttcc aggagagagg cccccaaacc ctctggccgg
2341 gtaataggcc tgggtcccac tcacccatgc cggcagctgt caccatgtga tttattcttg
2401 gatacctggg agggggccaa tgggggcctc agggggaggc cccctctgga aatgtggttc
2461 ccagggatgg gcctgtacat agaagccacc ggatggcact tccccaccgg atggacagtt
2521 attttgttga taagtaaccc tgtaattttc caaggaaaat aaagaacaga ctaactagtg
2581 tctttcaccc tgaaaaaaaa aaaaaa SEQ ID NO: 29 *Homo sapiens* KEAP1 cDNA, transcript variant 2
(NM_012289.3; CDS: 157-2031)
1 tctgcttagt catggtgacc tgcgcgcgct ccgcgcctcc cccacgcgca gcgatggagg
61 cgccggggct cgggcggtgg aggcggagcc ggagcgcggc catggcgggg tccctgagtg
121 ccagaggtgg tggtgttgct tatcttctgg aaccccatgc agccagatcc caggcctagc
181 ggggctgggg cctgctgccg attcctgccc ctgcagtcac agtgccctga gggggcaggg
241 gacgcggtga tgtacgcctc cactgagtgc aaggcggagg tgacgccctc ccagcatggc
301 aaccgcacct tcagctacac cctggaggat cataccaagc aggcctttgg catcatgaac
361 gagctgcggc tcagccagca gctgtgtgac gtcacactgc aggtcaagta ccaggatgca
421 ccggccgccc agttcatggc ccacaaggtg gtgctggcct catccagccc tgtcttcaag
481 gccatgttca ccaacgggct gcgggagcag ggcatggagg tggtgtccat tgagggtatc
541 caccccaagg tcatggagcg cctcattgaa ttcgcctaca cggcctccat ctccatgggc
601 gagaagtgtg tcctccacgt catgaacggt gctgtcatgt accagatcga cagcgttgtc
661 cgtgcctgca gtgacttcct ggtgcagcag ctggacccca gcaatgccat cggcatcgcc
721 aacttcgctg agcagattgg ctgtgtggag ttgcaccagc gtgcccggga gtacatctac
781 atgcattttg gggaggtggc caagcaagag gagttcttca acctgtccca ctgccaactg
841 gtgaccctca tcagccggga cgacctgaac gtgcgctgcg agtccgaggt cttccacgcc
901 tgcatcaact gggtcaagta cgactgcgaa cagcgacggt tctacgtcca ggcgctgctg
961 cgggccgtgc gctgccactc gttgacgccg aacttcctgc agatgcagct gcagaagtgc
1021 gagatcctgc agtccgactc ccgctgcaag gactacctgg tcaagatctt cgaggagctc
1081 accctgcaca agcccacgca ggtgatgccc tgccgggcgc ccaaggtggg ccgcctgatc
1141 tacaccgcgg gcggctactt ccgacagtcg ctcagctacc tggaggctta caaccccagt
1201 gacggcacct ggctccggtt ggcggacctg caggtgccgc ggagcggcct ggccggctgc
1261 gtggtgggcg ggctgttgta cgccgtgggc ggcaggaaca actcgcccga cggcaacacc
1321 gactccagcg ccctggactg ttacaacccc atgaccaatc agtggtcgcc ctgcgccccc
1381 atgagcgtgc cccgtaaccg catcggggtg ggggtcatcg atggccacat ctatgccgtc
1441 ggcggctccc acggctgcat ccaccacaac agtgtggaga ggtatgagcc agagcgggat
1501 gagtggcact tggtggcccc aatgctgaca cgaaggatcg gggtgggcgt ggctgtcctc
1561 aatcgtctcc tttatgccgt ggggggcttt gacgggacaa accgccttaa ttcagctgag
1621 tgttactacc cagagaggaa cgagtggcga atgatcacag caatgaacac catccgaagc
1681 ggggcaggcg tctgcgtcct gcacaactgt atctatgctg ctgggggcta tgatggtcag
1741 gaccagctga acagcgtgga gcgctacgat gtggaaacag agacgtggac tttcgtagcc
1801 cccatgaagc accggcgaag tgccctgggg atcactgtcc accaggggag aatctacgtc
1861 cttggaggct atgatggtca cacgttcctg gacagtgtgg agtgttacga cccagataca
1921 gacacctgga gcgaggtgac ccgaatgaca tcgggccgga gtggggtggg cgtggctgtc
1981 accatggagc cctgccggaa gcagattgac cagcagaact gtacctgttg aggcactttt TABLE 1B -continued KEAP1
Inhibiting mutations of NQO1, including loss-of-function mutations of NQO1
Inhibiting mutations of NRF2, including loss-of-function mutations of NRF2

2041 gtttcttggg caaaaataca gtccaatggg gagtatcatt gtttttgtac aaaaaccggg
2101 actaaaagaa aagacagcac tgcaaataac ccatcttccg ggaagggagg ccaggatgcc
2161 tcagtgttaa aatgacatct caaaagaagt ccaaagcggg aatcatgtgc cctcagcgg
2221 agccccggga gtgtccaaga cagcctggct gggaaagggg gtgtggaaag agcaggcttc
2281 caggagagag gcccccaaac cctctggccg ggtaataggc ctgggtccca ctcacccatg
2341 ccggcagctg tcaccatgtg atttattctt ggatacctgg gagggggcca atgggggcct
2401 cagggggagg cccccctctgg aaatgtggtt cccagggatg ggcctgtaca tagaagccac
2461 cggatggcac ttccccaccg gatggacagt tattttgttg ataagtaacc ctgtaatttt
2521 ccaaggaaaa taaagaacag actaactagt gtctttcacc ctgaaaaaaa aaaaaaa SEQ ID NO: 30 *Homo sapiens* KEAP1 amino acid sequence, isoform 1
(NP_987096.1)
1 mqpdprpsga gaccrflplq sqcpegagda vmyastecka evtpsqhgnr tfsytledht
61 kgafgimnel rlsqqlcdvt lqvkyqdapa aqfmahkvvl assspvfkam ftnglreqgm
121 evvsiegihp kvmerliefa ytasismgek cvlhvmngav myqidsvvra csdflvqqld
181 psnaigianf aegigcvelh qrareyiymh fgevakqeef fnlshcqlvt lisrddlnvr
241 cesevfhaci nwvkydceqr rfyvqallra vrchsltpnf lqmqlqkcel lqsdsrckdy
301 lvkifeeltl hkptqvmper apkvgrliyt aggyfrqsls yleaynpsdg twlrladlqv
361 prsglagcvv ggllyavggr nnspdgntds saldcynpmt nqwspcapms vprnrigvgv
421 idghiyavgg shgclhhnsv eryeperdew hlvapmltrr igvgvavinr llyavggfdg
481 tnrinsaecy ypernewrmi tamntirsga gvcvlhnciy aaggydgqdq lnsverydve
541 tetwtfvapm khrrsalgit vhqgrlyvlg gydghtflds vecydpdtdt wsevtrmtsg
601 rsgvgvavtm epcrkgidgq nctc SEQ ID NO: 31 *Homo sapiens* KEAP1 amino acid sequence, isoform 2
(NP_036421.2)
1 mqpdprpsga gaccrflplq sqcpegagda vmyastecka evtpsqhgnr tfsytledht
61 kgafgimnel rlsqqlcdvt lqvkyqdapa aqfmahkvvl assspvfkam ftnglreqgm
121 evvsiegihp kvmerliefa ytasismgek cvlhvmngav myqidsvvra csdflvqqld
181 psnaigianf aegigcvelh qrareyiymh fgevakqeef fnlshcqlvt lisrddlnvr
241 cesevfhaci nwvkydceqr rfyvqallra vrchsltpnf lqmqlqkcel lqsdsrckdy
301 lvkifeeltl hkptqvmper apkvgrliyt aggyfrqsls yleaynpsdg twlrladlqv
361 prsglagcvv ggllyavggr nnspdgntds saldcynpmt nqwspcapms vprnrigvgv
421 idghiyavgg shgclhhnsv eryeperdew hlvapmltrr igvgvavinr llyavggfdg
481 tnrinsaecy ypernewrmi tamntirsga gvcvlhnciy aaggydgqdq lnsverydve
541 tetwtfvapm khrrsalgit vhqgrlyvlg gydghtflds vecydpdtdt wsevtrmtsg
601 rsgvgvavtm epcrkgidgq nctc SEQ ID NO: 32 *Mus musculus* KEAP1 cDNA, transcript variant 1
(NM_001110305.1; CDS: 588-2462)
1 agacccacgc cctgctccct ccgcccggca cctgcaggaa gggctggaac tgcctctgcg
61 tacccgccgc ccgtttccgc cctcccgctc ctcccacgcg tgccgcccgg gaccccgcag
121 caccgctgcc ccgatccgag ccctccaccc ccactccggt ccccctcctc tcttcccgga
181 agcgcggcgc gtggcggccc ggcggcgcgg attggacgcg tggcacctac agagacaccc
241 gggggggtgg gacggaggtg agcgagcgcc cgcggaggat gcggtgggga gccagctccg
301 ggagctgccc gcggtcgcgc gtggggccgt gcacgcggtg gggggaagcg cgtgcccttc
361 tccaagcgcg caccccgccg ccgagcccgt gagccctcgt agggtggtgg ccgcggcgag
421 tagaggtagg ggtcgcccgc ggccggcgcc ccgggactct tattgtgaca gggtggcgcg
481 ctgtgcttag tcaccgtgac ccgcgcggcg gaggcggagg cagagcgcgg ccatggcggg
541 gcccctaacg gctagcagag gaactgtgtc ttgtcatcag gaaccccatg cagcccgaac
601 ccaagcttag cggggctccc cgcagcagcc agttcctgcc cctgtggtca aagtgccccg
661 agggggccgg ggacgcagtg atgtatgcct ccacggagtg caaggcagag gtgacgccct
721 cgcaggacgg taaccgaacc ttcagctaca cactagagga tcacaccaag caggcttttg
781 gcgtcatgaa cgagcttcgc ctgagccagc aactctgtga cgtgaccctg caggtcaaat
841 atgaggacat cccagctgcc caattcatgg ctcacaaagt ggtgctggcc tcctccagcc
901 cagtctttaa agccatgttc accaacgggc ttcgggagca gggcatggag gtggtgtcca
961 tcgaaggcat ccaccctaag gtcatggaaa ggcttattga gttcgcctac acggcctcca
1021 tctccgtggg cgagaagtgt gtcctgcacg tgatgaacgg ggcggtcatg taccagattg
1081 acagcgtggt tcgagcctgc agcgacttcc tcgtgcagca gctggacccc agcaacgcca
1141 ttggcatcgc caacttcgcg gagcagatcg gctgcactga actgcaccag cgtgcccggg
1201 agtatatcta catgcacttc ggggaggtgg ccaagcagga ggagttcttc aacctgtcac
1261 actgccagct ggccacgctc atcagccggg atgatctgaa cgtacgctgc gagtccgagg
1321 tgttccacgc gtgcatcgac tgggtcaaat acgactgccc gcagcggcgc ttctacgtgc
1381 aggcactgct gcgggccgtg cgctgccatg cgctcacgcc gcgcttcctg cagacgcagc
1441 tgcagaagtg tgagatcctg caggccgacg cgcgctgcaa ggactacctg gtgcagatat
1501 tccaggagct cacgctgcac aagcccacgc aggcagtgcc ctgccgcgcg cccaaagtgg
1561 gccgcctcat ctacacagcg ggcggttact tccgacagtc gctcagctac ctggaggcct
1621 acaacccgag caatggctcc tggctgcgcc tggccgatct acaggtgccg cgcagtgggc
1681 tggcaggctg cgtggtgggt gggctgctat acgctgtggg cggccgcaac aactctccgg
1741 atggcaacac tgactccagc gccctggact gctacaaccc catgaccaac cagtggtcgc
1801 cctgtgcctc tatgagcgtg ccacgcaacc gcatcggggt gggggtcata gatggccaca
1861 tctacgcagt cgggggttcc cacggctgca tccaccacag cagcgtggag agatatgagc
1921 cagagcggga cgagtggcat ctagtcgcgc caatgttgac acggaggatt ggcgtgggcg
1981 tggcagtgct caaccgcttg ctgtatgcag tgggggggctt tgacgggact aaccggctta
2041 actccgcaga atgttactat ccagagagga atgagtggcg gatgatcaca ccgatgaata
2101 ccatccggag cggggccggg gtctgcgtgc tgcacaactg tatctatgca gcaggggggct TABLE 1B -continued

| KEAP1<br>Inhibiting mutations of NQO1, including loss-of-function mutations of NQO1<br>Inhibiting mutations of NRF2, including loss-of-function mutations of NRF2 |
|---|

2161 acgatgggca ggaccagttg aacagtgtgg agcgctacga cgtggagaca gagacctgga
2221 ctttcgtagc ccccatgagg catcaccgta gtgcgctggg gattactgtg caccagggca
2281 agatctacgt cctcggaggc tatgatggcc acacttttct ggacagtgtg gaatgctatg
2341 acccggacag tgatacctgg agtgaggtga cccgcatgac atctggccgc agcggggtgg
2401 gtgtggccgt caccatggaa ccctgtcgga agcaaattga tcaacaaaac tgtacctgct
2461 gaagcacttg gaatacctga gcactgacaa caggacagaa aaacagtctg tgtatcactg
2521 cttctctgta ctaaagaaaa aagaagaaaa caaagcataa acagaaaaca cagggccgaa
2581 gaggcggcag aagaagtcat cccttcttcc aggaagggcg actgggatgc cttgtaaagg
2641 accttgtgga agaccagaac tcaaatccat gggcccatct gtcatagccc tggagcgtcc
2701 aagtctggga tggggtatgg gcggggcacc ctcacaggtg agaagccctt gaactcccac
2761 caccagaagg ggggggacag gcaaagcagg agatcacatg ttttttttctt tggttcctgc
2821 aactcggtga tcaattccag tggacagggg aagaagggac agctgaggcc aaggggctga
2881 ggctccctct ggaactgggg cccaagggac aagccggcac agagaagcct ctgggctctg
2941 agccctgaac agttatttg ttaaataacc ctgtaagttt cccatgggaa taaagaatgg
3001 agtaggcaca caggtcttca gagggcggtc ggaatccctc agggagagac agctcttcta
3061 ttgaaataca cgcagatcct gatggggctg gtatctgaaa cccgtctatt gtctctgctt
3121 gccattgtac attctgctca gacagggcat cttgcttctt gtgggacaca cagttgtctg
3181 tcagtttcag ggcattagaa gccaatgacc taacttctgt gcctcctaac ttctcctggg
3241 gcctcctgtg tttagcttta ttttgaggca gggactcacg tcgtccggga tggccttcag
3301 ttcagacctt gaactgacgc tgccgcctgt cccagcctac cgagtgctgg ggctacatct
3361 gtatagcgca atgcctggtt cctgcttatt atttttgtac ccaagcagga aaataaaggt
3421 ttctgggaca ttgg SEQ ID NO: 33 *Mus musculus* KEAP1 cDNA, transcript variant 2
(NM_001110306.1; CDS: 473-2347)
1 agacccacgc cctgctccct ccgcccggca cctgcaggaa gggctggaac tgcctctgcg
61 tacccgccgc ccgtttccgc cctcccgctc ctcccacgcg tgccgcccgg gaccccgcag
121 caccgctgcc ccgatccgag ccctccaccc ccactccggt ccccctcctc tcttcccgga
181 agcgcggcgc gtggcggccc ggcggcgcgg attggacgcg tggcacctac agagacaccc
241 gggggggtgg gacggaggtg agcgagcgcc cgcggaggat gcggtgggga gccagctccg
301 ggagctgccc gcggtcgcgc gtggggccgt gcacgcggtg gggggaagcg cgtgcccttc
361 tccaagcgcg caccccgccg ccgagcccgt gagccctcgt agggtggtgg ccgcggcgag
421 tagaggcccc taacggctag cagaggaact gtgtcttgtc atcaggaacc ccatgcagcc
481 cgaacccaag cttagcgggg ctccccgcag cagccagttc ctgcccctgt ggtcaaagtg
541 ccccgagggg gccggggacg cagtgatgta tgcctccacg gagtgcaagg cagaggtgac
601 gccctcgcag gacggtaacc gaaccttcag ctacacacta gaggatcaca ccaagcaggc
661 ttttggcgtc atgaacgagc ttcgcctgag ccagcaactc tgtgacgtga ccctgcaggt
721 caaatatgag gacatcccag ctgcccaatt catggctcac aaagtggtgc tggcctcctc
781 cagcccagtc tttaaagcca tgttcaccaa cgggcttcgg gagcagggca tggaggtggt
841 gtccatcgaa ggcatccacc ctaaggtcat ggaaaggctt attgagttcg cctacacggc
901 ctccatctcc gtgggcgaga agtgtgtcct gcacgtgatg aacggggcgg tcatgtacca
961 gattgacagc gtggttcgag cctgcagcga cttcctcgtg cagcagctgg accccagcaa
1021 cgccattggc atcgccaact tcgcggagca gatcggctgc actgaactgc accagcgtgc
1081 ccgggagtat atctacatgc acttcgggga ggtggccaag caggaggagt tcttcaacct
1141 gtcacactgc cagctggcca cgctcatcag ccgggatgat ctgaacgtac gctgcgagtc
1201 cgaggtgttc cacgcgtgca tcgactgggt caaatacgac tgcccgcagc ggcgcttcta
1261 cgtgcaggca ctgctgcggg ccgtgcgctg ccatgcgctc acgccgcgct tcctgcagac
1321 gcagctgcag aagtgtgaga tcctgcaggc cgacgcgcgc tgcaaggact acctggtgca
1381 gatattccag gagctcacgc tgcacaagcc cacgcaggca gtgccctgcc gcgcgcccaa
1441 agtgggccgc ctcatctaca cagcgggcgg ttacttccga cagtcgctca gctacctgga
1501 ggcctacaac ccgagcaatg gctcctggct gcgcctggcc gatctacagg tgccgcgcag
1561 tgggctggca ggctgcgtgg tgggtgggct gctatacgct gtgggcggcc gcaacaactc
1621 tccggatggc aacactgact ccagcgccct ggactgctac aaccccatga ccaaccagtg
1681 gtcgccctgt gcctctatga gcgtgccacg caaccgcatc ggggtggggg tcatagatgg
1741 ccacatctac gcagtcgggg gttcccacgg ctgcatccac cacagcagcg tggagagata
1801 tgagccagag cgggacgagt ggcatctagt cgcgccaatg ttgacacgga ggattggcgt
1861 gggcgtggca gtgctcaacc gcttgctgta tgcagtgggg ggctttgacg ggactaaccg
1921 gcttaactcc gcagaatgtt actatccaga gaggaatgag tggcggatga tcacaccgat
1981 gaataccatc cggagcgggg ccggggtctg cgtgctgcac aactgtatct atgcagcagg
2041 gggctacgat gggcaggacc agttgaacag tgtggagcgc tacgacgtgg agacagagac
2101 ctggactttc gtagcccccca tgaggcatca ccgtagtgcg ctggggatta ctgtgcacca
2161 gggcaagatc tacgtcctcg gaggctatga tggccacact tttctggaca gtgtggaatg
2221 ctatgacccg gacagtgata cctggagtga ggtgacccgc atgacatctg gccgcagcgg
2281 ggtgggtgtg gccgtcacca tggaaccctg tcggaagcaa attgatcaac aaaactgtac
2341 ctgctgaagc acttggaata cctgagcact gacaacagga cagaaaaaca gtctgtgtat
2401 cactgcttct ctgtactaaa gaaaaaagaa gaaaacaaag cataaacaga aaacacaggg
2461 ccgaagaggc ggcagaagaa gtcatccctt cttccaggaa gggcgactgg gatgccttgt
2521 aaaggacctt gtggaagacc agaactcaaa tccatgggcc catctgtcat agccctggag
2581 cgtccaagtc tgggatgggg tatgggcggg gcaccctcac aggtgagaag cccttgaact
2641 cccaccacca gaaggggggg gacaggcaaa gcaggagatc acatgttttt ttctttggtt
2701 cctgcaactc ggtgatcaat tccagtggac aggggaagaa gggacagctg aggccaaggg
2761 gctgaggctc cctctggaac tggggcccaa gggacaagcc ggcacagaga agcctctggg
2821 ctctgagccc tgaacagtta ttttgttaaa taaccctgta agtttcccat gggaataaag
2881 aatggagtag gcacacaggt cttcagaggg cggtcggaat ccctcaggga gagacagctc
2941 ttctattgaa atacacgcag atcctgatgg ggctggtatc tgaaacccgt ctattgtctc
3001 tgcttgccat tgtacattct gctcagacag ggcatcttgc ttcttgtggg acacacagtt TABLE 1B -continued KEAP1
Inhibiting mutations of NQO1, including loss-of-function mutations of NQO1
Inhibiting mutations of NRF2, including loss-of-function mutations of NRF2

3061 gtctgtcagt ttcagggcat tagaagccaa tgacctaact tctgtgcctc ctaacttctc
3121 ctggggcctc ctgtgtttag ctttattttg aggcagggac tcacgtcgtc cgggatggcc
3181 ttcagttcag accttgaact gacgctgccg cctgtcccag cctaccgagt gctggggcta
3241 catctgtata gcgcaatgcc tggttcctgc ttattatttt tgtacccaag caggaaaata
3301 aaggtttctg ggacattgg SEQ ID NO: 34 *Mus musculus* KEAP1 cDNA, transcript variant 3
(NM_001110307.1; CDS: 305-2179)
1 agacccacgc cctgctccct ccgcccggca cctgcaggaa gggctggaac tgcctctgcg
61 tacccgccgc ccgtttccgc cctcccgctc ctcccacgcg tgccgcccgg gaccccgcag
121 caccgctgcc ccgatccgag ccctccaccc ccactccggt ccccctcctc tcttcccgga
181 agcgcggcgc gtggcggccc ggcggcgcgg attggacgcg tggcacctac agagacaccc
241 ggggggggtgg gacggaggcc cctaacggct agcagaggaa ctgtgtcttg tcatcaggaa
301 ccccatgcag cccgaaccca agcttagcgg ggctccccgc agcagccagt tcctgcccct
361 gtggtcaaag tgccccgagg gggccgggga cgcagtgatg tatgcctcca cggagtgcaa
421 ggcagaggtg acgccctcgc aggacggtaa ccgaaccttc agctacacac tagaggatca
481 caccaagcag gcttttggcg tcatgaacga gcttcgcctg agccagcaac tctgtgacgt
541 gaccctgcag gtcaaatatg aggacatccc agctgcccaa ttcatggctc acaaagtggt
601 gctggcctcc tccagcccag tctttaaagc catgttcacc aacgggcttc gggagcaggg
661 catggaggtg gtgtccatcg aaggcatcca ccctaaggtc atggaaaggc ttattgagtt
721 cgcctacacg gcctccatct ccgtgggcga gaagtgtgtc ctgcacgtga tgaacggggc
781 ggtcatgtac cagattgaca gcgtggttcg agcctgcagc gacttcctcg tgcagcagct
841 ggaccccagc aacgccattg gcatcgccaa cttcgcggag cagatcggct gcactgaact
901 gcaccagcgt gcccgggagt atatctacat gcacttcggg gaggtggcca agcaggagga
961 gttcttcaac ctgtcacact gccagctggc cacgctcatc agccgggatg atctgaacgt
1021 acgctgcgag tccgaggtgt tccacgcgtg catcgactgg gtcaaatacg actgcccgca
1081 gcggcgcttc tacgtgcagg cactgctgcg ggccgtgcgc tgccatgcgc tcacgccgcg
1141 cttcctgcag acgcagctgc agaagtgtga gatcctgcag gccgacgcgc gctgcaagga
1201 ctacctggtg cagatattcc aggagctcac gctgcacaag cccacgcagg cagtgccctg
1261 ccgcgcgccc aaagtgggcc gcctcatcta cacagcgggc ggttacttcc gacagtcgct
1321 cagctacctg gaggcctaca acccgagcaa tggctcctgg ctgcgcctgg ccgatctaca
1381 ggtgccgcgc agtgggctgg caggctgcgt ggtgggtggg ctgctatacg ctgtgggcgg
1441 ccgcaacaac tctccggatg gcaacactga ctccagcgcc ctggactgct acaaccccat
1501 gaccaaccag tggtcgccct gtgcctctat gagcgtgcca cgcaaccgca tcggggtggg
1561 ggtcatagat ggccacatct acgcagtcgg gggttcccac ggctgcatcc accacagcag
1621 cgtggagaga tatgagccag agcgggacga gtggcatcta gtcgcgccaa tgttgacacg
1681 gaggattggc gtgggcgtgg cagtgctcaa ccgcttgctg tatgcagtgg ggggctttga
1741 cgggactaac cggcttaact ccgcagaatg ttactatcca gagaggaatg agtggcggat
1801 gatcacaccg atgaatacca tccggagcgg ggccggggtc tgcgtgctgc acaactgtat
1861 ctatgcagca ggggggctacg atgggcagga ccagttgaac agtgtggagc gctacgacgt
1921 ggagacagag acctggactt tcgtagcccc catgaggcat caccgtagtg cgctggggat
1981 tactgtgcac cagggcaaga tctacgtcct cggaggctat gatggccaca cttttctgga
2041 cagtgtggaa tgctatgacc cggacagtga tacctggagt gaggtgaccc gcatgacatc
2101 tggccgcagc ggggtgggtg tggccgtcac catggaaccc tgtcggaagc aaattgatca
2161 acaaaactgt acctgctgaa gcacttggaa tacctgagca ctgacaacag gacagaaaaa
2221 cagtctgtgt atcactgctt ctctgtacta aagaaaaaag aagaaaacaa agcataaaca
2281 gaaaacacag ggccgaagag gcggcagaag aagtcatccc ttcttccagg aagggcgact
2341 gggatgcctt gtaaaggacc ttgtggaaga ccagaactca aatccatggg cccatctgtc
2401 atagccctgg agcgtccaag tctgggatgg ggtatgggcg gggcaccctc acaggtgaga
2461 agcccttgaa ctcccaccac cagaaggggg gggacaggca aagcaggaga tcacatgttt
2521 ttttctttgg ttcctgcaac tcggtgatca attccagtgg acaggggaag aagggacagc
2581 tgaggccaag ggctgaggc tccctctgga actggggccc aagggacaag ccggcacaga
2641 gaagcctctg ggctctgagc cctgaacagt tattttgtta aataaccctg taagtttccc
2701 atgggaataa agaatggagt aggcacacag gtcttcagag ggcggtcgga atccctcagg
2761 gagagacagc tcttctattg aaatacacgc agatcctgat ggggctggta tctgaaaccc
2821 gtctattgtc tctgcttgcc attgtacatt ctgctcagac agggcatctt gcttcttgtg
2881 ggacacacag ttgtctgtca gtttcagggc attagaagcc aatgacctaa cttctgtgcc
2941 tcctaacttc tcctggggcc tcctgtgttt agctttattt tgaggcaggg actcacgtcg
3001 tccgggatgg ccttcagttc agaccttgaa ctgacgctgc cgcctgtccc agcctaccga
3061 gtgctggggc tacatctgta tagcgcaatg cctggttcct gcttattatt tttgtaccca
3121 agcaggaaaa taaaggtttc tgggacattg g SEQ ID NO: 35 *Mus musculus* KEAP1 cDNA, transcript variant 4 (NM_016679.4;
CDS: 1624-3498)
1 agacccacgc cctgctccct ccgcccggca cctgcaggaa gggctggaac tgcctctgcg
61 tacccgccgc ccgtttccgc cctcccgctc ctcccacgcg tgccgcccgg gaccccgcag
121 caccgctgcc ccgatccgag ccctccaccc ccactccggt ccccctcctc tcttcccgga
181 agcgcggcgc gtggcggccc ggcggcgcgg attggacgcg tggcacctac agagacaccc
241 ggggggggtgg gacggaggtg agcgagcgcc cgcggaggat gcggtgggga gccagctccg
301 ggagctgccc gcggtcgcgc gtggggccgt gcacgcggtg gggggaagcg cgtgcccttc
361 tccaagcgcg caccccgccg ccgagcccgt gagccctcgt agggtggtgg ccgcggcgag
421 tagaggtagg ggtcgcccgc ggccggcgcc ccgggactct tattgtgaca gggtggcgcg
481 ctgtgcttag tcaccgtgac ccgcgcggcg gaggcggagg cagagcgcgg ccatggcggg
541 gtgagtgagc cgctccaggc cgcggcccgg gaccaggccc tgcgggctct cccggcgtca
601 gggctgcgcc tccgagcggt ggggaggccg ctggagcagg cgccgggtac cgggcggccg
661 ctgcacagcc ccctgcgcaa tgccaggccc gagctccggc agtgtggtca cgcgtgacag TABLE 1B -continued KEAP1
Inhibiting mutations of NQO1, including loss-of-function mutations of NQO1
Inhibiting mutations of NRF2, including loss-of-function mutations of NRF2

721 tcgctcacta gctggggccc ctggagcatt tcatcccccc cctccccacg gtgatctaat
781 agacaaaaca cgcggagtcg cgactccagg ctgagcccag aacctgggga gccagacgca
841 gaccctctct tgtctcccca catcttcttt gaaagcataa ttcctcccct ggccccaggt
901 ctccaagggt ctcctgaatc cctccccgtg ggtgttccag atgctgcaca ctctcttgcc
961 ccaggagctt ggtgttcgct tagtgtttcc tatacagacc ttgctttatt tttaggcctt
1021 ttctgtcttc tcgctgtgtc tctggagctc agagcagtcc caaatacata aatggcaggc
1081 tctgtaaatg ttggtgtggt gttgaaagga atctgacatg ttggacgaag gcaaggggag
1141 ggaaggatgg ctggaacagt gaagaggttg gaaagcgggt gtggagtttt acaggccatt
1201 gacgatttgg ggtttccatt cttgggctcg gtgaaaggtg ttgggtgatt ctgagcagga
1261 aaaggaacat gatatgccct gaaggcccgc gagttgagaa gttagtttga atggagccgg
1321 ctgtgtccag tttacttggc ttggcaaaat ctgcacttag atatcattgc ttagtcttgc
1381 aaaaaaagaa gcctggctgg acatggtggc acatactgta atcccagcac tcgggaggag
1441 ccagctttgg ttgcatagtg agttggaagc cagcctaggc tatgtaagac cctgtctcaa
1501 ataaaataaa ataaagtggc agggtctggt ctaacccagc ctctgttccc agcgctgtgc
1561 tcttccctcc ctccaggccc ctaacggcta gcagaggaac tgtgtcttgt catcaggaac
1621 cccatgcagc ccgaacccaa gcttagcggg gctccccgca gcagccagtt cctgcccctg
1681 tggtcaaagt gccccgaggg ggccggggac gcagtgatgt atgcctccac ggagtgcaag
1741 gcagaggtga cgccctcgca ggacggtaac cgaaccttca gctacacact agaggatcac
1801 accaagcagg cttttggcgt catgaacgag cttcgcctga gccagcaact ctgtgacgtg
1861 accctgcagg tcaaatatga ggacatccca gctgcccaat tcatggctca caaagtggtg
1921 ctggcctcct ccagcccagt ctttaaagcc atgttcacca acgggcttcg ggagcagggc
1981 atggaggtgg tgtccatcga aggcatccac cctaaggtca tggaaaggct tattgagttc
2041 gcctacacgg cctccatctc cgtgggcgag aagtgtgtcc tgcacgtgat gaacggggcg
2101 gtcatgtacc agattgacag cgtggttcga gcctgcagcg acttcctcgt gcagcagctg
2161 gaccccagca acgccattgg catcgccaac ttcgcggagc agatcggctg cactgaactg
2221 caccagcgtg cccgggagta tatctacatg cacttcgggg aggtggccaa gcaggaggag
2281 ttcttcaacc tgtcacactg ccagctggcc acgctcatca gccgggatga tctgaacgta
2341 cgctgcgagt ccgaggtgtt ccacgcgtgc atcgactggg tcaaatacga ctgcccgcag
2401 cggcgcttct acgtgcaggc actgctgcgg gccgtgcgct gccatgcgct cacgccgcgc
2461 ttcctgcaga cgcagctgca gaagtgtgag atcctgcagg ccgacgcgcg ctgcaaggac
2521 tacctggtgc agatattcca ggagctcacg ctgcacaagc ccacgcaggc agtgccctgc
2581 cgcgcgccca aagtgggccg cctcatctac acagcgggcg gttacttccg acagtcgctc
2641 agctacctgg aggcctacaa cccgagcaat ggctcctggc tgcgcctggc cgatctacag
2701 gtgccgcgca gtgggctggc aggctgcgtg gtgggtgggc tgctatacgc tgtgggcggc
2761 cgcaacaact ctccggatgg caacactgac tccagcgccc tggactgcta caaccccatg
2821 accaaccagt ggtcgccctg tgcctctatg agcgtgccac gcaaccgcat cggggtgggg
2881 gtcatagatg gccacatcta cgcagtcggg ggttcccacg gctgcatcca ccacagcagc
2941 gtggagagat atgagccaga gcgggacgag tggcatctag tcgcgccaat gttgacacgg
3001 aggattggcg tgggcgtggc agtgctcaac cgcttgctgt atgcagtggg gggctttgac
3061 gggactaacc ggcttaactc cgcagaatgt tactatccag agaggaatga gtggcggatg
3121 atcacaccga tgaataccat ccggagcggg gccggggtct gcgtgctgca caactgtatc
3181 tatgcagcag gggctacga tgggcaggac cagttgaaca gtgtggagcg ctacgacgtg
3241 gagacagaga cctggacttt cgtagccccc atgaggcatc accgtagtgc gctggggatt
3301 actgtgcacc agggcaagat ctacgtcctc ggaggctatg atggccacac ttttctggac
3361 agtgtggaat gctatgaccc ggacagtgat acctggagtg aggtgacccg catgacatct
3421 ggccgcagcg gggtgggtgt ggccgtcacc atggaaccct gtcggaagca aattgatcaa
3481 caaaactgta cctgctgaag cacttggaat acctgagcac tgacaacagg acagaaaaac
3541 agtctgtgta tcactgcttc tctgtactaa agaaaaaaga agaaaacaaa gcataaacag
3601 aaaacacagg gccgaagagg cggcagaaga agtcatccct tcttccagga agggcgactg
3661 ggatgccttg taaaggacct tgtggaagac cagaactcaa atccatgggc ccatctgtca
3721 tagccctgga gcgtccaagt ctgggatggg gtatgggcgg ggcaccctca caggtgagaa
3781 gcccttgaac tcccaccacc agaagggggg ggacaggcaa agcaggagat cacatgtttt
3841 tttctttggt tcctgcaact cggtgatcaa ttccagtgga caggggaaga agggacagct
3901 gaggccaagg ggctgaggct ccctctggaa ctggggccca agggacaagc cggcacagag
3961 aagcctctgg gctctgagcc ctgaacagtt attttgttaa ataaccctgt aagtttccca
4021 tgggaataaa gaatggagta ggcacacagg tcttcagagg gcggtcggaa tccctcaggg
4081 agagacagct cttctattga aatacacgca gatcctgatg gggctggtat ctgaaacccg
4141 tctattgtct ctgcttgcca ttgtacattc tgctcagaca gggcatcttg cttcttgtgg
4201 gacacacagt tgtctgtcag tttcagggca ttagaagcca atgacctaac ttctgtgcct
4261 cctaacttct cctggggcct cctgtgttta gctttatttt gaggcaggga ctcacgtcgt
4321 ccgggatggc cttcagttca gaccttgaac tgacgctgcc gcctgtccca gcctaccgag
4381 tgctggggct acatctgtat agcgcaatgc ctggttcctg cttattattt ttgtacccaa
4441 gcaggaaaat aaaggtttct gggacattgg SEQ ID NO: 36 *Mus musculus* KEAP1 amino acid sequence, isoform 1 (NP_001103775.1)

1 mqpepklsga prssqflplw skcpegagda vmyastecka evtpsqdgnr tfsytledht
61 kgafgvmnel rlsqqlcdvt lqvkyedipa aqfmahkvvl assspvfkam ftnglreqgm
121 evvsiegihp kvmerliefa ytasisvgek cvlhvmngav myqidsvvra csdflvqqld
181 psnaigianf aegigctelh qrareyiymh fgevakqeef fnlshcqlat lisrddlnvr
241 cesevfhaci dwvkydcpqr rfyvqallra vrchaltprf lqtqlqkcei lqadarckdy
301 lvqifgeltl hkptgavpcr apkvgrliyt aggyfrqsls yleaynpsng swlrladlqv
361 prsglagcvv ggllyavggr nnspdgntds saldcynpmt nqwspcasms vprnrigvgv
421 idghiyavgg shgcihhssv eryeperdew hlvapmltrr igvgvavinr llyavggfdg
481 tnrinsaecy ypernewrmi tpmntirsga gvcvlhnciy aaggydgqdq lnsverydve
541 tetwtfvapm rhhrsalgit vhqgkiyvlg gydghtflds vecydpdsdt wsevtrmtsg TABLE 1B -continued KEAP1
Inhibiting mutations of NQO1, including loss-of-function mutations of NQO1
Inhibiting mutations of NRF2, including loss-of-function mutations of NRF2

```
601 rsgvgvavtm epcrkgidgq nctc
```

SEQ ID NO: 37 *Mus musculus* KEAP1 amino acid sequence, isoform 2 (NP_001103776.1)

```
  1 mqpepklsga prssqflplw skcpegagda vmyastecka evtpsqdgnr tfsytledht
 61 kgafgvmnel rlsqqlcdvt lqvkyedipa aqfmahkvvl assspvfkam ftnglreqgm
121 evvsiegihp kvmerliefa ytasisvgek cvlhvmngav myqidsvvra csdflvqqld
181 psnaigianf aegigctelh qrareyiymh fgevakqeef fnlshcqlat lisrddlnvr
241 cesevfhaci dwvkydcpqr rfyvqallra vrchaltprf lqtqlqkcei lqadarckdy
301 lvqifgeltl hkptgavpcr apkvgrliyt aggyfrqsls yleaynpsng swlrladlqv
361 prsglagcvv ggllyavggr nnspdgntds saldcynpmt nqwspcasms vprnrigvgv
421 idghiyavgg shgcihhssv eryeperdew hlvapmltrr igvgvavinr llyavggfdg
481 tnrinsaecy ypernewrmi tpmntirsga gvcvlhnciy aaggydgqdq lnsverydve
541 tetwtfvapm rhhrsalgit vhqgkiyvlg gydghtflds vecydpdsdt wsevtrmtsg
601 rsgvgvavtm epcrkgidgq nctc
```

SEQ ID NO: 38 *Mus musculus* KEAP1 amino acid sequence, isoform 3 (NP_001103777.1)

```
  1 mqpepklsga prssqflplw skcpegagda vmyastecka evtpsqdgnr tfsytledht
 61 kgafgvmnel rlsqqlcdvt lqvkyedipa aqfmahkvvl assspvfkam ftnglreqgm
121 evvsiegihp kvmerliefa ytasisvgek cvlhvmngav myqidsvvra csdflvqqld
181 psnaigianf aegigctelh qrareyiymh fgevakqeef fnlshcqlat lisrddlnvr
241 cesevfhaci dwvkydcpqr rfyvqallra vrchaltprf lqtqlqkcei lqadarckdy
301 lvqifgeltl hkptgavpcr apkvgrliyt aggyfrqsls yleaynpsng swlrladlqv
361 prsglagcvv ggllyavggr nnspdgntds saldcynpmt nqwspcasms vprnrigvgv
421 idghiyavgg shgcihhssv eryeperdew hlvapmltrr igvgvavinr llyavggfdg
481 tnrinsaecy ypernewrmi tpmntirsga gvcvlhnciy aaggydgqdq lnsverydve
541 tetwtfvapm rhhrsalgit vhqgkiyvlg gydghtflds vecydpdsdt wsevtrmtsg
601 rsgvgvavtm epcrkgidgq nctc
```

SEQ ID NO: 39 *Mus musculus* KEAP1 amino acid sequence, isoform 4 (NP_057888.1)

```
  1 mqpepklsga prssqflplw skcpegagda vmyastecka evtpsqdgnr tfsytledht
 61 kgafgvmnel rlsqqlcdvt lqvkyedipa aqfmahkvvl assspvfkam ftnglreqgm
121 evvsiegihp kvmerliefa ytasisvgek cvlhvmngav myqidsvvra csdflvqqld
181 psnaigianf aegigctelh qrareyiymh fgevakqeef fnlshcqlat lisrddlnvr
241 cesevfhaci dwvkydcpqr rfyvqallra vrchaltprf lqtqlqkcei lqadarckdy
301 lvqifgeltl hkptgavpcr apkvgrliyt aggyfrqsls yleaynpsng swlrladlqv
361 prsglagcvv ggllyavggr nnspdgntds saldcynpmt nqwspcasms vprnrigvgv
421 idghiyavgg shgcihhssv eryeperdew hlvapmltrr igvgvavinr llyavggfdg
481 tnrinsaecy ypernewrmi tpmntirsga gvcvlhnciy aaggydgqdq lnsverydve
541 tetwtfvapm rhhrsalgit vhqgkiyvlg gydghtflds vecydpdsdt wsevtrmtsg
601 rsgvgvavtm epcrkgidgq nctc
```

* Included in Table 1B are RNA nucleic acid molecules (e.g., thymines replaced with uridines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1B, or a portion thereof. Such nucleic acid molecules can have a function of the full-length nucleic acid as described further herein.
* Included in Table 1B are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1B, or a portion thereof. Such polypeptides can have a function of the full-length polypeptide as described further herein.
* Included in Table 1B are known NQO1, NRF2 and KEAP1 sequences, including those described herein and homologous sequences thereof, as well as NQO1 or NRF2 null mutations, missense mutations, nonsense mutations, frameshift mutations, insertion mutation, deletion mutations, and rearrangement mutations.

II. Subjects

In one embodiment, the subject for whom predicted likelihood of responsiveness to ML329 or a derivative thereof, is a mammal (e.g., mouse, rat, primate, non-human mammal, domestic animal, such as a dog, cat, cow, horse, and the like), and is preferably a human. In another embodiment, the subject is an animal model of a cancer, such as melanoma, lung cancer, head and neck squamous cell carcinomas, kidney cancer, pancreas cancer, prostate cancer, bladder cancer, uterine cancer, head&neck cancer, or esophagus cancer. For example, the animal model can be an orthotopic xenograft animal model of a human-derived cancer, such as melanoma, lung cancer, head and neck squamous cell carcinomas, kidney cancer, pancreas cancer, prostate cancer, bladder cancer, uterine cancer, head and neck cancer, or esophagus cancer.

In another embodiment of the methods encompassed by the present invention, the subject has not undergone treatment, such as chemotherapy, radiation therapy, targeted therapy, and/or treatment of ML329 or a derivative thereof. In still another embodiment, the subject has undergone treatment, such as chemotherapy, radiation therapy, targeted therapy, and/or treatment of ML329 or a derivative thereof.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods encompassed by the present invention can be used to determine the efficacy of ML329 or a derivative thereof for treating many different cancers in subjects such as those described herein.

III. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be responsive to ML329 or a derivative thereof. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising ML329 or a derivative thereof, alone or in combination with other anti-cancer agents.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments encompassed by the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement. In some embodiments encompassed by the present invention the change of biomarker amount and/or activity measurement(s) from the pre-determined level is about 0.5 fold, about 1.0 fold, about 1.5 fold, about 2.0 fold, about 2.5 fold, about 3.0 fold, about 3.5 fold, about 4.0 fold, about 4.5 fold, or about 5.0 fold or greater. In some embodiments, the fold change is less than about 1, less than about 5, less than about 10, less than about 20, less than about 30, less than about 40, or less than about 50. In other embodiments, the fold change in biomarker amount and/or activity measurement(s) compared to a predetermined level is more than about 1, more than about 5, more than about 10, more than about 20, more than about 30, more than about 40, or more than about 50.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect encompassed by the present invention pertains to the use of isolated nucleic acid molecules that correspond to biomarker nucleic acids (e.g., NQO1, NRF2 and/or KEAP1) that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule encompassed by the present invention can be isolated using standard molecular biology techniques and the sequence information in the database records described herein. Using all or a portion of such nucleic acid sequences, nucleic acid molecules encompassed by the present invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, NY, 1989).

A nucleic acid molecule encompassed by the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule encompassed by the present invention can be prepared by standard synthetic techniques, e.g., using an automated DNA synthesizer.

Moreover, a nucleic acid molecule encompassed by the present invention can comprise only a portion of a nucleic acid sequence, wherein the full length nucleic acid sequence comprises a marker encompassed by the present invention or which encodes a polypeptide corresponding to a marker encompassed by the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers encompassed by the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker encompassed by the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope encompassed by the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker encompassed by the present invention or to a nucleic acid molecule encoding a protein corresponding to a marker encompassed by the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule encompassed by the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect encompassed by the present invention pertains to nucleic acid molecules encoding a polypeptide encompassed by the present invention that contain changes in amino acid residues that are not essential for activity. Such polypeptides differ in amino acid sequence from the naturally-occurring proteins which correspond to the markers encompassed by the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids encompassed by the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid encompassed by the present invention, e.g., complementary to the coding strand of a double-stranded cDNA molecule corresponding to a marker encompassed by the present invention or complementary to an mRNA sequence corresponding to a marker encompassed by the present invention. Accordingly, an antisense nucleic acid molecule encompassed by the present invention can hydrogen bond to (i.e. anneal with) a sense nucleic acid encompassed by the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide encompassed by the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules encompassed by the present invention are typically administered to a subject or generated in situ such that they hybridize with or bind to cellular mRNA and/or genomic DNA encoding a polypeptide corresponding to a selected marker encompassed by the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules encompassed by the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule encompassed by the present invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215: 327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker encompassed by the present invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide encompassed by the present invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules encompassed by the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect encompassed by the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker encompassed by the present invention are produced by recombinant DNA techniques. Alternative to recombinant expression, a polypeptide corresponding to a marker encompassed by the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein encompassed by the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide encompassed by the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules encompassed by the present invention. BLAST protein searches can be performed with the XBLAST program, score=50, wordlength=3 to obtain amino acid sequences homologous to a protein molecules encompassed by the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker encompassed by the present invention operably linked to a heterologous polypeptide (i.e., a polypeptide other than the polypeptide corresponding to the marker). Within the fusion protein, the term "operably linked" is intended to indicate that the polypeptide encompassed by the present invention and the heterologous polypeptide are fused in-frame to each other. The heterologous polypeptide can be fused to the amino-terminus or the carboxyl-terminus of the polypeptide encompassed by the present invention.

One useful fusion protein is a GST fusion protein in which a polypeptide corresponding to a marker encompassed by the present invention is fused to the carboxyl terminus of GST sequences. Such fusion proteins can facilitate the purification of a recombinant polypeptide encompassed by the present invention.

In another embodiment, the fusion protein contains a heterologous signal sequence, immunoglobulin fusion protein, toxin, or other useful protein sequence. Chimeric and fusion proteins encompassed by the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide encompassed by the present invention can be cloned into such an expression vector such that the fusion moiety is linked in-frame to the polypeptide encompassed by the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein encompassed by the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides encompassed by the present invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker encompassed by the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein encompassed by the present invention (Arkin and Yourvan, 1992, *Proc. Natl. Acad. Sci. USA* 89:7811-7815; Delgrave et al., 1993, *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors encompassed by the present invention comprise a nucleic acid encompassed by the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, “operably linked” is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term “regulatory sequence” is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, CA (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors encompassed by the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker encompassed by the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, MA) and pRIT5 (Pharmacia, Piscataway, NJ) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, CA, 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, CA, 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences encompassed by the present invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, CA), and pPicZ (Invitrogen Corp, San Diego, CA).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid encompassed by the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide encompassed by the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect encompassed by the present invention pertains to host cells into which a recombinant expression vector encompassed by the present invention has been introduced. The terms “host cell” and “recombinant host cell” are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms “transformation” and “transfection” are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. The absence of one or more biomarkers listed in Table 1A and/or a copy number of at least 3, 4, 5, 6, 7, 8, 9, or 10 of one or more biomarkers listed in Table 1B is predictive of poorer outcome of the treatment of ML329 or a derivative thereof. The absence of one or more biomarkers listed in Table 1B and/or a copy number of at least 3, 4, 5, 6, 7, 8, 9, or 10 of one or more biomarkers listed in Table 1A is predictive of likely responsive to the treatment of ML329 or a derivative thereof.

Methods of evaluating the copy number of a biomarker locus include, but are not limited to, hybridization-based assays. Hybridization-based assays include, but are not limited to, traditional “direct probe” methods, such as Southern blots, in situ hybridization (e.g., FISH and FISH plus SKY) methods, and “comparative probe” methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402*; Methods in Molecular Biology*, Vol. 33: In situ Hybridization Protocols, Choo, ed., Humana Press, Totowa, N.J. (1994), etc.). In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods encompassed by the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of cancer cells are obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, NY).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope encompassed by the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see, e.g., U.S. Pat. Nos: 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to ML329 or a derivative thereof, treatment. Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}I$, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}I$, $^{121}I$), carbon ($^{14}C$), sulphur ($^{35}S$), tritium ($^{3}H$), indium ($^{112}In$), and technetium ($^{99}mTc$), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection.

Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify NQO1, NRF2 and/or KEAP1 protein that is overexpressed, overfunctional, and the like.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

VI. Anti-Cancer Therapies

The response of a cancer in a subject to the treatment of ML329 or a derivative thereof is predicted according to the methods described herein. In one embodiment, such treatment of ML329 or a derivative thereof can be administered once a subject is indicated as being a likely responder to ML329 or a derivative thereof. In another embodiment, such treatment of ML329 or a derivative thereof can be avoided once a subject is indicated as not being a likely responder to ML329 or a derivative thereof, and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with ML329 or a derivative thereof. ML329 or a derivative thereof described herein, have been described above.

The term "targeted therapy" refers to administration of agents that selectively interact with a chosen biomolecule to thereby treat cancer.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, mitochondrial cofactor therapy is useful. For example, vitamin E is known to block cell death via ferroptosis such that mitochondrial cofactor therapy can alleviate or improve any toxicity associated with ISC biosynthesis pathway inhibition. Mitochondrial cofactor therapies are well known in the art and include, for example, coenzyme Q10 (ubiquinone), riboflavin, thiamin, niacin, vitamin K (phylloquinone and menadione), creatine, carnitine, and other antioxidants such as ascorbic acid and lipoic acid (see, for example, Marriage et al. (2003) *J. Am. Diet. Assoc.* 103:1029-1038 and Parikh et al. (2009) *Curr. Treat. Options Neurol.* 11:414-430).

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, pro-apoptotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; pro-apoptotic agents: venetoclax (ABT-199), navitoclax and Obatoclax; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside (cytarabine); purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of 0-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term “laser” stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. In addition to its use to destroy the cancer, laser surgery is also used to help relieve symptoms caused by cancer (palliative care). It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with ML329 or a derivative thereof may vary according to the particular compound. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods encompassed by the present invention is a factor in determining optimal treatment doses and schedules.

Any means for the introduction of a polynucleotide into mammals, human or non-human, or cells thereof may be adapted to the practice encompassed by the present invention for the delivery of the various constructs encompassed by the present invention into the intended recipient. In one embodiment encompassed by the present invention, the DNA constructs are delivered to cells by transfection, i.e., by delivery of “naked” DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system encompassed by the present invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment encompassed by the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide encompassed by the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth, Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

VII. Clinical Efficacy

Clinical efficacy can be measured by any method known in the art. For example, the response to a therapy, such as treatment of ML329 or a derivative thereof, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) Breast (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular ML329 or a derivative thereof treatment regimen is at least 25%, 30%, 35%, 40%, 45%, 50%, 55%, 60%, 65%, 70%, 75%, 80%, 85%, or more.

Additional criteria for evaluating the response to the treatment of ML329 or a derivative thereof, and/or another agent, is related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular ML329 or a derivative thereof therapeutic regimen can be administered to a population of subjects and the outcome can be correlated to biomarker measurements that were determined prior to administration of any ML329 or a derivative thereof, and/or another agent. The outcome measurement may be pathologic response to therapy given in the neoadjuvant setting. Alternatively, outcome measures, such as overall survival and disease-free survival can be monitored over a period of time for subjects following the treatment of ML329 or a derivative thereof, and/or another agent, for whom biomarker measurement values are known. In certain embodiments, the same doses of ML329 or a derivative thereof, and/or another agent, are administered to each subject. In related embodiments, the doses administered are standard doses known in the art for ML329 or a derivative thereof, and/or another agent. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of treatment of ML329 or a derivative thereof, and/or another agent, can be determined using methods such as those described in the Examples section.

VIII. Further Uses and Methods Encompassed by the Present Invention

The methods described herein can be used in a variety of diagnostic, prognostic, and therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays. The compositions described herein can be used in a variety of diagnostic, prognostic, and therapeutic applications regarding biomarkers described herein, such as those listed in Table 1. Moreover, any method of diagnosis, prognosis, prevention, and the like described herein can be applied to a therapy or test agent of interest, such as ML329 or a derivative thereof, and another agent, and the like.

In addition, in some embodiments, methods encompassed by the present invention can involve the obtention or provision of a sample, such as cancer cells from a subject having cancer. In other embodiments, methods encompassed by the present invention involve analysis of results obtained from a sample having been obtained by another actor.

a. Screening Methods

One aspect encompassed by the present invention relates to screening assays, including non-cell based assays. In one embodiment, the assays provide a method for identifying whether a cancer is likely to respond to anti-cancer therapy (e.g., ML329 or a derivative thereof) and/or whether an agent can inhibit the growth of or kill a cancer cell that is likely to respond to anti-cancer therapy (e.g., ML329 or a derivative thereof).

In one embodiment, the present invention relates to assays for screening test agents which have a cytotoxic or cytostatic effect on cancer cells that have an increased copy number, amount and/or activity of biomarkers listed in Table 1A and/or a decreased copy number, amount, and/or activity of biomarkers listed in Table 1B. In one embodiment, a method for identifying such an agent entails determining the ability of the agent to reduce the viability and/or proliferation of the cancer cells.

In one embodiment, an assay is a cell-free or cell-based assay, comprising contacting at least one biomarker listed in Table 1, with a test agent, and determining the ability of the test agent to modulate (e.g. upregulate) the enzymatic activity of the biomarker, such as by measuring direct binding of substrates or by measuring indirect parameters as described below.

In another embodiment, an assay is a cell-free or cell-based assay, comprising contacting at least one biomarker listed in Table 1, with a test agent, and determining the ability of the test agent to modulate (e.g. upregulate) the ability of the biomarker to regulate translation of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies encompassed by the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and its natural binding partner can be accomplished by determining the ability of the test agent to modulate the activity of a polypeptide or other product that functions downstream or upstream of its position within the same pathway of the biomarker.

The present invention further pertains to novel agents identified by the above-described screening assays. Accordingly, it is within the scope encompassed by the present invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect encompassed by the present invention relates to diagnostic assays for determining the amount and/or activity level of a biomarker listed in Table 1 in the context of a biological sample (e.g., blood, serum, cells, or tissue) to thereby determine whether an individual afflicted with a cancer is likely to respond to the treatment of ML329 or a derivative thereof, whether in an original or recurrent cancer. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers listed in Table 1.

Another aspect encompassed by the present invention pertains to monitoring the influence of agents (e.g., drugs, compounds, and small nucleic acid-based molecules) on the expression or activity of a biomarker listed in Table 1. These and other agents are described in further detail in the following sections.

The skilled artisan will also appreciated that, in certain embodiments, the methods encompassed by the present invention implement a computer program and computer system. For example, a computer program can be used to perform the algorithms described herein. A computer system can also store and manipulate data generated by the methods encompassed by the present invention which comprises a plurality of biomarker signal changes/profiles which can be used by a computer system in implementing the methods encompassed by the present invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part encompassed by the present invention. Numerous types of computer systems can be used to implement the analytic methods encompassed by the present invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods encompassed by the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to treatment of ML329 or a derivative thereof. In some embodiments, the present invention is useful for classifying a sample (e.g., from a subject) as associated with or at risk for responding to or not responding to treatment of ML329 or a derivative thereof, using a statistical algorithm and/or empirical data (e.g., the amount or activity of a biomarker listed in Table 1).

An exemplary method for detecting the amount or activity of a biomarker listed in Table 1, and thus useful for classifying whether a sample is likely or unlikely to respond to treatment of ML329 or a derivative thereof, involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely ML329 or a derivative thereof, responder or progress or sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method encompassed by the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to treatment of ML329 or a derivative thereof, treatment), a biological sample from the subject during remission, or a biological sample from the subject during treatment for developing a cancer progressing despite treatment of ML329 or a derivative thereof, treatment.

d. Prognostic Assays

The diagnostic methods described herein can furthermore be utilized to identify subjects having or at risk of developing a cancer that is likely or unlikely to be responsive to treatment of ML329 or a derivative thereof. The assays described herein, such as the preceding diagnostic assays or the following assays, can be utilized to identify a subject having or at risk of developing a disorder associated with a misregulation of the amount or activity of at least one biomarker described in Table 1, such as in cancer. Alternatively, the prognostic assays can be utilized to identify a subject having or at risk for developing a disorder associated with a misregulation of the at least one biomarker described in Table 1, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

The compositions described herein (including dual binding antibodies and derivatives and conjugates thereof) can be used in a variety of in vitro and in vivo therapeutic applications using the formulations and/or combinations described herein. In one embodiment, ML329 or a derivative thereof, can be used to treat cancers determined to be responsive thereto.

Another aspect encompassed by the present invention pertains to methods of modulating the expression or activity of one or more biomarkers described herein (e.g., those listed in Table 1 and the Examples or fragments thereof) for therapeutic purposes. The biomarkers encompassed by the present invention have been demonstrated to correlate with cancers. Accordingly, the activity and/or expression of the biomarker, as well as the interaction between one or more biomarkers or a fragment thereof and its natural binding partner(s) or a fragment(s) thereof, can be modulated in order to treat cancers.

Another aspect encompassed by the present invention pertains to methods of modulating the expression or activity of one or more biomarkers described herein (e.g., those listed in Table 1 and the Examples or fragments thereof) for therapeutic purposes. The biomarkers encompassed by the present invention have been demonstrated to correlate with cancers. Accordingly, the activity and/or expression of the biomarker, as well as the interaction between one or more biomarkers or a fragment thereof and its natural binding partner(s) or a fragment(s) thereof, can be modulated in order to treat cancers.

Modulatory methods encompassed by the present invention involve contacting a cell with one or more biomarkers encompassed by the present invention, including one or more biomarkers encompassed by the present invention, including one or more biomarkers listed in Table 1 and the Examples or a fragment thereof or agent that modulates one or more of the activities of biomarker activity associated with the cell. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers encompassed by the present invention, including one or more biomarkers encompassed by the present invention, including one or more biomarkers listed in Table 1 and the Examples or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 μg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers encompassed by the present invention, including one or more biomarkers listed in Table 1 and the Examples or a fragment thereof. Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan). In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers encompassed by the present invention listed in Table 1 and the Examples or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular cancer, being treated, the extent of the disease and other factors familiar to the physician of skill in the art and can be determined by the physician.

IX. Pharmaceutical Compositions

In another aspect, the present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions encompassed by the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present invention. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods encompassed by the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods encompassed by the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope encompassed by the present invention.

Pharmaceutical compositions encompassed by the present invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions encompassed by the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents encompassed by the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions encompassed by the present invention may be determined by the methods encompassed by the present invention so as to obtain an amount of the active ingredient, which is effective to achieve the desired therapeutic response for a particular subject, composition, and mode of administration, without being toxic to the subject.

The nucleic acid molecules encompassed by the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit encompassed by the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

Other embodiments encompassed by the present invention are described in the following Examples. The present invention is further illustrated by the following examples which should not be construed as further limiting.

EXEMPLIFICATION

Figure 11A:
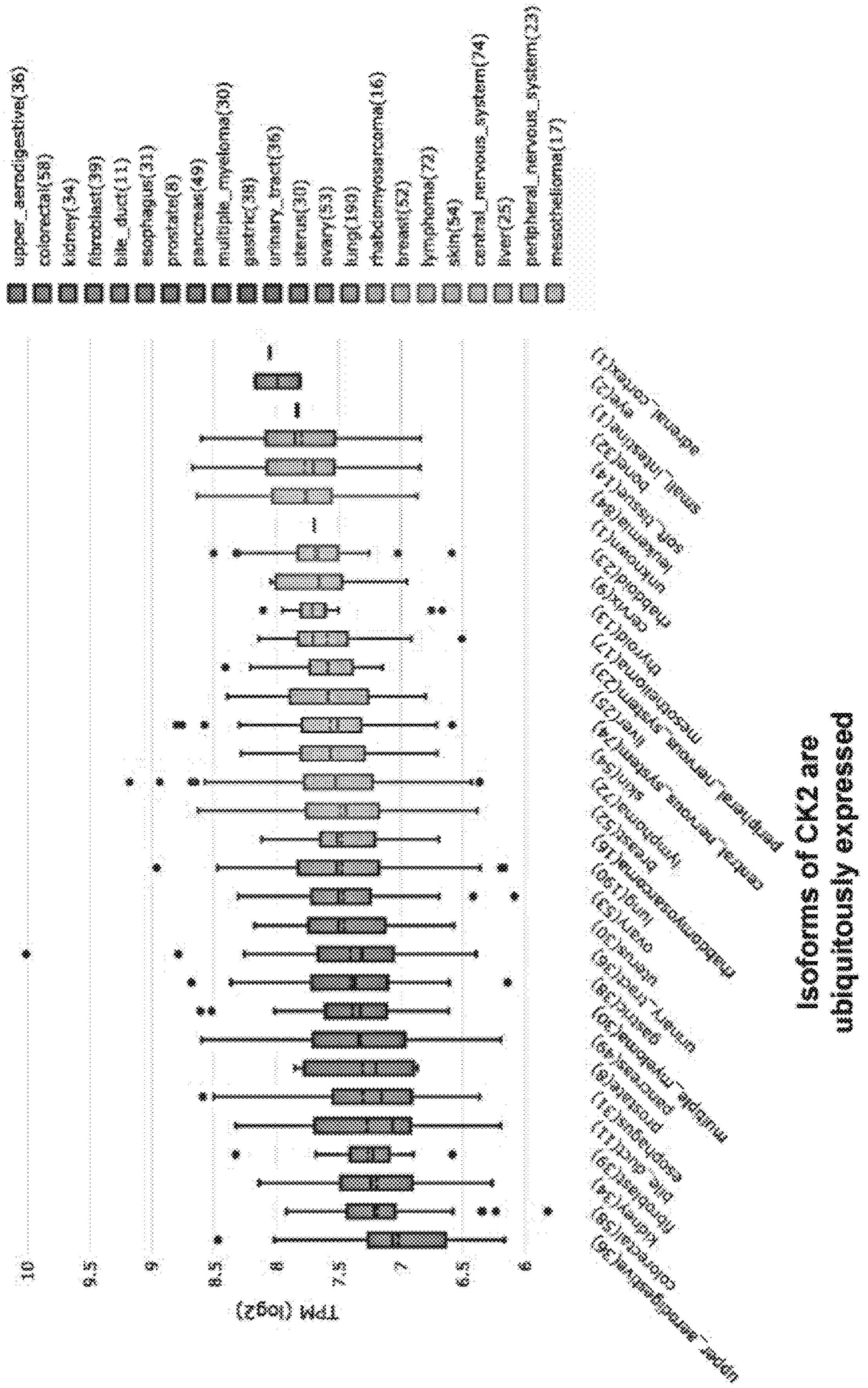
FIG. 11A and FIG. 11B show that CK2 is expressed ubiquitously and required for cellular survival.
Figure 11B:
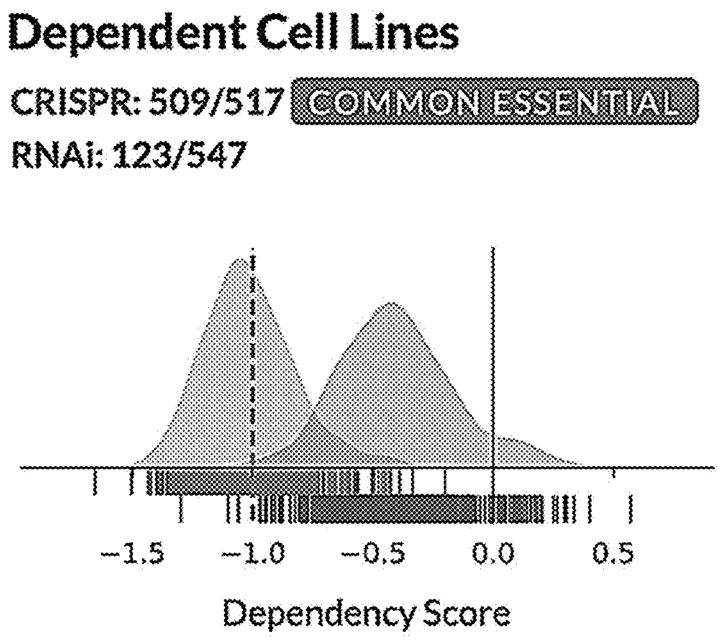
Figure 12:
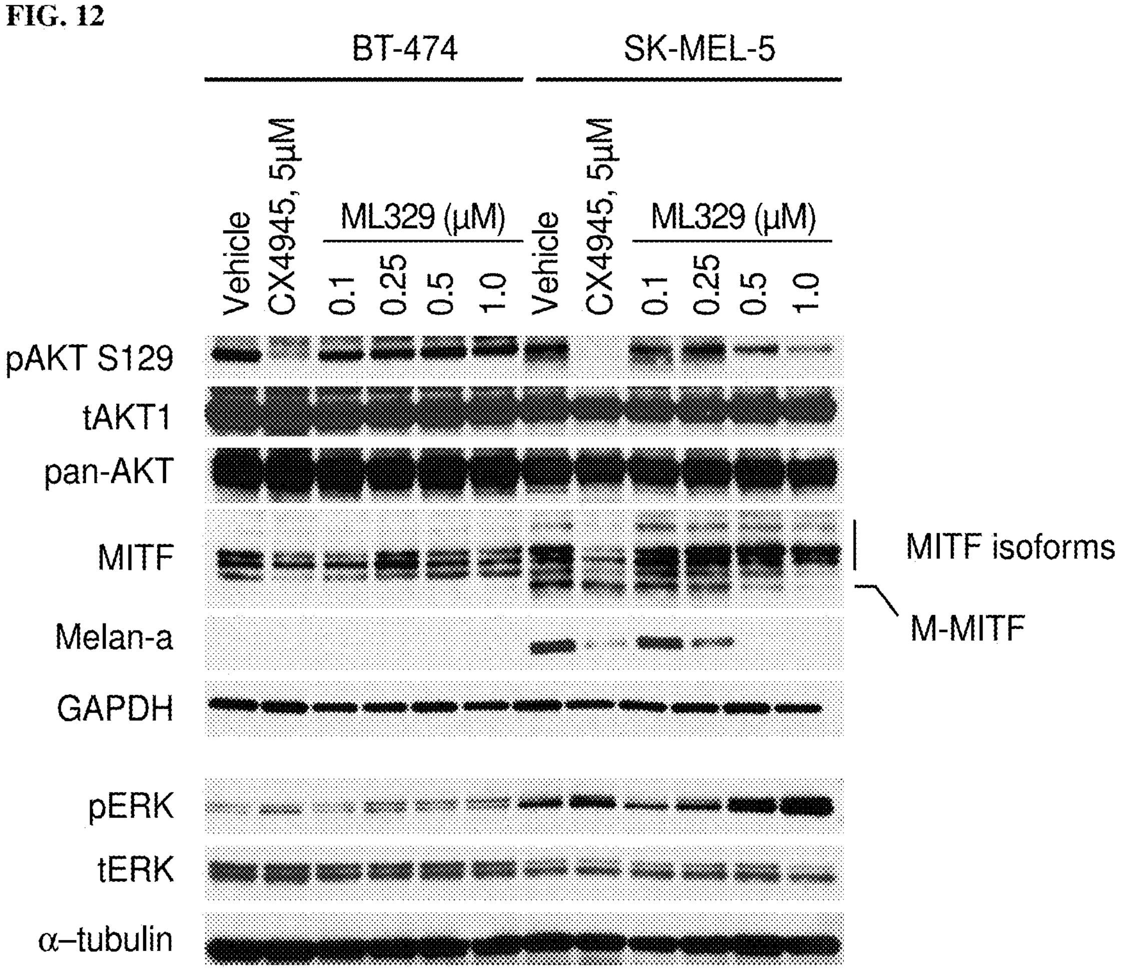
FIG. 12 shows that other CK2 inhibitors do not exhibit melanoma-specificity.
Figure 13:
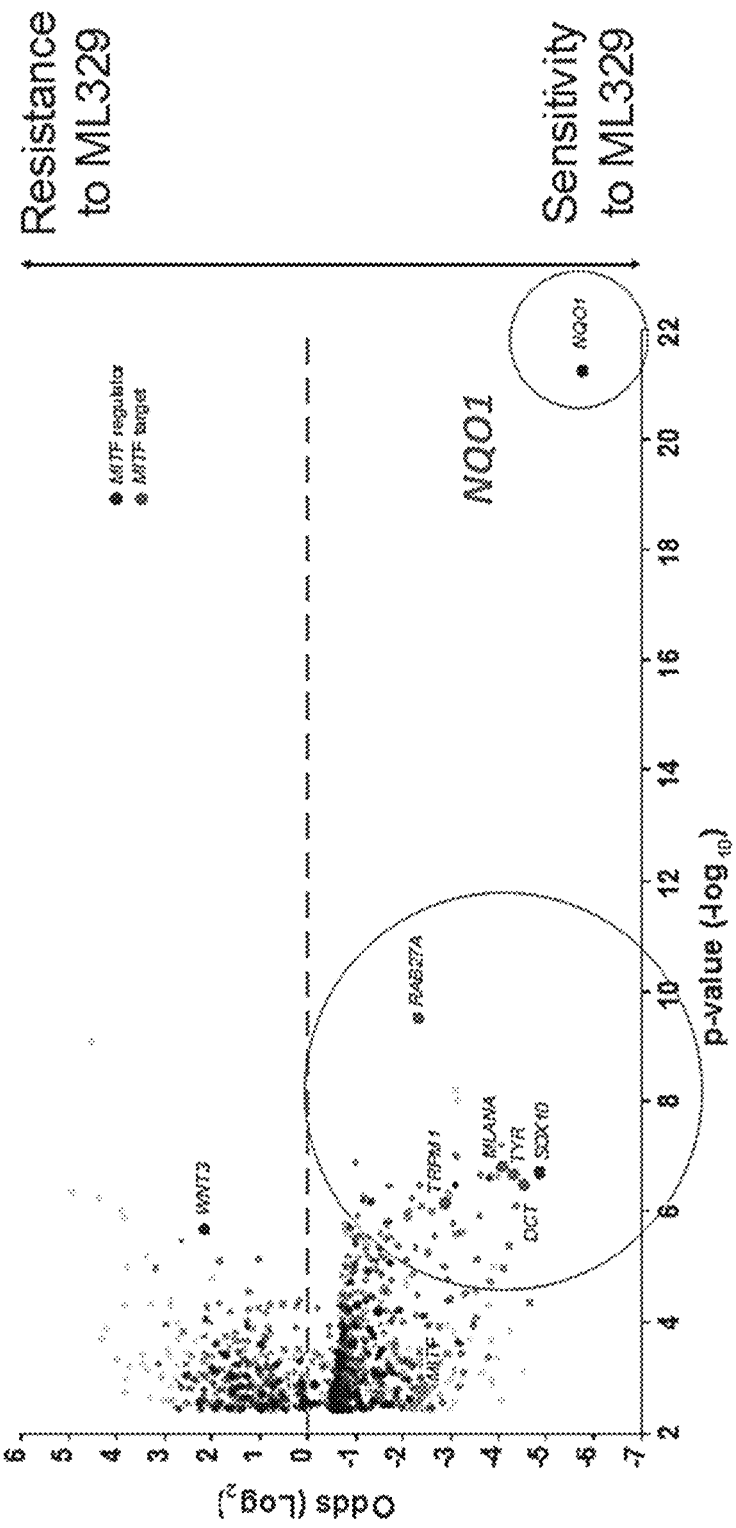
FIG. 13 shows the results of gene expression correlated with ML329 sensitivity in ~500 cell lines.
Figure 14:
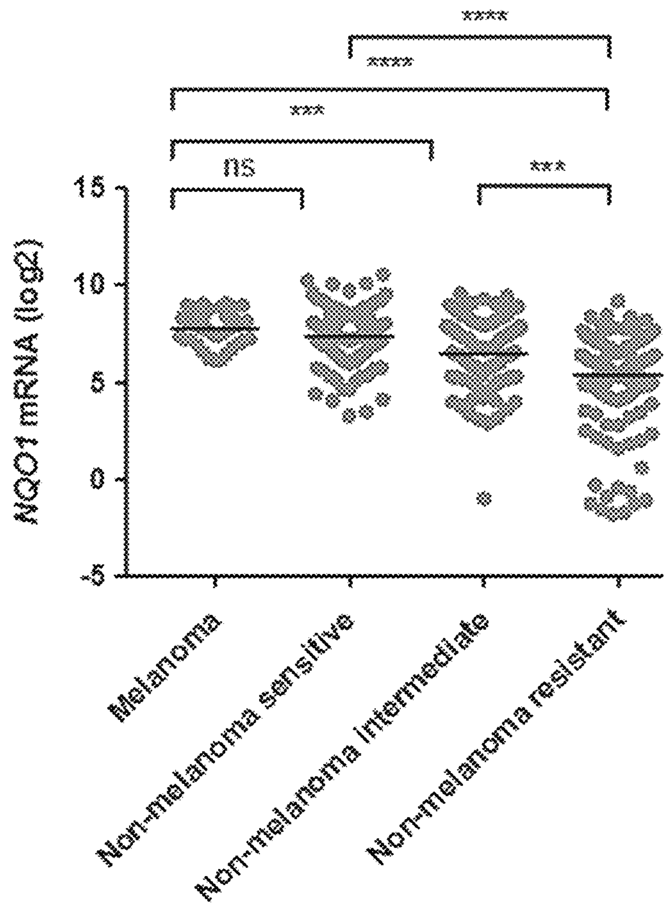
FIG. 14 shows that NQO1 is most highly expressed in melanoma.
Figure 15:
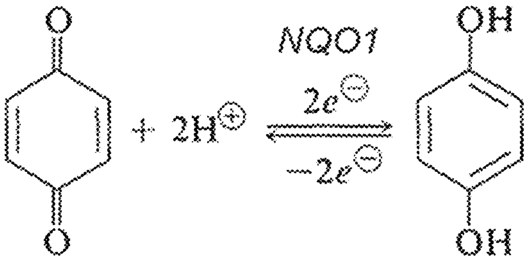
FIG. 15 shows that NQO1 is sufficient to reduce quinones.
Figure 15:
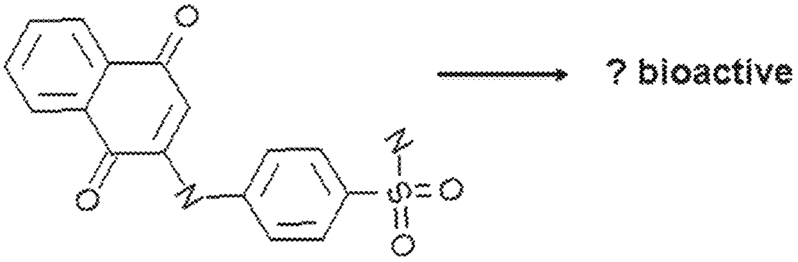
Figure 16A:
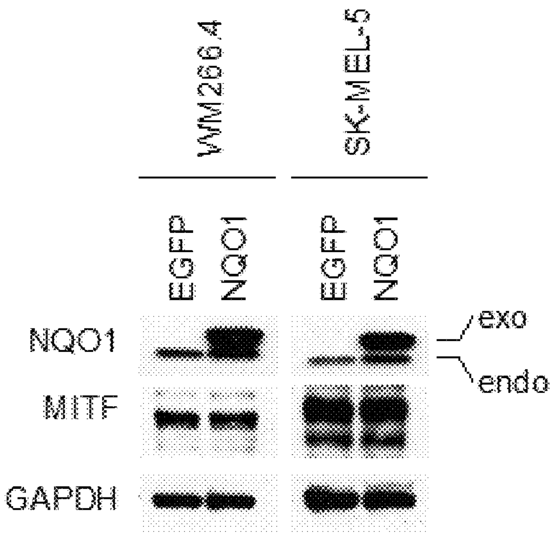
FIG. 16A-FIG. 16C show that NQO1 sensitizes cancer cells to ML329 cytotoxicity.
Figure 16B:
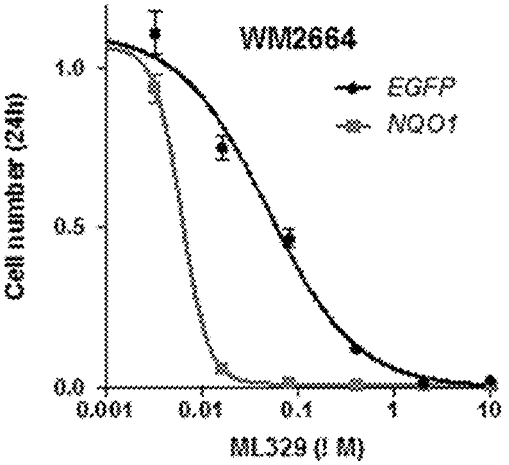
Figure 16C:
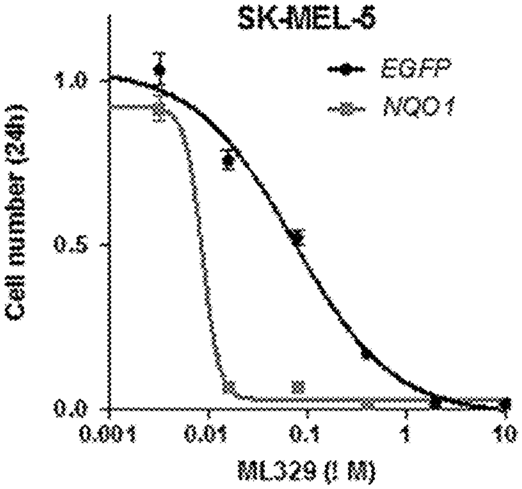
Figure 17:
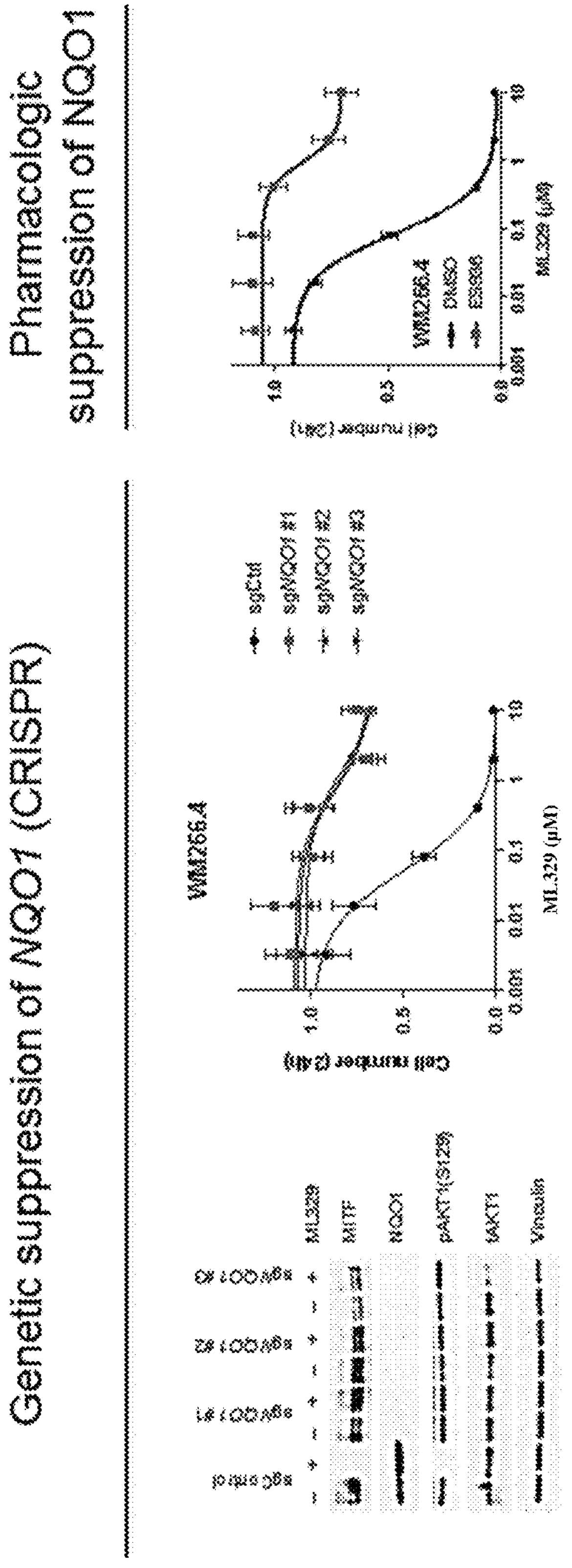
FIG. 17 shows that NQO1 is necessary for ML329 cytotoxicity and suppression of MITF.
Figure 18:
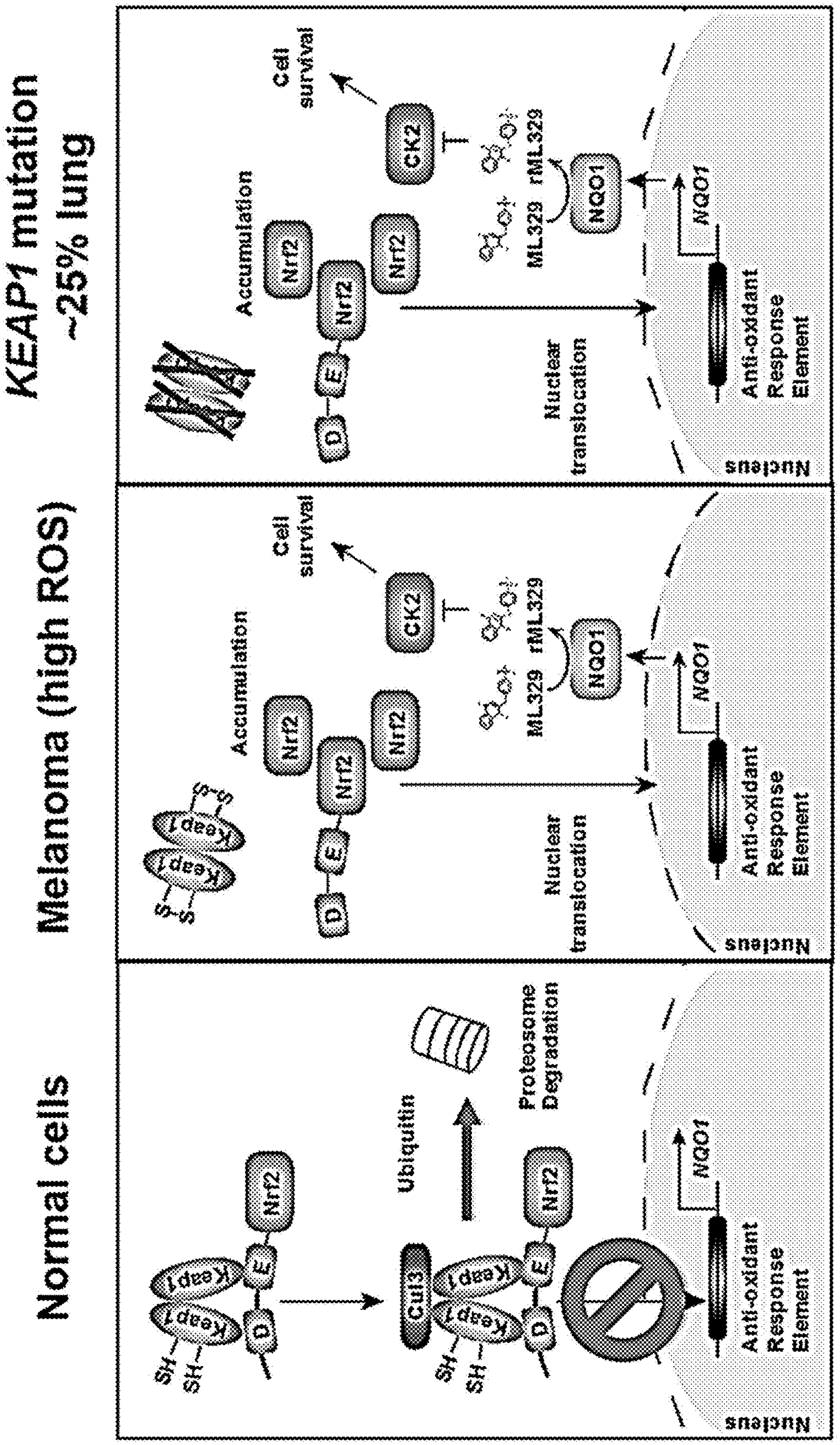
FIG. 18 shows a depiction of the mechanism of ML329 bioreduction and CK2 inhibition.
Figure 19:
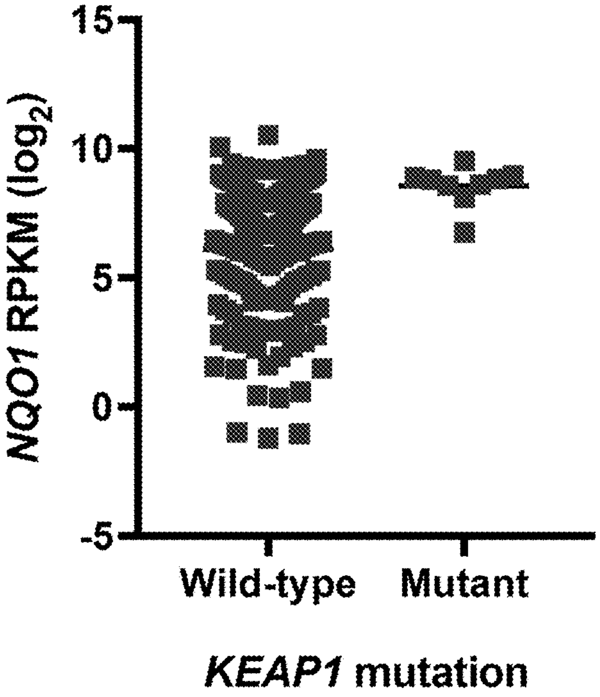
FIG. 19 shows that KEAP1-mutant lung cancer cells have elevated NQO1.
Figure 20:
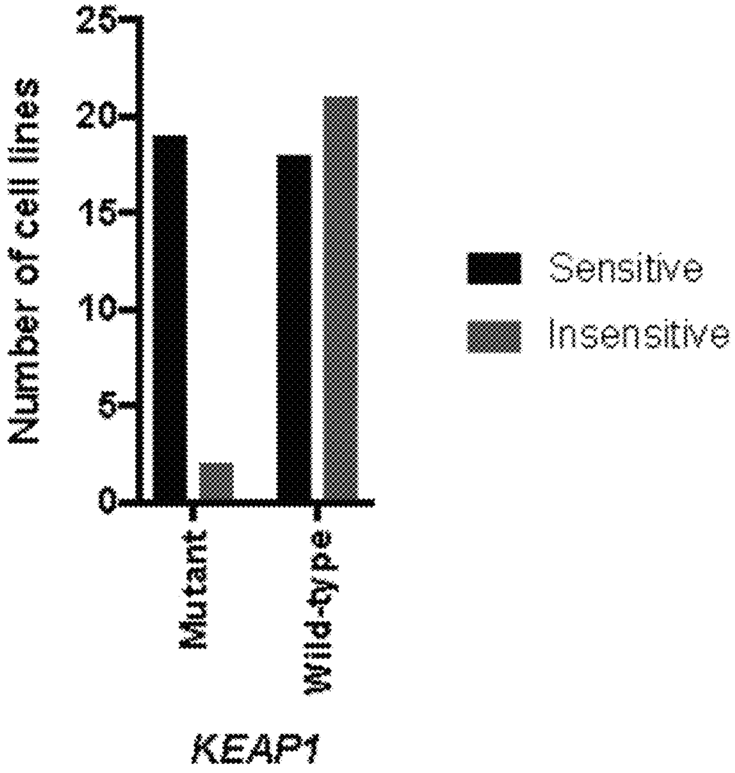
FIG. 20 shows that KEAP1-mutant lung cancer cells are sensitive to ML329.
Figure 21:
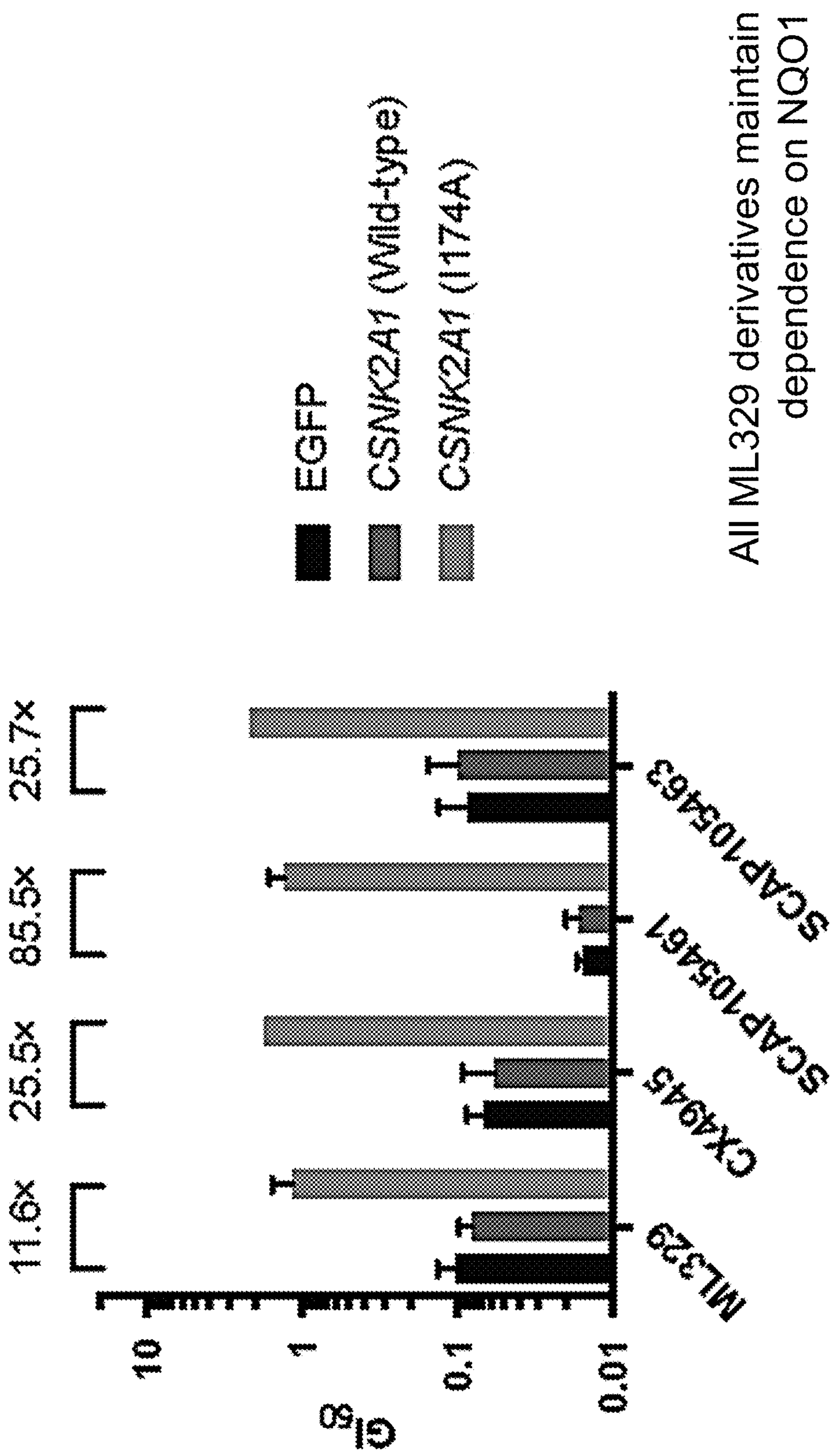
FIG. 21 shows that SAR identified more potent and selective NQO1-dependent CK2 inhibitors. All ML329 derivatices maintain dependence on NQO1.

Example 1: ML329 and Derivatives Thereof Selectively Target Cancer Cells with Increased NQO1 Expression and/or Activity ML329 (4-[(1,4-dioxo-1,4-dihydronapthalen-2-yl)amino] benzenesulfonamide; KUC114363) is a small molecule that was initially identified as an inhibitor of microphthalmia-associated transcription factor (MITF) (FIGS. 1-6). Briefly, Sk-MEL-5 melanoma cells expressing the promoter of MITF target TRPM1, upstreatm of a luciferase gene, were screened with a library of 331,578 compounds. Secondary screening was performed in two MITF-dependent melanoma cell links (SK-MEL-5 and MALME) and one non-MITF dependent cell line (A375). Candidate hits were tested for their effects on MITF target genes by qPCR. BRD-K45681478 was prioritized for medicinal chemistry. The lead compounds ML329 was used in subsequent studies. ML329 was found to associate with the protein kinase, CK2 (FIGS. 7-10). CK2 is an essential kinase and its reduction/inhibition is lethal (FIG. 11 and FIG. 12). Experiments were performed to determine that ML329 is bioreduced by an enzyme called NQO1, which is preferentially expressed in some cancer types, especially melanoma (FIGS. 13-15). Since ML329 is converted by cancer cells into an active form, it can avoid effects on normal cells. NQO1 is necessary and sufficient for the activity of ML329, thus enabling targeting of CK2 specifically to cancers with high NQO1 expression (FIGS. 16-18). For example, it was found that a group of lung cancers, characterized by a mutation in KEAP1 were selectively killed by ML329. NQO1 is highly expressed upon mutation of KEAP1 (FIG. 19), which is found in ~25% of lung cancers and smaller numbers of other cancer types. Greater than 90% of KEAP1-mutant lung cancers were determined to be sensitive to ML329 (FIG. 20). Other cancers that dysregulate KEAP1/NRF2 also exhibited sensitivity. SAR identified more potent and selective NQO1-dependent CK2 inhibitors, such as CX4945, SCAP105461, and SCAP105463 (FIG. 21).

Figure 22A:
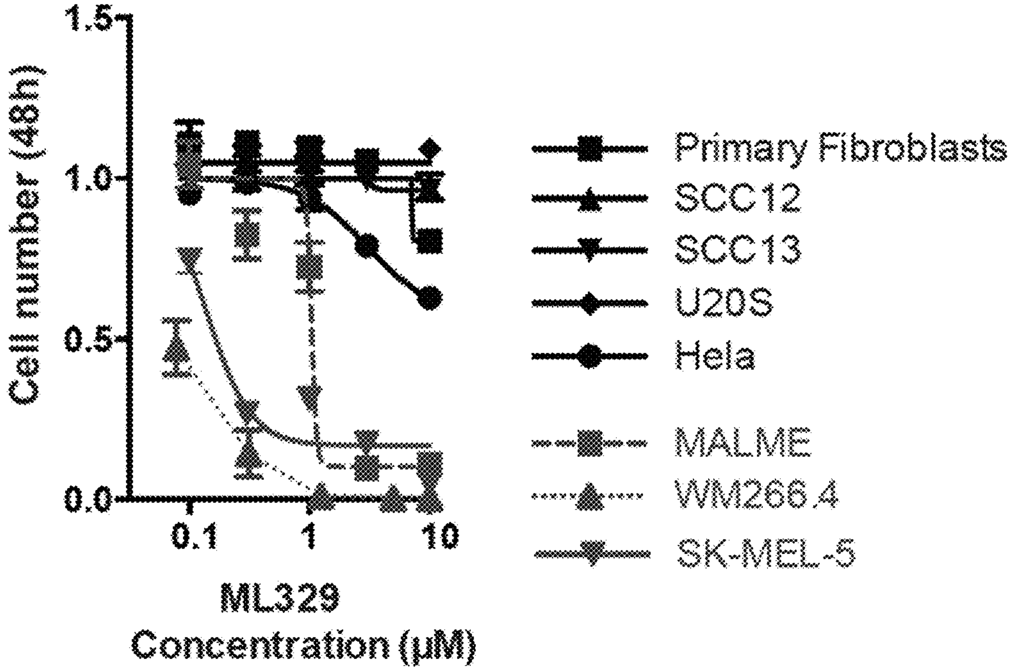
FIG. 22A and FIG. 22B show that ML329 suppresses MITF mRNA and target gene expression and suppresses growth of melanoma cells.
Figure 22B:
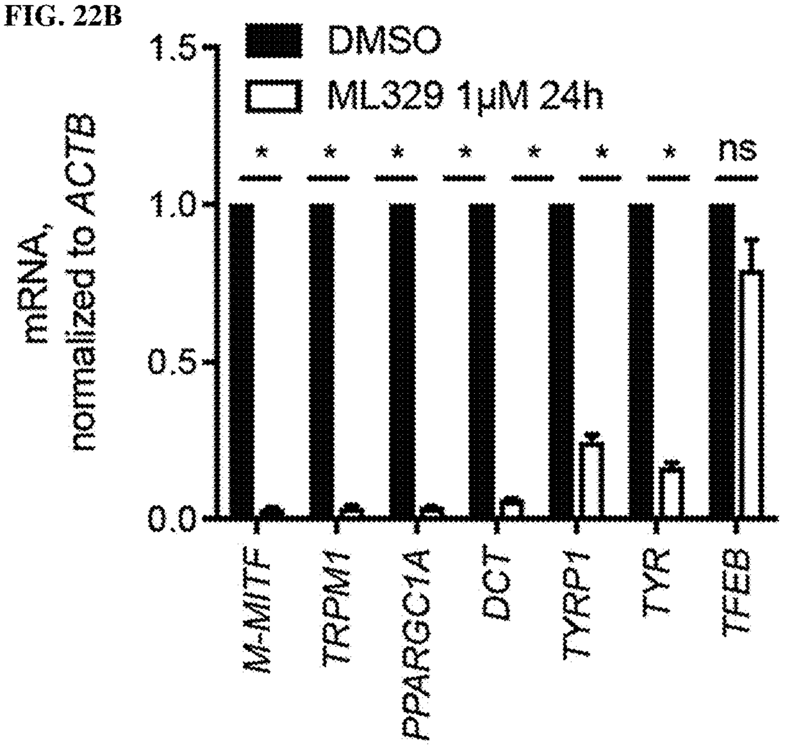
Figure 23A:
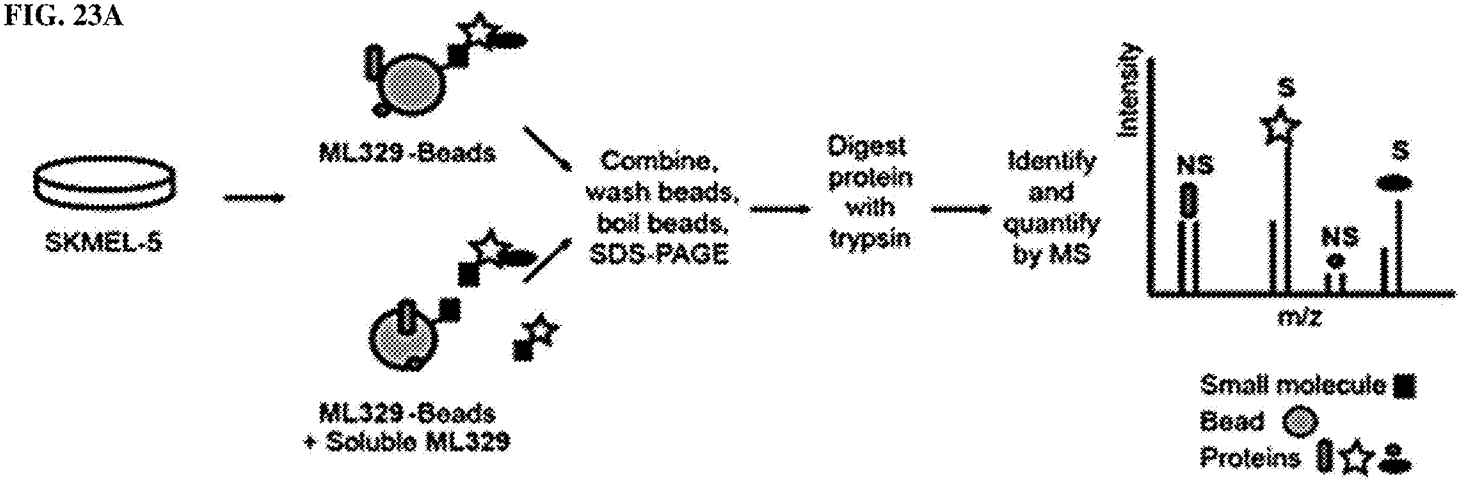
FIG. 23A-FIG. 23C show that ML329 binds to CK2 and suppresses CK2-dependent signaling specifically in melanomas.
Figure 23B:
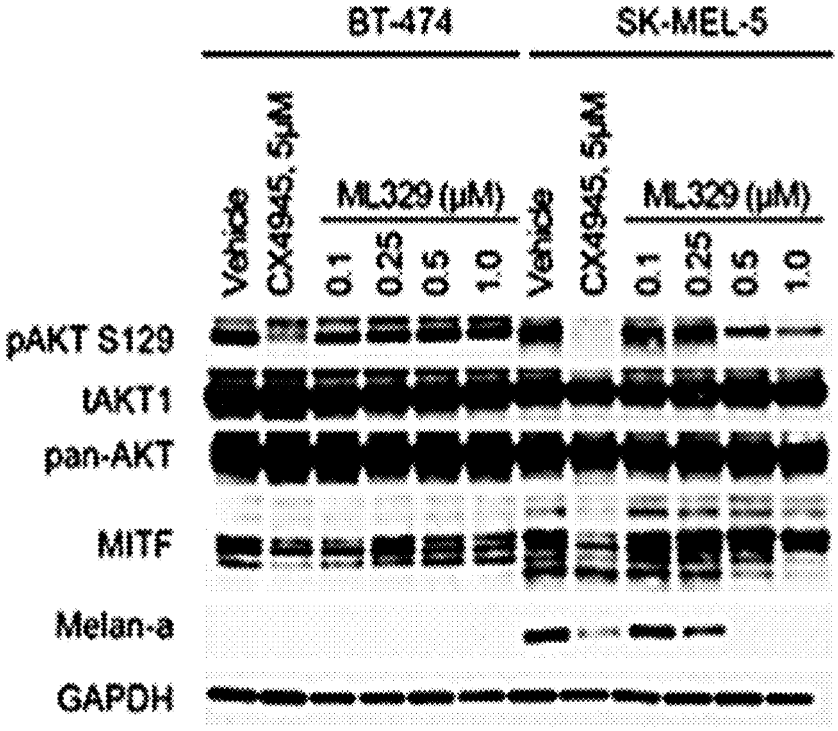
Figure 23C:
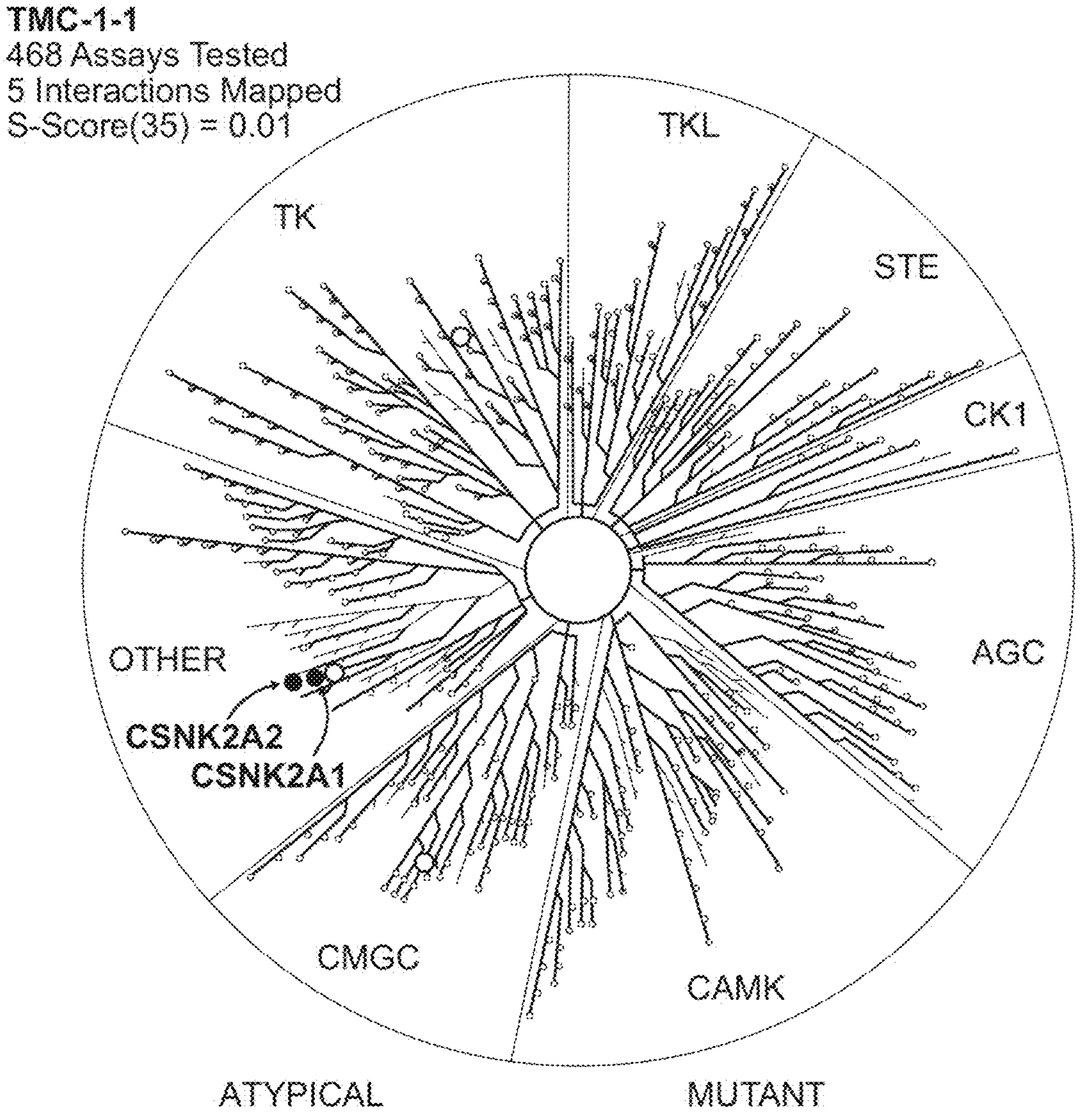
Figure 24A:
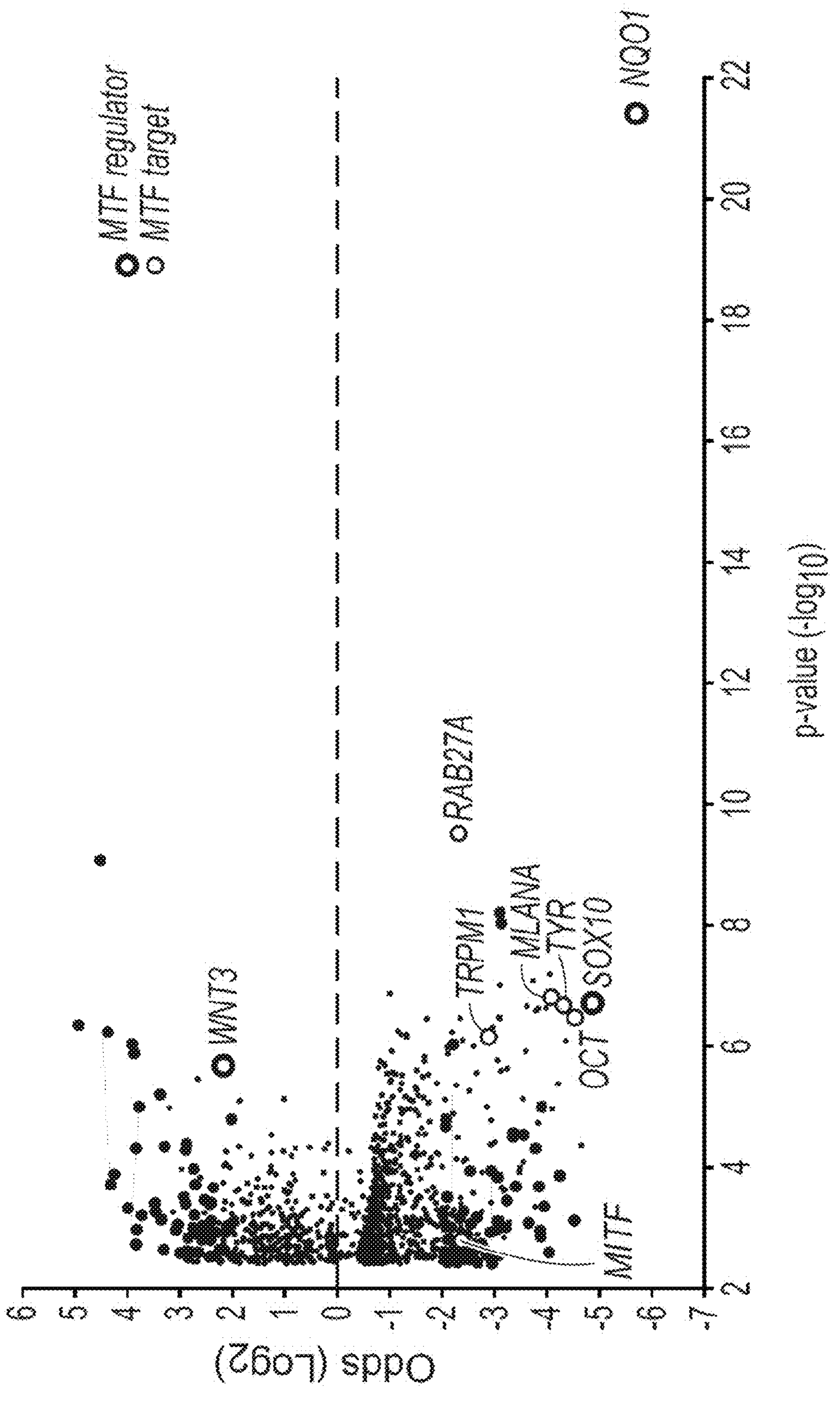
FIG. 24A-FIG. 24F show that NRF2 transcriptional target NQO1 is required for the activity of ML329.
Figure 24B:
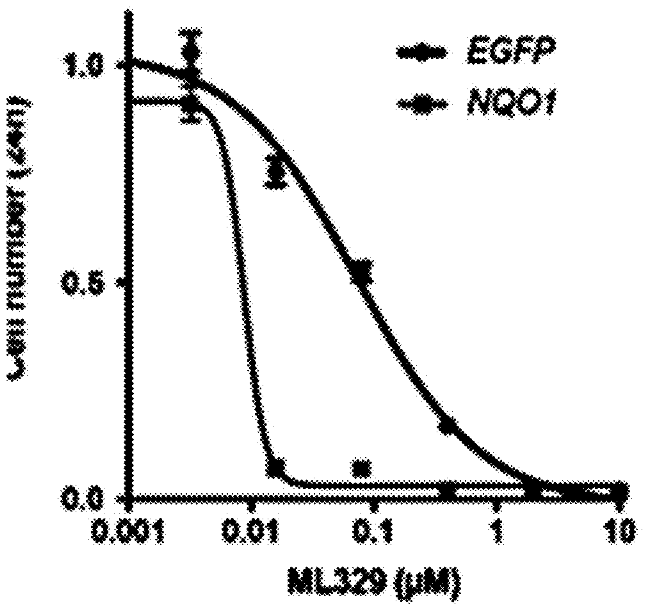
Figure 24C:
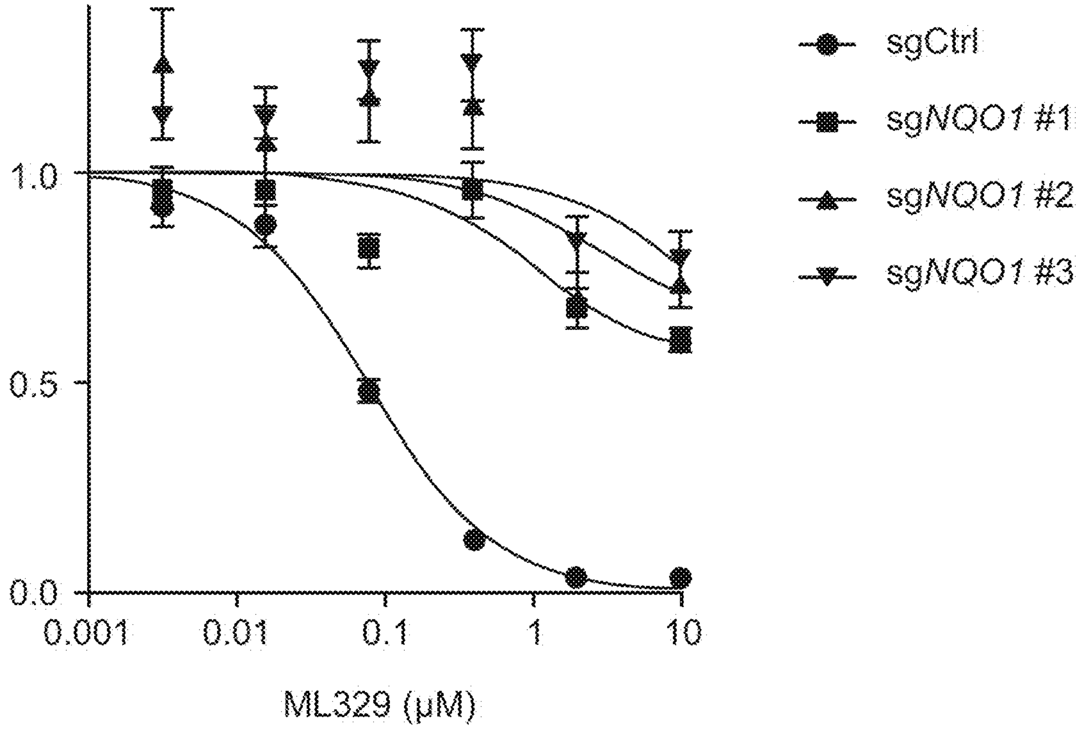
Figure 24D:
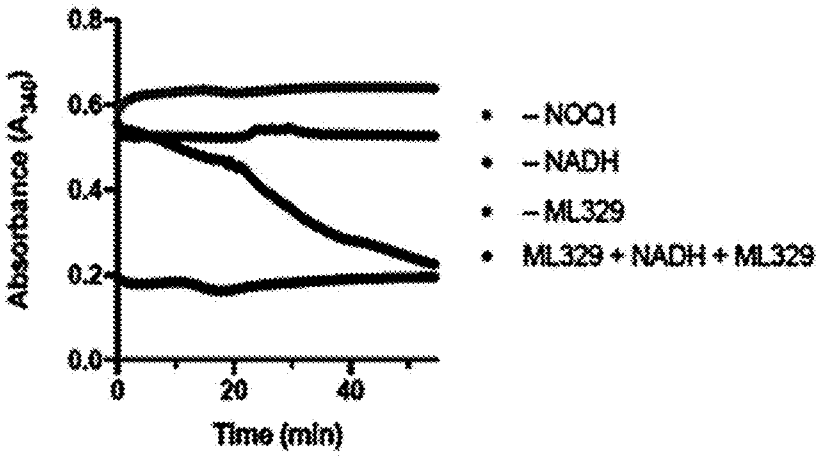
Figure 24E:
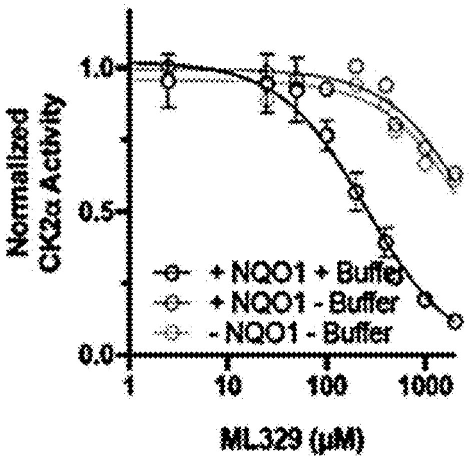
Figure 24F:
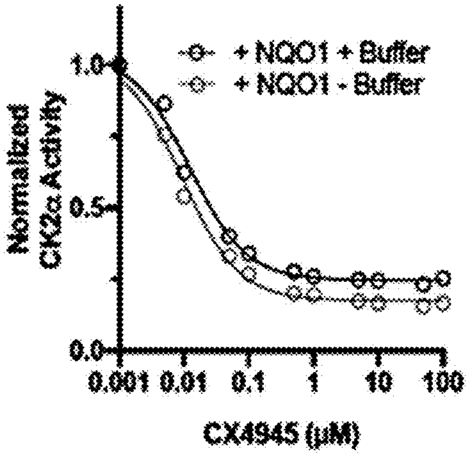
Figure 25:
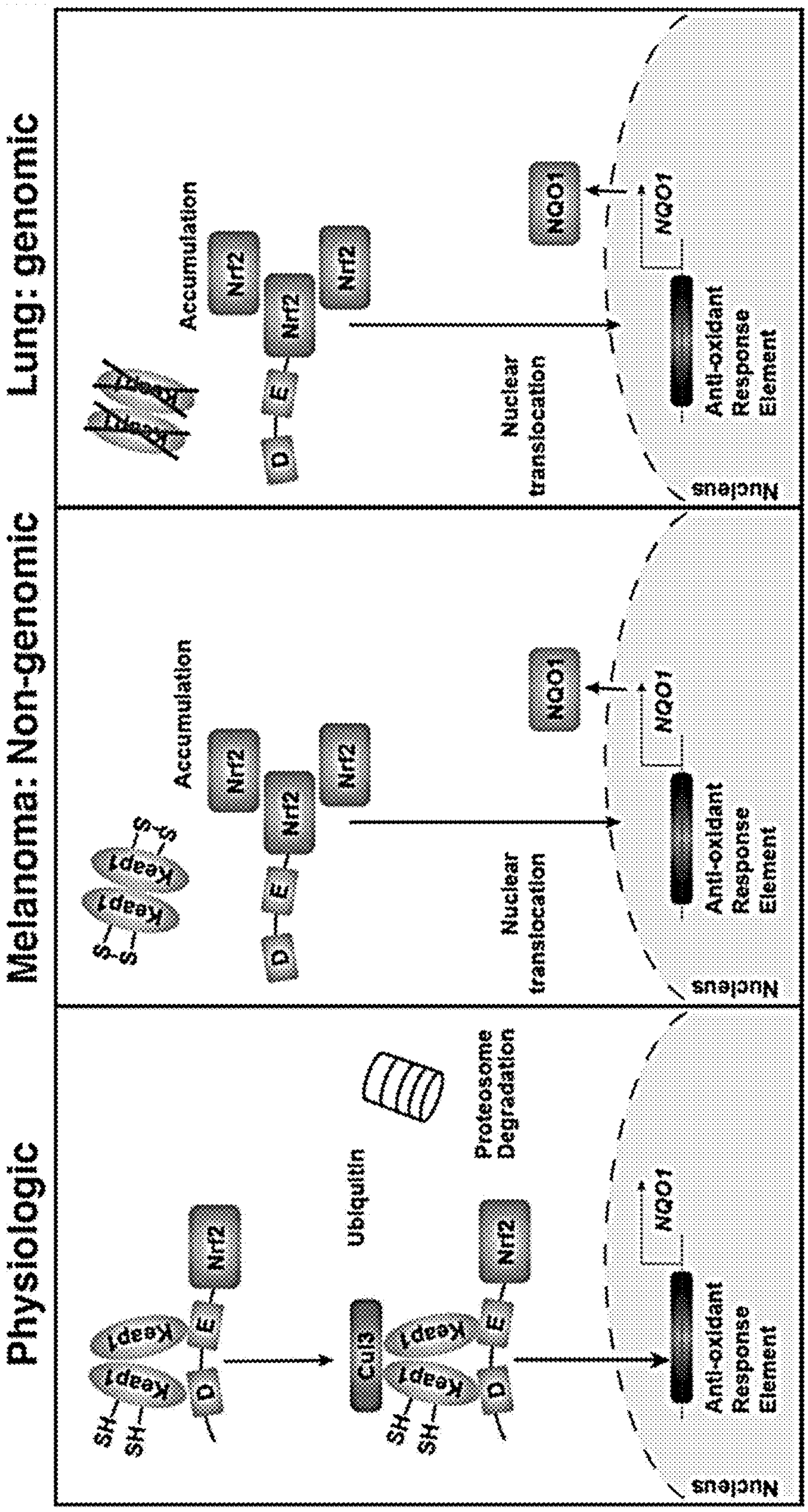
FIG. 25 shows a schematic description of the mechanism of ML329 bioreduction and CK2 inhibition.
Figure 26A:
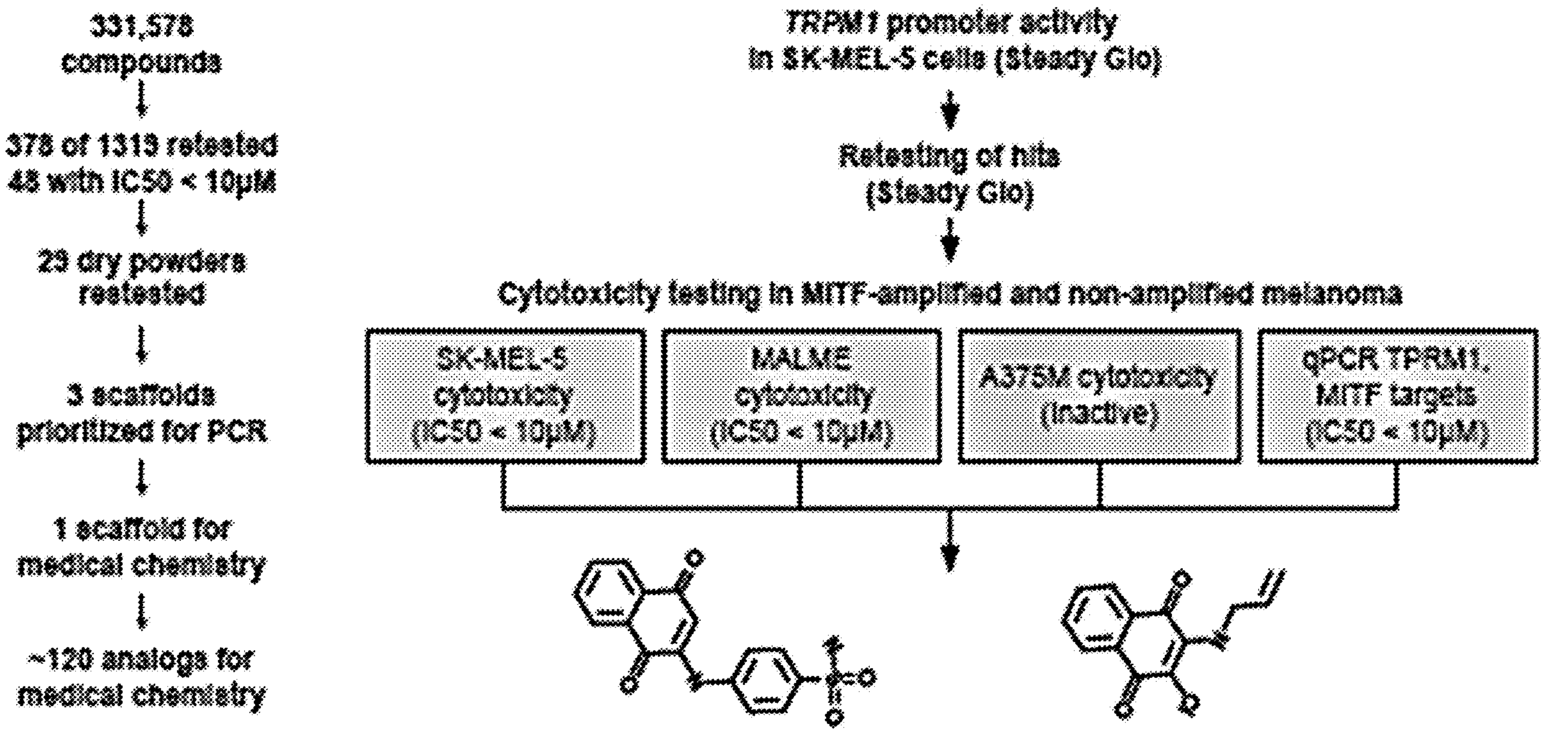
FIG. 26A-FIG. 26H show the results of a small molecule screen to identify regulators of lineage-specific melanoma oncogene MITF.
Figure 26B:
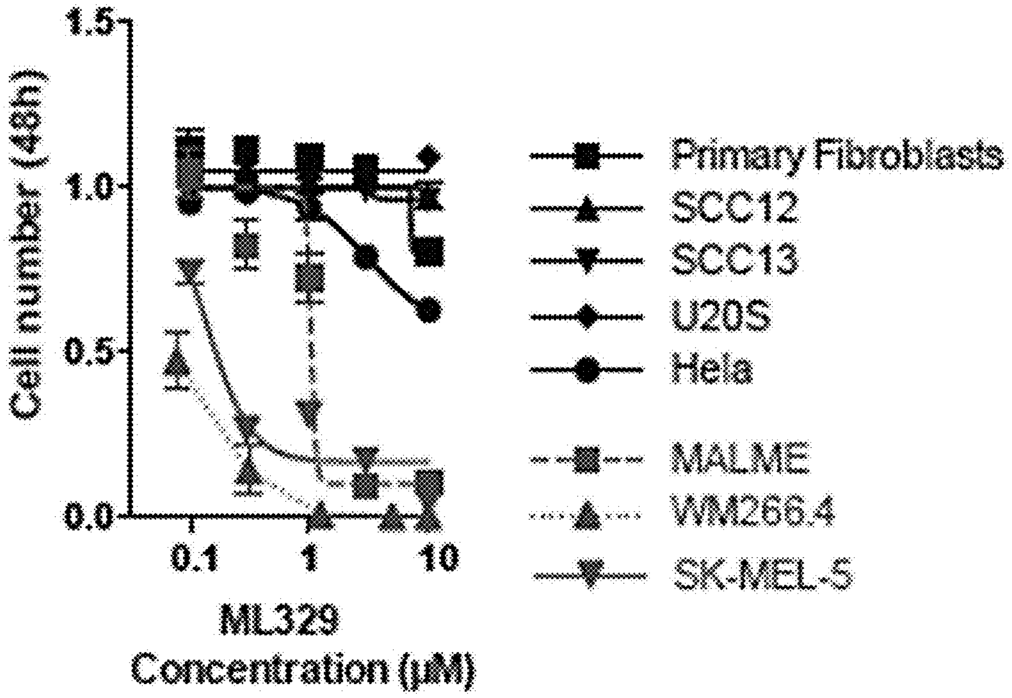
Figure 26C:
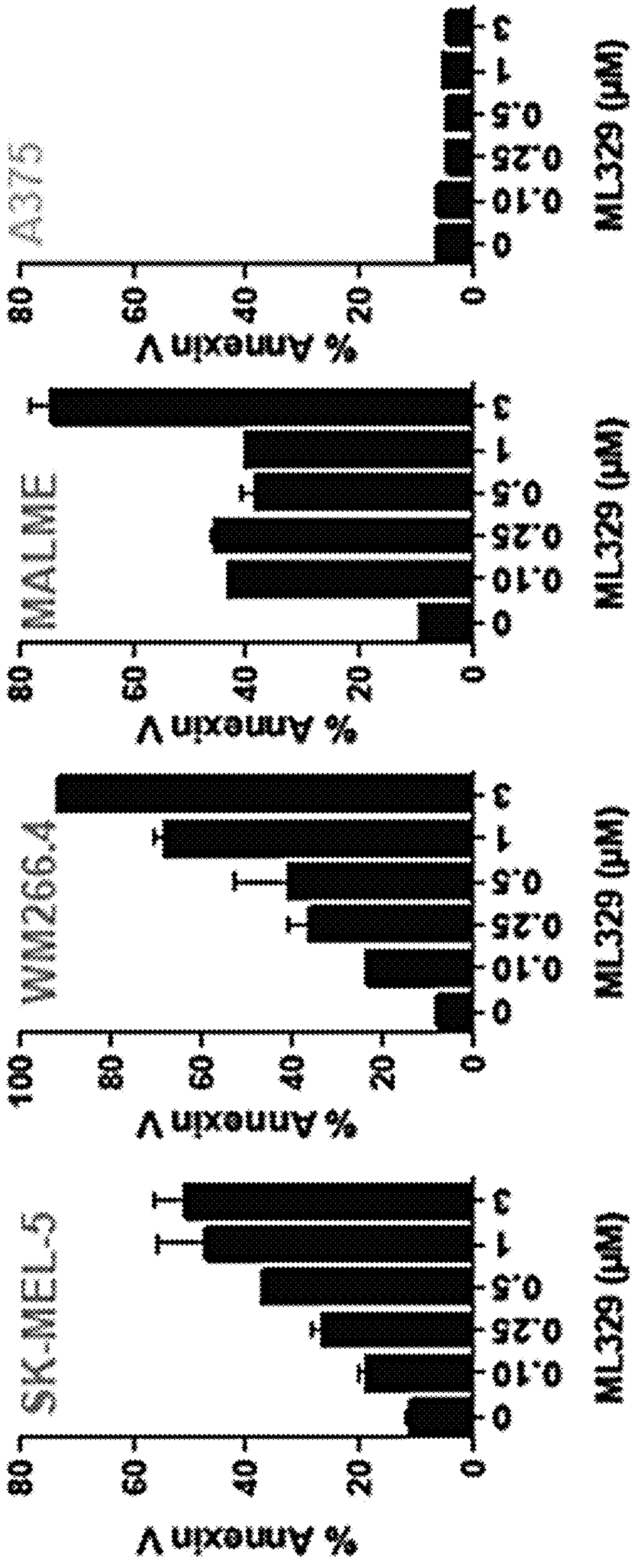
Figure 26D:
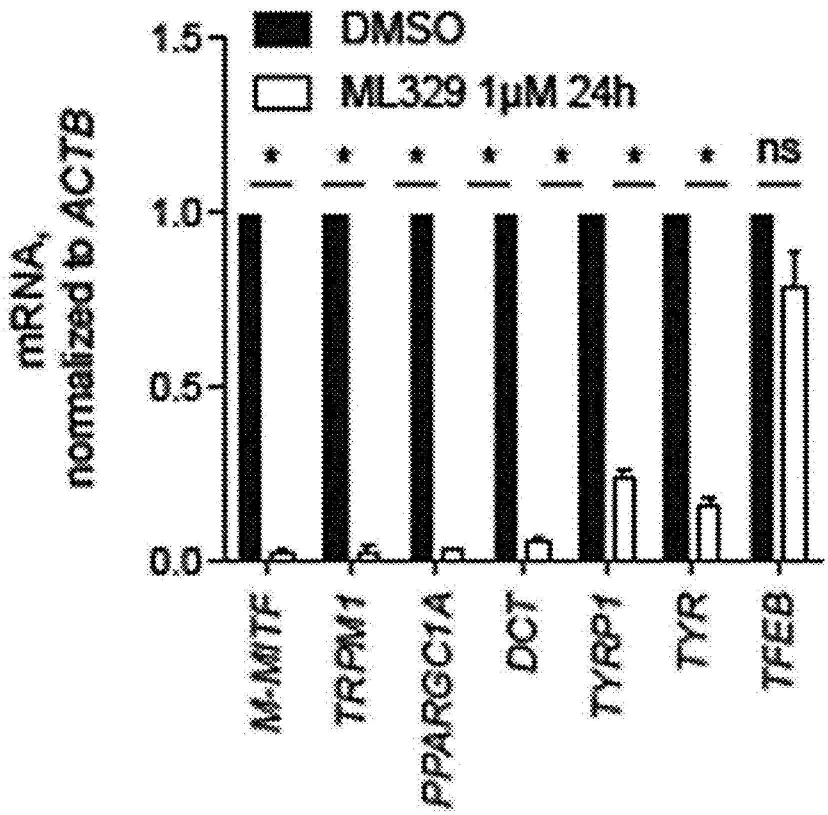
Figure 26:
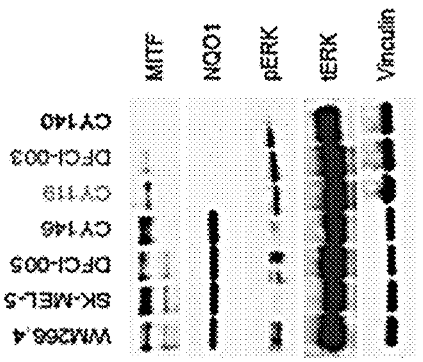
Figure 26:
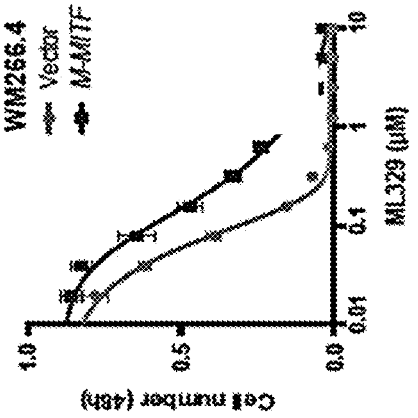
Figure 26:
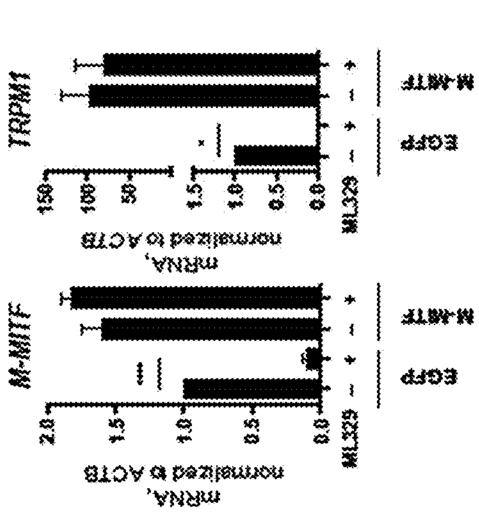
Figure 26:
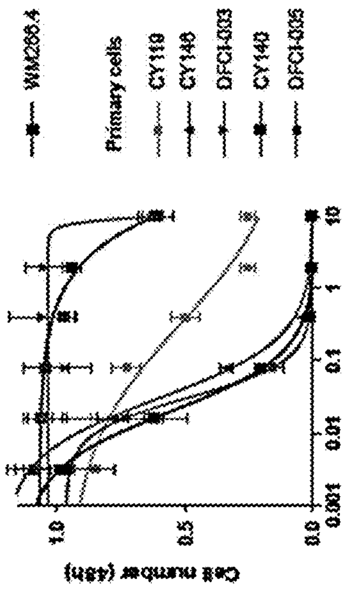
Figures 27A, 27B, 27C, 27D, 27E, 27F, 27G:
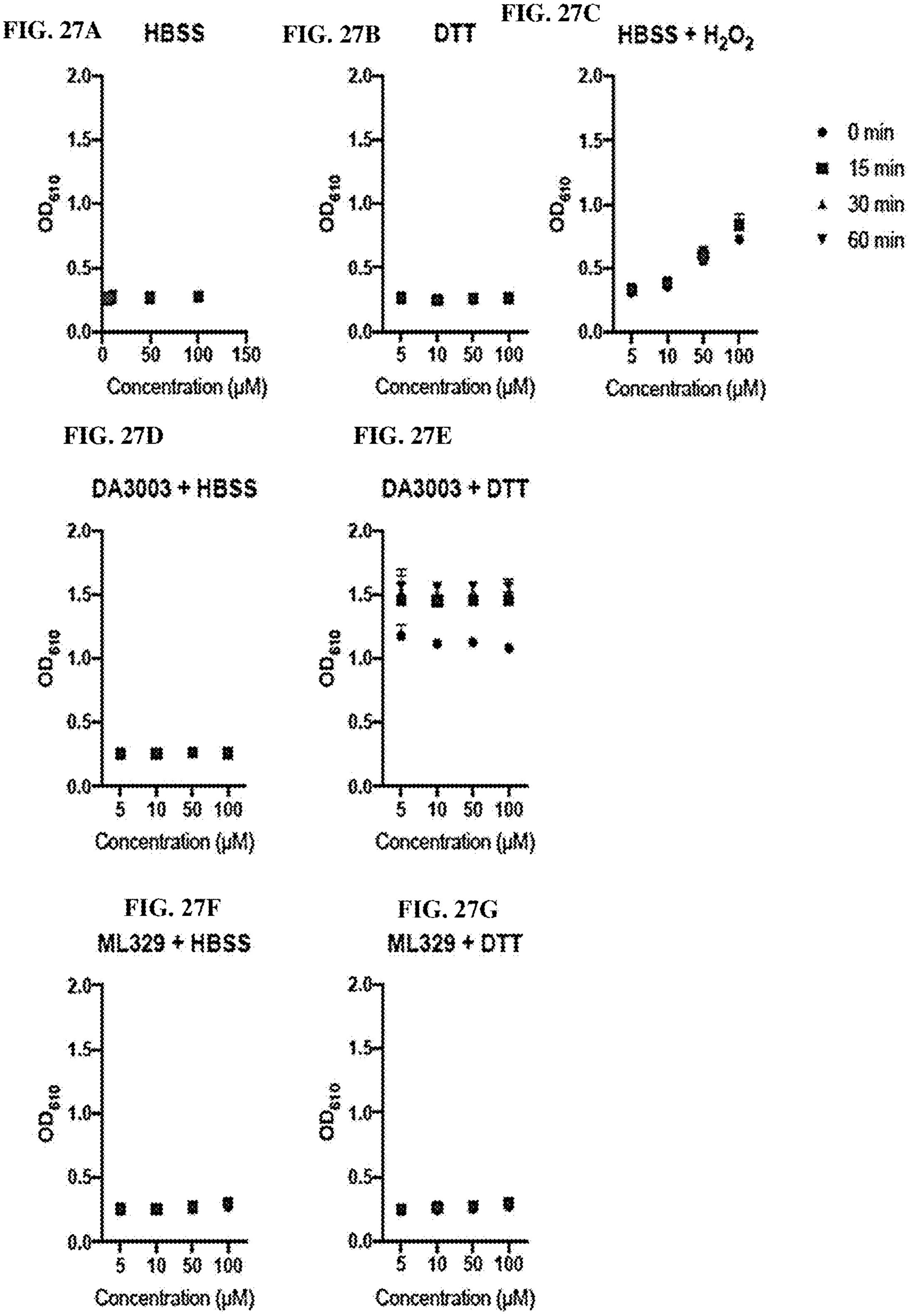
FIG. 27A-FIG. 27G show effects of ML329 on redox cycling, including quantification of hydrogen peroxide using a Phenol Red Horseradish/DTT peroxidase assay (PMID: 18699726) at indicated times.
Figure 28A:
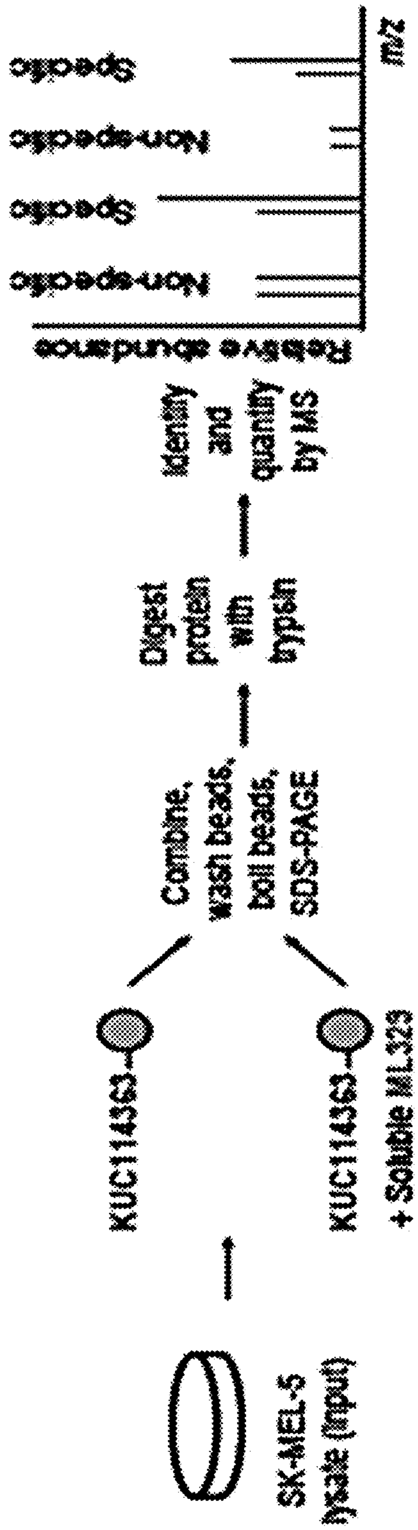
FIG. 28A-FIG. 28O show that ML329 suppresses MITF and melanoma growth via inhibition of CK2.
Figure 28C:
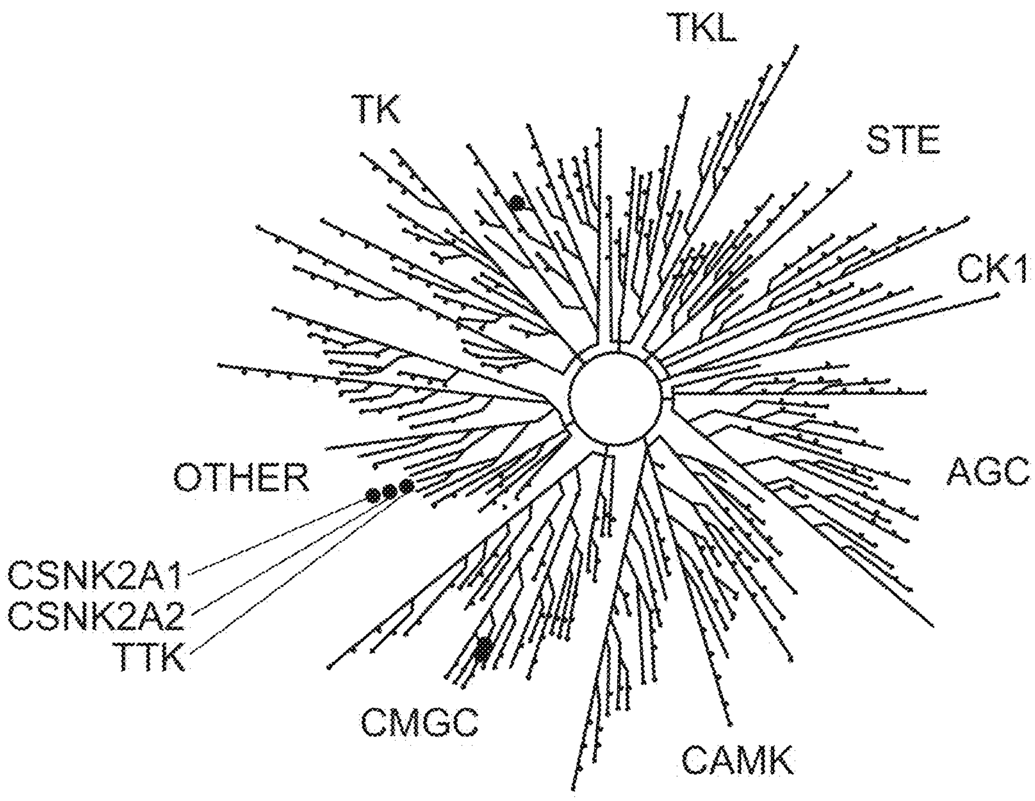
FIG. 28C shows binding of ML329 across 468 kinases using KINOMEScan profiling. Kinases found to bound are marked with red circles, where larger circles indicate higher-affinity binding. KINOMEScan image was generated using TREEspot™ Software Tool and reprinted with permission from KINOMEscan®, a division of DiscoveRx Corporation, © DISCOVERX CORPORATION 2010.
Figure 28D:
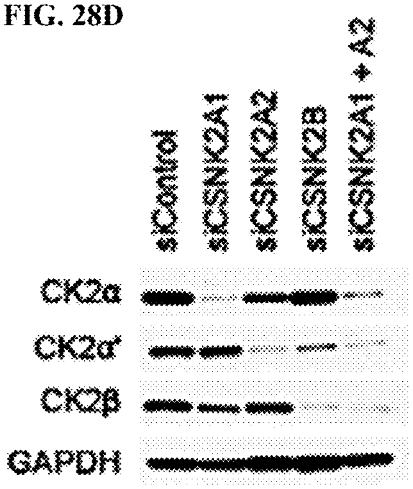
FIG. 28D shows CK2 subunit protein expression following transfection of WM266.4 melanoma cells with indicated siRNAs.
Figure 28E:
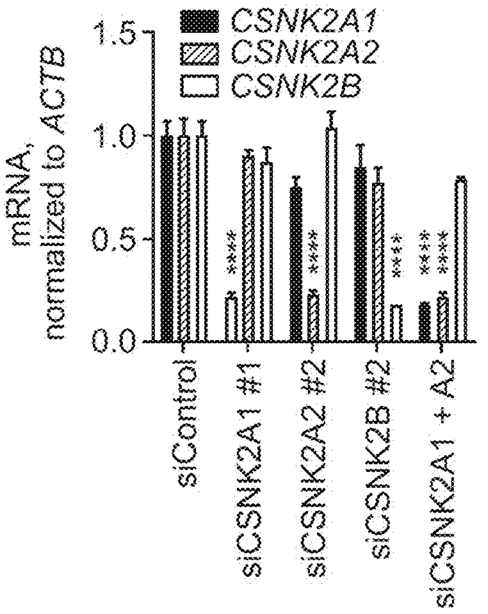
FIG. 28E shows quantification of CK2 subunit mRNA expression following transfection of WM266.4 cells with indicated siRNAs.
Figure 28F:
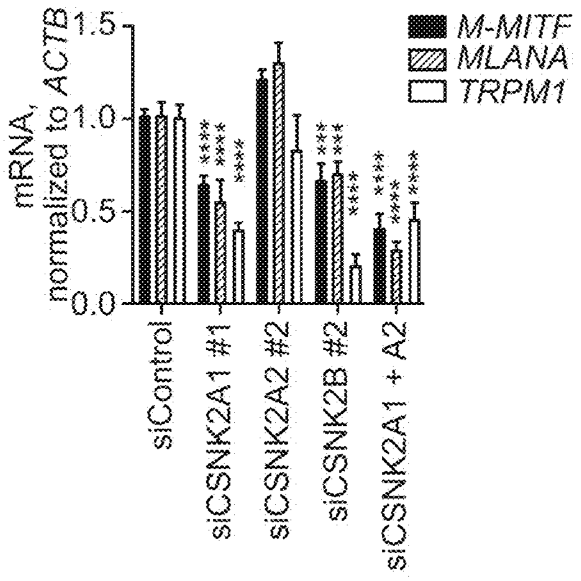
FIG. 28F shows quantification of MITF and MITF targets following transfection of WM266.4 cells with indicated siRNA.
Figure 28G:
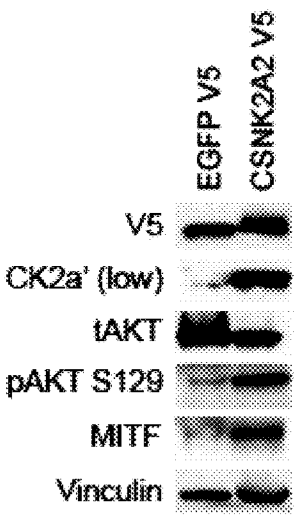
FIG. 28G shows levels of expression of indicated proteins in WM266.4 cells stably expressing CK2α' (CSNK2A2). FIG.
Figure 28H:
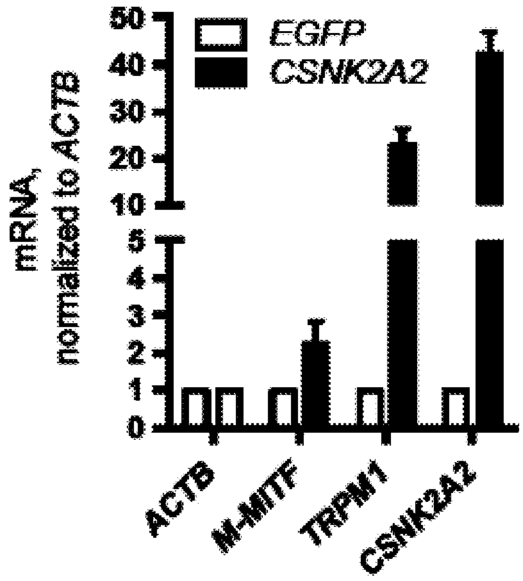
FIG. 28B shows putative targets of ML329 by mass spectrometry with indicated threshold (red).
FIG. 28I shows levels of CK2 dependent signaling proteins in SK-MEL-5 cells stably expressing wild-type or drug-resistant (I175A) mutant CK2α' (CSNK2A2).
FIG. 28J shows cell number after 48 h ML329 treatment of SK-MEL-5 cells stably expressing wild-type or drug-resistant (I175A) mutant CK2α' (CSNK2A2).
FIG. 28K shows cell number after 24 h treatment of WM266.4 cells with or without NQO1 inhibitor ES936 (1 μM).
FIG. 28L shows levels of CK2 dependent signaling proteins in SK-MEL-5 cells stably expressing wild-type or drug-resistant (I174A) mutant CK2a (CSNK2A1).
FIG. 28M shows levels of CK2 dependent signaling proteins in WM266.4 cells stably expressing wild-type or drug-resistant (I174A) mutant CK2a (CSNK2A1).
FIG. 28N shows cell number after 48 h ML329 treatment of SK-MEL-5 cells stably expressing wild-type or drug-resistant (I174A) mutant CK2a (CSNK2A1).
Figure 28I:
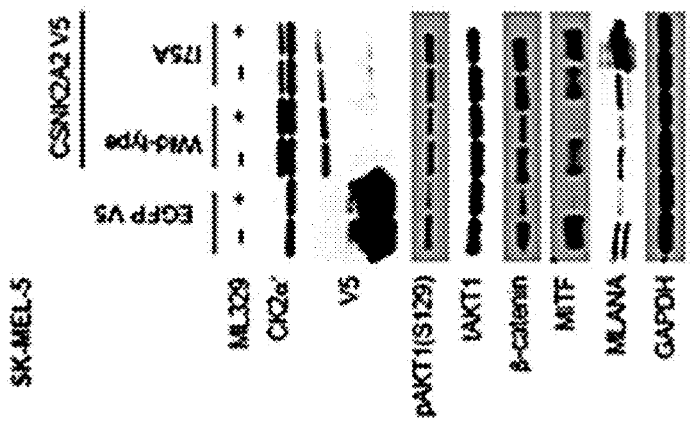
Figure 28J:
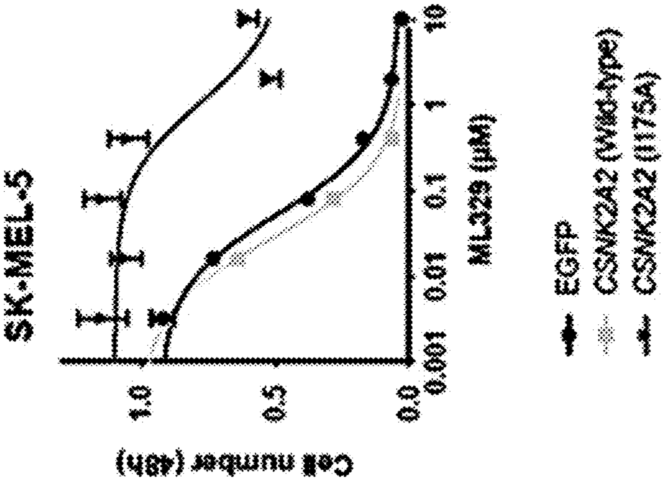
Figure 28K:
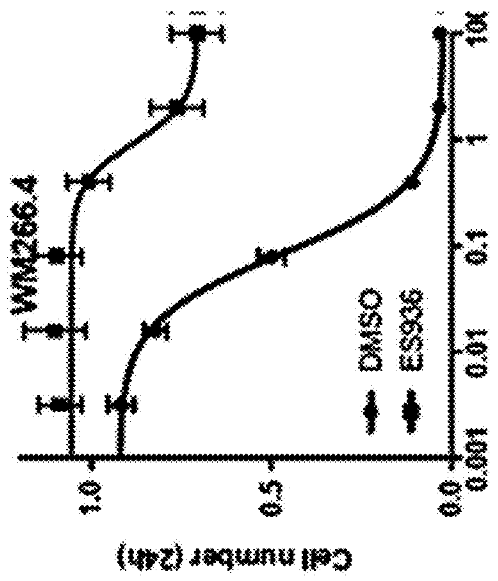
Figure 28L:
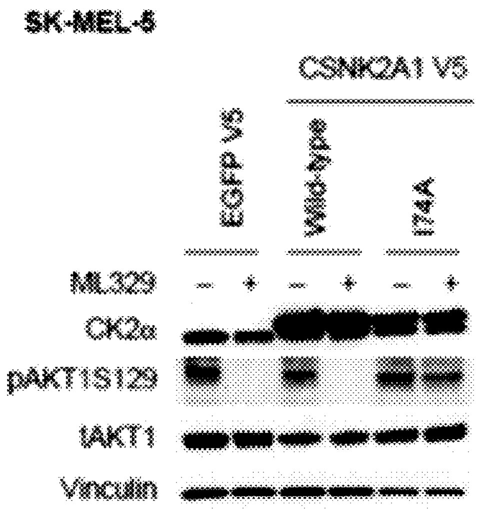
Figure 28M:
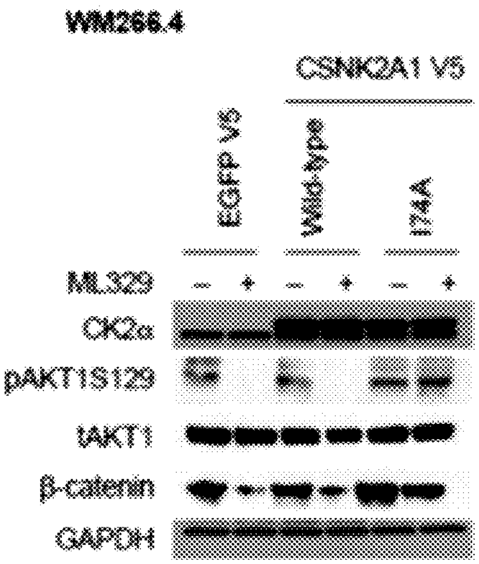
Figure 28N:
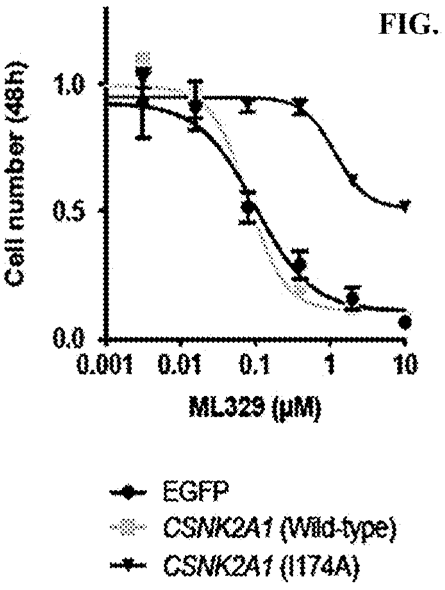
Figure 28O:
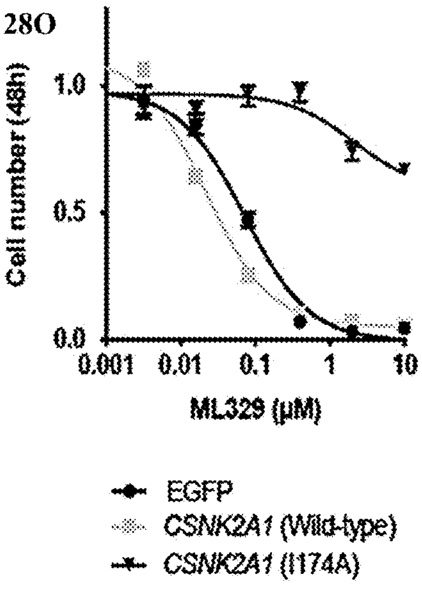
Figure 29A:
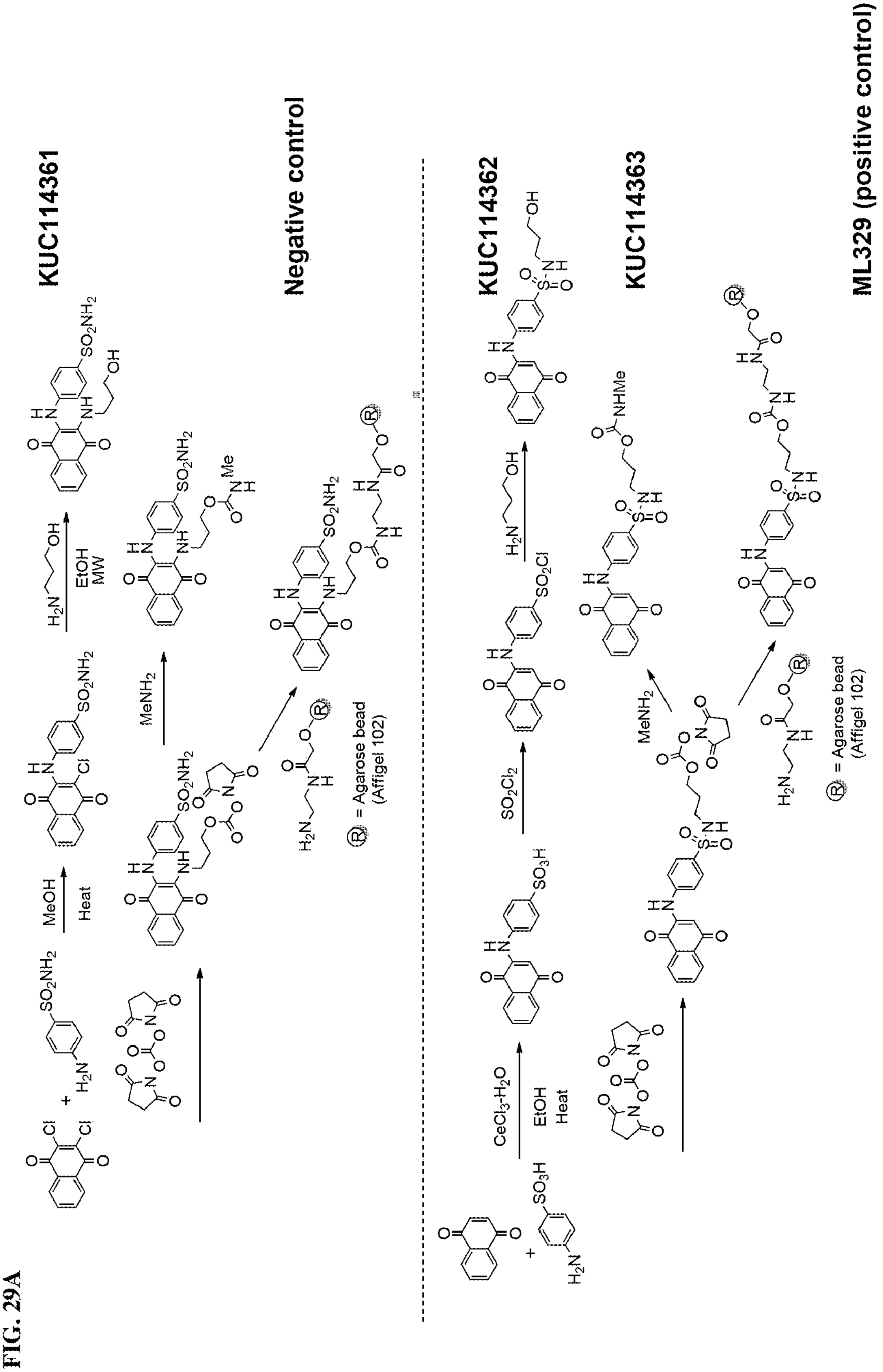
FIG. 29A-FIG. 29Z show structural, chemical, functional properties of ML329 derivatives.
Figure 29B:
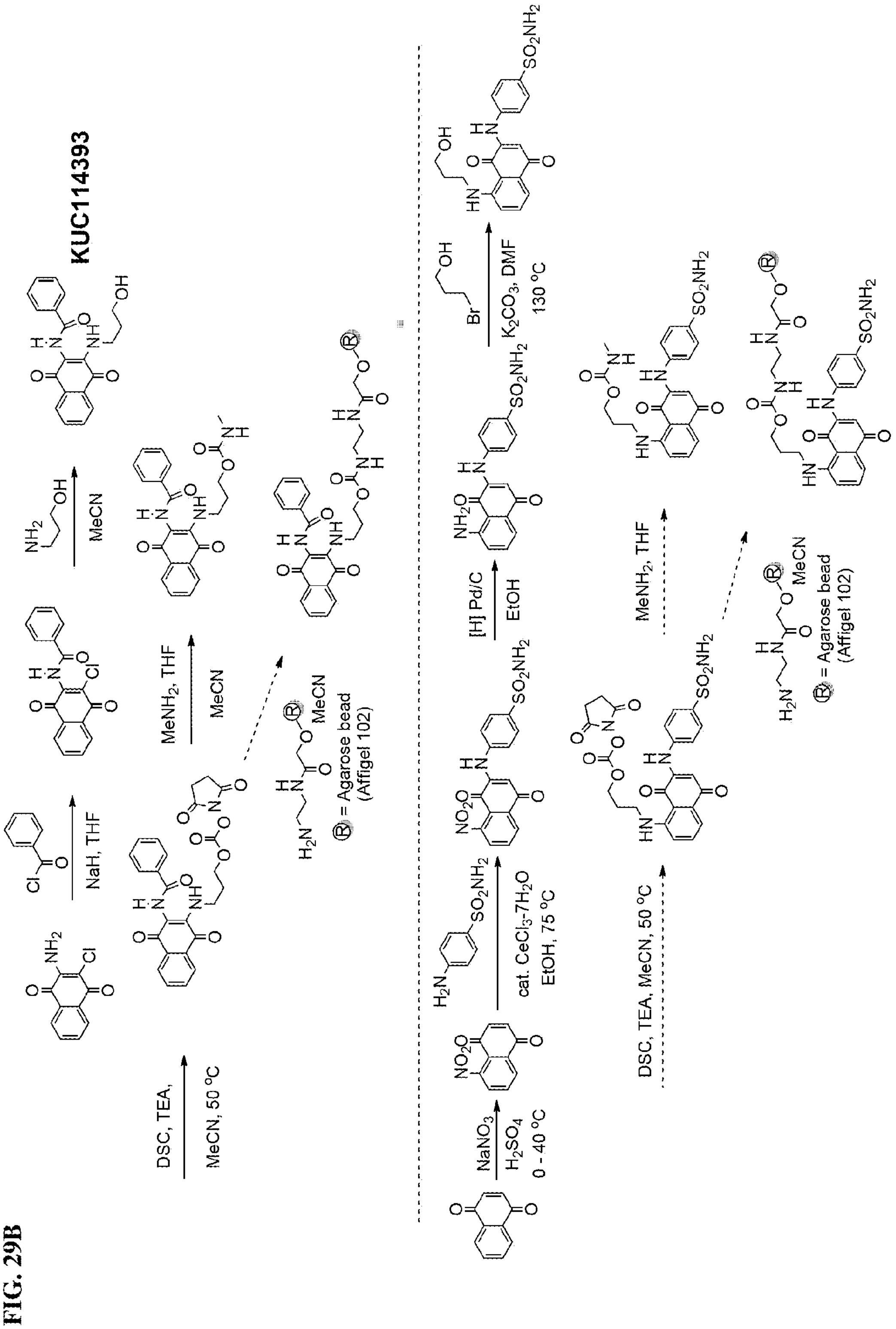
FIG. 29B shows chemical synthesis of KUC114393.
Figure 29C:
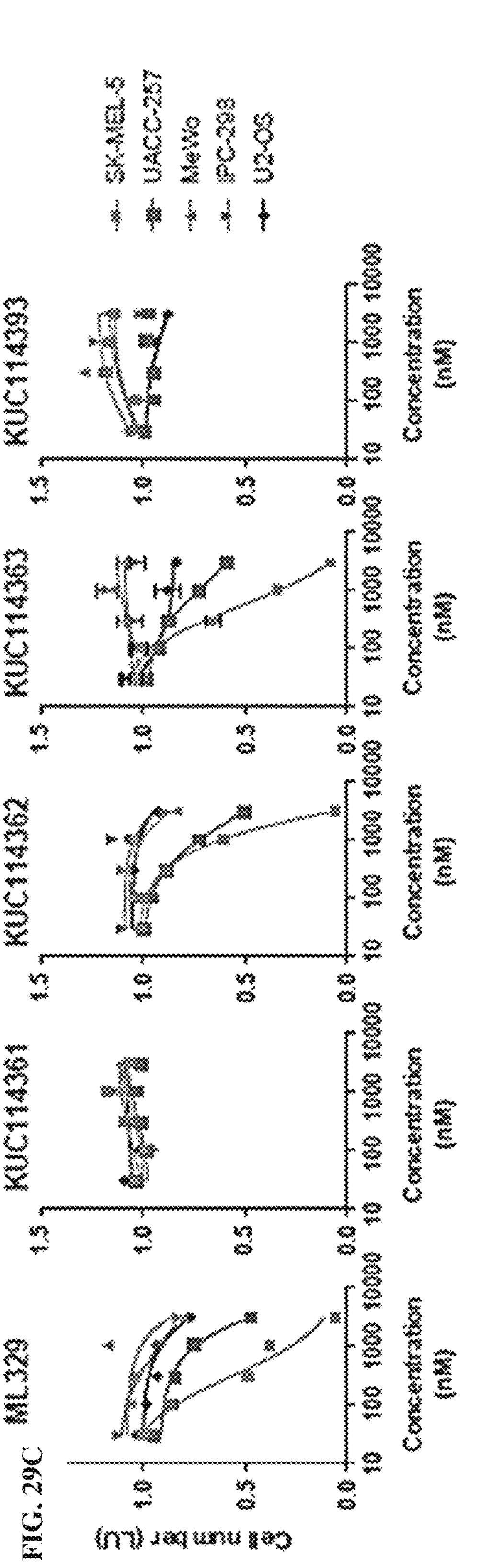
FIG. 29C shows cell number following treatment of indicated cell line with ML329 or ML329 derivatives.
Figure 29D:
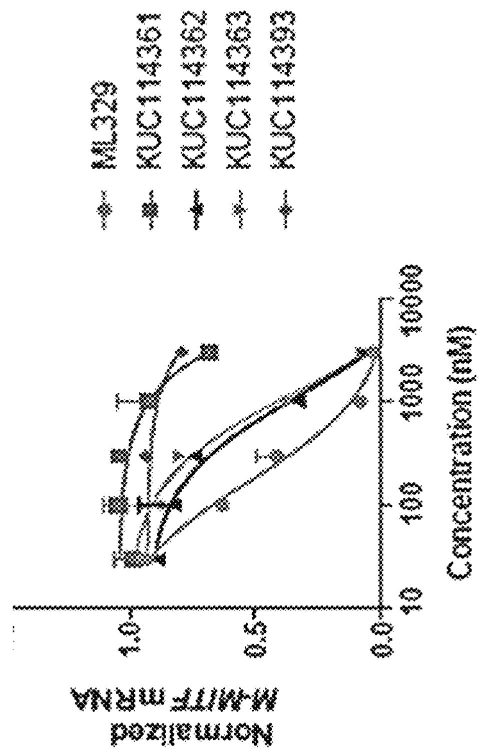
FIG. 29D shows quantification of M-MITF following treatment of SK-MEL-5 cell line with ML329 or derivatives (24 h).
Figure 29E:
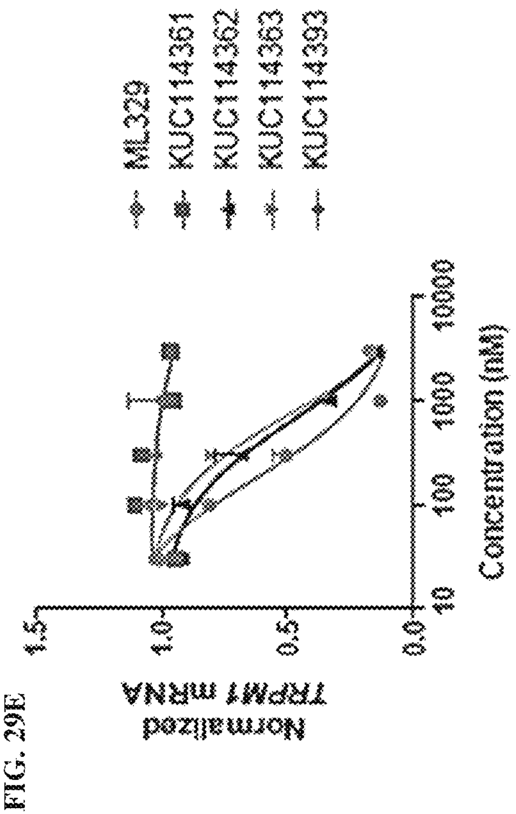
FIG. 29E shows quantification of M-MITF transcriptional target TRPM1 following treatment of SK-MEL-5 cell line with ML329 or derivatives (24 h).
Figures 29G, 29H, 29I, 29J, 29K:
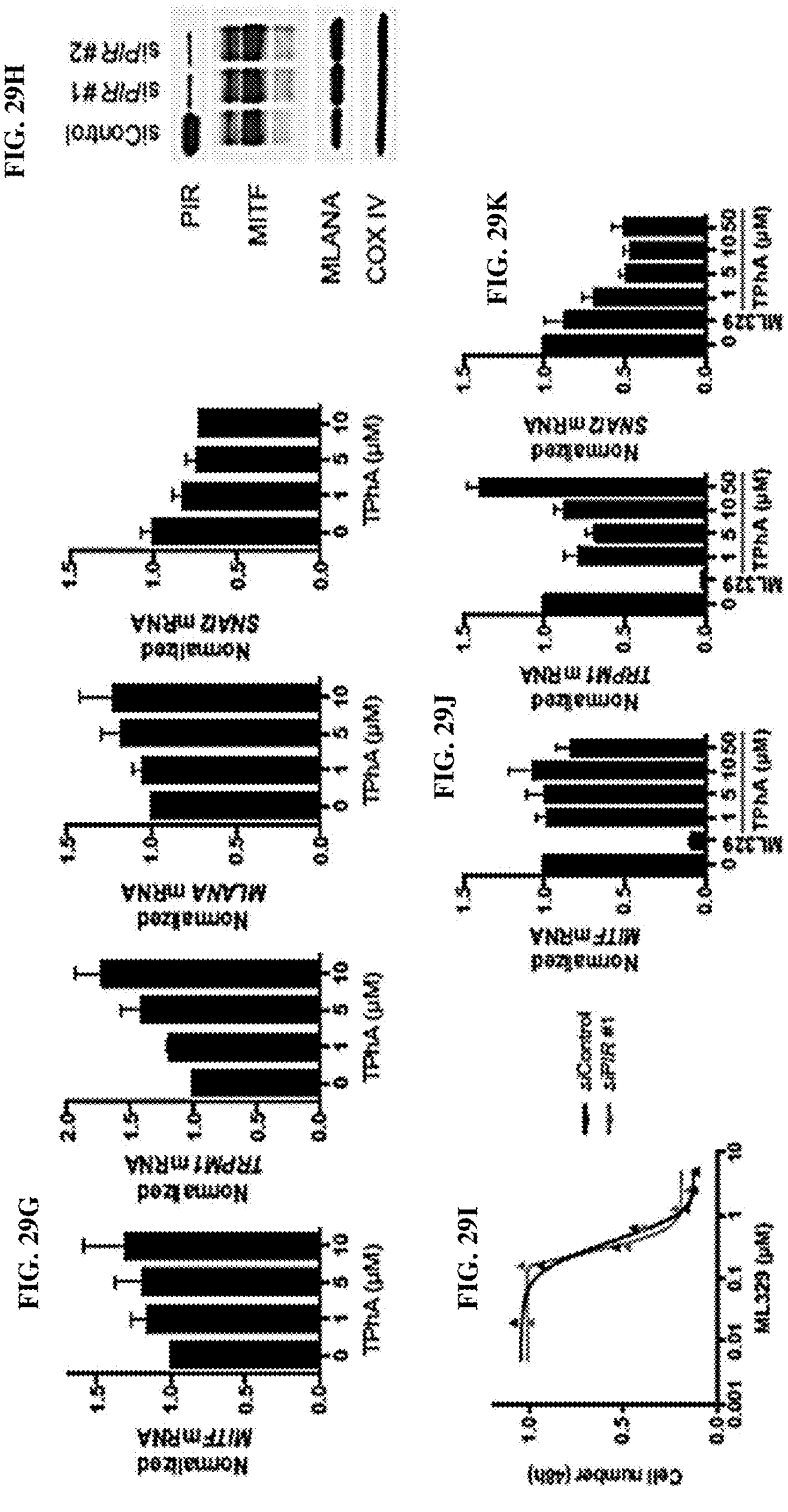
FIG. 29G shows quantification of M-MITF and transcriptional targets following 48 h treatment with Pirin inhibitor TPhA in SK-MEL-5 cells. The Pirin transcriptional target SNAI2 was also evaluated.
FIG. 29H shows protein levels of MITF and transcriptional targets in SK-MEL-5 cells transfected with siRNAs targeting PIR.
FIG. 29I shows cell number following ML329 treatment of SK-MEL-5 cells transfected with or without siRNAs targeting PIR.
FIG. 29J-FIG. 29K show quantification of M-MITF and transcriptional targets following ML329 (1 μM) or TPhA drug treatment (24 h) in SK-MEL-5 cells.
Figure 29L:
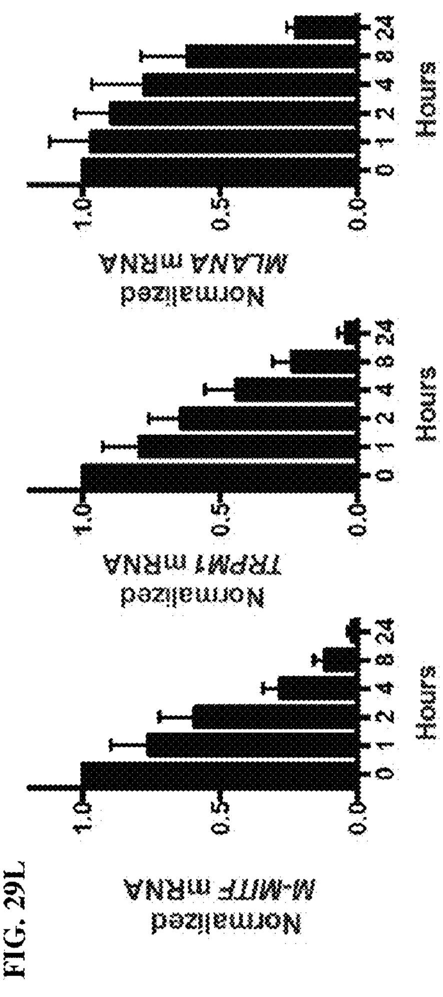
FIG. 29L shows quantification of M-MITF and transcriptional targets at indicated time after ML329 treatment of SK-MEL-5 melanoma cells.
Figure 29M:
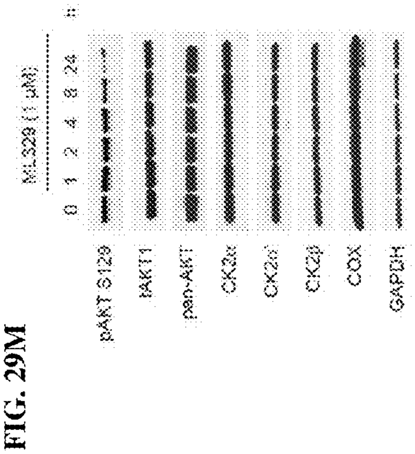
FIG. 29M shows levels of CK2 dependent signaling at indicated time after ML329 treatment of SK-MEL-5 melanoma cells.
Figure 29N:
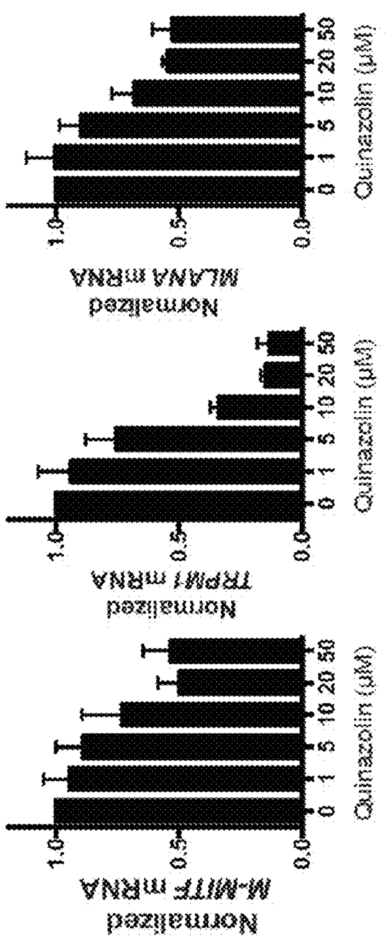
FIG. 29N shows quantification of M-MITF and transcriptional targets following indicated dose of the CK2 inhibitor quinazolin (24 h) in SK-MEL-5 cells.
Figure 29O:
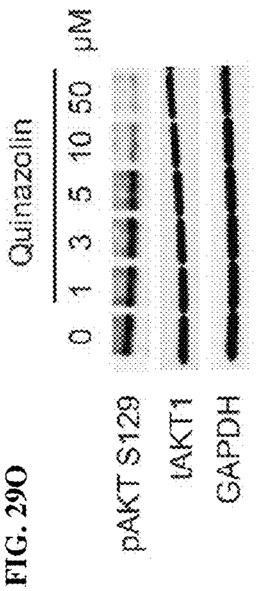
FIG. 29O shows levels of CK2 target phospho-AKT following treatment of SK-MEL-5 melanoma cells with quinazolin at indicated doses.
Figure 29P:
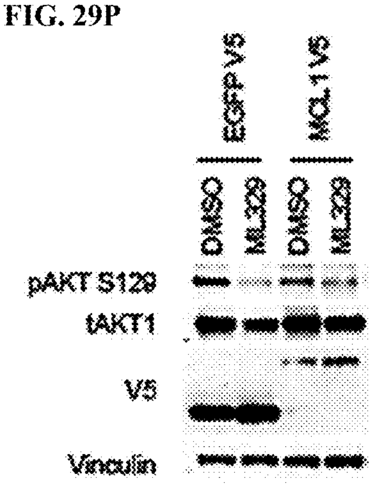
FIG. 29P shows protein levels in WM266.4 cells expressing MCL-1 anti-apopotic protein following 24 h treatment with ML329 (1 μM).
Figure 29Q:
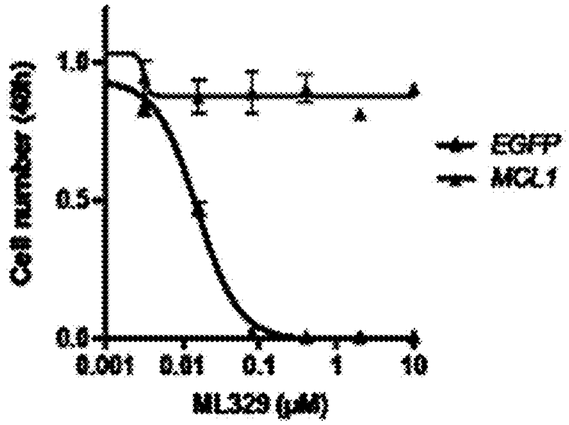
FIG. 29Q shows cell number after treatment of EGFP or MCL1 expressing cells with M1329 cells.
Figure 29R:
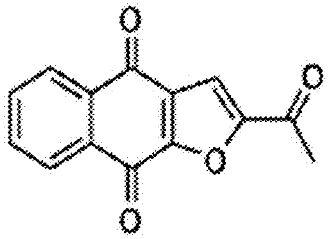
FIG. 29R shows structure of napabucasin, a STAT3 inhibitor.
Figure 29S:
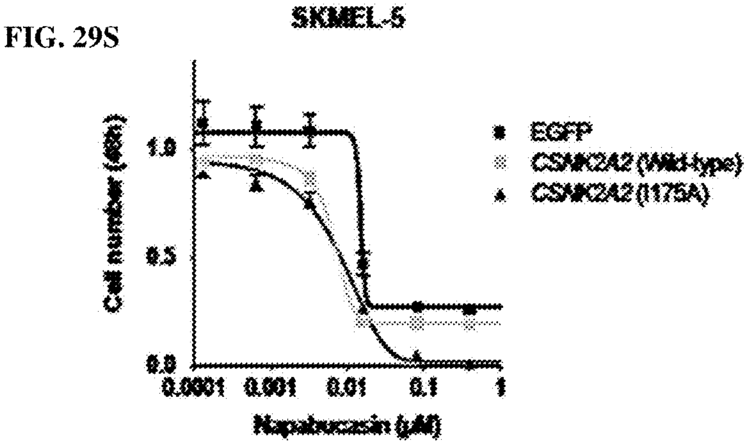
FIG. 29S shows cell number after 48 h napabucasin treatment of SK-MEL-S cells stably expressing wild-type or drug-resistant (I175A) mutant CK2α' (CSNK2A2).
Figure 29T:
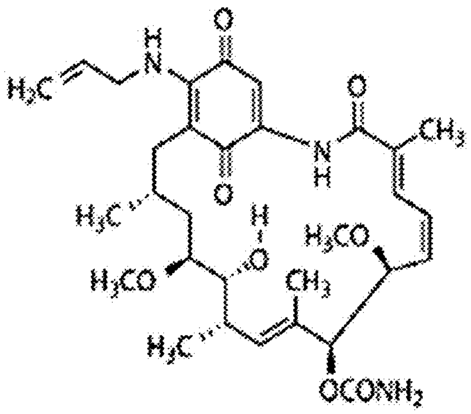
FIG. 29T shows structure of the quinone 17-AAG, a putative HSP90 inhibitor.
Figure 29U:
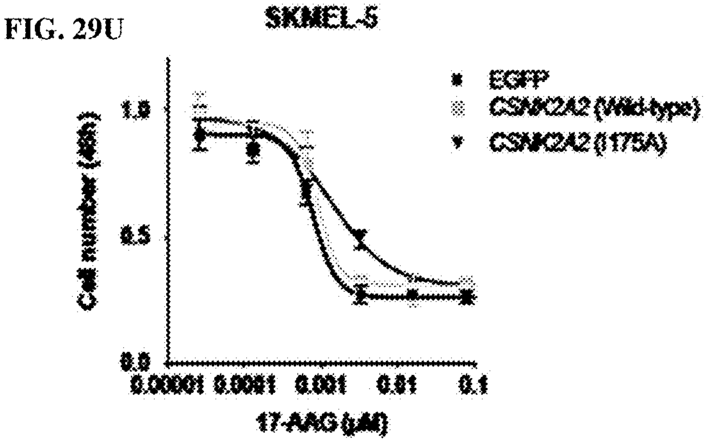
FIG. 29U shows cell number after 48 h 17-AAG treatment of SK-MEL-S cells stably expressing wild-type or drug-resistant (I175A) mutant CK2α' (CSNK2A2).
Figure 29W:
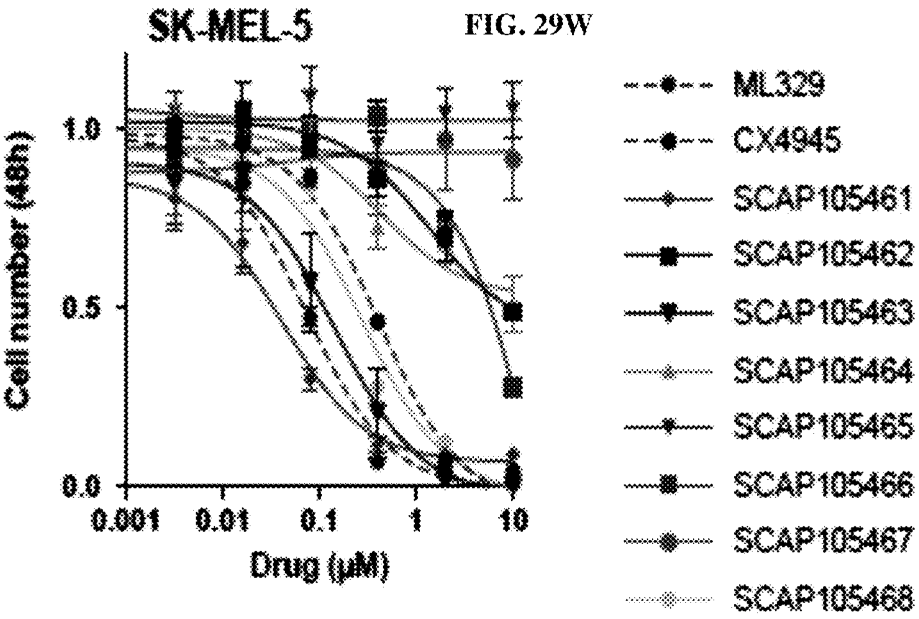
FIG. 29W shows cell number after 48 h treatment of SK-MEL-S cells with ML329 or chemical derivative.
Figure 29X:
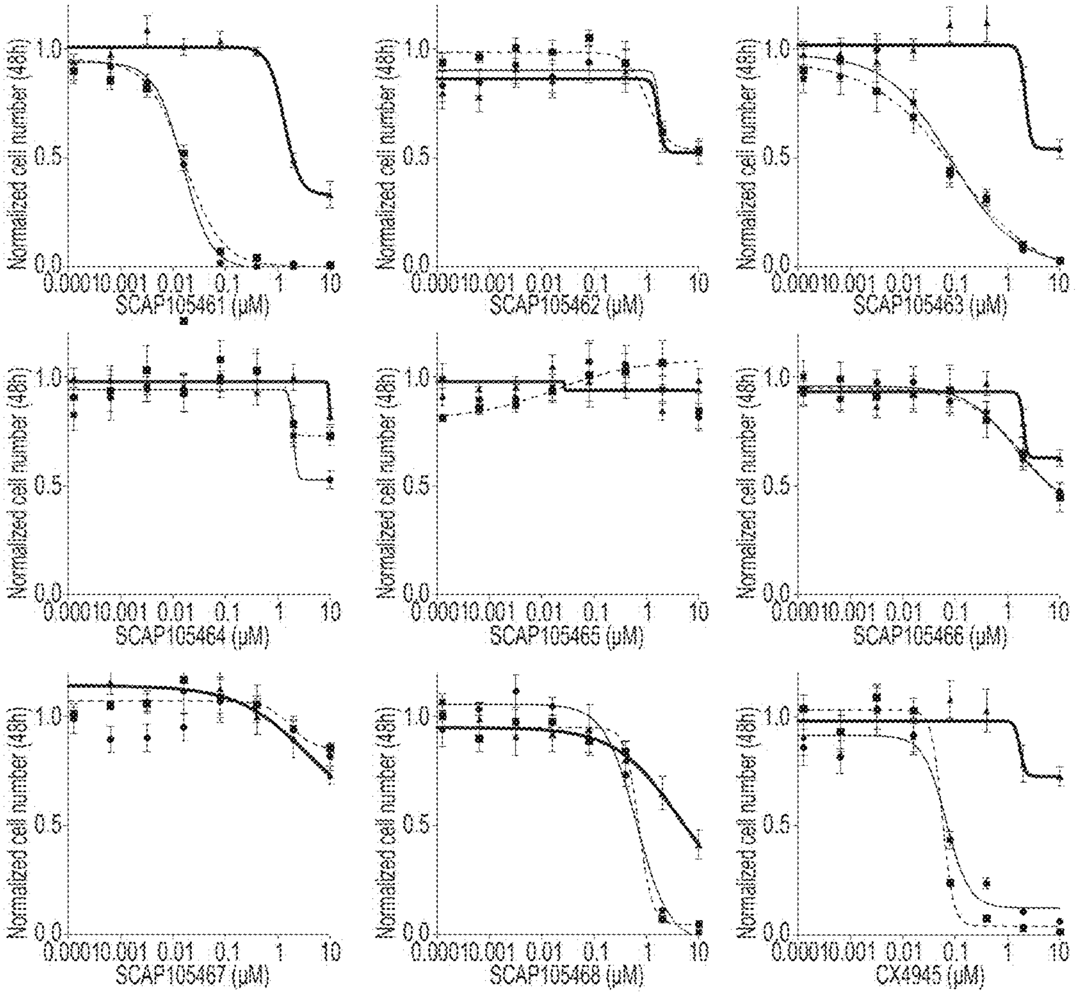
FIG. 29X shows cell number after 48 h treatment of SK-MEL-5 cells stably expressing empty vector (black solid line), wild-type CSNK2A1 (dotted black line), or I174A mutant CSNK2A1 (red line).
Figure 29Y:
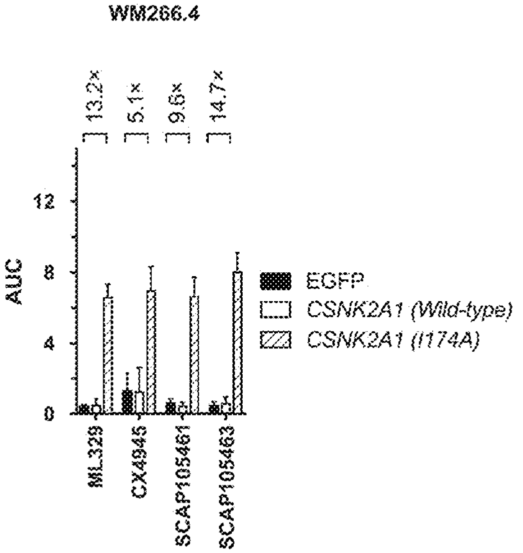
FIG. 29Y shows area-under-the-curve (AUC) for CX4945, ML329 or its derivatives in indicated WM266.4 cell line. The fold change in AUC between vector and drug-resistant CSNK2A1 expressing cell lines is indicated.
Figure 29Z:
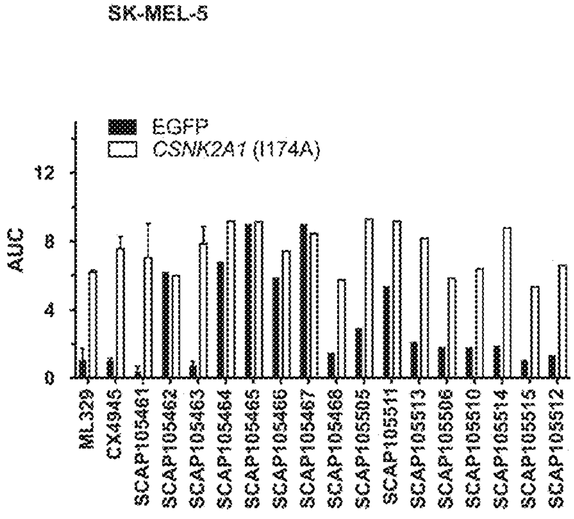
Figure 30A:
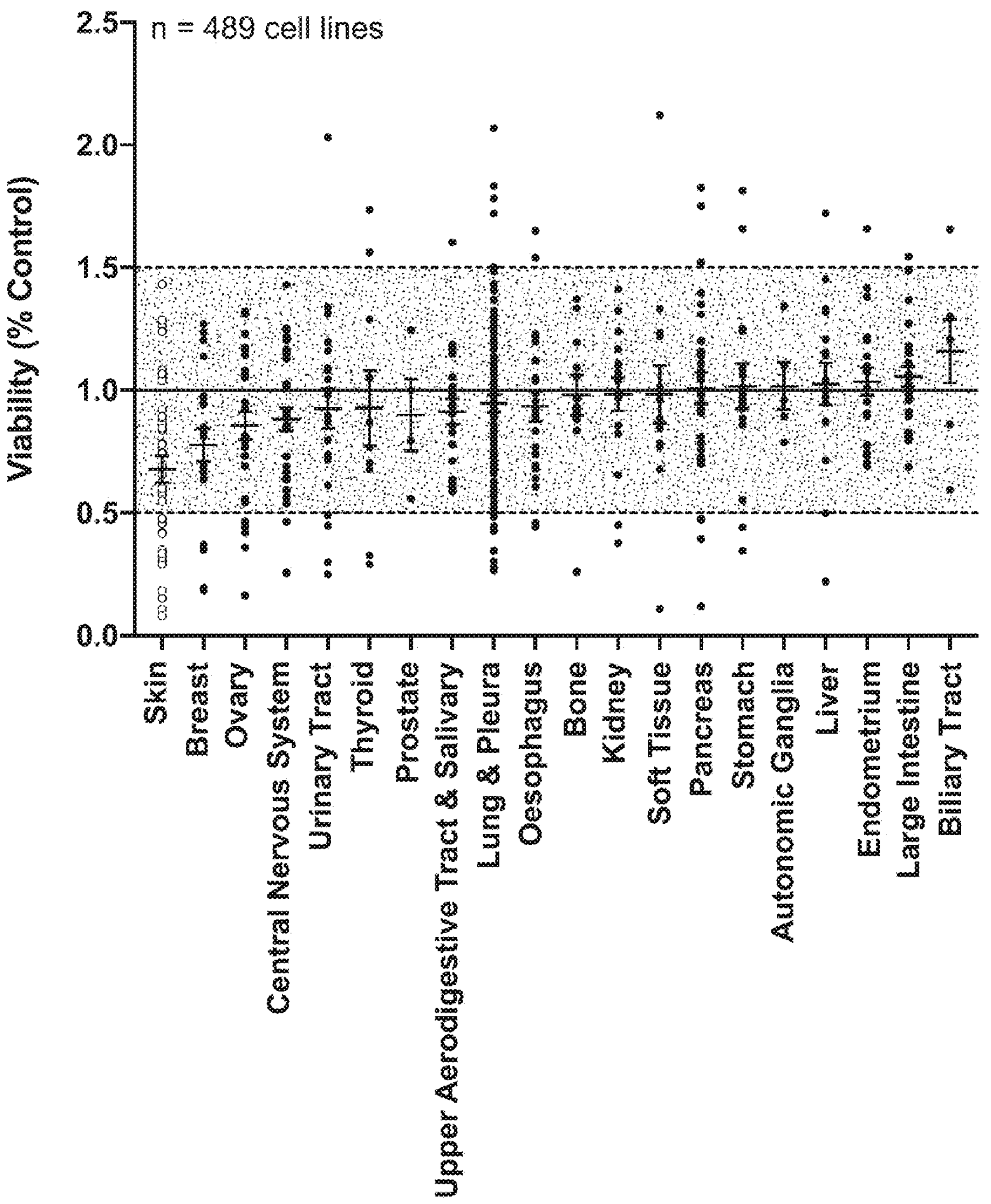
FIG. 30A-FIG. 30H show that ML329 is selectively cytotoxic in melanoma cells and associated with MITF dependent transcription.
Figure 30B:
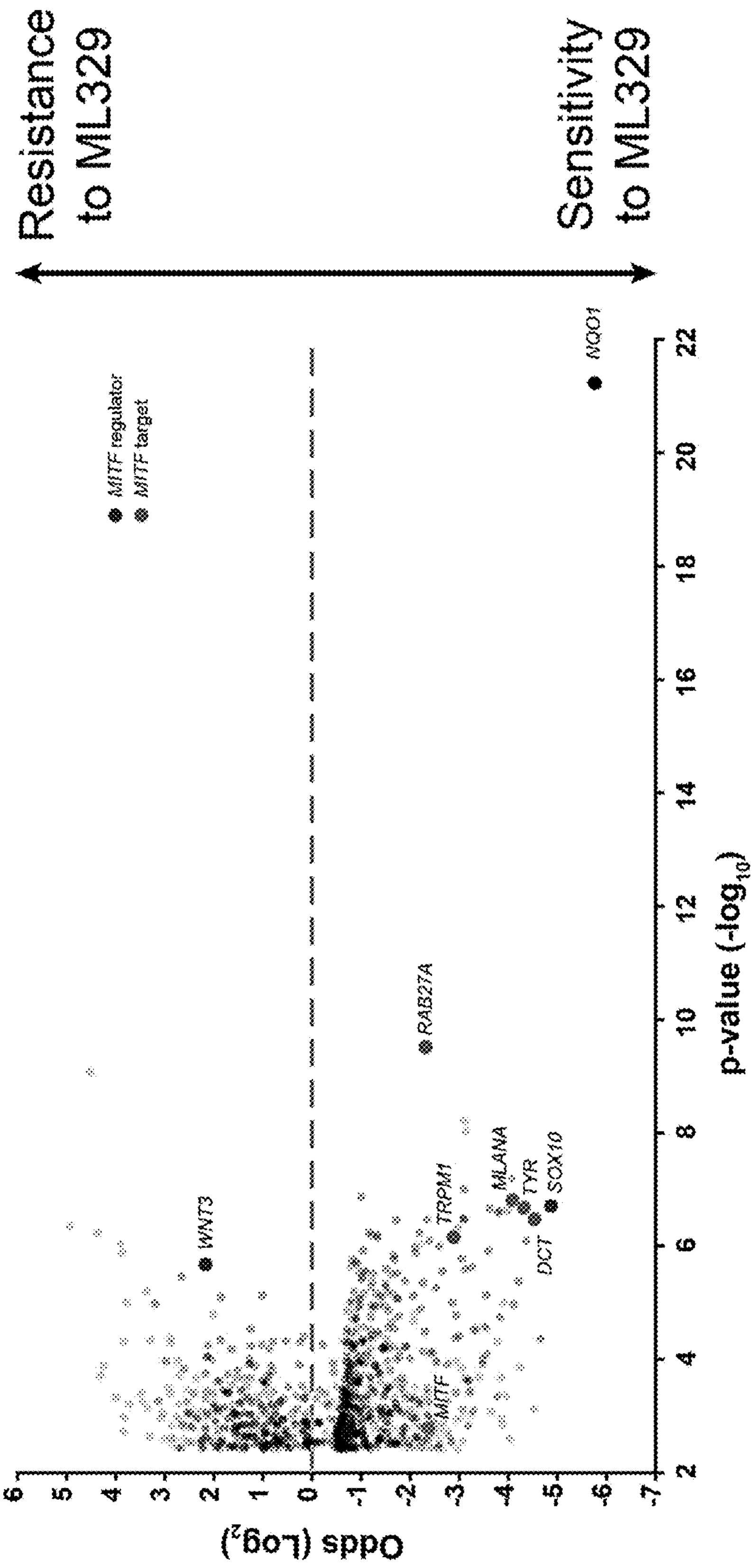
Figure 30C:
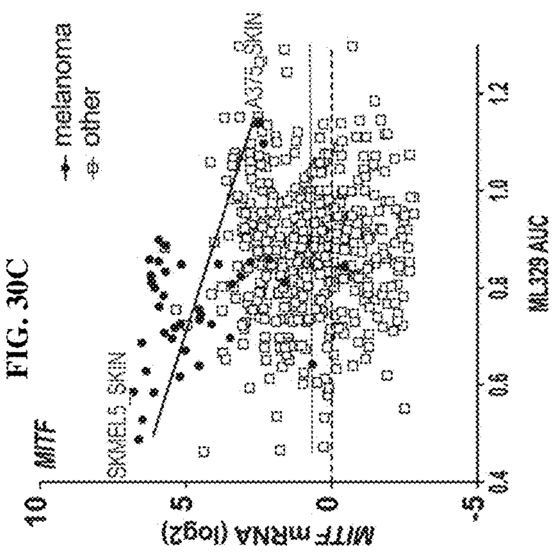
Figure 30D:
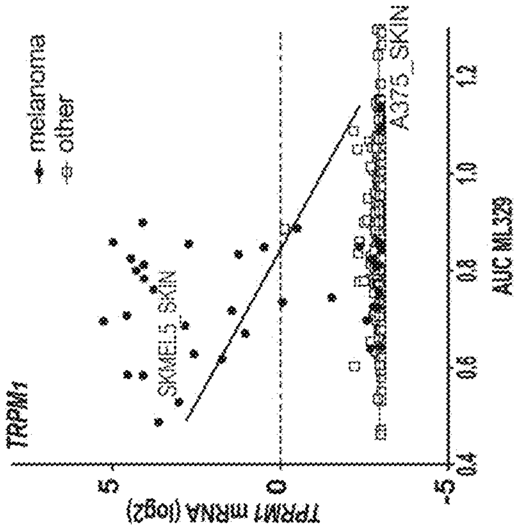
Figure 30E:
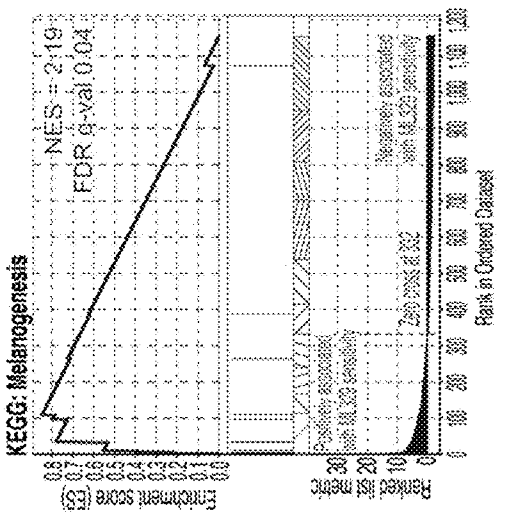
Figure 30F:
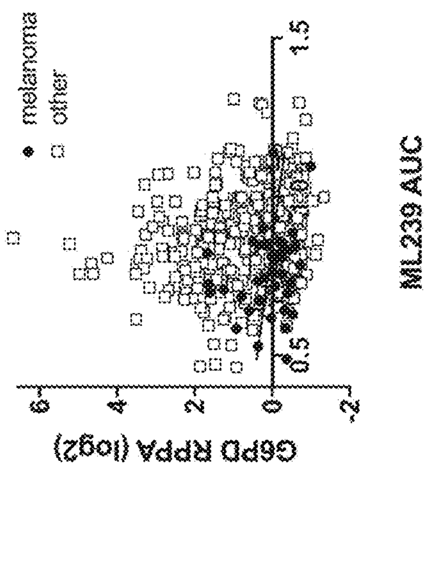
Figure 30G:
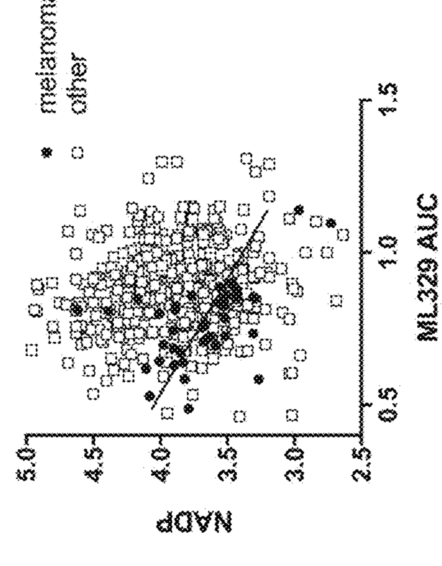
Figure 30H:
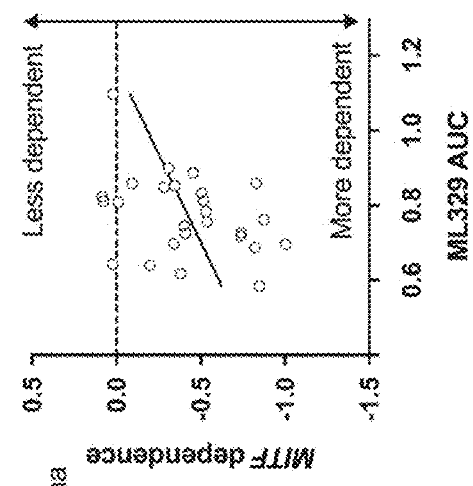
Figure 31A:
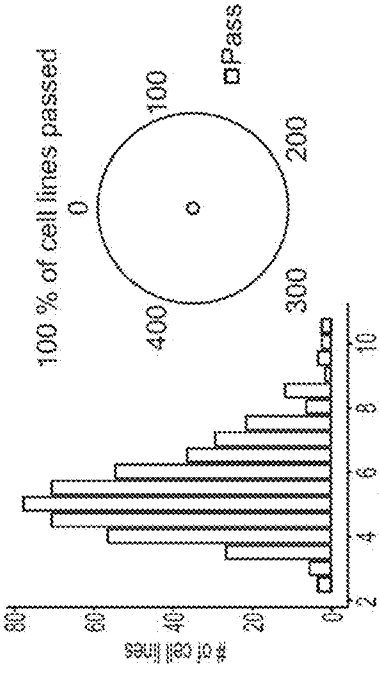
FIG. 31A-FIG. 31E shows genomic and molecular correlates of ML329 sensitivity across cancer cell lines.
Figure 31B:
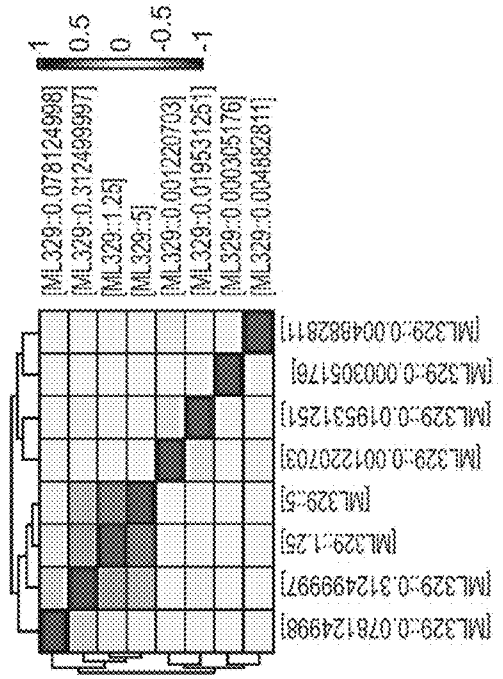
Figure 31C:
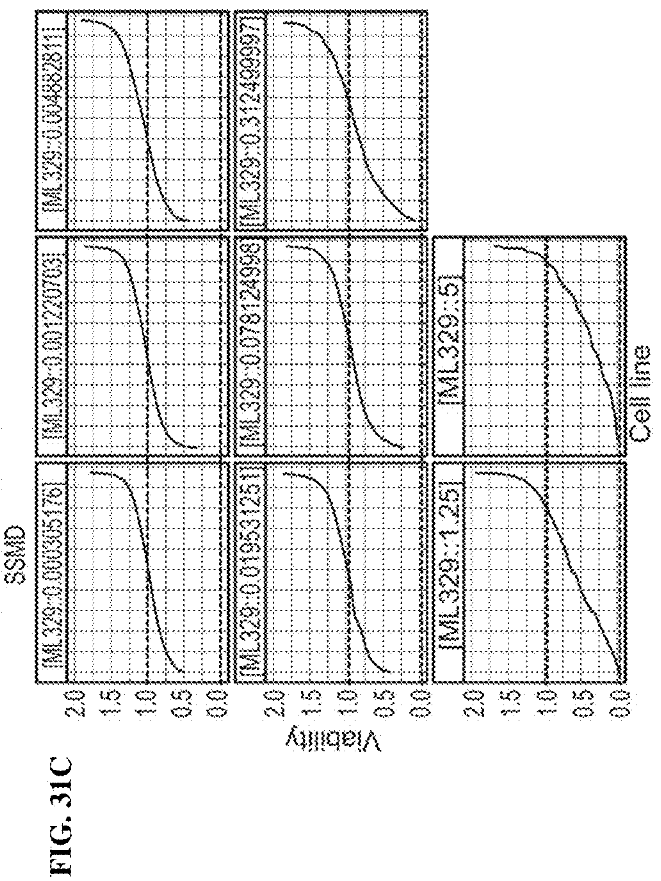
Figure 31D:
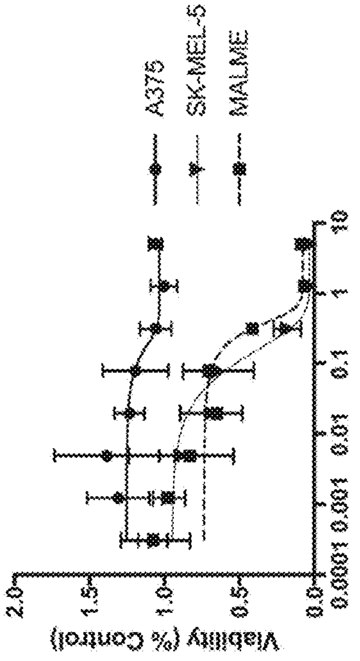
Figure 31:
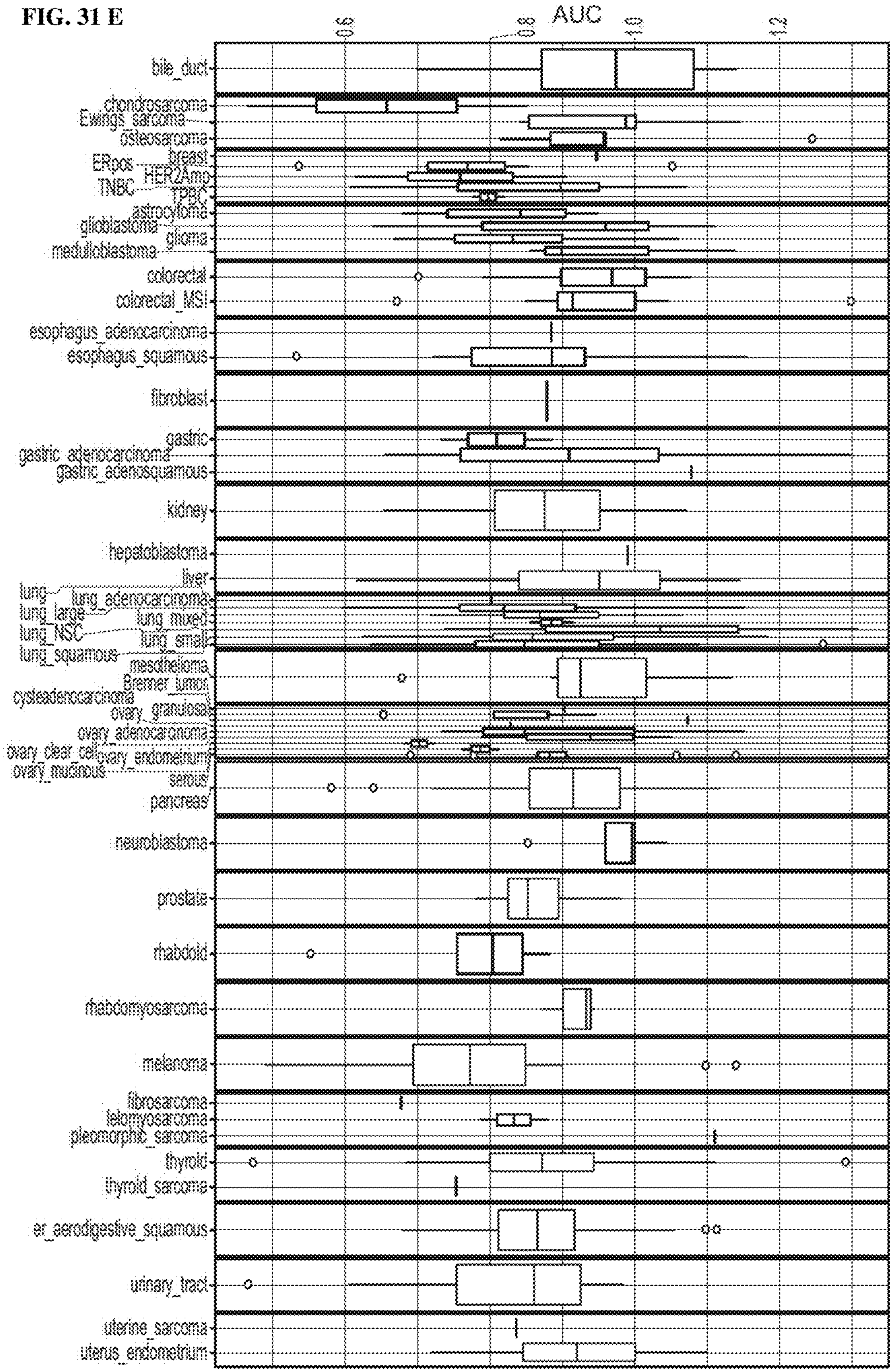
Figures 32A, 32B, 32C, 32D, 32E, 32F:
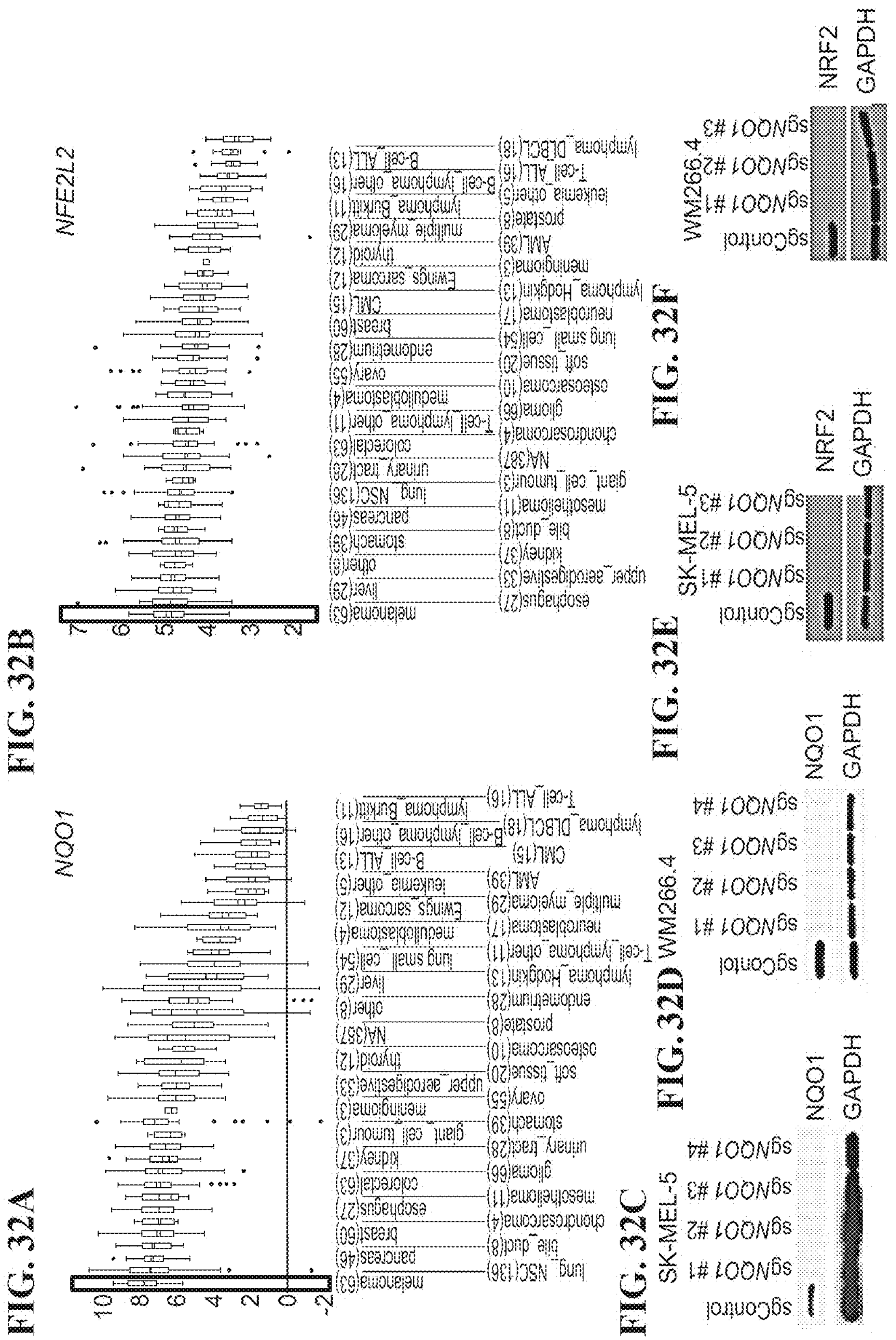
Figure 33:
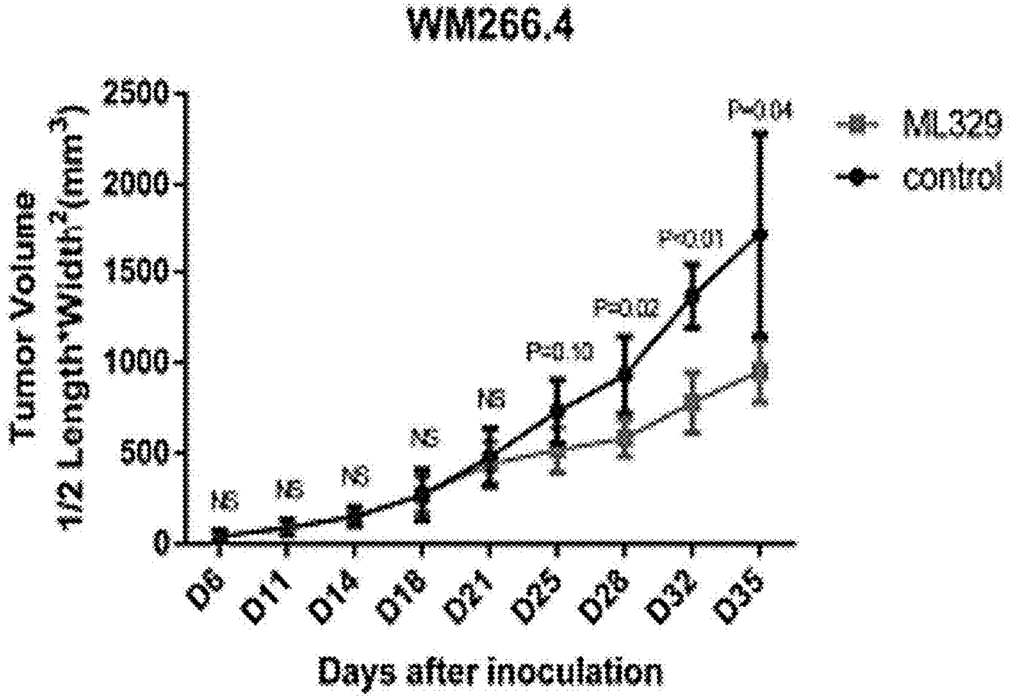
FIG. 33 shows that ML329 has in vivo activity in melanoma that requires NRF2/NQO1. The figure shows tumor volume in NSG mice xenografted with WM266.4 cells with twice daily treatment of ML329 (10 mg/kg) or vehicle.
Figure 34A:
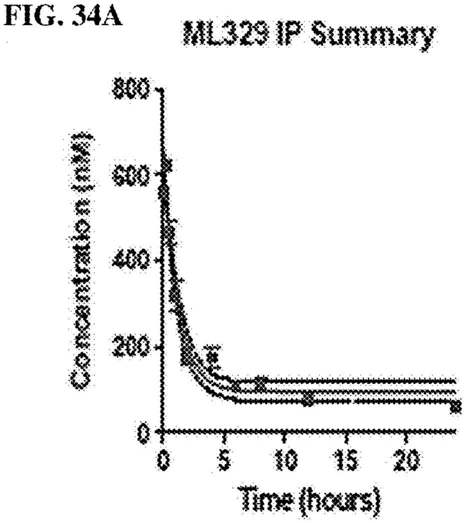
FIG. 34A-FIG. 34B shows pharmacokinetics of ML329 in vivo.
Figure 34B:
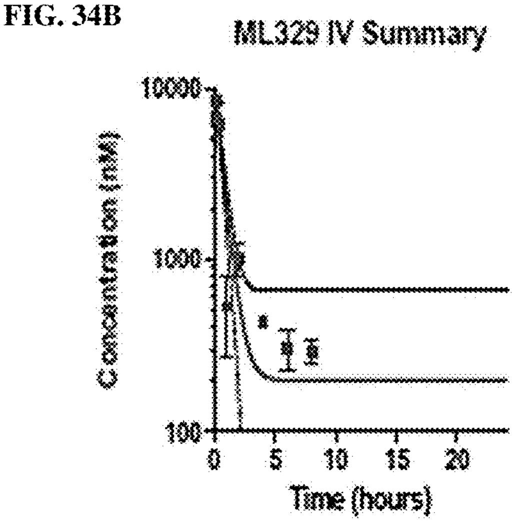
Figure 35A:
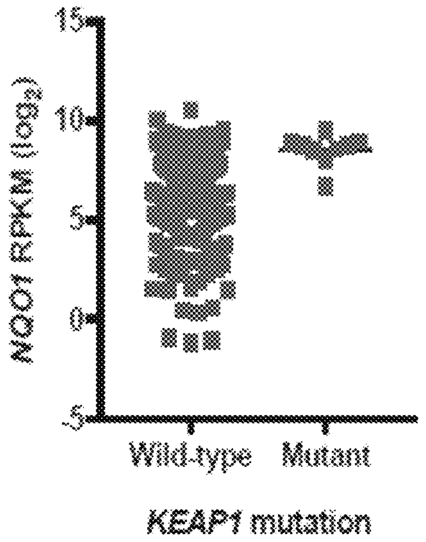
FIG. 35A-FIG. 35D shows that ML329 is preferentially active in KEAP1 deficient models of lung cancer.
Figure 35B:
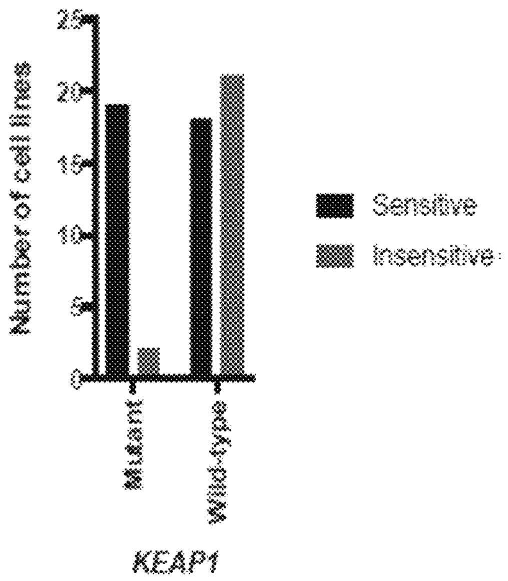
Figure 35C:
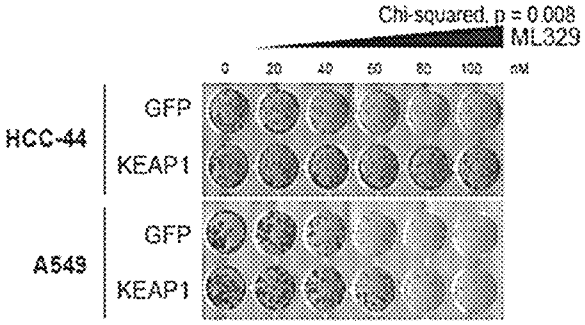
Figure 35D:
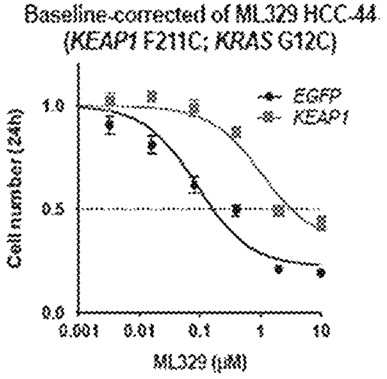
Figure 36:
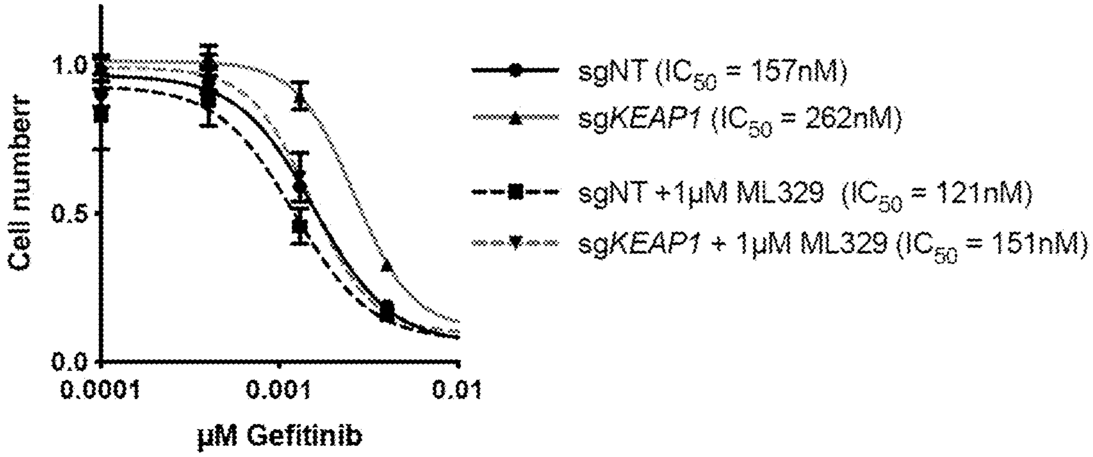
FIG. 36 shows that ML329 overcomes resistance to targeted therapies. The figure shows cell number of control or KEAP1-deleted HCC827 cell lines after 48 h treatment with gefinitib with or without ML329.

The results shown in FIGS. 22-24 further confirm the results shown in FIGS. 1-21, such as demonstrating effects of ML329 on melanoma cell lines MALME and WM266.4, further confirming effects on TRPM1 mRNA expression, further clarifying atypical and mutant kinases, further confirming that ML329 is a direct substrate of Nqo1 in vitro, and further confirming that Nqo1 is required for ML329 inhibition of CK2 in vitro. The results are consistent with a model schematized in FIG. 25. The model and other data are further confirmed by the data shown in FIGS. 26-36.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments encompassed by the present invention described herein. Such equivalents are intended to be encompassed by the following claims.

What is claimed is:

1. A method of treating a cancer in a subject likely to be responsive to 4-[(1,4-dioxo-1,4-dihydronapthalen-2-yl)amino]benzenesulfonamide (ML329) or an ML329 derivative selected from:

(SCAP105461)

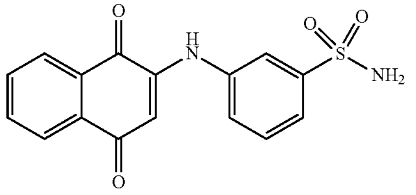

and (SCAP105463)

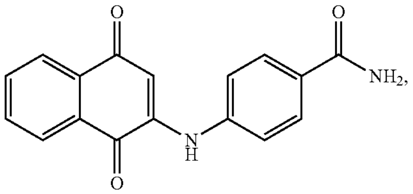

the method comprising:

i) selecting the subject likely to be responsive to ML329 or the ML329 derivative, the subject having been identified by determining the presence of a KEAP1 loss-of-function mutation in cancer cells from the subject wherein the presence of the kelch-like ECH-associated protein 1 (KEAP1) loss-of-function mutation identifies the subject as likely to be responsive to ML329 or the ML329 derivative; and ii) administering ML329 or the ML329 derivative to the selected subject.

2. The method of claim 1, wherein the subject's cancer cells have KEAP1 loss-of-function.

3. The method of claim 1, wherein the KEAP1 loss-of-function mutation is a coding region mutation.

4. The method of claim 1, wherein the cancer is selected from the group consisting of melanoma, lung cancer, head and neck squamous cell carcinomas, kidney cancer, pancreas cancer, prostate cancer, bladder cancer, uterine cancer, head and neck cancer, and esophagus cancer.

5. The method of claim 1, wherein the subject is likely to be responsive to ML329 and the method comprises administering ML329 to the selected subject.

6. The method of claim 1, wherein the subject is likely to be responsive to the ML329 derivative, SCAP105461, and the method comprises administering SCAP105461 to the selected subject.

7. The method of claim 1, wherein the subject is likely to be responsive to the ML329 derivative, SCAP105463, and the method comprises administering SCAP105463 to the selected subject.

8. The method of claim 1, wherein the subject is a) an animal model of cancer;

b) a mammal;

c) a mouse; or d) a human.

9. The method of claim 1, wherein the cancer is a lung cancer.

10. The method of claim 5, wherein the cancer is a lung cancer.

11. The method of claim 6, wherein the cancer is a lung cancer.

12. The method of claim 7, wherein the cancer is a lung cancer.

* * * * *

SEQUENCE LISTING

<160> NUMBER OF SEQ ID NOS: 39

<210> SEQ ID NO 1
<211> LENGTH: 2601
<212> TYPE: DNA
<213> ORGANISM: Homo sapiens

<400> SEQUENCE: 1
ccgcccttgt aggctgtcca cctcaaacgg gccggacagg atatataaga gagaatgcac 60
cgtgcactac acacgcgact cccacaaggt tgcagccgga gccgcccagc tcaccgagag 120
cctagttccg gccagggtcg ccccggcaac cacgagccca gccaatcagc gccccggact 180
gcaccagagc catggtcggc agaagagcac tgatcgtact ggctcactca gagaggacgt 240
ccttcaacta tgccatgaag gaggctgctg cagcggcttt gaagaagaaa ggatgggagg 300
tggtggagtc ggacctctat gccatgaact tcaatcccat catttccaga aaggacatca 360
caggtaaact gaaggaccct gcgaactttc agtatcctgc cgagtctgtt ctggcttata 420
aagaaggcca tctgagccca gatattgtgg ctgaacaaaa gaagctggaa gccgcagacc 480
ttgtgatatt ccagttcccc ctgcagtggt ttggagtccc tgccattctg aaaggctggt 540
ttgagcgagt gttcatagga gagtttgctt acacttacgc tgccatgtat gacaaaggac 600

-continued

```
ccttccggag taagaaggca gtgctttcca tcaccactgg tggcagtggc tccatgtact    660

ctctgcaagg gatccacggg gacatgaatg tcattctctg gccaattcag agtggcattc    720

tgcatttctg tggcttccaa gtcttagaac ctcaactgac atatagcatt gggcacactc    780

cagcagacgc ccgaattcaa atcctggaag gatggaagaa acgcctggag aatatttggg    840

atgagacacc actgtatttt gctccaagca gcctctttga cctaaacttc caggcaggat    900

tcttaatgaa aaaagaggta caggatgagg agaaaaacaa gaaatttggc ctttctgtgg    960

gccatcactt gggcaagtcc atcccaactg acaaccagat caaagctaga aaatgagatt   1020

ccttagcctg gatttccttc taacatgtta tcaaatctgg gtatctttcc aggcttccct   1080

gacttgcttt agtttttaag atttgtgttt ttctttttcc acaaggaata aatgagaggg   1140

aatcgactgt attcgtgcat ttttggatca tttttaactg attcttatga ttactatcat   1200

ggcatataac caaaatccga ctgggctcaa gaggccactt agggaaagat gtagaaagat   1260

gctagaaaaa tgttctttaa aggcatctac acaatttaat tcctcttttt agggctaaag   1320

ttttagggta cagtttggct aggtatcatt caactctcca atgttctatt aatcacctct   1380

ctgtagttta tggcagaagg gaattgctca gagaaggaaa agactgaatc tacctgccct   1440

aagggactta acttgtttgg tagttagcca tctaatgctt gtttatgata tttcttgctt   1500

tcaattacaa agcagttact aatatgccta gcacaagtac cactcttggt cagcttttgt   1560

tgtttatata cagtacacag ataccttgaa aggaagagct aataaatctc ttctttgctg   1620

cagtcatcta cttttttttt aattaaaaaa aatttttttt tgaagcagtc ttgctctgtt   1680

acccaggctg gagtgcagtg gtgtgatctc ggctcactgc aacctctgcc tcccaggttc   1740

cagcaattct cctgcctcag cctccctagt agctgggatg acaggcgcct gccatcatgc   1800

ctgactaatt tttgtatttt tagtagagac ggcgtttcac catgttggcc aggctggtct   1860

caaactcctg acctcaggtg atccgcctac ctcagcctcc caaagtgctg ggattacagg   1920

cgtgatccac cacacctggc ccttgcaatc ttctacttta aggtttgcag agataaacca   1980

ataaatccac accgtacatc tgcaatatga attcaagaaa ggaaatagta ccttcaatac   2040

ttaaaaatag tcttccacaa aaaatacttt atttctgatc tatacaaatt ttcagaaggt   2100

tattttcttt atcattgcta aactgatgac ttactatggg atggggtcca gtcccatgac   2160

cttggggtac aattgtaaac ctagagtttt atcaactttg gtgaacagtt ttggcataat   2220

agtcaatttc tacttctgga agtcatctca ttccactgtt ggtattatat aattcaagga   2280

gaatatgata aaacactgcc ctcttgtggt gcattgaaag aagagatgag aaatgatgaa   2340

aaggttgcct gaaaaatggg agacagcctc ttacttgcca agaaaatgaa gggattggac   2400

cgagctggaa aacctccttt accagatgct gactggcact ggtggttttt gctctcgaca   2460

gtatccacaa tagctgacgg ctgggtgttt cagtttgaaa atattttgtt gccttcatct   2520

tcactgcaat tttgtgtaaa tttctcaaag atctgaatta aataaataaa attcatttct   2580

acagacccac aaaaaaaaaa a                                             2601
```

<210> SEQ ID NO 2
<211> LENGTH: 2499
<212> TYPE: DNA
<213> ORGANISM: Homo sapiens

<400> SEQUENCE: 2

```
ccgcccttgt aggctgtcca cctcaaacgg gccggacagg atatataaga gagaatgcac     60

cgtgcactac acacgcgact cccacaaggt tgcagccgga gccgcccagc tcaccgagag    120
```

-continued

```
cctagttccg gccagggtcg ccccggcaac cacgagccca gccaatcagc gccccggact    180
gcaccagagc catggtcggc agaagagcac tgatcgtact ggctcactca gagaggacgt    240
ccttcaacta tgccatgaag gaggctgctg cagcggcttt gaagaagaaa ggatgggagg    300
tggtggagtc ggacctctat gccatgaact tcaatcccat catttccaga aaggacatca    360
caggtaaact gaaggaccct gcgaactttc agtatcctgc cgagtctgtt ctggcttata    420
aagaaggcca tctgagccca gatattgtgg ctgaacaaaa gaagctggaa gccgcagacc    480
ttgtgatatt ccagttcccc ctgcagtggt ttggagtccc tgccattctg aaaggctggt    540
ttgagcgagt gttcatagga gagtttgctt acacttacgc tgccatgtat gacaaaggac    600
ccttccggag tggcattctg catttctgtg gcttccaagt cttagaacct caactgacat    660
atagcattgg gcacactcca gcagacgccc gaattcaaat cctggaagga tggaagaaac    720
gcctggagaa tatttgggat gagacaccac tgtattttgc tccaagcagc ctctttgacc    780
taaacttcca ggcaggattc ttaatgaaaa aagaggtaca ggatgaggag aaaaacaaga    840
aatttggcct ttctgtgggc catcacttgg gcaagtccat cccaactgac aaccagatca    900
aagctagaaa atgagattcc ttagcctgga tttccttcta acatgttatc aaatctgggt    960
atctttccag gcttccctga cttgctttag tttttaagat ttgtgttttt ctttttccac   1020
aaggaataaa tgagagggaa tcgactgtat tcgtgcattt ttggatcatt tttaactgat   1080
tcttatgatt actatcatgg catataacca aaatccgact gggctcaaga ggccacttag   1140
ggaaagatgt agaaagatgc tagaaaaatg ttctttaaag gcatctacac aatttaattc   1200
ctctttttag ggctaaagtt ttagggtaca gtttggctag gtatcattca actctccaat   1260
gttctattaa tcacctctct gtagtttatg gcagaaggga attgctcaga gaaggaaaag   1320
actgaatcta cctgccctaa gggacttaac ttgtttggta gttagccatc taatgcttgt   1380
ttatgatatt tcttgctttc aattacaaag cagttactaa tatgcctagc acaagtacca   1440
ctcttggtca gcttttgttg tttatataca gtacacagat accttgaaag gaagagctaa   1500
taaatctctt ctttgctgca gtcatctact ttttttttaa ttaaaaaaaa ttttttttttg   1560
aagcagtctt gctctgttac ccaggctgga gtgcagtggt gtgatctcgg ctcactgcaa   1620
cctctgcctc ccaggttcca gcaattctcc tgcctcagcc tccctagtag ctgggatgac   1680
aggcgcctgc catcatgcct gactaatttt tgtattttta gtagagacgg cgtttcacca   1740
tgttggccag gctggtctca aactcctgac ctcaggtgat ccgcctacct cagcctccca   1800
aagtgctggg attacaggcg tgatccacca cacctggccc ttgcaatctt ctactttaag   1860
gtttgcagag ataaaccaat aaatccacac cgtacatctg caatatgaat tcaagaaagg   1920
aaatagtacc ttcaatactt aaaaatagtc ttccacaaaa aatactttat ttctgatcta   1980
tacaaatttt cagaaggtta ttttctttat cattgctaaa ctgatgactt actatgggat   2040
ggggtccagt cccatgacct tggggtacaa ttgtaaacct agagttttat caactttggt   2100
gaacagtttt ggcataatag tcaatttcta cttctggaag tcatctcatt ccactgttgg   2160
tattatataa ttcaaggaga atatgataaa acactgccct cttgtggtgc attgaaagaa   2220
gagatgagaa atgatgaaaa ggttgcctga aaaatgggag acagcctctt acttgccaag   2280
aaaatgaagg gattggaccg agctggaaaa cctcctttac cagatgctga ctggcactgg   2340
tggtttttgc tctcgacagt atccacaata gctgacggct gggtgtttca gtttgaaaat   2400
attttgttgc cttcatcttc actgcaattt tgtgtaaatt tctcaaagat ctgaattaaa   2460
```

taaataaaat tcatttctac agacccacaa aaaaaaaaa 2499

<210> SEQ ID NO 3
<211> LENGTH: 2487
<212> TYPE: DNA
<213> ORGANISM: Homo sapiens

<400> SEQUENCE: 3
ccgcccttgt aggctgtcca cctcaaacgg gccggacagg atatataaga gagaatgcac 60
cgtgcactac acacgcgact cccacaaggt tgcagccgga gccgcccagc tcaccgagag 120
cctagttccg gccagggtcg ccccggcaac cacgagccca gccaatcagc gccccggact 180
gcaccagagc catggtcggc agaagagcac tgatcgtact ggctcactca gagaggacgt 240
ccttcaacta tgccatgaag gaggctgctg cagcggcttt gaagaagaaa ggatgggagg 300
tggtggagtc ggacctctat gccatgaact tcaatcccat catttccaga aaggacatca 360
caggtaaact gaaggaccct gcgaactttc agtatcctgc cgagtctgtt ctggcttata 420
aagaaggcca tctgagccca gatattgtgg ctgaacaaaa gaagctggaa gccgcagacc 480
ttgtgatatt ccagagtaag aaggcagtgc tttccatcac cactggtggc agtggctcca 540
tgtactctct gcaagggatc cacggggaca tgaatgtcat tctctggcca attcagagtg 600
gcattctgca tttctgtggc ttccaagtct tagaacctca actgacatat agcattgggc 660
acactccagc agacgcccga attcaaatcc tggaaggatg gaagaaacgc ctggagaata 720
tttgggatga gacaccactg tattttgctc caagcagcct ctttgaccta aacttccagg 780
caggattctt aatgaaaaaa gaggtacagg atgaggagaa aaacaagaaa tttggccttt 840
ctgtgggcca tcacttgggc aagtccatcc caactgacaa ccagatcaaa gctagaaaat 900
gagattcctt agcctggatt tccttctaac atgttatcaa atctgggtat ctttccaggc 960
ttccctgact tgctttagtt tttaagattt gtgtttttct ttttccacaa ggaataaatg 1020
agagggaatc gactgtattc gtgcattttt ggatcatttt taactgattc ttatgattac 1080
tatcatggca tataaccaaa atccgactgg gctcaagagg ccacttaggg aaagatgtag 1140
aaagatgcta gaaaaatgtt ctttaaaggc atctacacaa tttaattcct ctttttaggg 1200
ctaaagtttt agggtacagt ttggctaggt atcattcaac tctccaatgt tctattaatc 1260
acctctctgt agtttatggc agaagggaat tgctcagaga aggaaaagac tgaatctacc 1320
tgccctaagg gacttaactt gtttggtagt tagccatcta atgcttgttt atgatatttc 1380
ttgctttcaa ttacaaagca gttactaata tgcctagcac aagtaccact cttggtcagc 1440
ttttgttgtt tatatacagt acacagatac cttgaaagga agagctaata aatctcttct 1500
ttgctgcagt catctacttt ttttttaatt aaaaaaaatt ttttttgaa gcagtcttgc 1560 tctgttaccc aggctggagt gcagtggtgt gatctcggct cactgcaacc tctgcctccc 1620
aggttccagc aattctcctg cctcagcctc cctagtagct gggatgacag gcgcctgcca 1680
tcatgcctga ctaatttttg tatttttagt agagacggcg tttcaccatg ttggccaggc 1740
tggtctcaaa ctcctgacct caggtgatcc gcctacctca gcctcccaaa gtgctgggat 1800
tacaggcgtg atccaccaca cctggccctt gcaatcttct actttaaggt ttgcagagat 1860
aaaccaataa atccacaccg tacatctgca atatgaattc aagaaaggaa atagtacctt 1920
caatacttaa aaatagtctt ccacaaaaaa tactttattt ctgatctata caaattttca 1980
gaaggttatt ttctttatca ttgctaaact gatgacttac tatgggatgg ggtccagtcc 2040
catgaccttg gggtacaatt gtaaacctag agttttatca actttggtga acagttttgg 2100

-continued

```
cataatagtc aatttctact tctggaagtc atctcattcc actgttggta ttatataatt   2160

caaggagaat atgataaaac actgccctct tgtggtgcat tgaaagaaga gatgagaaat   2220

gatgaaaagg ttgcctgaaa aatgggagac agcctcttac ttgccaagaa aatgaaggga   2280

ttggaccgag ctggaaaacc tcctttacca gatgctgact ggcactggtg gtttttgctc   2340

tcgacagtat ccacaatagc tgacggctgg gtgtttcagt ttgaaaatat tttgttgcct   2400

tcatcttcac tgcaattttg tgtaaatttc tcaaagatct gaattaaata aataaaattc   2460

atttctacag acccacaaaa aaaaaaa                                       2487
```

<210> SEQ ID NO 4
<211> LENGTH: 2423
<212> TYPE: DNA
<213> ORGANISM: Homo sapiens

<400> SEQUENCE: 4

```
atcctccgcc cagcacccca ggattcaggc gttgggtccc gcccttgtag gctgtccacc     60

tcaaacgggc cggacaggat atataagaga gaatgcaccg tgcactacac acgcgactcc    120

cacaaggttg cagccggagc cgcccagctc accgagagcc tagttccggc cagggtcgcc    180

ccggcaacca cgagcccagc caatcagcgc cccggactgc accagagcca tggtcggcag    240

aagagcactg atcgtactgg ctcactcaga gaggacgtcc ttcaactatg ccatgaagga    300

ggctgctgca gcggctttga agaagaaagg atgggaggtg gtggagtcgg acctctatgc    360

catgaacttc aatcccatca tttccagaaa ggacatcaca ggtaaactga aggaccctgc    420

gaactttcag tatcctgccg agtctgttct ggcttataaa gaaggccatc tgagcccaga    480

tattgtggct gaacaaaaga agctggaagc cgcagacctt gtgatattcc agagtggcat    540

tctgcatttc tgtggcttcc aagtcttaga acctcaactg acatatagca ttgggcacac    600

tccagcagac gcccgaattc aaatcctgga aggatggaag aaacgcctgg agaatatttg    660

ggatgagaca ccactgtatt ttgctccaag cagcctcttt gacctaaact tccaggcagg    720

attcttaatg aaaaaagagg tacaggatga ggagaaaaac aagaaatttg gcctttctgt    780

gggccatcac ttgggcaagt ccatcccaac tgacaaccag atcaaagcta gaaaatgaga    840

ttccttagcc tggatttcct tctaacatgt tatcaaatct gggtatcttt ccaggcttcc    900

ctgacttgct ttagttttta agatttgtgt ttttcttttt ccacaaggaa taaatgagag    960

ggaatcgact gtattcgtgc atttttggat catttttaac tgattcttat gattactatc   1020

atggcatata accaaaatcc gactgggctc aagaggccac ttagggaaag atgtagaaag   1080

atgctagaaa aatgttcttt aaaggcatct acacaattta attcctcttt ttagggctaa   1140

agttttaggg tacagtttgg ctaggtatca ttcaactctc caatgttcta ttaatcacct   1200

ctctgtagtt tatggcagaa gggaattgct cagagaagga aaagactgaa tctacctgcc   1260

ctaagggact taacttgttt ggtagttagc catctaatgc ttgtttatga tatttcttgc   1320

tttcaattac aaagcagtta ctaatatgcc tagcacaagt accactcttg gtcagctttt   1380

gttgtttata tacagtacac agataccttg aaaggaagag ctaataaatc tcttctttgc   1440

tgcagtcatc tacttttttt ttaattaaaa aaaatttttt tttgaagcag tcttgctctg   1500

ttacccaggc tggagtgcag tggtgtgatc tcggctcact gcaacctctg cctcccaggt   1560

tccagcaatt ctcctgcctc agcctcccta gtagctggga tgacaggcgc ctgccatcat   1620

gcctgactaa tttttgtatt tttagtagag acggcgtttc accatgttgg ccaggctggt   1680
```

-continued

```
ctcaaactcc tgacctcagg tgatccgcct acctcagcct cccaaagtgc tgggattaca   1740

ggcgtgatcc accacacctg gcccttgcaa tcttctactt taaggtttgc agagataaac   1800

caataaatcc acaccgtaca tctgcaatat gaattcaaga aaggaaatag taccttcaat   1860

acttaaaaat agtcttccac aaaaaatact ttatttctga tctatacaaa ttttcagaag   1920

gttattttct ttatcattgc taaactgatg acttactatg ggatggggtc cagtcccatg   1980

accttggggt acaattgtaa acctagagtt ttatcaactt tggtgaacag ttttggcata   2040

atagtcaatt tctacttctg gaagtcatct cattccactg ttggtattat ataattcaag   2100

gagaatatga taaaacactg ccctcttgtg gtgcattgaa agaagagatg agaaatgatg   2160

aaaaggttgc ctgaaaaatg ggagacagcc tcttacttgc caagaaaatg aagggattgg   2220

accgagctgg aaaacctcct ttaccagatg ctgactggca ctggtggttt ttgctctcga   2280

cagtatccac aatagctgac ggctgggtgt ttcagtttga aaatattttg ttgccttcat   2340

cttcactgca attttgtgta aatttctcaa agatctgaat taaataaata aaattcattt   2400

ctacagaccc acaaaaaaaa aaa                                            2423
```

```
<210> SEQ ID NO 5
<211> LENGTH: 274
<212> TYPE: PRT
<213> ORGANISM: Homo sapiens

<400> SEQUENCE: 5

Met Val Gly Arg Arg Ala Leu Ile Val Leu Ala His Ser Glu Arg Thr
1               5                   10                  15

Ser Phe Asn Tyr Ala Met Lys Glu Ala Ala Ala Ala Ala Leu Lys Lys
            20                  25                  30

Lys Gly Trp Glu Val Val Glu Ser Asp Leu Tyr Ala Met Asn Phe Asn
        35                  40                  45

Pro Ile Ile Ser Arg Lys Asp Ile Thr Gly Lys Leu Lys Asp Pro Ala
    50                  55                  60

Asn Phe Gln Tyr Pro Ala Glu Ser Val Leu Ala Tyr Lys Glu Gly His
65                  70                  75                  80

Leu Ser Pro Asp Ile Val Ala Glu Gln Lys Lys Leu Glu Ala Ala Asp
                85                  90                  95

Leu Val Ile Phe Gln Phe Pro Leu Gln Trp Phe Gly Val Pro Ala Ile
            100                 105                 110

Leu Lys Gly Trp Phe Glu Arg Val Phe Ile Gly Glu Phe Ala Tyr Thr
        115                 120                 125

Tyr Ala Ala Met Tyr Asp Lys Gly Pro Phe Arg Ser Lys Lys Ala Val
    130                 135                 140

Leu Ser Ile Thr Thr Gly Gly Ser Gly Ser Met Tyr Ser Leu Gln Gly
145                 150                 155                 160

Ile His Gly Asp Met Asn Val Ile Leu Trp Pro Ile Gln Ser Gly Ile
                165                 170                 175

Leu His Phe Cys Gly Phe Gln Val Leu Glu Pro Gln Leu Thr Tyr Ser
            180                 185                 190

Ile Gly His Thr Pro Ala Asp Ala Arg Ile Gln Ile Leu Glu Gly Trp
        195                 200                 205

Lys Lys Arg Leu Glu Asn Ile Trp Asp Glu Thr Pro Leu Tyr Phe Ala
    210                 215                 220

Pro Ser Ser Leu Phe Asp Leu Asn Phe Gln Ala Gly Phe Leu Met Lys
225                 230                 235                 240
```

-continued

```
Lys Glu Val Gln Asp Glu Glu Lys Asn Lys Lys Phe Gly Leu Ser Val
                245                 250                 255

Gly His His Leu Gly Lys Ser Ile Pro Thr Asp Asn Gln Ile Lys Ala
            260                 265                 270

Arg Lys


<210> SEQ ID NO 6
<211> LENGTH: 240
<212> TYPE: PRT
<213> ORGANISM: Homo sapiens

<400> SEQUENCE: 6

Met Val Gly Arg Arg Ala Leu Ile Val Leu Ala His Ser Glu Arg Thr
1               5                   10                  15

Ser Phe Asn Tyr Ala Met Lys Glu Ala Ala Ala Ala Ala Leu Lys Lys
            20                  25                  30

Lys Gly Trp Glu Val Val Glu Ser Asp Leu Tyr Ala Met Asn Phe Asn
        35                  40                  45

Pro Ile Ile Ser Arg Lys Asp Ile Thr Gly Lys Leu Lys Asp Pro Ala
    50                  55                  60

Asn Phe Gln Tyr Pro Ala Glu Ser Val Leu Ala Tyr Lys Glu Gly His
65                  70                  75                  80

Leu Ser Pro Asp Ile Val Ala Glu Gln Lys Lys Leu Glu Ala Ala Asp
                85                  90                  95

Leu Val Ile Phe Gln Phe Pro Leu Gln Trp Phe Gly Val Pro Ala Ile
            100                 105                 110

Leu Lys Gly Trp Phe Glu Arg Val Phe Ile Gly Glu Phe Ala Tyr Thr
        115                 120                 125

Tyr Ala Ala Met Tyr Asp Lys Gly Pro Phe Arg Ser Gly Ile Leu His
    130                 135                 140

Phe Cys Gly Phe Gln Val Leu Glu Pro Gln Leu Thr Tyr Ser Ile Gly
145                 150                 155                 160

His Thr Pro Ala Asp Ala Arg Ile Gln Ile Leu Glu Gly Trp Lys Lys
                165                 170                 175

Arg Leu Glu Asn Ile Trp Asp Glu Thr Pro Leu Tyr Phe Ala Pro Ser
            180                 185                 190

Ser Leu Phe Asp Leu Asn Phe Gln Ala Gly Phe Leu Met Lys Lys Glu
        195                 200                 205

Val Gln Asp Glu Glu Lys Asn Lys Lys Phe Gly Leu Ser Val Gly His
    210                 215                 220

His Leu Gly Lys Ser Ile Pro Thr Asp Asn Gln Ile Lys Ala Arg Lys
225                 230                 235                 240


<210> SEQ ID NO 7
<211> LENGTH: 236
<212> TYPE: PRT
<213> ORGANISM: Homo sapiens

<400> SEQUENCE: 7

Met Val Gly Arg Arg Ala Leu Ile Val Leu Ala His Ser Glu Arg Thr
1               5                   10                  15

Ser Phe Asn Tyr Ala Met Lys Glu Ala Ala Ala Ala Ala Leu Lys Lys
            20                  25                  30

Lys Gly Trp Glu Val Val Glu Ser Asp Leu Tyr Ala Met Asn Phe Asn
        35                  40                  45

Pro Ile Ile Ser Arg Lys Asp Ile Thr Gly Lys Leu Lys Asp Pro Ala
```

-continued

```
    50                  55                  60

Asn Phe Gln Tyr Pro Ala Glu Ser Val Leu Ala Tyr Lys Glu Gly His
65                  70                  75                  80

Leu Ser Pro Asp Ile Val Ala Glu Gln Lys Lys Leu Glu Ala Ala Asp
                85                  90                  95

Leu Val Ile Phe Gln Ser Lys Lys Ala Val Leu Ser Ile Thr Thr Gly
            100                 105                 110

Gly Ser Gly Ser Met Tyr Ser Leu Gln Gly Ile His Gly Asp Met Asn
        115                 120                 125

Val Ile Leu Trp Pro Ile Gln Ser Gly Ile Leu His Phe Cys Gly Phe
    130                 135                 140

Gln Val Leu Glu Pro Gln Leu Thr Tyr Ser Ile Gly His Thr Pro Ala
145                 150                 155                 160

Asp Ala Arg Ile Gln Ile Leu Glu Gly Trp Lys Lys Arg Leu Glu Asn
                165                 170                 175

Ile Trp Asp Glu Thr Pro Leu Tyr Phe Ala Pro Ser Ser Leu Phe Asp
            180                 185                 190

Leu Asn Phe Gln Ala Gly Phe Leu Met Lys Lys Glu Val Gln Asp Glu
        195                 200                 205

Glu Lys Asn Lys Lys Phe Gly Leu Ser Val Gly His His Leu Gly Lys
    210                 215                 220

Ser Ile Pro Thr Asp Asn Gln Ile Lys Ala Arg Lys
225                 230                 235


<210> SEQ ID NO 8
<211> LENGTH: 202
<212> TYPE: PRT
<213> ORGANISM: Homo sapiens

<400> SEQUENCE: 8

Met Val Gly Arg Arg Ala Leu Ile Val Leu Ala His Ser Glu Arg Thr
1               5                   10                  15

Ser Phe Asn Tyr Ala Met Lys Glu Ala Ala Ala Ala Ala Leu Lys Lys
            20                  25                  30

Lys Gly Trp Glu Val Val Glu Ser Asp Leu Tyr Ala Met Asn Phe Asn
        35                  40                  45

Pro Ile Ile Ser Arg Lys Asp Ile Thr Gly Lys Leu Lys Asp Pro Ala
    50                  55                  60

Asn Phe Gln Tyr Pro Ala Glu Ser Val Leu Ala Tyr Lys Glu Gly His
65                  70                  75                  80

Leu Ser Pro Asp Ile Val Ala Glu Gln Lys Lys Leu Glu Ala Ala Asp
                85                  90                  95

Leu Val Ile Phe Gln Ser Gly Ile Leu His Phe Cys Gly Phe Gln Val
            100                 105                 110

Leu Glu Pro Gln Leu Thr Tyr Ser Ile Gly His Thr Pro Ala Asp Ala
        115                 120                 125

Arg Ile Gln Ile Leu Glu Gly Trp Lys Lys Arg Leu Glu Asn Ile Trp
    130                 135                 140

Asp Glu Thr Pro Leu Tyr Phe Ala Pro Ser Ser Leu Phe Asp Leu Asn
145                 150                 155                 160

Phe Gln Ala Gly Phe Leu Met Lys Lys Glu Val Gln Asp Glu Glu Lys
                165                 170                 175

Asn Lys Lys Phe Gly Leu Ser Val Gly His His Leu Gly Lys Ser Ile
            180                 185                 190
```

-continued

```
Pro Thr Asp Asn Gln Ile Lys Ala Arg Lys
        195                 200


<210> SEQ ID NO 9
<211> LENGTH: 1553
<212> TYPE: DNA
<213> ORGANISM: Mus musculus

<400> SEQUENCE: 9

aggctcagct cttactagcc tagcctgtag ccagccctaa ggatbctctc cgaagagctt     60

tagggtcgtc ttggcaacca gctgctcagc caatcagcgt tcggtattac gatcctccct    120

caacatctgg agccatggcg gcgagaagag ccctgattgt actggcccat tcagagaaga    180

catcattcaa ctacgccatg aaggaggctg ctgtagaggc tctgaagaag agaggatggg    240

aggtactcga atctgacctc tatgctatga acttcaaccc catcatttcc agaaatgaca    300

tcacaggtga gctgaaggac tcgaagaact ttcagtatcc ttccgagtca tctctagcat    360

ataaggaagg acgcctgagc ccagatattg tggccgaaca caagaagctg gaagctgcag    420

acctggtgat atttcagttc ccattgcagt ggtttggggt gccagccatt ctgaaaggct    480

ggtttgagag agtgctcgta gcaggatttg cctacacata tgctgccatg tacgacaacg    540

gtcctttcca gaataagaag accttgcttt ctatcaccac tgggggtagc ggctccatgt    600

actctcttca gggtgtccac ggggacatga acgtcattct ctggccgatt cagagtggca    660

tcctgcgttt ctgtggcttc caggtcttag aacctcaact ggtttacagc attggccaca    720

ctccaccaga tgcccgcatg cagatcctgg aaggatggaa gaaacgtctg gaaaccgtct    780

gggaggagac cccactctat tttgctccaa gcagcctgtt tgacctaaac tttcaggcag    840

gattcttaat gaaaaaggaa gttcaagagg agcagaagaa gaacaagttt ggcctctctg    900

tgggccatca cctgggcaag tccattccag ctgacaacca gatcaaagct agaaaataag    960

gatttttttc ctaacatata gttagacgca gctttctttt tccccagctt gtctgacttg   1020

ctttcatttt tttcctttgc tccacgagga tgggaaaagg agtaagtttg cttcatgctt   1080

tttttttttt tttgatagtt ctgccataac aacaaaatga atgaagtcag attaggagcc   1140

tcagggcaag gtgcagaagc gagctggaaa tactcttcta ggtcatttat gcaatattcg   1200

ccatttcctt cgggctagtc ccagttagat ggcatccagt cctccatcaa gattcgttgt   1260

ctataattac ctctctgtgg tttagggcag aagggaattg ctcaaagtaa acaatggccg   1320

agggactaac ttgtttagca gttagcagtt agctaaagcc tgtttatgat acatcctggt   1380

ttcaattact gtgcagtgac tgacatggcg cccagggggt tggctctcca gctcttttct   1440

gtcttgtaca cagcacaccc aggtcctggg aaaggaattt taaaacagat ctccgtctca   1500

ttctttctat ttcttttttt ttttaatcga aataaatgaa tacatcacac atc          1553


<210> SEQ ID NO 10
<211> LENGTH: 274
<212> TYPE: PRT
<213> ORGANISM: Mus musculus

<400> SEQUENCE: 10

Met Ala Ala Arg Arg Ala Leu Ile Val Leu Ala His Ser Glu Lys Thr
1               5                   10                  15

Ser Phe Asn Tyr Ala Met Lys Glu Ala Ala Val Glu Ala Leu Lys Lys
            20                  25                  30

Arg Gly Trp Glu Val Leu Glu Ser Asp Leu Tyr Ala Met Asn Phe Asn
        35                  40                  45
```

-continued

```
Pro Ile Ile Ser Arg Asn Asp Ile Thr Gly Glu Leu Lys Asp Ser Lys
    50                  55                  60

Asn Phe Gln Tyr Pro Ser Glu Ser Ser Leu Ala Tyr Lys Glu Gly Arg
65                  70                  75                  80

Leu Ser Pro Asp Ile Val Ala Glu His Lys Lys Leu Glu Ala Ala Asp
                85                  90                  95

Leu Val Ile Phe Gln Phe Pro Leu Gln Trp Phe Gly Val Pro Ala Ile
            100                 105                 110

Leu Lys Gly Trp Phe Glu Arg Val Leu Val Ala Gly Phe Ala Tyr Thr
        115                 120                 125

Tyr Ala Ala Met Tyr Asp Asn Gly Pro Phe Gln Asn Lys Lys Thr Leu
    130                 135                 140

Leu Ser Ile Thr Thr Gly Gly Ser Gly Ser Met Tyr Ser Leu Gln Gly
145                 150                 155                 160

Val His Gly Asp Met Asn Val Ile Leu Trp Pro Ile Gln Ser Gly Ile
                165                 170                 175

Leu Arg Phe Cys Gly Phe Gln Val Leu Glu Pro Gln Leu Val Tyr Ser
            180                 185                 190

Ile Gly His Thr Pro Pro Asp Ala Arg Met Gln Ile Leu Glu Gly Trp
        195                 200                 205

Lys Lys Arg Leu Glu Thr Val Trp Glu Glu Thr Pro Leu Tyr Phe Ala
    210                 215                 220

Pro Ser Ser Leu Phe Asp Leu Asn Phe Gln Ala Gly Phe Leu Met Lys
225                 230                 235                 240

Lys Glu Val Gln Glu Glu Gln Lys Lys Asn Lys Phe Gly Leu Ser Val
                245                 250                 255

Gly His His Leu Gly Lys Ser Ile Pro Ala Asp Asn Gln Ile Lys Ala
            260                 265                 270

Arg Lys


<210> SEQ ID NO 11
<211> LENGTH: 2859
<212> TYPE: DNA
<213> ORGANISM: Homo sapiens

<400> SEQUENCE: 11

aaatcaggga ggcgcagctc ctacaccaac gcctttccgg ggctccgggt gtgtttgttc      60

caactgttta aactgtttca aagcgtccga actccagcga ccttcgcaaa caactcttta     120

tctcgcgggc gagagcgctg cccttatttg cgggggaggg caaactgaac gccggcaccg     180

gggagctaac ggagacctcc tctaggtccc ccgcctgctg ggaccccagc tggcagtccc     240

ttcccgcccc cggaccgcga gcttcttgcg tcagccccgg cgcgggtggg ggattttcgg     300

aagctcagcc cgcgcggccg gcgggggaag gaagggcccg gactcttgcc ccgcccttgt     360

ggggcgggag gcggagcggg gcaggggccc gccggcgtgt agccgattac cgagtgccgg     420

ggagcccgga ggagccgccg acgcagccgc caccgccgcc gccgccgcca ccagagccgc     480

cctgtccgcg ccgcgcctcg gcagccggaa cagggccgcc gtcggggagc cccaacacac     540

ggtccacagc tcatcatgat ggacttggag ctgccgccgc cgggactccc gtcccagcag     600

gacatggatt tgattgacat actttggagg caagatatag atcttggagt aagtcgagaa     660

gtatttgact tcagtcagcg acggaaagag tatgagctgg aaaaacagaa aaaacttgaa     720

aaggaaagac aagaacaact ccaaaaggag caagagaaag cctttttcgc tcagttacaa     780
```

-continued

```
ctagatgaag agacaggtga atttctccca attcagccag cccagcacat ccagtcagaa    840
accagtggat ctgccaacta ctcccaggtt gcccacattc ccaaatcaga tgctttgtac    900
tttgatgact gcatgcagct tttggcgcag acattcccgt ttgtagatga caatgaggtt    960
tcttcggcta cgtttcagtc acttgttcct gatattcccg gtcacatcga gagcccagtc   1020
ttcattgcta ctaatcaggc tcagtcacct gaaacttctg ttgctcaggt agcccctgtt   1080
gatttagacg gtatgcaaca ggacattgag caagtttggg aggagctatt atccattcct   1140
gagttacagt gtcttaatat tgaaaatgac aagctggttg agactaccat ggttccaagt   1200
ccagaagcca aactgacaga agttgacaat tatcattttt actcatctat accctcaatg   1260
gaaaaagaag taggtaactg tagtccacat tttcttaatg cttttgagga ttccttcagc   1320
agcatcctct ccacagaaga ccccaaccag ttgacagtga actcattaaa ttcagatgcc   1380
acagtcaaca cagattttgg tgatgaattt tattctgctt tcatagctga gcccagtatc   1440
agcaacagca tgccctcacc tgctacttta agccattcac tctctgaact tctaaatggg   1500
cccattgatg tttctgatct atcactttgc aaagctttca accaaaacca ccctgaaagc   1560
acagcagaat tcaatgattc tgactccggc atttcactaa acacaagtcc cagtgtggca   1620
tcaccagaac actcagtgga atcttccagc tatggagaca cactacttgg cctcagtgat   1680
tctgaagtgg aagagctaga tagtgcccct ggaagtgtca aacagaatgg tcctaaaaca   1740
ccagtacatt cttctgggga tatggtacaa cccttgtcac catctcaggg gcagagcact   1800
cacgtgcatg atgcccaatg tgagaacaca ccagagaaag aattgcctgt aagtcctggt   1860
catcggaaaa ccccattcac aaaagacaaa cattcaagcc gcttggaggc tcatctcaca   1920
agagatgaac ttagggcaaa agctctccat atcccattcc ctgtagaaaa aatcattaac   1980
ctccctgttg ttgacttcaa cgaaatgatg tccaaagagc agttcaatga agctcaactt   2040
gcattaattc gggatatacg taggaggggt aagaataaag tggctgctca gaattgcaga   2100
aaaagaaaac tggaaaatat agtagaacta gagcaagatt tagatcattt gaaagatgaa   2160
aaagaaaaat tgctcaaaga aaaaggagaa aatgacaaaa gccttcacct actgaaaaaa   2220
caactcagca ccttatatct cgaagttttc agcatgctac gtgatgaaga tggaaaacct   2280
tattctccta gtgaatactc cctgcagcaa acaagagatg gcaatgtttt ccttgttccc   2340
aaaagtaaga agccagatgt taagaaaaac tagatttagg aggatttgac cttttctgag   2400
ctagtttttt tgtactatta tactaaaagc tcctactgtg atgtgaaatg ctcatacttt   2460
ataagtaatt ctatgcaaaa tcatagccaa aactagtata gaaaataata cgaaacttta   2520
aaaagcattg gagtgtcagt atgttgaatc agtagtttca ctttaactgt aaacaatttc   2580
ttaggacacc atttgggcta gtttctgtgt aagtgtaaat actacaaaaa cttatttata   2640
ctgttcttat gtcatttgtt atattcatag atttatatga tgatatgaca tctggctaaa   2700
aagaaattat tgcaaaacta accactatgt acttttttat aaatactgta tggacaaaaa   2760
atggcatttt ttatattaaa ttgtttagct ctggcaaaaa aaaaaaattt taagagctgg   2820
tactaataaa ggattattat gactgttaaa ttattaaaa                          2859
```

<210> SEQ ID NO 12
<211> LENGTH: 2988
<212> TYPE: DNA
<213> ORGANISM: Homo sapiens

<400> SEQUENCE: 12

```
ggcccttccg gggctgcgcg gctccccccgc ctcggtgccg gcaaaaatgt gcctagtcac     60
```

```
ggggccgctc tcgggggaac tgaggtcgcc ttcgggctgg gacccggagc cccttcgccg    120
cgccccaaga cctccttgag tgcgggctgc gacgcgctca ccccgctggg ccgtctgtgg    180
gcgcggcttt gcgaagtcat ccatctctcg gatcactctc tggcagcctt gagctctctt    240
gaaagcccag ccccgggacg agggaggagc gccttaagtg cccagcgggc tcagaagccc    300
cgacgtgtgg cggctgagcc gggccccgcg cactttctcg gccggggagg ggttcgggct    360
cgggcacccg gagttggccc ctcgtaacgc cgcgggaaag tgcgggcgag ggcagtggac    420
tctgaggccg gagtcggcgg cacccggggc ttctagttcg gacgcggtgc cccctggtgg    480
cgctcaccgc gcgcgtggcc ttggcttccg tgacagcgct cggttggccg tcacagcagc    540
cctcggttgg ccctttcctg ctttatagcg tgcaaacctc gccgcgccag ggccaaggga    600
caggttggag ctgttgatct gttgcgcaat tgctattttc cccagagcgg ctttgtcttt    660
ggatttagcg tttcagaatt gcaattccaa aatgtgtaag acgggatatt ctcttctgtg    720
ctgtcaaggg acatggattt gattgacata ctttggaggc aagatataga tcttggagta    780
agtcgagaag tatttgactt cagtcagcga cggaaagagt atgagctgga aaaacagaaa    840
aaacttgaaa aggaaagaca agaacaactc caaaaggagc aagagaaagc ctttttcgct    900
cagttacaac tagatgaaga gacaggtgaa tttctcccaa ttcagccagc ccagcacatc    960
cagtcagaaa ccagtggatc tgccaactac tcccaggttg cccacattcc caaatcagat   1020
gctttgtact ttgatgactg catgcagctt ttggcgcaga cattcccgtt tgtagatgac   1080
aatgaggttt cttcggctac gtttcagtca cttgttcctg atattcccgg tcacatcgag   1140
agcccagtct tcattgctac taatcaggct cagtcacctg aaacttctgt tgctcaggta   1200
gcccctgttg atttagacgg tatgcaacag gacattgagc aagtttggga ggagctatta   1260
tccattcctg agttacagtg tcttaatatt gaaaatgaca agctggttga gactaccatg   1320
gttccaagtc cagaagccaa actgacagaa gttgacaatt atcattttta ctcatctata   1380
ccctcaatgg aaaaagaagt aggtaactgt agtccacatt ttcttaatgc ttttgaggat   1440
tccttcagca gcatcctctc cacagaagac cccaaccagt tgacagtgaa ctcattaaat   1500
tcagatgcca cagtcaacac agattttggt gatgaatttt attctgcttt catagctgag   1560
cccagtatca gcaacagcat gccctcacct gctactttaa gccattcact ctctgaactt   1620
ctaaatgggc ccattgatgt ttctgatcta tcactttgca aagctttcaa ccaaaaccac   1680
cctgaaagca cagcagaatt caatgattct gactccggca tttcactaaa cacaagtccc   1740
agtgtggcat caccagaaca ctcagtggaa tcttccagct atggagacac actacttggc   1800
ctcagtgatt ctgaagtgga agagctagat agtgcccctg gaagtgtcaa acagaatggt   1860
cctaaaacac cagtacattc ttctggggat atggtacaac ccttgtcacc atctcagggg   1920
cagagcactc acgtgcatga tgcccaatgt gagaacacac cagagaaaga attgcctgta   1980
agtcctggtc atcggaaaac cccattcaca aaagacaaac attcaagccg cttggaggct   2040
catctcacaa gagatgaact tagggcaaaa gctctccata tcccattccc tgtagaaaaa   2100
atcattaacc tccctgttgt tgacttcaac gaaatgatgt ccaaagagca gttcaatgaa   2160
gctcaacttg cattaattcg ggatatacgt aggaggggta agaataaagt ggctgctcag   2220
aattgcagaa aaagaaaact ggaaaatata gtagaactag agcaagattt agatcatttg   2280
aaagatgaaa aagaaaaatt gctcaaagaa aaaggagaaa atgacaaaag ccttcaccta   2340
ctgaaaaaac aactcagcac cttatatctc gaagttttca gcatgctacg tgatgaagat   2400
```

ggaaaacctt attctcctag tgaatactcc ctgcagcaaa caagagatgg caatgttttc 2460
cttgttccca aaagtaagaa gccagatgtt aagaaaaact agatttagga ggatttgacc 2520
ttttctgagc tagtttttt gtactattat actaaaagct cctactgtga tgtgaaatgc 2580
tcatacttta taagtaattc tatgcaaaat catagccaaa actagtatag aaaataatac 2640
gaaactttaa aaagcattgg agtgtcagta tgttgaatca gtagtttcac tttaactgta 2700
aacaatttct taggacacca tttgggctag tttctgtgta agtgtaaata ctacaaaaac 2760
ttatttatac tgttcttatg tcatttgtta tattcataga tttatatgat gatatgacat 2820
ctggctaaaa agaaattatt gcaaaactaa ccactatgta cttttttata aatactgtat 2880
ggacaaaaaa tggcattttt tatattaaat tgtttagctc tggcaaaaaa aaaaaatttt 2940
aagagctggt actaataaag gattattatg actgttaaat tattaaaa 2988

<210> SEQ ID NO 13
<211> LENGTH: 2967
<212> TYPE: DNA
<213> ORGANISM: Homo sapiens

<400> SEQUENCE: 13
ggcccttccg gggctgcgcg gctccccgc ctcggtgccg gcaaaaatgt gcctagtcac 60
ggggccgctc tcgggggaac tgaggtcgcc ttcgggctgg gacccggagc cccttcgccg 120
cgccccaaga cctccttgag tgcgggctgc gacgcgctca ccccgctggg ccgtctgtgg 180
gcgcggcttt gcgaagtcat ccatctctcg gatcactctc tggcagcctt gagctctctt 240
gaaagcccag ccccgggacg agggaggagc gccttaagtg cccagcgggc tcagaagccc 300
cgacgtgtgg cggctgagcc gggccccgcg cactttctcg gccggggagg ggttcgggct 360
cgggcacccg gagttggccc ctcgtaacgc cgcgggaaag tgcgggcgag ggcagtggac 420
tctgaggccg gagtcggcgg cacccggggc ttctagttcg gacgcggtgc cccctggtgg 480
cgctcaccgc gcgcgtggcc ttggcttccg tgacagcgct cggttggccg tcacagcagc 540
cctcggttgg ccctttcctg ctttatagcg tgcaaacctc gccgcgccag ggccaaggga 600
caggttggag ctgttgatct gttgcgcaat tgctattttc cccagagcgg ctttgtcttt 660
ggatttagcg tttcagaatt gcaattccaa aatgtgtaag acgggatatt ctcttctgtg 720
ctgtcaaggg acatggattt gattgacata ctttggaggc aagatataga tcttggagta 780
agtcgagaag tatttgactt cagtcagcga cggaaagagt atgagctgga aaaacagaaa 840
aaacttgaaa aggaaagaca agaacaactc caaaaggagc aagagaaagc ctttttcgct 900
cagttacaac tagatgaaga gacaggtgaa tttctcccaa ttcagccagc ccagcacatc 960
cagtcagaaa ccagtggatc tgccaactac tcccaggttg cccacattcc caaatcagat 1020
gctttgtact ttgatgactg catgcagctt ttggcgcaga cattcccgtt tgtagatgac 1080
aatgagtcac ttgttcctga tattcccggt cacatcgaga gcccagtctt cattgctact 1140
aatcaggctc agtcacctga aacttctgtt gctcaggtag cccctgttga tttagacggt 1200
atgcaacagg acattgagca agtttgggag gagctattat ccattcctga gttacagtgt 1260
cttaatattg aaaatgacaa gctggttgag actaccatgg ttccaagtcc agaagccaaa 1320
ctgacagaag ttgacaatta tcatttttac tcatctatac cctcaatgga aaaagaagta 1380
ggtaactgta gtccacattt tcttaatgct tttgaggatt ccttcagcag catcctctcc 1440
acagaagacc ccaaccagtt gacagtgaac tcattaaatt cagatgccac agtcaacaca 1500
gattttggtg atgaatttta ttctgctttc atagctgagc ccagtatcag caacagcatg 1560

-continued

```
ccctcacctg ctactttaag ccattcactc tctgaacttc taaatgggcc cattgatgtt   1620
tctgatctat cactttgcaa agctttcaac caaaaccacc ctgaaagcac agcagaattc   1680
aatgattctg actccggcat ttcactaaac acaagtccca gtgtggcatc accagaacac   1740
tcagtggaat cttccagcta tggagacaca ctacttggcc tcagtgattc tgaagtggaa   1800
gagctagata gtgcccctgg aagtgtcaaa cagaatggtc ctaaaacacc agtacattct   1860
tctggggata tggtacaacc cttgtcacca tctcaggggc agagcactca cgtgcatgat   1920
gcccaatgtg agaacacacc agagaaagaa ttgcctgtaa gtcctggtca tcggaaaacc   1980
ccattcacaa aagacaaaca ttcaagccgc ttggaggctc atctcacaag agatgaactt   2040
agggcaaaag ctctccatat cccattccct gtagaaaaaa tcattaacct ccctgttgtt   2100
gacttcaacg aaatgatgtc caaagagcag ttcaatgaag ctcaacttgc attaattcgg   2160
gatatacgta ggaggggtaa gaataaagtg gctgctcaga attgcagaaa aagaaaactg   2220
gaaaatatag tagaactaga gcaagattta gatcatttga aagatgaaaa agaaaaattg   2280
ctcaaagaaa aaggagaaaa tgacaaaagc cttcacctac tgaaaaaaca actcagcacc   2340
ttatatctcg aagttttcag catgctacgt gatgaagatg gaaaacctta ttctcctagt   2400
gaatactccc tgcagcaaac aagagatggc aatgttttcc ttgttcccaa aagtaagaag   2460
ccagatgtta agaaaaacta gatttaggag gatttgacct tttctgagct agtttttttg   2520
tactattata ctaaaagctc ctactgtgat gtgaaatgct catactttat aagtaattct   2580
atgcaaaatc atagccaaaa ctagtataga aaataatacg aaactttaaa aagcattgga   2640
gtgtcagtat gttgaatcag tagtttcact ttaactgtaa acaatttctt aggacaccat   2700
ttgggctagt ttctgtgtaa gtgtaaatac tacaaaaact tatttatact gttcttatgt   2760
catttgttat attcatagat ttatatgatg atatgacatc tggctaaaaa gaaattattg   2820
caaaactaac cactatgtac ttttttataa atactgtatg gacaaaaaat ggcatttttt   2880
atattaaatt gtttagctct ggcaaaaaaa aaaaatttta agagctggta ctaataaagg   2940
attattatga ctgttaaatt attaaaa                                        2967
```

<210> SEQ ID NO 14
<211> LENGTH: 2862
<212> TYPE: DNA
<213> ORGANISM: Homo sapiens

<400> SEQUENCE: 14

```
ggcccttccg gggctgcgcg gctcccccgc ctcggtgccg gcaaaaatgt gcctagtcac     60
ggggccgctc tcgggggaac tgaggtcgcc ttcgggctgg gacccggagc cccttcgccg    120
cgccccaaga cctccttgag tgcgggctgc gacgcgctca ccccgctggg ccgtctgtgg    180
gcgcggcttt gcgaagtcat ccatctctcg gatcactctc tggcagcctt gagctctctt    240
gaaagcccag ccccgggacg agggaggagc gccttaagtg cccagcgggc tcagaagccc    300
cgacgtgtgg cggctgagcc gggccccgcg cactttctcg gccggggagg ggttcgggct    360
cgggcacccg gagttggccc ctcgtaacgc cgcgggaaag tgcgggcgag ggcagtggac    420
tctgaggccg gagtcggcgg cacccggggc ttctagttcg gacgcggtgc cccctggtgg    480
cgctcaccgc gcgcgtggcc ttggcttccg tgacagcgct cggttggccg tcacagcagc    540
cctcggttgg ccctttcctg ctttatagcg tgcaaacctc gccgcgccag ggccaaggga    600
caggacatgg atttgattga catactttgg aggcaagata tagatcttgg agtaagtcga    660
```

-continued

```
gaagtatttg acttcagtca gcgacggaaa gagtatgagc tggaaaaaca gaaaaaactt    720
gaaaaggaaa gacaagaaca actccaaaag gagcaagaga aagccttttt cgctcagtta    780
caactagatg aagagacagg tgaatttctc ccaattcagc cagcccagca catccagtca    840
gaaaccagtg gatctgccaa ctactcccag gttgcccaca ttcccaaatc agatgctttg    900
tactttgatg actgcatgca gcttttggcg cagacattcc cgtttgtaga tgacaatgag    960
gtttcttcgg ctacgtttca gtcacttgtt cctgatattc ccggtcacat cgagagccca   1020
gtcttcattg ctactaatca ggctcagtca cctgaaactt ctgttgctca ggtagcccct   1080
gttgatttag acggtatgca acaggacatt gagcaagttt gggaggagct attatccatt   1140
cctgagttac agtgtcttaa tattgaaaat gacaagctgg ttgagactac catggttcca   1200
agtccagaag ccaaactgac agaagttgac aattatcatt tttactcatc tataccctca   1260
atggaaaaag aagtaggtaa ctgtagtcca cattttctta atgcttttga ggattccttc   1320
agcagcatcc tctccacaga agaccccaac cagttgacag tgaactcatt aaattcagat   1380
gccacagtca acacagattt tggtgatgaa ttttattctg ctttcatagc tgagcccagt   1440
atcagcaaca gcatgccctc acctgctact ttaagccatt cactctctga acttctaaat   1500
gggcccattg atgtttctga tctatcactt tgcaaagctt tcaaccaaaa ccaccctgaa   1560
agcacagcag aattcaatga ttctgactcc ggcatttcac taaacacaag tcccagtgtg   1620
gcatcaccag aacactcagt ggaatcttcc agctatggag acacactact tggcctcagt   1680
gattctgaag tggaagagct agatagtgcc cctggaagtg tcaaacagaa tggtcctaaa   1740
acaccagtac attcttctgg ggatatggta caacccttgt caccatctca ggggcagagc   1800
actcacgtgc atgatgccca atgtgagaac acaccagaga aagaattgcc tgtaagtcct   1860
ggtcatcgga aaaccccatt cacaaaagac aaacattcaa gccgcttgga ggctcatctc   1920
acaagagatg aacttagggc aaaagctctc catatcccat tccctgtaga aaaaatcatt   1980
aacctccctg ttgttgactt caacgaaatg atgtccaaag agcagttcaa tgaagctcaa   2040
cttgcattaa ttcgggatat acgtaggagg ggtaagaata aagtggctgc tcagaattgc   2100
agaaaaaagaa aactggaaaa tatagtagaa ctagagcaag atttagatca tttgaaagat   2160
gaaaaagaaa aattgctcaa agaaaaagga gaaaatgaca aaagccttca cctactgaaa   2220
aaacaactca gcaccttata tctcgaagtt ttcagcatgc tacgtgatga agatggaaaa   2280
ccttattctc ctagtgaata ctccctgcag caaacaagag atggcaatgt tttccttgtt   2340
cccaaaagta agaagccaga tgttaagaaa aactagattt aggaggattt gaccttttct   2400
gagctagttt ttttgtacta ttatactaaa agctcctact gtgatgtgaa atgctcatac   2460
tttataagta attctatgca aaatcatagc caaaactagt atagaaaata atacgaaact   2520
ttaaaaagca ttggagtgtc agtatgttga atcagtagtt tcactttaac tgtaaacaat   2580
ttcttaggac accatttggg ctagtttctg tgtaagtgta aatactacaa aaacttattt   2640
atactgttct tatgtcattt gttatattca tagatttata tgatgatatg acatctggct   2700
aaaaagaaat tattgcaaaa ctaaccacta tgtacttttt tataaatact gtatggacaa   2760
aaaatggcat tttttatatt aaattgttta gctctggcaa aaaaaaaaaa ttttaagagc   2820
tggtactaat aaaggattat tatgactgtt aaattattaa aa                       2862
```

<210> SEQ ID NO 15
<211> LENGTH: 2954
<212> TYPE: DNA
<213> ORGANISM: Homo sapiens

<400> SEQUENCE: 15
ggcccttccg gggctgcgcg gctcccccgc ctcggtgccg gcaaaaatgt gcctagtcac 60
ggggccgctc tcgggggaac tgaggtcgcc ttcgggctgg gacccggagc cccttcgccg 120
cgccccaaga cctccttgag tgcgggctgc gacgcgctca ccccgctggg ccgtctgtgg 180
gcgcggcttt gcgaagtcat ccatctctcg gatcactctc tggcagcctt gagctctctt 240
gaaagcccag ccccgggacg agggaggagc gccttaagtg cccagcgggc tcagaagccc 300
cgacgtgtgg cggctgagcc gggccccgcg cactttctcg gccggggagg ggttcgggct 360
cgggcacccg gagttggccc ctcgtaacgc cgcgggaaag tgcgggcgag ggcagtggac 420
tctgaggccg gagtcggcgg cacccggggc ttctagttcg gacgcggtgc cccctggtgg 480
cgctcaccgc gcgcgtggcc ttggcttccg tgacagcgct cggttggccg tcacagcagc 540
cctcggttgg ccctttcctg ctttatagcg tgcaaacctc gccgcgccag ggccaaggga 600
caggttggag ctgttgatct gttgcgcaat tgctattttc cccagagcgg ctttgtcttt 660
ggatttagcg tttcagaatt gcaattccaa aatgtgacat ggatttgatt gacatacttt 720
ggaggcaaga tatagatctt ggagtaagtc gagaagtatt tgacttcagt cagcgacgga 780
aagagtatga gctggaaaaa cagaaaaaac ttgaaaagga aagacaagaa caactccaaa 840
aggagcaaga gaaagccttt ttcgctcagt tacaactaga tgaagagaca ggtgaatttc 900
tcccaattca gccagcccag cacatccagt cagaaaccag tggatctgcc aactactccc 960
aggttgccca cattcccaaa tcagatgctt tgtactttga tgactgcatg cagcttttgg 1020
cgcagacatt cccgtttgta gatgacaatg aggtttcttc ggctacgttt cagtcacttg 1080
ttcctgatat tcccggtcac atcgagagcc cagtcttcat tgctactaat caggctcagt 1140
cacctgaaac ttctgttgct caggtagccc ctgttgattt agacggtatg caacaggaca 1200
ttgagcaagt ttgggaggag ctattatcca ttcctgagtt acagtgtctt aatattgaaa 1260
atgacaagct ggttgagact accatggttc caagtccaga agccaaactg acagaagttg 1320
acaattatca tttttactca tctataccct caatggaaaa agaagtaggt aactgtagtc 1380
cacattttct taatgctttt gaggattcct tcagcagcat cctctccaca gaagacccca 1440
accagttgac agtgaactca ttaaattcag atgccacagt caacacagat tttggtgatg 1500
aattttattc tgctttcata gctgagccca gtatcagcaa cagcatgccc tcacctgcta 1560
ctttaagcca ttcactctct gaacttctaa atgggcccat tgatgtttct gatctatcac 1620
tttgcaaagc tttcaaccaa aaccaccctg aaagcacagc agaattcaat gattctgact 1680
ccggcatttc actaaacaca agtcccagtg tggcatcacc agaacactca gtggaatctt 1740
ccagctatgg agacacacta cttggcctca gtgattctga agtggaagag ctagatagtg 1800
cccctggaag tgtcaaacag aatggtccta aaacaccagt acattcttct ggggatatgg 1860
tacaaccctt gtcaccatct caggggcaga gcactcacgt gcatgatgcc caatgtgaga 1920
acacaccaga gaaagaattg cctgtaagtc ctggtcatcg gaaaacccca ttcacaaaag 1980
acaaacattc aagccgcttg gaggctcatc tcacaagaga tgaacttagg gcaaaagctc 2040
tccatatccc attccctgta gaaaaaatca ttaacctccc tgttgttgac ttcaacgaaa 2100
tgatgtccaa agagcagttc aatgaagctc aacttgcatt aattcgggat atacgtagga 2160
ggggtaagaa taaagtggct gctcagaatt gcagaaaaag aaaactggaa aatatagtag 2220
aactagagca agatttagat catttgaaag atgaaaaaga aaaattgctc aaagaaaaag 2280

-continued gagaaaatga caaaagcctt cacctactga aaaaacaact cagcacctta tatctcgaag 2340
ttttcagcat gctacgtgat gaagatggaa aaccttattc tcctagtgaa tactccctgc 2400
agcaaacaag agatggcaat gttttccttg ttcccaaaag taagaagcca gatgttaaga 2460
aaaactagat ttaggaggat ttgacctttt ctgagctagt ttttttgtac tattatacta 2520
aaagctccta ctgtgatgtg aaatgctcat actttataag taattctatg caaaatcata 2580
gccaaaacta gtatagaaaa taatacgaaa ctttaaaaag cattggagtg tcagtatgtt 2640
gaatcagtag tttcacttta actgtaaaca atttcttagg acaccatttg ggctagtttc 2700
tgtgtaagtg taaatactac aaaaacttat ttatactgtt cttatgtcat ttgttatatt 2760
catagattta tatgatgata tgacatctgg ctaaaaagaa attattgcaa aactaaccac 2820
tatgtacttt tttataaata ctgtatggac aaaaaatggc attttttata ttaaattgtt 2880
tagctctggc aaaaaaaaaa aattttaaga gctggtacta ataaaggatt attatgactg 2940
ttaaattatt aaaa 2954

<210> SEQ ID NO 16
<211> LENGTH: 2769
<212> TYPE: DNA
<213> ORGANISM: Homo sapiens

<400> SEQUENCE: 16
aaatcaggga ggcgcagctc ctacaccaac gcctttccgg ggctccgggt gtgtttgttc 60
caactgttta aactgtttca aagcgtccga actccagcga ccttcgcaaa caactcttta 120
tctcgcgggc gagagcgctg cccttatttg cgggggaggg caaactgaac gccggcaccg 180
gggagctaac ggagacctcc tctaggtccc ccgcctgctg ggaccccagc tggcagtccc 240
ttcccgcccc cggaccgcga gcttcttgcg tcagccccgg cgcgggtggg ggattttcgg 300
aagctcagcc cgcgcggccg gcgggggaag gaagggcccg gactcttgcc ccgcccttgt 360
ggggcgggag gcggagcggg gcaggggccc gccggcgtgt agccgattac cgagtgccgg 420
ggagcccgga ggagccgccg acgcagccgc caccgccgcc gccgccgcca ccagagccgc 480
cctgtccgcg ccgcgcctcg gcagccggaa cagggccgcc gtcggggagc cccaacacac 540
ggtccacagc tcatcatgat ggacttggag ctgccgccgc cgggactccc gtcccagcag 600
gacatggatt tgattgacat actttggagg caagatatag atcttggagt aagtcgagaa 660
gtatttgact tcagtcagcg acggaaagag tatgagctgg aaaaacagaa aaaacttgaa 720
aaggaaagac aagaacaact ccaaaaggag caagagaaag ccttttttcgc tcagttacaa 780 ctagatgaag agacaggtga atttctccca attcagccag cccagcacat ccagtcagaa 840
accagtggat ctgccaacta ctcccaggtt tcttcggcta cgtttcagtc acttgttcct 900
gatattcccg gtcacatcga gagcccagtc ttcattgcta ctaatcaggc tcagtcacct 960
gaaacttctg ttgctcaggt agcccctgtt gatttagacg gtatgcaaca ggacattgag 1020
caagtttggg aggagctatt atccattcct gagttacagt gtcttaatat tgaaaatgac 1080
aagctggttg agactaccat ggttccaagt ccagaagcca aactgacaga agttgacaat 1140
tatcattttt actcatctat accctcaatg gaaaaagaag taggtaactg tagtccacat 1200
tttcttaatg cttttgagga ttccttcagc agcatcctct ccacagaaga ccccaaccag 1260
ttgacagtga actcattaaa ttcagatgcc acagtcaaca cagattttgg tgatgaattt 1320
tattctgctt tcatagctga gcccagtatc agcaacagca tgccctcacc tgctacttta 1380
agccattcac tctctgaact tctaaatggg cccattgatg tttctgatct atcactttgc 1440
aaagctttca accaaaacca ccctgaaagc acagcagaat tcaatgattc tgactccggc 1500
atttcactaa acacaagtcc cagtgtggca tcaccagaac actcagtgga atcttccagc 1560
tatggagaca cactacttgg cctcagtgat tctgaagtgg aagagctaga tagtgcccct 1620
ggaagtgtca aacagaatgg tcctaaaaca ccagtacatt cttctgggga tatggtacaa 1680
cccttgtcac catctcaggg gcagagcact cacgtgcatg atgcccaatg tgagaacaca 1740
ccagagaaag aattgcctgt aagtcctggt catcggaaaa ccccattcac aaaagacaaa 1800
cattcaagcc gcttggaggc tcatctcaca agagatgaac ttagggcaaa agctctccat 1860
atcccattcc ctgtagaaaa aatcattaac ctccctgttg ttgacttcaa cgaaatgatg 1920
tccaaagagc agttcaatga agctcaactt gcattaattc gggatatacg taggaggggt 1980
aagaataaag tggctgctca gaattgcaga aaaagaaaac tggaaaatat agtagaacta 2040
gagcaagatt tagatcattt gaaagatgaa aaagaaaaat tgctcaaaga aaaaggagaa 2100
aatgacaaaa gccttcacct actgaaaaaa caactcagca ccttatatct cgaagttttc 2160
agcatgctac gtgatgaaga tggaaaacct tattctccta gtgaatactc cctgcagcaa 2220
acaagagatg gcaatgtttt ccttgttccc aaaagtaaga agccagatgt taagaaaaac 2280
tagatttagg aggatttgac cttttctgag ctagtttttt tgtactatta tactaaaagc 2340
tcctactgtg atgtgaaatg ctcatacttt ataagtaatt ctatgcaaaa tcatagccaa 2400
aactagtata gaaaataata cgaaacttta aaaagcattg gagtgtcagt atgttgaatc 2460
agtagtttca ctttaactgt aaacaatttc ttaggacacc atttgggcta gtttctgtgt 2520
aagtgtaaat actacaaaaa cttatttata ctgttcttat gtcatttgtt atattcatag 2580
atttatatga tgatatgaca tctggctaaa aagaaattat tgcaaaacta accactatgt 2640 actttttat aaatactgta tggacaaaaa atggcatttt ttatattaaa ttgtttagct 2700
ctggcaaaaa aaaaaaattt taagagctgg tactaataaa ggattattat gactgttaaa 2760
ttattaaaa 2769

<210> SEQ ID NO 17
<211> LENGTH: 2640
<212> TYPE: DNA
<213> ORGANISM: Homo sapiens

<400> SEQUENCE: 17
aaatcaggga ggcgcagctc ctacaccaac gcctttccgg ggctccgggt gtgtttgttc 60
caactgttta aactgtttca aagcgtccga actccagcga ccttcgcaaa caactcttta 120
tctcgcgggc gagagcgctg cccttatttg cgggggaggg caaactgaac gccggcaccg 180
gggagctaac ggagacctcc tctaggtccc ccgcctgctg ggaccccagc tggcagtccc 240
ttcccgcccc cggaccgcga gcttcttgcg tcagccccgg cgcgggtggg ggattttcgg 300
aagctcagcc cgcgcggccg gcgggggaag gaagggcccg gactcttgcc ccgcccttgt 360
ggggcgggag gcggagcggg gcaggggccc gccggcgtgt agccgattac cgagtgccgg 420
ggagcccgga ggagccgccg acgcagccgc caccgccgcc gccgccgcca ccagagccgc 480
cctgtccgcg ccgcgcctcg gcagccggaa cagggccgcc gtcggggagc cccaacacac 540
ggtccacagc tcatcatgat ggacttggag ctgccgccgc cgggactccc gtcccagcag 600
gacatggatt tgattgacat actttggagg caagatatag atcttggagt tgcccacatt 660
cccaaatcag atgctttgta ctttgatgac tgcatgcagc ttttggcgca gacattcccg 720

-continued

```
tttgtagatg acaatgaggt ttcttcggct acgtttcagt cacttgttcc tgatattccc     780
ggtcacatcg agagcccagt cttcattgct actaatcagg ctcagtcacc tgaaacttct     840
gttgctcagg tagcccctgt tgatttagac ggtatgcaac aggacattga gcaagtttgg     900
gaggagctat tatccattcc tgagttacag tgtcttaata ttgaaaatga caagctggtt     960
gagactacca tggttccaag tccagaagcc aaactgacag aagttgacaa ttatcatttt    1020
tactcatcta taccctcaat ggaaaaagaa gtaggtaact gtagtccaca ttttcttaat    1080
gcttttgagg attccttcag cagcatcctc tccacagaag accccaacca gttgacagtg    1140
aactcattaa attcagatgc cacagtcaac acagattttg gtgatgaatt ttattctgct    1200
ttcatagctg agcccagtat cagcaacagc atgccctcac ctgctacttt aagccattca    1260
ctctctgaac ttctaaatgg gcccattgat gtttctgatc tatcactttg caaagctttc    1320
aaccaaaacc accctgaaag cacagcagaa ttcaatgatt ctgactccgg catttcacta    1380
aacacaagtc ccagtgtggc atcaccagaa cactcagtgg aatcttccag ctatggagac    1440
acactacttg gcctcagtga ttctgaagtg gaagagctag atagtgcccc tggaagtgtc    1500
aaacagaatg gtcctaaaac accagtacat tcttctgggg atatggtaca acccttgtca    1560
ccatctcagg ggcagagcac tcacgtgcat gatgcccaat gtgagaacac accagagaaa    1620
gaattgcctg taagtcctgg tcatcggaaa accccattca caaaagacaa acattcaagc    1680
cgcttggagg ctcatctcac aagagatgaa cttagggcaa aagctctcca tatcccattc    1740
cctgtagaaa aaatcattaa cctccctgtt gttgacttca acgaaatgat gtccaaagag    1800
cagttcaatg aagctcaact tgcattaatt cgggatatac gtaggagggg taagaataaa    1860
gtggctgctc agaattgcag aaaaagaaaa ctggaaaata tagtagaact agagcaagat    1920
ttagatcatt tgaaagatga aaaagaaaaa ttgctcaaag aaaaaggaga aaatgacaaa    1980
agccttcacc tactgaaaaa acaactcagc accttatatc tcgaagtttt cagcatgcta    2040
cgtgatgaag atggaaaacc ttattctcct agtgaatact ccctgcagca aacaagagat    2100
ggcaatgttt tccttgttcc caaaagtaag aagccagatg ttaagaaaaa ctagatttag    2160
gaggatttga ccttttctga gctagttttt ttgtactatt atactaaaag ctcctactgt    2220
gatgtgaaat gctcatactt tataagtaat tctatgcaaa atcatagcca aaactagtat    2280
agaaaataat acgaaacttt aaaaagcatt ggagtgtcag tatgttgaat cagtagtttc    2340
actttaactg taaacaattt cttaggacac catttgggct agtttctgtg taagtgtaaa    2400
tactacaaaa acttatttat actgttctta tgtcatttgt tatattcata gatttatatg    2460
atgatatgac atctggctaa aaagaaatta ttgcaaaact aaccactatg tacttttttta    2520
taaatactgt atggacaaaa aatggcattt tttatattaa attgtttagc tctggcaaaa    2580
aaaaaaaatt ttaagagctg gtactaataa aggattatta tgactgttaa attattaaaa    2640
```

<210> SEQ ID NO 18
<211> LENGTH: 2917
<212> TYPE: DNA
<213> ORGANISM: Homo sapiens

<400> SEQUENCE: 18

```
ggcccttccg ggctgcgcg gctccccgc ctcggtgccg gcaaaaatgt gcctagtcac      60
ggggccgctc tcgggggaac tgaggtcgcc ttcgggctgg gacccggagc cccttcgccg    120
cgccccaaga cctccttgag tgcgggctgc gacgcgctca ccccgctggg ccgtctgtgg    180
gcgcggcttt gcgaagtcat ccatctctcg gatcactctc tggcagcctt gagctctctt    240
```

-continued

```
gaaagcccag ccccgggacg agggaggagc gccttaagtg cccagcgggc tcagaagccc    300
cgacgtgtgg cggctgagcc gggccccgcg cactttctcg gccggggagg ggttcgggct    360
cgggcacccg gagttggccc ctcgtaacgc cgcgggaaag tgcgggcgag ggcagtggac    420
tctgaggccg gagtcggcgg cacccggggc ttctagttcg gacgcggtgc cccctggtgg    480
cgctcaccgc gcgcgtggcc ttggcttccg tgacagcgct cggttggccg tcacagcagc    540
cctcggttgg ccctttcctg ctttatagcg tgcaaacctc gccgcgccag ggccaaggga    600
caggttggag ctgttgatct gttgcgcaat tgctattttc cccagagcgg ctttgtcttt    660
ggatttagcg tttcagaatt gcaattccaa aatgtgtaag acgggatatt ctcttctgtg    720
ctgtcaaggg acatggattt gattgacata ctttggaggc aagatataga tcttggagta    780
agtcgagaag tatttgactt cagtcagcga cggaaagagt atgagctgga aaaacagaaa    840
aaacttgaaa aggaaagaca agaacaactc caaaaggagc aagagaaagc ctttttcgct    900
cagttacaac tagatgaaga gacaggttgc ccacattccc aaatcagatg ctttgtactt    960
tgatgactgc atgcagcttt tggcgcagac attcccgttt gtagatgaca atgaggtttc   1020
ttcggctacg tttcagtcac ttgttcctga tattcccggt cacatcgaga gcccagtctt   1080
cattgctact aatcaggctc agtcacctga aacttctgtt gctcaggtag cccctgttga   1140
tttagacggt atgcaacagg acattgagca agtttgggag gagctattat ccattcctga   1200
gttacagtgt cttaatattg aaaatgacaa gctggttgag actaccatgg ttccaagtcc   1260
agaagccaaa ctgacagaag ttgacaatta tcatttttac tcatctatac cctcaatgga   1320
aaaagaagta ggtaactgta gtccacattt tcttaatgct tttgaggatt ccttcagcag   1380
catcctctcc acagaagacc ccaaccagtt gacagtgaac tcattaaatt cagatgccac   1440
agtcaacaca gattttggtg atgaatttta ttctgctttc atagctgagc ccagtatcag   1500
caacagcatg ccctcacctg ctactttaag ccattcactc tctgaacttc taaatgggcc   1560
cattgatgtt tctgatctat cactttgcaa agctttcaac caaaaccacc ctgaaagcac   1620
agcagaattc aatgattctg actccggcat ttcactaaac acaagtccca gtgtggcatc   1680
accagaacac tcagtggaat cttccagcta tggagacaca ctacttggcc tcagtgattc   1740
tgaagtggaa gagctagata gtgcccctgg aagtgtcaaa cagaatggtc ctaaaacacc   1800
agtacattct tctggggata tggtacaacc cttgtcacca tctcaggggc agagcactca   1860
cgtgcatgat gcccaatgtg agaacacacc agagaaagaa ttgcctgtaa gtcctggtca   1920
tcggaaaacc ccattcacaa aagacaaaca ttcaagccgc ttggaggctc atctcacaag   1980
agatgaactt agggcaaaag ctctccatat cccattccct gtagaaaaaa tcattaacct   2040
ccctgttgtt gacttcaacg aaatgatgtc caaagagcag ttcaatgaag ctcaacttgc   2100
attaattcgg gatatacgta ggaggggtaa gaataaagtg gctgctcaga attgcagaaa   2160
aagaaaactg gaaaatatag tagaactaga gcaagattta gatcatttga aagatgaaaa   2220
agaaaaattg ctcaaagaaa aaggagaaaa tgacaaaagc cttcacctac tgaaaaaaca   2280
actcagcacc ttatatctcg aagttttcag catgctacgt gatgaagatg gaaaacctta   2340
ttctcctagt gaatactccc tgcagcaaac aagagatggc aatgttttcc ttgttcccaa   2400
aagtaagaag ccagatgtta agaaaaacta gatttaggag gatttgacct tttctgagct   2460
agttttttttg tactattata ctaaaagctc ctactgtgat gtgaaatgct catactttat   2520
aagtaattct atgcaaaatc atagccaaaa ctagtataga aaataatacg aaactttaaa   2580
```

-continued

```
aagcattgga gtgtcagtat gttgaatcag tagtttcact ttaactgtaa acaatttctt   2640

aggacaccat ttgggctagt ttctgtgtaa gtgtaaatac tacaaaaact tatttatact   2700

gttcttatgt catttgttat attcatagat ttatatgatg atatgacatc tggctaaaaa   2760

gaaattattg caaaactaac cactatgtac tttttttataa atactgtatg gacaaaaaat   2820

ggcatttttt atattaaatt gtttagctct ggcaaaaaaa aaaaatttta agagctggta   2880

ctaataaagg attattatga ctgttaaatt attaaaa                            2917
```

```
<210> SEQ ID NO 19
<211> LENGTH: 605
<212> TYPE: PRT
<213> ORGANISM: Homo sapiens

<400> SEQUENCE: 19

Met Met Asp Leu Glu Leu Pro Pro Pro Gly Leu Pro Ser Gln Gln Asp
1               5                   10                  15

Met Asp Leu Ile Asp Ile Leu Trp Arg Gln Asp Ile Asp Leu Gly Val
            20                  25                  30

Ser Arg Glu Val Phe Asp Phe Ser Gln Arg Arg Lys Glu Tyr Glu Leu
        35                  40                  45

Glu Lys Gln Lys Lys Leu Glu Lys Glu Arg Gln Glu Gln Leu Gln Lys
    50                  55                  60

Glu Gln Glu Lys Ala Phe Phe Ala Gln Leu Gln Leu Asp Glu Glu Thr
65                  70                  75                  80

Gly Glu Phe Leu Pro Ile Gln Pro Ala Gln His Ile Gln Ser Glu Thr
                85                  90                  95

Ser Gly Ser Ala Asn Tyr Ser Gln Val Ala His Ile Pro Lys Ser Asp
            100                 105                 110

Ala Leu Tyr Phe Asp Asp Cys Met Gln Leu Leu Ala Gln Thr Phe Pro
        115                 120                 125

Phe Val Asp Asp Asn Glu Val Ser Ser Ala Thr Phe Gln Ser Leu Val
    130                 135                 140

Pro Asp Ile Pro Gly His Ile Glu Ser Pro Val Phe Ile Ala Thr Asn
145                 150                 155                 160

Gln Ala Gln Ser Pro Glu Thr Ser Val Ala Gln Val Ala Pro Val Asp
                165                 170                 175

Leu Asp Gly Met Gln Gln Asp Ile Glu Gln Val Trp Glu Glu Leu Leu
            180                 185                 190

Ser Ile Pro Glu Leu Gln Cys Leu Asn Ile Glu Asn Asp Lys Leu Val
        195                 200                 205

Glu Thr Thr Met Val Pro Ser Pro Glu Ala Lys Leu Thr Glu Val Asp
    210                 215                 220

Asn Tyr His Phe Tyr Ser Ser Ile Pro Ser Met Glu Lys Glu Val Gly
225                 230                 235                 240

Asn Cys Ser Pro His Phe Leu Asn Ala Phe Glu Asp Ser Phe Ser Ser
                245                 250                 255

Ile Leu Ser Thr Glu Asp Pro Asn Gln Leu Thr Val Asn Ser Leu Asn
            260                 265                 270

Ser Asp Ala Thr Val Asn Thr Asp Phe Gly Asp Glu Phe Tyr Ser Ala
        275                 280                 285

Phe Ile Ala Glu Pro Ser Ile Ser Asn Ser Met Pro Ser Pro Ala Thr
    290                 295                 300

Leu Ser His Ser Leu Ser Glu Leu Leu Asn Gly Pro Ile Asp Val Ser
305                 310                 315                 320
```

Asp Leu Ser Leu Cys Lys Ala Phe Asn Gln Asn His Pro Glu Ser Thr
325 330 335

Ala Glu Phe Asn Asp Ser Asp Ser Gly Ile Ser Leu Asn Thr Ser Pro
340 345 350

Ser Val Ala Ser Pro Glu His Ser Val Glu Ser Ser Ser Tyr Gly Asp
355 360 365

Thr Leu Leu Gly Leu Ser Asp Ser Glu Val Glu Glu Leu Asp Ser Ala
370 375 380

Pro Gly Ser Val Lys Gln Asn Gly Pro Lys Thr Pro Val His Ser Ser
385 390 395 400

Gly Asp Met Val Gln Pro Leu Ser Pro Ser Gln Gly Gln Ser Thr His
405 410 415

Val His Asp Ala Gln Cys Glu Asn Thr Pro Glu Lys Glu Leu Pro Val
420 425 430

Ser Pro Gly His Arg Lys Thr Pro Phe Thr Lys Asp Lys His Ser Ser
435 440 445

Arg Leu Glu Ala His Leu Thr Arg Asp Glu Leu Arg Ala Lys Ala Leu
450 455 460

His Ile Pro Phe Pro Val Glu Lys Ile Ile Asn Leu Pro Val Val Asp
465 470 475 480

Phe Asn Glu Met Met Ser Lys Glu Gln Phe Asn Glu Ala Gln Leu Ala
485 490 495

Leu Ile Arg Asp Ile Arg Arg Arg Gly Lys Asn Lys Val Ala Ala Gln
500 505 510

Asn Cys Arg Lys Arg Lys Leu Glu Asn Ile Val Glu Leu Glu Gln Asp
515 520 525

Leu Asp His Leu Lys Asp Glu Lys Glu Lys Leu Leu Lys Glu Lys Gly
530 535 540

Glu Asn Asp Lys Ser Leu His Leu Leu Lys Lys Gln Leu Ser Thr Leu
545 550 555 560

Tyr Leu Glu Val Phe Ser Met Leu Arg Asp Glu Asp Gly Lys Pro Tyr
565 570 575

Ser Pro Ser Glu Tyr Ser Leu Gln Gln Thr Arg Asp Gly Asn Val Phe
580 585 590

Leu Val Pro Lys Ser Lys Lys Pro Asp Val Lys Lys Asn
595 600 605

<210> SEQ ID NO 20
<211> LENGTH: 589
<212> TYPE: PRT
<213> ORGANISM: Homo sapiens

<400> SEQUENCE: 20

Met Asp Leu Ile Asp Ile Leu Trp Arg Gln Asp Ile Asp Leu Gly Val
1 5 10 15

Ser Arg Glu Val Phe Asp Phe Ser Gln Arg Arg Lys Glu Tyr Glu Leu
20 25 30

Glu Lys Gln Lys Lys Leu Glu Lys Glu Arg Gln Glu Gln Leu Gln Lys
35 40 45

Glu Gln Glu Lys Ala Phe Phe Ala Gln Leu Gln Leu Asp Glu Glu Thr
50 55 60

Gly Glu Phe Leu Pro Ile Gln Pro Ala Gln His Ile Gln Ser Glu Thr
65 70 75 80

Ser Gly Ser Ala Asn Tyr Ser Gln Val Ala His Ile Pro Lys Ser Asp

-continued

```
                85                  90                  95

Ala Leu Tyr Phe Asp Asp Cys Met Gln Leu Leu Ala Gln Thr Phe Pro
            100                 105                 110

Phe Val Asp Asp Asn Glu Val Ser Ser Ala Thr Phe Gln Ser Leu Val
        115                 120                 125

Pro Asp Ile Pro Gly His Ile Glu Ser Pro Val Phe Ile Ala Thr Asn
    130                 135                 140

Gln Ala Gln Ser Pro Glu Thr Ser Val Ala Gln Val Ala Pro Val Asp
145                 150                 155                 160

Leu Asp Gly Met Gln Gln Asp Ile Glu Gln Val Trp Glu Glu Leu Leu
                165                 170                 175

Ser Ile Pro Glu Leu Gln Cys Leu Asn Ile Glu Asn Asp Lys Leu Val
            180                 185                 190

Glu Thr Thr Met Val Pro Ser Pro Glu Ala Lys Leu Thr Glu Val Asp
        195                 200                 205

Asn Tyr His Phe Tyr Ser Ser Ile Pro Ser Met Glu Lys Glu Val Gly
    210                 215                 220

Asn Cys Ser Pro His Phe Leu Asn Ala Phe Glu Asp Ser Phe Ser Ser
225                 230                 235                 240

Ile Leu Ser Thr Glu Asp Pro Asn Gln Leu Thr Val Asn Ser Leu Asn
                245                 250                 255

Ser Asp Ala Thr Val Asn Thr Asp Phe Gly Asp Glu Phe Tyr Ser Ala
            260                 265                 270

Phe Ile Ala Glu Pro Ser Ile Ser Asn Ser Met Pro Ser Pro Ala Thr
        275                 280                 285

Leu Ser His Ser Leu Ser Glu Leu Leu Asn Gly Pro Ile Asp Val Ser
    290                 295                 300

Asp Leu Ser Leu Cys Lys Ala Phe Asn Gln Asn His Pro Glu Ser Thr
305                 310                 315                 320

Ala Glu Phe Asn Asp Ser Asp Ser Gly Ile Ser Leu Asn Thr Ser Pro
                325                 330                 335

Ser Val Ala Ser Pro Glu His Ser Val Glu Ser Ser Ser Tyr Gly Asp
            340                 345                 350

Thr Leu Leu Gly Leu Ser Asp Ser Glu Val Glu Glu Leu Asp Ser Ala
        355                 360                 365

Pro Gly Ser Val Lys Gln Asn Gly Pro Lys Thr Pro Val His Ser Ser
    370                 375                 380

Gly Asp Met Val Gln Pro Leu Ser Pro Ser Gln Gly Gln Ser Thr His
385                 390                 395                 400

Val His Asp Ala Gln Cys Glu Asn Thr Pro Glu Lys Glu Leu Pro Val
                405                 410                 415

Ser Pro Gly His Arg Lys Thr Pro Phe Thr Lys Asp Lys His Ser Ser
            420                 425                 430

Arg Leu Glu Ala His Leu Thr Arg Asp Glu Leu Arg Ala Lys Ala Leu
        435                 440                 445

His Ile Pro Phe Pro Val Glu Lys Ile Ile Asn Leu Pro Val Val Asp
    450                 455                 460

Phe Asn Glu Met Met Ser Lys Glu Gln Phe Asn Glu Ala Gln Leu Ala
465                 470                 475                 480

Leu Ile Arg Asp Ile Arg Arg Arg Gly Lys Asn Lys Val Ala Ala Gln
                485                 490                 495

Asn Cys Arg Lys Arg Lys Leu Glu Asn Ile Val Glu Leu Glu Gln Asp
            500                 505                 510
```

```
Leu Asp His Leu Lys Asp Glu Lys Glu Lys Leu Leu Lys Glu Lys Gly
        515                 520                 525

Glu Asn Asp Lys Ser Leu His Leu Leu Lys Lys Gln Leu Ser Thr Leu
    530                 535                 540

Tyr Leu Glu Val Phe Ser Met Leu Arg Asp Glu Asp Gly Lys Pro Tyr
545                 550                 555                 560

Ser Pro Ser Glu Tyr Ser Leu Gln Gln Thr Arg Asp Gly Asn Val Phe
                565                 570                 575

Leu Val Pro Lys Ser Lys Lys Pro Asp Val Lys Lys Asn
            580                 585


<210> SEQ ID NO 21
<211> LENGTH: 582
<212> TYPE: PRT
<213> ORGANISM: Homo sapiens

<400> SEQUENCE: 21

Met Asp Leu Ile Asp Ile Leu Trp Arg Gln Asp Ile Asp Leu Gly Val
1               5                   10                  15

Ser Arg Glu Val Phe Asp Phe Ser Gln Arg Arg Lys Glu Tyr Glu Leu
            20                  25                  30

Glu Lys Gln Lys Lys Leu Glu Lys Glu Arg Gln Glu Gln Leu Gln Lys
        35                  40                  45

Glu Gln Glu Lys Ala Phe Phe Ala Gln Leu Gln Leu Asp Glu Glu Thr
    50                  55                  60

Gly Glu Phe Leu Pro Ile Gln Pro Ala Gln His Ile Gln Ser Glu Thr
65                  70                  75                  80

Ser Gly Ser Ala Asn Tyr Ser Gln Val Ala His Ile Pro Lys Ser Asp
                85                  90                  95

Ala Leu Tyr Phe Asp Asp Cys Met Gln Leu Leu Ala Gln Thr Phe Pro
            100                 105                 110

Phe Val Asp Asp Asn Glu Ser Leu Val Pro Asp Ile Pro Gly His Ile
        115                 120                 125

Glu Ser Pro Val Phe Ile Ala Thr Asn Gln Ala Gln Ser Pro Glu Thr
    130                 135                 140

Ser Val Ala Gln Val Ala Pro Val Asp Leu Asp Gly Met Gln Gln Asp
145                 150                 155                 160

Ile Glu Gln Val Trp Glu Glu Leu Leu Ser Ile Pro Glu Leu Gln Cys
                165                 170                 175

Leu Asn Ile Glu Asn Asp Lys Leu Val Glu Thr Thr Met Val Pro Ser
            180                 185                 190

Pro Glu Ala Lys Leu Thr Glu Val Asp Asn Tyr His Phe Tyr Ser Ser
        195                 200                 205

Ile Pro Ser Met Glu Lys Glu Val Gly Asn Cys Ser Pro His Phe Leu
    210                 215                 220

Asn Ala Phe Glu Asp Ser Phe Ser Ser Ile Leu Ser Thr Glu Asp Pro
225                 230                 235                 240

Asn Gln Leu Thr Val Asn Ser Leu Asn Ser Asp Ala Thr Val Asn Thr
                245                 250                 255

Asp Phe Gly Asp Glu Phe Tyr Ser Ala Phe Ile Ala Glu Pro Ser Ile
            260                 265                 270

Ser Asn Ser Met Pro Ser Pro Ala Thr Leu Ser His Ser Leu Ser Glu
        275                 280                 285

Leu Leu Asn Gly Pro Ile Asp Val Ser Asp Leu Ser Leu Cys Lys Ala
```

-continued 290 295 300

Phe Asn Gln Asn His Pro Glu Ser Thr Ala Glu Phe Asn Asp Ser Asp
305 310 315 320

Ser Gly Ile Ser Leu Asn Thr Ser Pro Ser Val Ala Ser Pro Glu His
325 330 335

Ser Val Glu Ser Ser Ser Tyr Gly Asp Thr Leu Leu Gly Leu Ser Asp
340 345 350

Ser Glu Val Glu Glu Leu Asp Ser Ala Pro Gly Ser Val Lys Gln Asn
355 360 365

Gly Pro Lys Thr Pro Val His Ser Ser Gly Asp Met Val Gln Pro Leu
370 375 380

Ser Pro Ser Gln Gly Gln Ser Thr His Val His Asp Ala Gln Cys Glu
385 390 395 400

Asn Thr Pro Glu Lys Glu Leu Pro Val Ser Pro Gly His Arg Lys Thr
405 410 415

Pro Phe Thr Lys Asp Lys His Ser Ser Arg Leu Glu Ala His Leu Thr
420 425 430

Arg Asp Glu Leu Arg Ala Lys Ala Leu His Ile Pro Phe Pro Val Glu
435 440 445

Lys Ile Ile Asn Leu Pro Val Val Asp Phe Asn Glu Met Met Ser Lys
450 455 460

Glu Gln Phe Asn Glu Ala Gln Leu Ala Leu Ile Arg Asp Ile Arg Arg
465 470 475 480

Arg Gly Lys Asn Lys Val Ala Ala Gln Asn Cys Arg Lys Arg Lys Leu
485 490 495

Glu Asn Ile Val Glu Leu Glu Gln Asp Leu Asp His Leu Lys Asp Glu
500 505 510

Lys Glu Lys Leu Leu Lys Glu Lys Gly Glu Asn Asp Lys Ser Leu His
515 520 525

Leu Leu Lys Lys Gln Leu Ser Thr Leu Tyr Leu Glu Val Phe Ser Met
530 535 540

Leu Arg Asp Glu Asp Gly Lys Pro Tyr Ser Pro Ser Glu Tyr Ser Leu
545 550 555 560

Gln Gln Thr Arg Asp Gly Asn Val Phe Leu Val Pro Lys Ser Lys Lys
565 570 575

Pro Asp Val Lys Lys Asn
580

<210> SEQ ID NO 22
<211> LENGTH: 575
<212> TYPE: PRT
<213> ORGANISM: Homo sapiens

<400> SEQUENCE: 22

Met Met Asp Leu Glu Leu Pro Pro Pro Gly Leu Pro Ser Gln Gln Asp
1 5 10 15

Met Asp Leu Ile Asp Ile Leu Trp Arg Gln Asp Ile Asp Leu Gly Val
20 25 30

Ser Arg Glu Val Phe Asp Phe Ser Gln Arg Arg Lys Glu Tyr Glu Leu
35 40 45

Glu Lys Gln Lys Lys Leu Glu Lys Glu Arg Gln Glu Gln Leu Gln Lys
50 55 60

Glu Gln Glu Lys Ala Phe Phe Ala Gln Leu Gln Leu Asp Glu Glu Thr
65 70 75 80

-continued

```
Gly Glu Phe Leu Pro Ile Gln Pro Ala Gln His Ile Gln Ser Glu Thr
                85                  90                  95

Ser Gly Ser Ala Asn Tyr Ser Gln Val Ser Ser Ala Thr Phe Gln Ser
            100                 105                 110

Leu Val Pro Asp Ile Pro Gly His Ile Glu Ser Pro Val Phe Ile Ala
        115                 120                 125

Thr Asn Gln Ala Gln Ser Pro Glu Thr Ser Val Ala Gln Val Ala Pro
    130                 135                 140

Val Asp Leu Asp Gly Met Gln Gln Asp Ile Glu Gln Val Trp Glu Glu
145                 150                 155                 160

Leu Leu Ser Ile Pro Glu Leu Gln Cys Leu Asn Ile Glu Asn Asp Lys
                165                 170                 175

Leu Val Glu Thr Thr Met Val Pro Ser Pro Glu Ala Lys Leu Thr Glu
            180                 185                 190

Val Asp Asn Tyr His Phe Tyr Ser Ser Ile Pro Ser Met Glu Lys Glu
        195                 200                 205

Val Gly Asn Cys Ser Pro His Phe Leu Asn Ala Phe Glu Asp Ser Phe
    210                 215                 220

Ser Ser Ile Leu Ser Thr Glu Asp Pro Asn Gln Leu Thr Val Asn Ser
225                 230                 235                 240

Leu Asn Ser Asp Ala Thr Val Asn Thr Asp Phe Gly Asp Glu Phe Tyr
                245                 250                 255

Ser Ala Phe Ile Ala Glu Pro Ser Ile Ser Asn Ser Met Pro Ser Pro
            260                 265                 270

Ala Thr Leu Ser His Ser Leu Ser Glu Leu Leu Asn Gly Pro Ile Asp
        275                 280                 285

Val Ser Asp Leu Ser Leu Cys Lys Ala Phe Asn Gln Asn His Pro Glu
    290                 295                 300

Ser Thr Ala Glu Phe Asn Asp Ser Asp Ser Gly Ile Ser Leu Asn Thr
305                 310                 315                 320

Ser Pro Ser Val Ala Ser Pro Glu His Ser Val Glu Ser Ser Ser Tyr
                325                 330                 335

Gly Asp Thr Leu Leu Gly Leu Ser Asp Ser Glu Val Glu Glu Leu Asp
            340                 345                 350

Ser Ala Pro Gly Ser Val Lys Gln Asn Gly Pro Lys Thr Pro Val His
        355                 360                 365

Ser Ser Gly Asp Met Val Gln Pro Leu Ser Pro Ser Gln Gly Gln Ser
    370                 375                 380

Thr His Val His Asp Ala Gln Cys Glu Asn Thr Pro Glu Lys Glu Leu
385                 390                 395                 400

Pro Val Ser Pro Gly His Arg Lys Thr Pro Phe Thr Lys Asp Lys His
                405                 410                 415

Ser Ser Arg Leu Glu Ala His Leu Thr Arg Asp Glu Leu Arg Ala Lys
            420                 425                 430

Ala Leu His Ile Pro Phe Pro Val Glu Lys Ile Ile Asn Leu Pro Val
        435                 440                 445

Val Asp Phe Asn Glu Met Met Ser Lys Glu Gln Phe Asn Glu Ala Gln
    450                 455                 460

Leu Ala Leu Ile Arg Asp Ile Arg Arg Arg Gly Lys Asn Lys Val Ala
465                 470                 475                 480

Ala Gln Asn Cys Arg Lys Arg Lys Leu Glu Asn Ile Val Glu Leu Glu
                485                 490                 495

Gln Asp Leu Asp His Leu Lys Asp Glu Lys Glu Lys Leu Leu Lys Glu
```

```
            500                 505                 510

Lys Gly Glu Asn Asp Lys Ser Leu His Leu Leu Lys Lys Gln Leu Ser
        515                 520                 525

Thr Leu Tyr Leu Glu Val Phe Ser Met Leu Arg Asp Glu Asp Gly Lys
    530                 535                 540

Pro Tyr Ser Pro Ser Glu Tyr Ser Leu Gln Gln Thr Arg Asp Gly Asn
545                 550                 555                 560

Val Phe Leu Val Pro Lys Ser Lys Lys Pro Asp Val Lys Lys Asn
                565                 570                 575


<210> SEQ ID NO 23
<211> LENGTH: 532
<212> TYPE: PRT
<213> ORGANISM: Homo sapiens

<400> SEQUENCE: 23

Met Met Asp Leu Glu Leu Pro Pro Pro Gly Leu Pro Ser Gln Gln Asp
1               5                   10                  15

Met Asp Leu Ile Asp Ile Leu Trp Arg Gln Asp Ile Asp Leu Gly Val
            20                  25                  30

Ala His Ile Pro Lys Ser Asp Ala Leu Tyr Phe Asp Asp Cys Met Gln
        35                  40                  45

Leu Leu Ala Gln Thr Phe Pro Phe Val Asp Asp Asn Glu Val Ser Ser
    50                  55                  60

Ala Thr Phe Gln Ser Leu Val Pro Asp Ile Pro Gly His Ile Glu Ser
65                  70                  75                  80

Pro Val Phe Ile Ala Thr Asn Gln Ala Gln Ser Pro Glu Thr Ser Val
                85                  90                  95

Ala Gln Val Ala Pro Val Asp Leu Asp Gly Met Gln Gln Asp Ile Glu
            100                 105                 110

Gln Val Trp Glu Glu Leu Leu Ser Ile Pro Glu Leu Gln Cys Leu Asn
        115                 120                 125

Ile Glu Asn Asp Lys Leu Val Glu Thr Thr Met Val Pro Ser Pro Glu
    130                 135                 140

Ala Lys Leu Thr Glu Val Asp Asn Tyr His Phe Tyr Ser Ser Ile Pro
145                 150                 155                 160

Ser Met Glu Lys Glu Val Gly Asn Cys Ser Pro His Phe Leu Asn Ala
                165                 170                 175

Phe Glu Asp Ser Phe Ser Ser Ile Leu Ser Thr Glu Asp Pro Asn Gln
            180                 185                 190

Leu Thr Val Asn Ser Leu Asn Ser Asp Ala Thr Val Asn Thr Asp Phe
        195                 200                 205

Gly Asp Glu Phe Tyr Ser Ala Phe Ile Ala Glu Pro Ser Ile Ser Asn
    210                 215                 220

Ser Met Pro Ser Pro Ala Thr Leu Ser His Ser Leu Ser Glu Leu Leu
225                 230                 235                 240

Asn Gly Pro Ile Asp Val Ser Asp Leu Ser Leu Cys Lys Ala Phe Asn
                245                 250                 255

Gln Asn His Pro Glu Ser Thr Ala Glu Phe Asn Asp Ser Asp Ser Gly
            260                 265                 270

Ile Ser Leu Asn Thr Ser Pro Ser Val Ala Ser Pro Glu His Ser Val
        275                 280                 285

Glu Ser Ser Ser Tyr Gly Asp Thr Leu Leu Gly Leu Ser Asp Ser Glu
    290                 295                 300
```

```
Val Glu Glu Leu Asp Ser Ala Pro Gly Ser Val Lys Gln Asn Gly Pro
305                 310                 315                 320

Lys Thr Pro Val His Ser Ser Gly Asp Met Val Gln Pro Leu Ser Pro
                325                 330                 335

Ser Gln Gly Gln Ser Thr His Val His Asp Ala Gln Cys Glu Asn Thr
            340                 345                 350

Pro Glu Lys Glu Leu Pro Val Ser Pro Gly His Arg Lys Thr Pro Phe
        355                 360                 365

Thr Lys Asp Lys His Ser Ser Arg Leu Glu Ala His Leu Thr Arg Asp
    370                 375                 380

Glu Leu Arg Ala Lys Ala Leu His Ile Pro Phe Pro Val Glu Lys Ile
385                 390                 395                 400

Ile Asn Leu Pro Val Val Asp Phe Asn Glu Met Met Ser Lys Glu Gln
                405                 410                 415

Phe Asn Glu Ala Gln Leu Ala Leu Ile Arg Asp Ile Arg Arg Arg Gly
            420                 425                 430

Lys Asn Lys Val Ala Ala Gln Asn Cys Arg Lys Arg Lys Leu Glu Asn
        435                 440                 445

Ile Val Glu Leu Glu Gln Asp Leu Asp His Leu Lys Asp Glu Lys Glu
    450                 455                 460

Lys Leu Leu Lys Glu Lys Gly Glu Asn Asp Lys Ser Leu His Leu Leu
465                 470                 475                 480

Lys Lys Gln Leu Ser Thr Leu Tyr Leu Glu Val Phe Ser Met Leu Arg
                485                 490                 495

Asp Glu Asp Gly Lys Pro Tyr Ser Pro Ser Glu Tyr Ser Leu Gln Gln
            500                 505                 510

Thr Arg Asp Gly Asn Val Phe Leu Val Pro Lys Ser Lys Lys Pro Asp
        515                 520                 525

Val Lys Lys Asn
    530


<210> SEQ ID NO 24
<211> LENGTH: 505
<212> TYPE: PRT
<213> ORGANISM: Homo sapiens

<400> SEQUENCE: 24

Met Lys Arg Gln Val Ala His Ile Pro Lys Ser Asp Ala Leu Tyr Phe
1               5                   10                  15

Asp Asp Cys Met Gln Leu Leu Ala Gln Thr Phe Pro Phe Val Asp Asp
            20                  25                  30

Asn Glu Val Ser Ser Ala Thr Phe Gln Ser Leu Val Pro Asp Ile Pro
        35                  40                  45

Gly His Ile Glu Ser Pro Val Phe Ile Ala Thr Asn Gln Ala Gln Ser
    50                  55                  60

Pro Glu Thr Ser Val Ala Gln Val Ala Pro Val Asp Leu Asp Gly Met
65                  70                  75                  80

Gln Gln Asp Ile Glu Gln Val Trp Glu Glu Leu Leu Ser Ile Pro Glu
                85                  90                  95

Leu Gln Cys Leu Asn Ile Glu Asn Asp Lys Leu Val Glu Thr Thr Met
            100                 105                 110

Val Pro Ser Pro Glu Ala Lys Leu Thr Glu Val Asp Asn Tyr His Phe
        115                 120                 125

Tyr Ser Ser Ile Pro Ser Met Glu Lys Glu Val Gly Asn Cys Ser Pro
    130                 135                 140
```

-continued

His Phe Leu Asn Ala Phe Glu Asp Ser Phe Ser Ser Ile Leu Ser Thr
145 150 155 160

Glu Asp Pro Asn Gln Leu Thr Val Asn Ser Leu Asn Ser Asp Ala Thr
165 170 175

Val Asn Thr Asp Phe Gly Asp Glu Phe Tyr Ser Ala Phe Ile Ala Glu
180 185 190

Pro Ser Ile Ser Asn Ser Met Pro Ser Pro Ala Thr Leu Ser His Ser
195 200 205

Leu Ser Glu Leu Leu Asn Gly Pro Ile Asp Val Ser Asp Leu Ser Leu
210 215 220

Cys Lys Ala Phe Asn Gln Asn His Pro Glu Ser Thr Ala Glu Phe Asn
225 230 235 240

Asp Ser Asp Ser Gly Ile Ser Leu Asn Thr Ser Pro Ser Val Ala Ser
245 250 255

Pro Glu His Ser Val Glu Ser Ser Ser Tyr Gly Asp Thr Leu Leu Gly
260 265 270

Leu Ser Asp Ser Glu Val Glu Glu Leu Asp Ser Ala Pro Gly Ser Val
275 280 285

Lys Gln Asn Gly Pro Lys Thr Pro Val His Ser Ser Gly Asp Met Val
290 295 300

Gln Pro Leu Ser Pro Ser Gln Gly Gln Ser Thr His Val His Asp Ala
305 310 315 320

Gln Cys Glu Asn Thr Pro Glu Lys Glu Leu Pro Val Ser Pro Gly His
325 330 335

Arg Lys Thr Pro Phe Thr Lys Asp Lys His Ser Ser Arg Leu Glu Ala
340 345 350

His Leu Thr Arg Asp Glu Leu Arg Ala Lys Ala Leu His Ile Pro Phe
355 360 365

Pro Val Glu Lys Ile Ile Asn Leu Pro Val Val Asp Phe Asn Glu Met
370 375 380

Met Ser Lys Glu Gln Phe Asn Glu Ala Gln Leu Ala Leu Ile Arg Asp
385 390 395 400

Ile Arg Arg Arg Gly Lys Asn Lys Val Ala Ala Gln Asn Cys Arg Lys
405 410 415

Arg Lys Leu Glu Asn Ile Val Glu Leu Glu Gln Asp Leu Asp His Leu
420 425 430

Lys Asp Glu Lys Glu Lys Leu Leu Lys Glu Lys Gly Glu Asn Asp Lys
435 440 445

Ser Leu His Leu Leu Lys Lys Gln Leu Ser Thr Leu Tyr Leu Glu Val
450 455 460

Phe Ser Met Leu Arg Asp Glu Asp Gly Lys Pro Tyr Ser Pro Ser Glu
465 470 475 480

Tyr Ser Leu Gln Gln Thr Arg Asp Gly Asn Val Phe Leu Val Pro Lys
485 490 495

Ser Lys Lys Pro Asp Val Lys Lys Asn
500 505

<210> SEQ ID NO 25
<211> LENGTH: 2497
<212> TYPE: DNA
<213> ORGANISM: Mus musculus

<400> SEQUENCE: 25
ctccatgccc ttgtcctgcc tctggccctt gcctcttgcc ctagcctttt ctccgcctct 60

```
aagttcttgt cccgtcccta ggtccttgtt ccgcccccag ggggcggggg cggggcggac    120
taaggctggc ctgccactcc agcgagcagg ctatctccta gttctccgct gctcggacta    180
gccattgccg ccgcctcacc tctgctgcaa gtagcctcgc cgtcggggag ccctaccaca    240
gcgtccgccc tcagcatgat ggacttggag ttgccaccgc caggactaca gtcccagcag    300
gacatggatt tgattgacat cctttggagg caagacatag atcttggagt aagtcgagaa    360
gtgtttgact ttagtcagcg acagaaggac tatgagctgg aaaaacagaa aaaactcgaa    420
aaggaaagac aagagcaact ccagaaggaa caggagaagg cctttttgc tcagtttcaa    480
ctggatgaag aaacaggaga attcctccca attcagccgg cccagcacat ccagacagac    540
accagtggat ccgccagcta ctcccaggtt gcccacattc ccaaacaaga tgccttgtac    600
tttgaagact gtatgcagct tttggcagag acattcccat ttgtagatga ccatgagtcg    660
cttgccctgg atatccccag ccacgctgaa agttcagtct tcactgcccc tcatcaggcc    720
cagtccctca atagctctct ggaggcagcc atgactgatt taagcagcat agagcaggac    780
atggagcaag tttggcagga gctattttcc attcccgaat tacagtgtct taataccgaa    840
aacaagcagc tggctgatac taccgctgtt cccagcccag aagccacact gacagaaatg    900
gacagcaatt accattttta ctcatcgatc tcctcgctgg aaaaagaagt gggcaactgt    960
ggtccacatt tccttcatgg ttttgaggat tctttcagca gcatcctctc cactgatgat   1020
gccagccagc tgacctcctt agactcaaat cccaccttaa acacagattt tggcgatgaa   1080
ttttattctg ctttcatagc agagcccagt gacggtggca gcatgccttc ctccgctgcc   1140
atcagtcagt cactctctga actcctggac gggactattg aaggctgtga cctgtcactg   1200
tgtaaagctt tcaacccgaa gcacgctgaa ggcacaatgg aattcaatga ctctgactct   1260
ggcatttcac tgaacacgag tcccagccga gcgtccccag agcactccgt ggagtcttcc   1320
atttacggag acccaccgcc tgggttcagt gactcggaaa tggaggagct agatagtgcc   1380
cctggaagtg tcaaacagaa cggccctaaa gcacagccag cacattctcc tggagacaca   1440
gtacagcctc tgtcaccagc tcaagggcac agtgctccta tgcgtgaatc ccaatgtgaa   1500
aatacaacaa aaaaagaagt tcccgtgagt cctggtcatc aaaaagcccc attcacaaaa   1560
gacaaacatt caagccgctt agaggctcat ctcacacgag atgagcttag ggcaaaagct   1620
ctccatattc cattccctgt cgaaaaaatc attaacctcc ctgttgatga cttcaatgaa   1680
atgatgtcca aggagcaatt caatgaagct cagctcgcat tgatccgaga tatacgcagg   1740
agaggtaaga ataaagtcgc cgcccagaac tgtaggaaaa ggaagctgga gaacattgtc   1800
gagctggagc aagacttggg ccacttaaaa gacgagagag aaaaactact cagagaaaag   1860
ggagaaaacg acagaaacct ccatctactg aaaaggcggc tcagcacctt gtatcttgaa   1920
gtcttcagca tgttacgtga tgaggatgga aagccttact ctcccagtga atactctctg   1980
cagcaaacca gagatggcaa tgtgttcctt gttcccaaaa gcaagaagcc agatacaaag   2040
aaaaactagg ttcgggagga tggagccttt tctgagctag tgtttgtttt gtactgctaa   2100
aacttcctac tgtgatgtga aatgcagaaa cactttataa gtaactatgc agaattatag   2160
ccaaagctag tatagcaata atatgaaact ttacaaagca ttaaagtctc aatgttgaat   2220
cagtttcatt ttaactctca agttaatttc ttaggcacca tttgggagag tttctgttta   2280
agtgtaaata ctacagaact tatttatact gttctcactt gttacagtca tagacttata   2340
tgacatctgg ctaaaagcaa actattgaaa actaaccaga ccactatact tttttatata   2400
```

ctgtatgaac aggaaatgac atttttatat taaattgttt agctcataaa aattaaaagg 2460
agctagcact aataaaagaa tatcatgact taaacta 2497

<210> SEQ ID NO 26
<211> LENGTH: 1621
<212> TYPE: DNA
<213> ORGANISM: Mus musculus

<400> SEQUENCE: 26
ctccatgccc ttgtcctgcc tctggccctt gcctcttgcc ctagcctttt ctccgcctct 60
aagttcttgt cccgtcccta ggtccttgtt ccgcccccag ggggcggggg cggggcggac 120
taaggctggc ctgccactcc agcgagcagg ctatctccta gttctccgct gctcggacta 180
gccattgccg ccgcctcacc tctgctgcaa gtagcctcgc cgtcggggag ccctaccaca 240
gcgtccgccc tcagcatgat ggacttggag ttgccaccgc caggactaca gtcccagcag 300
agtgatggtt gcccacttgg tggattgctg tgcgtccaga cgaggcggta caagttttgg 360
aaggaggttt ctgagcacgc agaaagtgtg tgatcagagg tggctgctct tgttgcagtg 420
cagtgtctac tttatctgga cttagaccat ccccacgttg taaccttccg ttctcaaaac 480
ccagtgtgac cagtgtctca cacaactcta tagtagattt ttaatctgct ttttatgtat 540
atgggtgttt tgcctgtatg tatttctgtg taccatacat gtactcgatg ccttcagagt 600
ccagaagaga gcatcagatt acagacagtt gtgagttgcc atataggttc catgaacaga 660
tccagcttct gtgtaagagc agtgagtgct cttaaccact ggtttagcca tctctccagt 720
ccctagtaat cctttttata ggcccaaatt gcattgtagt agtcagcaac aatagtgagt 780
accatgatgc actttcagat atatacatat gaaagtagtt gaaatataat ttctaagctc 840
agggttaatt tatgtcttta ttgggaacac agagcccttt tacatgacgt gtttagtagc 900
catggtaatc atctcatttg taaattatgc tattatggaa taatatgaaa aactattgag 960
tttagtcatt aagagccctc tttgtgattc agattcacac cagctctttg gagtaattgc 1020
taatgatacc tagagtagtt tggaagggct aatgtccaca gttgtagcct cgggaagttg 1080
ttagccacac atttgcttag aggacacccg aggagggcat gggccatagt ggggaccgct 1140
gcagggctgc gctgtccacc accgcagcca ctagtcacct tgcagtctgg aaatgtgatg 1200
agtgacagaa accaagaggc tggagcttta gtgttaatga gcatgacatt tataaacagc 1260
agaaacgact tttctggtta ataagcctta ggtagtcctc tagctcagga ggaggctcgg 1320
ggctcctggt cctgcctttg tagggcagca ttgtgcgctg tcttgtgggt aagattattg 1380
tgctctgtca cctttaatat cacaacaata ctgttaacat gttaaaatgc tattggacca 1440
aattggatta aatacgttgt tcaaattaaa ttcactgtgt tgtttttgtt attgtgtctg 1500
agctgcaaac aatatcagtt acatatgtta ttcacattat atttcttatg aagttccttt 1560
agagcattct gtaatctaaa attagtgtgt atttttacat taaaatgaat tttcaattgt 1620
a 1621

<210> SEQ ID NO 27
<211> LENGTH: 597
<212> TYPE: PRT
<213> ORGANISM: Mus musculus

<400> SEQUENCE: 27

Met Met Asp Leu Glu Leu Pro Pro Pro Gly Leu Gln Ser Gln Gln Asp
1 5 10 15

-continued

```
Met Asp Leu Ile Asp Ile Leu Trp Arg Gln Asp Ile Asp Leu Gly Val
            20                  25                  30

Ser Arg Glu Val Phe Asp Phe Ser Gln Arg Gln Lys Asp Tyr Glu Leu
        35                  40                  45

Glu Lys Gln Lys Lys Leu Glu Lys Glu Arg Gln Glu Gln Leu Gln Lys
    50                  55                  60

Glu Gln Glu Lys Ala Phe Phe Ala Gln Phe Gln Leu Asp Glu Glu Thr
65                  70                  75                  80

Gly Glu Phe Leu Pro Ile Gln Pro Ala Gln His Ile Gln Thr Asp Thr
                85                  90                  95

Ser Gly Ser Ala Ser Tyr Ser Gln Val Ala His Ile Pro Lys Gln Asp
            100                 105                 110

Ala Leu Tyr Phe Glu Asp Cys Met Gln Leu Leu Ala Glu Thr Phe Pro
        115                 120                 125

Phe Val Asp Asp His Glu Ser Leu Ala Leu Asp Ile Pro Ser His Ala
    130                 135                 140

Glu Ser Ser Val Phe Thr Ala Pro His Gln Ala Gln Ser Leu Asn Ser
145                 150                 155                 160

Ser Leu Glu Ala Ala Met Thr Asp Leu Ser Ser Ile Glu Gln Asp Met
                165                 170                 175

Glu Gln Val Trp Gln Glu Leu Phe Ser Ile Pro Glu Leu Gln Cys Leu
            180                 185                 190

Asn Thr Glu Asn Lys Gln Leu Ala Asp Thr Thr Ala Val Pro Ser Pro
        195                 200                 205

Glu Ala Thr Leu Thr Glu Met Asp Ser Asn Tyr His Phe Tyr Ser Ser
    210                 215                 220

Ile Ser Ser Leu Glu Lys Glu Val Gly Asn Cys Gly Pro His Phe Leu
225                 230                 235                 240

His Gly Phe Glu Asp Ser Phe Ser Ser Ile Leu Ser Thr Asp Asp Ala
                245                 250                 255

Ser Gln Leu Thr Ser Leu Asp Ser Asn Pro Thr Leu Asn Thr Asp Phe
            260                 265                 270

Gly Asp Glu Phe Tyr Ser Ala Phe Ile Ala Glu Pro Ser Asp Gly Gly
        275                 280                 285

Ser Met Pro Ser Ser Ala Ala Ile Ser Gln Ser Leu Ser Glu Leu Leu
    290                 295                 300

Asp Gly Thr Ile Glu Gly Cys Asp Leu Ser Leu Cys Lys Ala Phe Asn
305                 310                 315                 320

Pro Lys His Ala Glu Gly Thr Met Glu Phe Asn Asp Ser Asp Ser Gly
                325                 330                 335

Ile Ser Leu Asn Thr Ser Pro Ser Arg Ala Ser Pro Glu His Ser Val
            340                 345                 350

Glu Ser Ser Ile Tyr Gly Asp Pro Pro Pro Gly Phe Ser Asp Ser Glu
        355                 360                 365

Met Glu Glu Leu Asp Ser Ala Pro Gly Ser Val Lys Gln Asn Gly Pro
    370                 375                 380

Lys Ala Gln Pro Ala His Ser Pro Gly Asp Thr Val Gln Pro Leu Ser
385                 390                 395                 400

Pro Ala Gln Gly His Ser Ala Pro Met Arg Glu Ser Gln Cys Glu Asn
                405                 410                 415

Thr Thr Lys Lys Glu Val Pro Val Ser Pro Gly His Gln Lys Ala Pro
            420                 425                 430

Phe Thr Lys Asp Lys His Ser Ser Arg Leu Glu Ala His Leu Thr Arg
```

```
        435                 440                 445

Asp Glu Leu Arg Ala Lys Ala Leu His Ile Pro Phe Pro Val Glu Lys
    450                 455                 460

Ile Ile Asn Leu Pro Val Asp Asp Phe Asn Glu Met Met Ser Lys Glu
465                 470                 475                 480

Gln Phe Asn Glu Ala Gln Leu Ala Leu Ile Arg Asp Ile Arg Arg Arg
                485                 490                 495

Gly Lys Asn Lys Val Ala Ala Gln Asn Cys Arg Lys Arg Lys Leu Glu
            500                 505                 510

Asn Ile Val Glu Leu Glu Gln Asp Leu Gly His Leu Lys Asp Glu Arg
        515                 520                 525

Glu Lys Leu Leu Arg Glu Lys Gly Glu Asn Asp Arg Asn Leu His Leu
    530                 535                 540

Leu Lys Arg Arg Leu Ser Thr Leu Tyr Leu Glu Val Phe Ser Met Leu
545                 550                 555                 560

Arg Asp Glu Asp Gly Lys Pro Tyr Ser Pro Ser Glu Tyr Ser Leu Gln
                565                 570                 575

Gln Thr Arg Asp Gly Asn Val Phe Leu Val Pro Lys Ser Lys Lys Pro
            580                 585                 590

Asp Thr Lys Lys Asn
        595


<210> SEQ ID NO 28
<211> LENGTH: 2606
<212> TYPE: DNA
<213> ORGANISM: Homo sapiens

<400> SEQUENCE: 28

ctttccgccc tctccccgcc tccttttcgg gcgtcccgag gccgctcccc aaccgacaac      60

caagaccccg caggccacgc agccctggag ccgaggcccc ccgacggcgg aggcgcccgc     120

gggtccccta cagccaaggt ccctgagtgc cagaggtggt ggtgttgctt atcttctgga     180

accccatgca gccagatccc aggcctagcg gggctggggc ctgctgccga ttcctgcccc     240

tgcagtcaca gtgccctgag ggggcagggg acgcggtgat gtacgcctcc actgagtgca     300

aggcggaggt gacgccctcc cagcatggca accgcacctt cagctacacc ctggaggatc     360

ataccaagca ggcctttggc atcatgaacg agctgcggct cagccagcag ctgtgtgacg     420

tcacactgca ggtcaagtac caggatgcac cggccgccca gttcatggcc cacaaggtgg     480

tgctggcctc atccagccct gtcttcaagg ccatgttcac caacgggctg cgggagcagg     540

gcatggaggt ggtgtccatt gagggtatcc accccaaggt catggagcgc ctcattgaat     600

tcgcctacac ggcctccatc tccatgggcg agaagtgtgt cctccacgtc atgaacggtg     660

ctgtcatgta ccagatcgac agcgttgtcc gtgcctgcag tgacttcctg gtgcagcagc     720

tggaccccag caatgccatc ggcatcgcca acttcgctga gcagattggc tgtgtggagt     780

tgcaccagcg tgcccgggag tacatctaca tgcattttgg ggaggtggcc aagcaagagg     840

agttcttcaa cctgtcccac tgccaactgg tgaccctcat cagccgggac gacctgaacg     900

tgcgctgcga gtccgaggtc ttccacgcct gcatcaactg ggtcaagtac gactgcgaac     960

agcgacggtt ctacgtccag gcgctgctgc gggccgtgcg ctgccactcg ttgacgccga    1020

acttcctgca gatgcagctg cagaagtgcg agatcctgca gtccgactcc cgctgcaagg    1080

actacctggt caagatcttc gaggagctca ccctgcacaa gcccacgcag gtgatgccct    1140

gccgggcgcc caaggtgggc cgcctgatct acaccgcggg cggctacttc cgacagtcgc    1200
```

tcagctacct ggaggcttac aaccccagtg acggcacctg gctccggttg gcggacctgc 1260
aggtgccgcg gagcggcctg gccggctgcg tggtgggcgg gctgttgtac gccgtgggcg 1320
gcaggaacaa ctcgcccgac ggcaacaccg actccagcgc cctggactgt tacaacccca 1380
tgaccaatca gtggtcgccc tgcgccccca tgagcgtgcc ccgtaaccgc atcggggtgg 1440
gggtcatcga tggccacatc tatgccgtcg gcggctccca cggctgcatc caccacaaca 1500
gtgtggagag gtatgagcca gagcgggatg agtggcactt ggtggcccca atgctgacac 1560
gaaggatcgg ggtgggcgtg gctgtcctca atcgtctcct ttatgccgtg gggggctttg 1620
acgggacaaa ccgccttaat tcagctgagt gttactaccc agagaggaac gagtggcgaa 1680
tgatcacagc aatgaacacc atccgaagcg gggcaggcgt ctgcgtcctg cacaactgta 1740
tctatgctgc tgggggctat gatggtcagg accagctgaa cagcgtggag cgctacgatg 1800
tggaaacaga gacgtggact ttcgtagccc ccatgaagca ccggcgaagt gccctgggga 1860
tcactgtcca ccaggggaga atctacgtcc ttggaggcta tgatggtcac acgttcctgg 1920
acagtgtgga gtgttacgac ccagatacag acacctggag cgaggtgacc cgaatgacat 1980
cgggccggag tggggtgggc gtggctgtca ccatggagcc ctgccggaag cagattgacc 2040
agcagaactg tacctgttga ggcacttttg tttcttgggc aaaaatacag tccaatgggg 2100
agtatcattg tttttgtaca aaaaccggga ctaaaagaaa agacagcact gcaaataacc 2160
catcttccgg gaagggaggc caggatgcct cagtgttaaa atgacatctc aaaagaagtc 2220
caaagcggga atcatgtgcc cctcagcgga gccccgggag tgtccaagac agcctggctg 2280
ggaaaggggg tgtggaaaga gcaggcttcc aggagagagg cccccaaacc ctctggccgg 2340
gtaataggcc tgggtcccac tcacccatgc cggcagctgt caccatgtga tttattcttg 2400
gatacctggg agggggccaa tgggggcctc agggggaggc cccctctgga aatgtggttc 2460
ccagggatgg gcctgtacat agaagccacc ggatggcact tccccaccgg atggacagtt 2520
attttgttga taagtaaccc tgtaattttc caaggaaaat aaagaacaga ctaactagtg 2580
tctttcaccc tgaaaaaaaa aaaaaa 2606

<210> SEQ ID NO 29
<211> LENGTH: 2577
<212> TYPE: DNA
<213> ORGANISM: Homo sapiens

<400> SEQUENCE: 29
tctgcttagt catggtgacc tgcgcgcgct ccgcgcctcc cccacgcgca gcgatggagg 60
cgccggggct cgggcggtgg aggcggagcc ggagcgcggc catggcgggg tccctgagtg 120
ccagaggtgg tggtgttgct tatcttctgg aaccccatgc agccagatcc caggcctagc 180
ggggctgggg cctgctgccg attcctgccc ctgcagtcac agtgccctga gggggcaggg 240
gacgcggtga tgtacgcctc cactgagtgc aaggcggagg tgacgccctc ccagcatggc 300
aaccgcacct tcagctacac cctggaggat cataccaagc aggcctttgg catcatgaac 360
gagctgcggc tcagccagca gctgtgtgac gtcacactgc aggtcaagta ccaggatgca 420
ccggccgccc agttcatggc ccacaaggtg gtgctggcct catccagccc tgtcttcaag 480
gccatgttca ccaacgggct gcgggagcag ggcatggagg tggtgtccat tgagggtatc 540
caccccaagg tcatggagcg cctcattgaa ttcgcctaca cggcctccat ctccatgggc 600
gagaagtgtg tcctccacgt catgaacggt gctgtcatgt accagatcga cagcgttgtc 660

```
cgtgcctgca gtgacttcct ggtgcagcag ctggacccca gcaatgccat cggcatcgcc    720
aacttcgctg agcagattgg ctgtgtggag ttgcaccagc gtgcccggga gtacatctac    780
atgcattttg gggaggtggc caagcaagag gagttcttca acctgtccca ctgccaactg    840
gtgaccctca tcagccggga cgacctgaac gtgcgctgcg agtccgaggt cttccacgcc    900
tgcatcaact gggtcaagta cgactgcgaa cagcgacggt tctacgtcca ggcgctgctg    960
cgggccgtgc gctgccactc gttgacgccg aacttcctgc agatgcagct gcagaagtgc   1020
gagatcctgc agtccgactc ccgctgcaag gactacctgg tcaagatctt cgaggagctc   1080
accctgcaca agcccacgca ggtgatgccc tgccgggcgc ccaaggtggg ccgcctgatc   1140
tacaccgcgg gcggctactt ccgacagtcg ctcagctacc tggaggctta caaccccagt   1200
gacggcacct ggctccggtt ggcggacctg caggtgccgc ggagcggcct ggccggctgc   1260
gtggtgggcg ggctgttgta cgccgtgggc ggcaggaaca actcgcccga cggcaacacc   1320
gactccagcg ccctggactg ttacaacccc atgaccaatc agtggtcgcc ctgcgccccc   1380
atgagcgtgc cccgtaaccg catcggggtg ggggtcatcg atggccacat ctatgccgtc   1440
ggcggctccc acggctgcat ccaccacaac agtgtggaga ggtatgagcc agagcgggat   1500
gagtggcact tggtggcccc aatgctgaca cgaaggatcg gggtgggcgt ggctgtcctc   1560
aatcgtctcc tttatgccgt ggggggcttt gacgggacaa accgccttaa ttcagctgag   1620
tgttactacc cagagaggaa cgagtggcga atgatcacag caatgaacac catccgaagc   1680
ggggcaggcg tctgcgtcct gcacaactgt atctatgctg ctgggggcta tgatggtcag   1740
gaccagctga acagcgtgga gcgctacgat gtggaaacag agacgtggac tttcgtagcc   1800
cccatgaagc accggcgaag tgccctgggg atcactgtcc accaggggag aatctacgtc   1860
cttggaggct atgatggtca cacgttcctg gacagtgtgg agtgttacga cccagataca   1920
gacacctgga gcgaggtgac ccgaatgaca tcgggccgga gtggggtggg cgtggctgtc   1980
accatggagc cctgccggaa gcagattgac cagcagaact gtacctgttg aggcactttt   2040
gtttcttggg caaaaataca gtccaatggg gagtatcatt gtttttgtac aaaaaccggg   2100
actaaaagaa aagacagcac tgcaaataac ccatcttccg ggaagggagg ccaggatgcc   2160
tcagtgttaa aatgacatct caaaagaagt ccaaagcggg aatcatgtgc ccctcagcgg   2220
agccccggga gtgtccaaga cagcctggct gggaaagggg gtgtggaaag agcaggcttc   2280
caggagagag gcccccaaac cctctggccg ggtaataggc ctgggtccca ctcacccatg   2340
ccggcagctg tcaccatgtg atttattctt ggatacctgg gagggggcca atgggggcct   2400
cagggggagg ccccctctgg aaatgtggtt cccagggatg ggcctgtaca tagaagccac   2460
cggatggcac ttccccaccg gatggacagt tattttgttg ataagtaacc ctgtaatttt   2520
ccaaggaaaa taaagaacag actaactagt gtctttcacc ctgaaaaaaa aaaaaaa      2577
```

<210> SEQ ID NO 30
<211> LENGTH: 624
<212> TYPE: PRT
<213> ORGANISM: Homo sapiens

<400> SEQUENCE: 30

```
Met Gln Pro Asp Pro Arg Pro Ser Gly Ala Gly Ala Cys Cys Arg Phe
1               5                   10                  15

Leu Pro Leu Gln Ser Gln Cys Pro Glu Gly Ala Gly Asp Ala Val Met
            20                  25                  30

Tyr Ala Ser Thr Glu Cys Lys Ala Glu Val Thr Pro Ser Gln His Gly
```

-continued

```
        35                  40                  45

Asn Arg Thr Phe Ser Tyr Thr Leu Glu Asp His Thr Lys Gln Ala Phe
    50                  55                  60

Gly Ile Met Asn Glu Leu Arg Leu Ser Gln Gln Leu Cys Asp Val Thr
65                  70                  75                  80

Leu Gln Val Lys Tyr Gln Asp Ala Pro Ala Ala Gln Phe Met Ala His
                85                  90                  95

Lys Val Val Leu Ala Ser Ser Ser Pro Val Phe Lys Ala Met Phe Thr
            100                 105                 110

Asn Gly Leu Arg Glu Gln Gly Met Glu Val Val Ser Ile Glu Gly Ile
        115                 120                 125

His Pro Lys Val Met Glu Arg Leu Ile Glu Phe Ala Tyr Thr Ala Ser
    130                 135                 140

Ile Ser Met Gly Glu Lys Cys Val Leu His Val Met Asn Gly Ala Val
145                 150                 155                 160

Met Tyr Gln Ile Asp Ser Val Val Arg Ala Cys Ser Asp Phe Leu Val
                165                 170                 175

Gln Gln Leu Asp Pro Ser Asn Ala Ile Gly Ile Ala Asn Phe Ala Glu
            180                 185                 190

Gln Ile Gly Cys Val Glu Leu His Gln Arg Ala Arg Glu Tyr Ile Tyr
        195                 200                 205

Met His Phe Gly Glu Val Ala Lys Gln Glu Glu Phe Phe Asn Leu Ser
    210                 215                 220

His Cys Gln Leu Val Thr Leu Ile Ser Arg Asp Asp Leu Asn Val Arg
225                 230                 235                 240

Cys Glu Ser Glu Val Phe His Ala Cys Ile Asn Trp Val Lys Tyr Asp
                245                 250                 255

Cys Glu Gln Arg Arg Phe Tyr Val Gln Ala Leu Leu Arg Ala Val Arg
            260                 265                 270

Cys His Ser Leu Thr Pro Asn Phe Leu Gln Met Gln Leu Gln Lys Cys
        275                 280                 285

Glu Ile Leu Gln Ser Asp Ser Arg Cys Lys Asp Tyr Leu Val Lys Ile
    290                 295                 300

Phe Glu Glu Leu Thr Leu His Lys Pro Thr Gln Val Met Pro Cys Arg
305                 310                 315                 320

Ala Pro Lys Val Gly Arg Leu Ile Tyr Thr Ala Gly Gly Tyr Phe Arg
                325                 330                 335

Gln Ser Leu Ser Tyr Leu Glu Ala Tyr Asn Pro Ser Asp Gly Thr Trp
            340                 345                 350

Leu Arg Leu Ala Asp Leu Gln Val Pro Arg Ser Gly Leu Ala Gly Cys
        355                 360                 365

Val Val Gly Gly Leu Leu Tyr Ala Val Gly Gly Arg Asn Asn Ser Pro
    370                 375                 380

Asp Gly Asn Thr Asp Ser Ser Ala Leu Asp Cys Tyr Asn Pro Met Thr
385                 390                 395                 400

Asn Gln Trp Ser Pro Cys Ala Pro Met Ser Val Pro Arg Asn Arg Ile
                405                 410                 415

Gly Val Gly Val Ile Asp Gly His Ile Tyr Ala Val Gly Gly Ser His
            420                 425                 430

Gly Cys Ile His His Asn Ser Val Glu Arg Tyr Glu Pro Glu Arg Asp
        435                 440                 445

Glu Trp His Leu Val Ala Pro Met Leu Thr Arg Arg Ile Gly Val Gly
    450                 455                 460
```

```
Val Ala Val Leu Asn Arg Leu Leu Tyr Ala Val Gly Gly Phe Asp Gly
465                 470                 475                 480

Thr Asn Arg Leu Asn Ser Ala Glu Cys Tyr Tyr Pro Glu Arg Asn Glu
                485                 490                 495

Trp Arg Met Ile Thr Ala Met Asn Thr Ile Arg Ser Gly Ala Gly Val
            500                 505                 510

Cys Val Leu His Asn Cys Ile Tyr Ala Ala Gly Gly Tyr Asp Gly Gln
        515                 520                 525

Asp Gln Leu Asn Ser Val Glu Arg Tyr Asp Val Glu Thr Glu Thr Trp
    530                 535                 540

Thr Phe Val Ala Pro Met Lys His Arg Arg Ser Ala Leu Gly Ile Thr
545                 550                 555                 560

Val His Gln Gly Arg Ile Tyr Val Leu Gly Gly Tyr Asp Gly His Thr
                565                 570                 575

Phe Leu Asp Ser Val Glu Cys Tyr Asp Pro Asp Thr Asp Thr Trp Ser
            580                 585                 590

Glu Val Thr Arg Met Thr Ser Gly Arg Ser Gly Val Gly Val Ala Val
        595                 600                 605

Thr Met Glu Pro Cys Arg Lys Gln Ile Asp Gln Gln Asn Cys Thr Cys
    610                 615                 620


<210> SEQ ID NO 31
<211> LENGTH: 624
<212> TYPE: PRT
<213> ORGANISM: Homo sapiens

<400> SEQUENCE: 31

Met Gln Pro Asp Pro Arg Pro Ser Gly Ala Gly Ala Cys Cys Arg Phe
1               5                   10                  15

Leu Pro Leu Gln Ser Gln Cys Pro Glu Gly Ala Gly Asp Ala Val Met
            20                  25                  30

Tyr Ala Ser Thr Glu Cys Lys Ala Glu Val Thr Pro Ser Gln His Gly
        35                  40                  45

Asn Arg Thr Phe Ser Tyr Thr Leu Glu Asp His Thr Lys Gln Ala Phe
    50                  55                  60

Gly Ile Met Asn Glu Leu Arg Leu Ser Gln Gln Leu Cys Asp Val Thr
65                  70                  75                  80

Leu Gln Val Lys Tyr Gln Asp Ala Pro Ala Ala Gln Phe Met Ala His
                85                  90                  95

Lys Val Val Leu Ala Ser Ser Ser Pro Val Phe Lys Ala Met Phe Thr
            100                 105                 110

Asn Gly Leu Arg Glu Gln Gly Met Glu Val Val Ser Ile Glu Gly Ile
        115                 120                 125

His Pro Lys Val Met Glu Arg Leu Ile Glu Phe Ala Tyr Thr Ala Ser
    130                 135                 140

Ile Ser Met Gly Glu Lys Cys Val Leu His Val Met Asn Gly Ala Val
145                 150                 155                 160

Met Tyr Gln Ile Asp Ser Val Val Arg Ala Cys Ser Asp Phe Leu Val
                165                 170                 175

Gln Gln Leu Asp Pro Ser Asn Ala Ile Gly Ile Ala Asn Phe Ala Glu
            180                 185                 190

Gln Ile Gly Cys Val Glu Leu His Gln Arg Ala Arg Glu Tyr Ile Tyr
        195                 200                 205

Met His Phe Gly Glu Val Ala Lys Gln Glu Glu Phe Phe Asn Leu Ser
```

```
    210                 215                 220

His Cys Gln Leu Val Thr Leu Ile Ser Arg Asp Asp Leu Asn Val Arg
225                 230                 235                 240

Cys Glu Ser Glu Val Phe His Ala Cys Ile Asn Trp Val Lys Tyr Asp
                245                 250                 255

Cys Glu Gln Arg Arg Phe Tyr Val Gln Ala Leu Leu Arg Ala Val Arg
            260                 265                 270

Cys His Ser Leu Thr Pro Asn Phe Leu Gln Met Gln Leu Gln Lys Cys
        275                 280                 285

Glu Ile Leu Gln Ser Asp Ser Arg Cys Lys Asp Tyr Leu Val Lys Ile
    290                 295                 300

Phe Glu Glu Leu Thr Leu His Lys Pro Thr Gln Val Met Pro Cys Arg
305                 310                 315                 320

Ala Pro Lys Val Gly Arg Leu Ile Tyr Thr Ala Gly Gly Tyr Phe Arg
                325                 330                 335

Gln Ser Leu Ser Tyr Leu Glu Ala Tyr Asn Pro Ser Asp Gly Thr Trp
            340                 345                 350

Leu Arg Leu Ala Asp Leu Gln Val Pro Arg Ser Gly Leu Ala Gly Cys
        355                 360                 365

Val Val Gly Gly Leu Leu Tyr Ala Val Gly Gly Arg Asn Asn Ser Pro
    370                 375                 380

Asp Gly Asn Thr Asp Ser Ser Ala Leu Asp Cys Tyr Asn Pro Met Thr
385                 390                 395                 400

Asn Gln Trp Ser Pro Cys Ala Pro Met Ser Val Pro Arg Asn Arg Ile
                405                 410                 415

Gly Val Gly Val Ile Asp Gly His Ile Tyr Ala Val Gly Gly Ser His
            420                 425                 430

Gly Cys Ile His His Asn Ser Val Glu Arg Tyr Glu Pro Glu Arg Asp
        435                 440                 445

Glu Trp His Leu Val Ala Pro Met Leu Thr Arg Arg Ile Gly Val Gly
    450                 455                 460

Val Ala Val Leu Asn Arg Leu Leu Tyr Ala Val Gly Gly Phe Asp Gly
465                 470                 475                 480

Thr Asn Arg Leu Asn Ser Ala Glu Cys Tyr Tyr Pro Glu Arg Asn Glu
                485                 490                 495

Trp Arg Met Ile Thr Ala Met Asn Thr Ile Arg Ser Gly Ala Gly Val
            500                 505                 510

Cys Val Leu His Asn Cys Ile Tyr Ala Ala Gly Gly Tyr Asp Gly Gln
        515                 520                 525

Asp Gln Leu Asn Ser Val Glu Arg Tyr Asp Val Glu Thr Glu Thr Trp
    530                 535                 540

Thr Phe Val Ala Pro Met Lys His Arg Arg Ser Ala Leu Gly Ile Thr
545                 550                 555                 560

Val His Gln Gly Arg Ile Tyr Val Leu Gly Gly Tyr Asp Gly His Thr
                565                 570                 575

Phe Leu Asp Ser Val Glu Cys Tyr Asp Pro Asp Thr Asp Thr Trp Ser
            580                 585                 590

Glu Val Thr Arg Met Thr Ser Gly Arg Ser Gly Val Gly Val Ala Val
        595                 600                 605

Thr Met Glu Pro Cys Arg Lys Gln Ile Asp Gln Gln Asn Cys Thr Cys
    610                 615                 620
```

<210> SEQ ID NO 32

<211> LENGTH: 3434
<212> TYPE: DNA
<213> ORGANISM: Mus musculus

<400> SEQUENCE: 32
agacccacgc cctgctccct ccgcccggca cctgcaggaa gggctggaac tgcctctgcg 60
tacccgccgc ccgtttccgc cctcccgctc ctcccacgcg tgccgcccgg gaccccgcag 120
caccgctgcc ccgatccgag ccctccaccc ccactccggt ccccctcctc tcttcccgga 180
agcgcggcgc gtggcggccc ggcggcgcgg attggacgcg tggcacctac agagacaccc 240 ggggggggtgg gacggaggtg agcgagcgcc cgcggaggat gcggtgggga gccagctccg 300
ggagctgccc gcggtcgcgc gtggggccgt gcacgcggtg gggggaagcg cgtgcccttc 360
tccaagcgcg caccccgccg ccgagcccgt gagccctcgt agggtggtgg ccgcggcgag 420
tagaggtagg ggtcgcccgc ggccggcgcc ccgggactct tattgtgaca gggtggcgcg 480
ctgtgcttag tcaccgtgac ccgcgcggcg gaggcggagg cagagcgcgg ccatggcggg 540
gcccctaacg gctagcagag gaactgtgtc ttgtcatcag gaacccccatg cagcccgaac 600 ccaagcttag cggggctccc cgcagcagcc agttcctgcc cctgtggtca aagtgccccg 660
agggggccgg ggacgcagtg atgtatgcct ccacggagtg caaggcagag gtgacgccct 720
cgcaggacgg taaccgaacc ttcagctaca cactagagga tcacaccaag caggcttttg 780
gcgtcatgaa cgagcttcgc ctgagccagc aactctgtga cgtgaccctg caggtcaaat 840
atgaggacat cccagctgcc caattcatgg ctcacaaagt ggtgctggcc tcctccagcc 900
cagtctttaa agccatgttc accaacgggc ttcgggagca gggcatggag gtggtgtcca 960
tcgaaggcat ccaccctaag gtcatggaaa ggcttattga gttcgcctac acggcctcca 1020
tctccgtggg cgagaagtgt gtcctgcacg tgatgaacgg ggcggtcatg taccagattg 1080
acagcgtggt tcgagcctgc agcgacttcc tcgtgcagca gctggacccc agcaacgcca 1140
ttggcatcgc caacttcgcg gagcagatcg gctgcactga actgcaccag cgtgcccggg 1200
agtatatcta catgcacttc ggggaggtgg ccaagcagga ggagttcttc aacctgtcac 1260
actgccagct ggccacgctc atcagccggg atgatctgaa cgtacgctgc gagtccgagg 1320
tgttccacgc gtgcatcgac tgggtcaaat acgactgccc gcagcggcgc ttctacgtgc 1380
aggcactgct gcgggccgtg cgctgccatg cgctcacgcc gcgcttcctg cagacgcagc 1440
tgcagaagtg tgagatcctg caggccgacg cgcgctgcaa ggactacctg gtgcagatat 1500
tccaggagct cacgctgcac aagcccacgc aggcagtgcc ctgccgcgcg cccaaagtgg 1560
gccgcctcat ctacacagcg ggcggttact tccgacagtc gctcagctac ctggaggcct 1620
acaacccgag caatggctcc tggctgcgcc tggccgatct acaggtgccg cgcagtgggc 1680
tggcaggctg cgtggtgggt gggctgctat acgctgtggg cggccgcaac aactctccgg 1740
atggcaacac tgactccagc gccctggact gctacaaccc catgaccaac cagtggtcgc 1800
cctgtgcctc tatgagcgtg ccacgcaacc gcatcggggt gggggtcata gatggccaca 1860
tctacgcagt cgggggttcc cacggctgca tccaccacag cagcgtggag agatatgagc 1920
cagagcggga cgagtggcat ctagtcgcgc caatgttgac acggaggatt ggcgtgggcg 1980
tggcagtgct caaccgcttg ctgtatgcag tgggggggctt tgacgggact aaccggctta 2040
actccgcaga atgttactat ccagagagga atgagtggcg gatgatcaca ccgatgaata 2100
ccatccggag cggggccggg gtctgcgtgc tgcacaactg tatctatgca gcaggggggct 2160 acgatgggca ggaccagttg aacagtgtgg agcgctacga cgtggagaca gagacctgga 2220
ctttcgtagc ccccatgagg catcaccgta gtgcgctggg gattactgtg caccagggca 2280
agatctacgt cctcggaggc tatgatggcc acacttttct ggacagtgtg gaatgctatg 2340
acccggacag tgatacctgg agtgaggtga cccgcatgac atctggccgc agcggggtgg 2400
gtgtggccgt caccatggaa ccctgtcgga agcaaattga tcaacaaaac tgtacctgct 2460
gaagcacttg gaatacctga gcactgacaa caggacagaa aaacagtctg tgtatcactg 2520
cttctctgta ctaaagaaaa aagaagaaaa caaagcataa acagaaaaca cagggccgaa 2580
gaggcggcag aagaagtcat cccttcttcc aggaagggcg actgggatgc cttgtaaagg 2640
accttgtgga agaccagaac tcaaatccat gggcccatct gtcatagccc tggagcgtcc 2700
aagtctggga tggggtatgg gcggggcacc ctcacaggtg agaagccctt gaactcccac 2760
caccagaagg ggggggacag gcaaagcagg agatcacatg tttttttctt tggttcctgc 2820
aactcggtga tcaattccag tggacagggg aagaagggac agctgaggcc aaggggctga 2880
ggctccctct ggaactgggg cccaagggac aagccggcac agagaagcct ctgggctctg 2940
agccctgaac agttattttg ttaaataacc ctgtaagttt cccatgggaa taaagaatgg 3000
agtaggcaca caggtcttca gagggcggtc ggaatccctc agggagagac agctcttcta 3060
ttgaaataca cgcagatcct gatggggctg gtatctgaaa cccgtctatt gtctctgctt 3120
gccattgtac attctgctca gacagggcat cttgcttctt gtgggacaca cagttgtctg 3180
tcagtttcag ggcattagaa gccaatgacc taacttctgt gcctcctaac ttctcctggg 3240
gcctcctgtg tttagcttta ttttgaggca gggactcacg tcgtccggga tggccttcag 3300
ttcagacctt gaactgacgc tgccgcctgt cccagcctac cgagtgctgg ggctacatct 3360
gtatagcgca atgcctggtt cctgcttatt atttttgtac ccaagcagga aaataaaggt 3420
ttctgggaca ttgg 3434

<210> SEQ ID NO 33
<211> LENGTH: 3319
<212> TYPE: DNA
<213> ORGANISM: Mus musculus

<400> SEQUENCE: 33
agacccacgc cctgctccct ccgcccggca cctgcaggaa gggctggaac tgcctctgcg 60
tacccgccgc ccgtttccgc cctcccgctc ctcccacgcg tgccgcccgg gaccccgcag 120
caccgctgcc ccgatccgag ccctccaccc ccactccggt cccccctcctc tcttcccgga 180 agcgcggcgc gtggcggccc ggcggcgcgg attggacgcg tggcacctac agagacaccc 240
gggggggtgg gacggaggtg agcgagcgcc cgcggaggat gcggtgggga gccagctccg 300
ggagctgccc gcggtcgcgc gtggggccgt gcacgcggtg gggggaagcg cgtgcccttc 360
tccaagcgcg caccccgccg ccgagcccgt gagccctcgt agggtggtgg ccgcggcgag 420
tagaggcccc taacggctag cagaggaact gtgtcttgtc atcaggaacc ccatgcagcc 480
cgaacccaag cttagcgggg ctccccgcag cagccagttc ctgcccctgt ggtcaaagtg 540
ccccgagggg gccggggacg cagtgatgta tgcctccacg gagtgcaagg cagaggtgac 600
gccctcgcag gacggtaacc gaaccttcag ctacacacta gaggatcaca ccaagcaggc 660
ttttggcgtc atgaacgagc ttcgcctgag ccagcaactc tgtgacgtga ccctgcaggt 720
caaatatgag gacatcccag ctgcccaatt catggctcac aaagtggtgc tggcctcctc 780
cagcccagtc tttaaagcca tgttcaccaa cgggcttcgg gagcagggca tggaggtggt 840

-continued

```
gtccatcgaa ggcatccacc ctaaggtcat ggaaaggctt attgagttcg cctacacggc    900
ctccatctcc gtgggcgaga agtgtgtcct gcacgtgatg aacggggcgg tcatgtacca    960
gattgacagc gtggttcgag cctgcagcga cttcctcgtg cagcagctgg accccagcaa   1020
cgccattggc atcgccaact tcgcggagca gatcggctgc actgaactgc accagcgtgc   1080
ccgggagtat atctacatgc acttcgggga ggtggccaag caggaggagt tcttcaacct   1140
gtcacactgc cagctggcca cgctcatcag ccgggatgat ctgaacgtac gctgcgagtc   1200
cgaggtgttc cacgcgtgca tcgactgggt caaatacgac tgcccgcagc ggcgcttcta   1260
cgtgcaggca ctgctgcggg ccgtgcgctg ccatgcgctc acgccgcgct tcctgcagac   1320
gcagctgcag aagtgtgaga tcctgcaggc cgacgcgcgc tgcaaggact acctggtgca   1380
gatattccag gagctcacgc tgcacaagcc cacgcaggca gtgccctgcc gcgcgcccaa   1440
agtgggccgc ctcatctaca cagcgggcgg ttacttccga cagtcgctca gctacctgga   1500
ggcctacaac ccgagcaatg gctcctggct gcgcctggcc gatctacagg tgccgcgcag   1560
tgggctggca ggctgcgtgg tgggtgggct gctatacgct gtgggcggcc gcaacaactc   1620
tccggatggc aacactgact ccagcgccct ggactgctac aaccccatga ccaaccagtg   1680
gtcgccctgt gcctctatga gcgtgccacg caaccgcatc ggggtggggg tcatagatgg   1740
ccacatctac gcagtcgggg gttcccacgg ctgcatccac cacagcagcg tggagagata   1800
tgagccagag cgggacgagt ggcatctagt cgcgccaatg ttgacacgga ggattggcgt   1860
gggcgtggca gtgctcaacc gcttgctgta tgcagtgggg ggctttgacg ggactaaccg   1920
gcttaactcc gcagaatgtt actatccaga gaggaatgag tggcggatga tcacaccgat   1980
gaataccatc cggagcgggg ccggggtctg cgtgctgcac aactgtatct atgcagcagg   2040
gggctacgat gggcaggacc agttgaacag tgtggagcgc tacgacgtgg agacagagac   2100
ctggactttc gtagccccca tgaggcatca ccgtagtgcg ctggggatta ctgtgcacca   2160
gggcaagatc tacgtcctcg gaggctatga tggccacact tttctggaca gtgtggaatg   2220
ctatgacccg gacagtgata cctggagtga ggtgacccgc atgacatctg gccgcagcgg   2280
ggtgggtgtg gccgtcacca tggaaccctg tcggaagcaa attgatcaac aaaactgtac   2340
ctgctgaagc acttggaata cctgagcact gacaacagga cagaaaaaca gtctgtgtat   2400
cactgcttct ctgtactaaa gaaaaaagaa gaaaacaaag cataaacaga aaacacaggg   2460
ccgaagaggc ggcagaagaa gtcatccctt cttccaggaa gggcgactgg gatgccttgt   2520
aaaggacctt gtggaagacc agaactcaaa tccatgggcc catctgtcat agccctggag   2580
cgtccaagtc tgggatgggg tatgggcggg gcaccctcac aggtgagaag cccttgaact   2640
cccaccacca gaaggggggg gacaggcaaa gcaggagatc acatgttttt ttctttggtt   2700
cctgcaactc ggtgatcaat tccagtggac aggggaagaa gggacagctg aggccaaggg   2760
gctgaggctc cctctggaac tggggcccaa gggacaagcc ggcacagaga agcctctggg   2820
ctctgagccc tgaacagtta ttttgttaaa taaccctgta agtttcccat gggaataaag   2880
aatggagtag gcacacaggt cttcagaggg cggtcggaat ccctcaggga gagacagctc   2940
ttctattgaa atacacgcag atcctgatgg ggctggtatc tgaaacccgt ctattgtctc   3000
tgcttgccat tgtacattct gctcagacag ggcatcttgc ttcttgtggg acacacagtt   3060
gtctgtcagt ttcagggcat tagaagccaa tgacctaact tctgtgcctc ctaacttctc   3120
ctggggcctc ctgtgtttag ctttattttg aggcagggac tcacgtcgtc cgggatggcc   3180
ttcagttcag accttgaact gacgctgccg cctgtcccag cctaccgagt gctggggcta   3240
```

```
catctgtata gcgcaatgcc tggttcctgc ttattatttt tgtacccaag caggaaaata   3300

aaggtttctg ggacattgg                                                3319


<210> SEQ ID NO 34
<211> LENGTH: 3151
<212> TYPE: DNA
<213> ORGANISM: Mus musculus

<400> SEQUENCE: 34

agacccacgc cctgctccct ccgcccggca cctgcaggaa gggctggaac tgcctctgcg     60

tacccgccgc ccgtttccgc cctcccgctc ctcccacgcg tgccgcccgg gaccccgcag    120

caccgctgcc ccgatccgag ccctccaccc ccactccggt ccccctcctc tcttcccgga    180

agcgcggcgc gtggcggccc ggcggcgcgg attggacgcg tggcacctac agagacaccc    240

ggggggggtgg gacggaggcc cctaacggct agcagaggaa ctgtgtcttg tcatcaggaa   300

ccccatgcag cccgaaccca agcttagcgg ggctccccgc agcagccagt tcctgcccct    360

gtggtcaaag tgccccgagg gggccgggga cgcagtgatg tatgcctcca cggagtgcaa    420

ggcagaggtg acgccctcgc aggacggtaa ccgaaccttc agctacacac tagaggatca    480

caccaagcag gcttttggcg tcatgaacga gcttcgcctg agccagcaac tctgtgacgt    540

gaccctgcag gtcaaatatg aggacatccc agctgcccaa ttcatggctc acaaagtggt    600

gctggcctcc tccagcccag tctttaaagc catgttcacc aacgggcttc gggagcaggg    660

catggaggtg gtgtccatcg aaggcatcca ccctaaggtc atggaaaggc ttattgagtt    720

cgcctacacg gcctccatct ccgtgggcga gaagtgtgtc ctgcacgtga tgaacggggc    780

ggtcatgtac cagattgaca gcgtggttcg agcctgcagc gacttcctcg tgcagcagct    840

ggaccccagc aacgccattg gcatcgccaa cttcgcggag cagatcggct gcactgaact    900

gcaccagcgt gcccgggagt atatctacat gcacttcggg gaggtggcca agcaggagga    960

gttcttcaac ctgtcacact gccagctggc cacgctcatc agccgggatg atctgaacgt   1020

acgctgcgag tccgaggtgt tccacgcgtg catcgactgg gtcaaatacg actgcccgca   1080

gcggcgcttc tacgtgcagg cactgctgcg ggccgtgcgc tgccatgcgc tcacgccgcg   1140

cttcctgcag acgcagctgc agaagtgtga gatcctgcag gccgacgcgc gctgcaagga   1200

ctacctggtg cagatattcc aggagctcac gctgcacaag cccacgcagg cagtgccctg   1260

ccgcgcgccc aaagtgggcc gcctcatcta cacagcgggc ggttacttcc gacagtcgct   1320

cagctacctg gaggcctaca acccgagcaa tggctcctgg ctgcgcctgg ccgatctaca   1380

ggtgccgcgc agtgggctgg caggctgcgt ggtgggtggg ctgctatacg ctgtgggcgg   1440

ccgcaacaac tctccggatg gcaacactga ctccagcgcc ctggactgct acaaccccat   1500

gaccaaccag tggtcgccct gtgcctctat gagcgtgcca cgcaaccgca tcggggtggg   1560

ggtcatagat ggccacatct acgcagtcgg gggttcccac ggctgcatcc accacagcag   1620

cgtggagaga tatgagccag agcgggacga gtggcatcta gtcgcgccaa tgttgacacg   1680

gaggattggc gtgggcgtgg cagtgctcaa ccgcttgctg tatgcagtgg ggggctttga   1740

cgggactaac cggcttaact ccgcagaatg ttactatcca gagaggaatg agtggcggat   1800

gatcacaccg atgaatacca tccggagcgg ggccggggtc tgcgtgctgc acaactgtat   1860

ctatgcagca gggggctacg atgggcagga ccagttgaac agtgtggagc gctacgacgt   1920

ggagacagag acctggactt tcgtagcccc catgaggcat caccgtagtg cgctggggat   1980
```

-continued

```
tactgtgcac cagggcaaga tctacgtcct cggaggctat gatggccaca cttttctgga   2040

cagtgtggaa tgctatgacc cggacagtga tacctggagt gaggtgaccc gcatgacatc   2100

tggccgcagc ggggtgggtg tggccgtcac catggaaccc tgtcggaagc aaattgatca   2160

acaaaactgt acctgctgaa gcacttggaa tacctgagca ctgacaacag gacagaaaaa   2220

cagtctgtgt atcactgctt ctctgtacta aagaaaaaag aagaaaacaa agcataaaca   2280

gaaaacacag ggccgaagag gcggcagaag aagtcatccc ttcttccagg aagggcgact   2340

gggatgcctt gtaaaggacc ttgtggaaga ccagaactca aatccatggg cccatctgtc   2400

atagccctgg agcgtccaag tctgggatgg ggtatgggcg ggcaccctc acaggtgaga   2460

agcccttgaa ctcccaccac cagaaggggg gggacaggca aagcaggaga tcacatgttt   2520

ttttctttgg ttcctgcaac tcggtgatca attccagtgg acaggggaag aagggacagc   2580

tgaggccaag gggctgaggc tccctctgga actggggccc aagggacaag ccggcacaga   2640

gaagcctctg ggctctgagc cctgaacagt tattttgtta aataaccctg taagtttccc   2700

atgggaataa agaatggagt aggcacacag gtcttcagag ggcggtcgga atccctcagg   2760

gagagacagc tcttctattg aaatacacgc agatcctgat ggggctggta tctgaaaccc   2820

gtctattgtc tctgcttgcc attgtacatt ctgctcagac agggcatctt gcttcttgtg   2880

ggacacacag ttgtctgtca gtttcagggc attagaagcc aatgacctaa cttctgtgcc   2940

tcctaacttc tcctggggcc tcctgtgttt agctttattt tgaggcaggg actcacgtcg   3000

tccgggatgg ccttcagttc agaccttgaa ctgacgctgc cgcctgtccc agcctaccga   3060

gtgctggggc tacatctgta tagcgcaatg cctggttcct gcttattatt tttgtaccca   3120

agcaggaaaa taaaggtttc tgggacattg g                                  3151
```

<210> SEQ ID NO 35
<211> LENGTH: 4470
<212> TYPE: DNA
<213> ORGANISM: Mus musculus

<400> SEQUENCE: 35

```
agacccacgc cctgctccct ccgcccggca cctgcaggaa gggctggaac tgcctctgcg     60

tacccgccgc ccgtttccgc cctcccgctc ctcccacgcg tgccgcccgg gaccccgcag    120

caccgctgcc ccgatccgag ccctccaccc ccactccggt ccccctcctc tcttcccgga    180

agcgcggcgc gtggcggccc ggcggcgcgg attggacgcg tggcacctac agagacaccc    240

gggggggtgg gacggaggtg agcgagcgcc cgcggaggat gcggtgggga gccagctccg    300

ggagctgccc gcggtcgcgc gtggggccgt gcacgcggtg gggggaagcg cgtgcccttc    360

tccaagcgcg caccccgccg ccgagcccgt gagccctcgt agggtggtgg ccgcggcgag    420

tagaggtagg ggtcgcccgc ggccggcgcc ccgggactct tattgtgaca gggtggcgcg    480

ctgtgcttag tcaccgtgac ccgcgcggcg gaggcggagg cagagcgcgg ccatggcggg    540

gtgagtgagc cgctccaggc cgcggcccgg gaccaggccc tgcgggctct cccggcgtca    600

gggctgcgcc tccgagcggt ggggaggccg ctggagcagg cgccgggtac cgggcggccg    660

ctgcacagcc ccctgcgcaa tgccaggccc gagctccggc agtgtggtca cgcgtgacag    720

tcgctcacta gctggggccc ctggagcatt tcatcccccc cctccccacg gtgatctaat    780

agacaaaaca cgcggagtcg cgactccagg ctgagcccag aacctgggga gccagacgca    840

gaccctctct tgtctcccca catcttcttt gaaagcataa ttcctcccct ggccccaggt    900

ctccaagggt ctcctgaatc cctccccgtg ggtgttccag atgctgcaca ctctcttgcc    960
```

-continued

```
ccaggagctt ggtgttcgct tagtgtttcc tatacagacc ttgctttatt tttaggcctt   1020
ttctgtcttc tcgctgtgtc tctggagctc agagcagtcc caaatacata aatggcaggc   1080
tctgtaaatg ttggtgtggt gttgaaagga atctgacatg ttggacgaag gcaaggggag   1140
ggaaggatgg ctggaacagt gaagaggttg gaaagcgggt gtggagtttt acaggccatt   1200
gacgatttgg ggtttccatt cttgggctcg gtgaaaggtg ttgggtgatt ctgagcagga   1260
aaaggaacat gatatgccct gaaggcccgc gagttgagaa gttagtttga atggagccgg   1320
ctgtgtccag tttacttggc ttggcaaaat ctgcacttag atatcattgc ttagtcttgc   1380
aaaaaaagaa gcctggctgg acatggtggc acatactgta atcccagcac tcgggaggag   1440
ccagctttgg ttgcatagtg agttggaagc cagcctaggc tatgtaagac cctgtctcaa   1500
ataaaataaa ataaagtggc agggtctggt ctaacccagc ctctgttccc agcgctgtgc   1560
tcttccctcc ctccaggccc ctaacggcta gcagaggaac tgtgtcttgt catcaggaac   1620
cccatgcagc ccgaacccaa gcttagcggg gctccccgca gcagccagtt cctgcccctg   1680
tggtcaaagt gccccgaggg ggccggggac gcagtgatgt atgcctccac ggagtgcaag   1740
gcagaggtga cgccctcgca ggacggtaac cgaaccttca gctacacact agaggatcac   1800
accaagcagg cttttggcgt catgaacgag cttcgcctga gccagcaact ctgtgacgtg   1860
accctgcagg tcaaatatga ggacatccca gctgcccaat tcatggctca caaagtggtg   1920
ctggcctcct ccagcccagt ctttaaagcc atgttcacca acgggcttcg ggagcagggc   1980
atggaggtgg tgtccatcga aggcatccac cctaaggtca tggaaaggct tattgagttc   2040
gcctacacgg cctccatctc cgtgggcgag aagtgtgtcc tgcacgtgat gaacggggcg   2100
gtcatgtacc agattgacag cgtggttcga gcctgcagcg acttcctcgt gcagcagctg   2160
gaccccagca acgccattgg catcgccaac ttcgcggagc agatcggctg cactgaactg   2220
caccagcgtg cccgggagta tatctacatg cacttcgggg aggtggccaa gcaggaggag   2280
ttcttcaacc tgtcacactg ccagctggcc acgctcatca gccgggatga tctgaacgta   2340
cgctgcgagt ccgaggtgtt ccacgcgtgc atcgactggg tcaaatacga ctgcccgcag   2400
cggcgcttct acgtgcaggc actgctgcgg gccgtgcgct gccatgcgct cacgccgcgc   2460
ttcctgcaga cgcagctgca gaagtgtgag atcctgcagg ccgacgcgcg ctgcaaggac   2520
tacctggtgc agatattcca ggagctcacg ctgcacaagc ccacgcaggc agtgccctgc   2580
cgcgcgccca aagtgggccg cctcatctac acagcgggcg gttacttccg acagtcgctc   2640
agctacctgg aggcctacaa cccgagcaat ggctcctggc tgcgcctggc cgatctacag   2700
gtgccgcgca gtgggctggc aggctgcgtg gtgggtgggc tgctatacgc tgtgggcggc   2760
cgcaacaact ctccggatgg caacactgac tccagcgccc tggactgcta caaccccatg   2820
accaaccagt ggtcgccctg tgcctctatg agcgtgccac gcaaccgcat cggggtgggg   2880
gtcatagatg gccacatcta cgcagtcggg ggttcccacg gctgcatcca ccacagcagc   2940
gtggagagat atgagccaga gcgggacgag tggcatctag tcgcgccaat gttgacacgg   3000
aggattggcg tgggcgtggc agtgctcaac cgcttgctgt atgcagtggg gggctttgac   3060
gggactaacc ggcttaactc cgcagaatgt tactatccag agaggaatga gtggcggatg   3120
atcacaccga tgaataccat ccggagcggg gccggggtct gcgtgctgca caactgtatc   3180
tatgcagcag gggctacga tgggcaggac cagttgaaca gtgtggagcg ctacgacgtg   3240
gagacagaga cctggacttt cgtagccccc atgaggcatc accgtagtgc gctggggatt   3300
```

```
actgtgcacc agggcaagat ctacgtcctc ggaggctatg atggccacac ttttctggac   3360

agtgtggaat gctatgaccc ggacagtgat acctggagtg aggtgacccg catgacatct   3420

ggccgcagcg gggtgggtgt ggccgtcacc atggaaccct gtcggaagca aattgatcaa   3480

caaaactgta cctgctgaag cacttggaat acctgagcac tgacaacagg acagaaaaac   3540

agtctgtgta tcactgcttc tctgtactaa agaaaaaaga agaaaacaaa gcataaacag   3600

aaaacacagg gccgaagagg cggcagaaga agtcatccct tcttccagga agggcgactg   3660

ggatgccttg taaaggacct tgtggaagac cagaactcaa atccatgggc ccatctgtca   3720

tagccctgga gcgtccaagt ctgggatggg gtatgggcgg ggcaccctca caggtgagaa   3780

gcccttgaac tcccaccacc agaagggggg ggacaggcaa agcaggagat cacatgtttt   3840

tttctttggt tcctgcaact cggtgatcaa ttccagtgga caggggaaga agggacagct   3900

gaggccaagg ggctgaggct ccctctggaa ctggggccca agggacaagc cggcacagag   3960

aagcctctgg gctctgagcc ctgaacagtt attttgttaa ataaccctgt aagtttccca   4020

tgggaataaa gaatggagta ggcacacagg tcttcagagg gcggtcggaa tccctcaggg   4080

agagacagct cttctattga aatacacgca gatcctgatg gggctggtat ctgaaacccg   4140

tctattgtct ctgcttgcca ttgtacattc tgctcagaca gggcatcttg cttcttgtgg   4200

gacacacagt tgtctgtcag tttcagggca ttagaagcca atgacctaac ttctgtgcct   4260

cctaacttct cctggggcct cctgtgttta gctttatttt gaggcaggga ctcacgtcgt   4320

ccgggatggc cttcagttca gaccttgaac tgacgctgcc gcctgtccca gcctaccgag   4380

tgctggggct acatctgtat agcgcaatgc ctggttcctg cttattattt ttgtacccaa   4440

gcaggaaaat aaaggtttct gggacattgg                                    4470
```

<210> SEQ ID NO 36
<211> LENGTH: 624
<212> TYPE: PRT
<213> ORGANISM: Mus musculus

<400> SEQUENCE: 36

```
Met Gln Pro Glu Pro Lys Leu Ser Gly Ala Pro Arg Ser Ser Gln Phe
1               5                   10                  15

Leu Pro Leu Trp Ser Lys Cys Pro Glu Gly Ala Gly Asp Ala Val Met
            20                  25                  30

Tyr Ala Ser Thr Glu Cys Lys Ala Glu Val Thr Pro Ser Gln Asp Gly
        35                  40                  45

Asn Arg Thr Phe Ser Tyr Thr Leu Glu Asp His Thr Lys Gln Ala Phe
    50                  55                  60

Gly Val Met Asn Glu Leu Arg Leu Ser Gln Gln Leu Cys Asp Val Thr
65                  70                  75                  80

Leu Gln Val Lys Tyr Glu Asp Ile Pro Ala Ala Gln Phe Met Ala His
                85                  90                  95

Lys Val Val Leu Ala Ser Ser Ser Pro Val Phe Lys Ala Met Phe Thr
            100                 105                 110

Asn Gly Leu Arg Glu Gln Gly Met Glu Val Val Ser Ile Glu Gly Ile
        115                 120                 125

His Pro Lys Val Met Glu Arg Leu Ile Glu Phe Ala Tyr Thr Ala Ser
    130                 135                 140

Ile Ser Val Gly Glu Lys Cys Val Leu His Val Met Asn Gly Ala Val
145                 150                 155                 160

Met Tyr Gln Ile Asp Ser Val Val Arg Ala Cys Ser Asp Phe Leu Val
```

-continued

```
                165                 170                 175

Gln Gln Leu Asp Pro Ser Asn Ala Ile Gly Ile Ala Asn Phe Ala Glu
            180                 185                 190

Gln Ile Gly Cys Thr Glu Leu His Gln Arg Ala Arg Glu Tyr Ile Tyr
        195                 200                 205

Met His Phe Gly Glu Val Ala Lys Gln Glu Glu Phe Phe Asn Leu Ser
    210                 215                 220

His Cys Gln Leu Ala Thr Leu Ile Ser Arg Asp Asp Leu Asn Val Arg
225                 230                 235                 240

Cys Glu Ser Glu Val Phe His Ala Cys Ile Asp Trp Val Lys Tyr Asp
                245                 250                 255

Cys Pro Gln Arg Arg Phe Tyr Val Gln Ala Leu Leu Arg Ala Val Arg
            260                 265                 270

Cys His Ala Leu Thr Pro Arg Phe Leu Gln Thr Gln Leu Gln Lys Cys
        275                 280                 285

Glu Ile Leu Gln Ala Asp Ala Arg Cys Lys Asp Tyr Leu Val Gln Ile
    290                 295                 300

Phe Gln Glu Leu Thr Leu His Lys Pro Thr Gln Ala Val Pro Cys Arg
305                 310                 315                 320

Ala Pro Lys Val Gly Arg Leu Ile Tyr Thr Ala Gly Gly Tyr Phe Arg
                325                 330                 335

Gln Ser Leu Ser Tyr Leu Glu Ala Tyr Asn Pro Ser Asn Gly Ser Trp
            340                 345                 350

Leu Arg Leu Ala Asp Leu Gln Val Pro Arg Ser Gly Leu Ala Gly Cys
        355                 360                 365

Val Val Gly Gly Leu Leu Tyr Ala Val Gly Gly Arg Asn Asn Ser Pro
    370                 375                 380

Asp Gly Asn Thr Asp Ser Ser Ala Leu Asp Cys Tyr Asn Pro Met Thr
385                 390                 395                 400

Asn Gln Trp Ser Pro Cys Ala Ser Met Ser Val Pro Arg Asn Arg Ile
                405                 410                 415

Gly Val Gly Val Ile Asp Gly His Ile Tyr Ala Val Gly Gly Ser His
            420                 425                 430

Gly Cys Ile His His Ser Ser Val Glu Arg Tyr Glu Pro Glu Arg Asp
        435                 440                 445

Glu Trp His Leu Val Ala Pro Met Leu Thr Arg Arg Ile Gly Val Gly
    450                 455                 460

Val Ala Val Leu Asn Arg Leu Leu Tyr Ala Val Gly Gly Phe Asp Gly
465                 470                 475                 480

Thr Asn Arg Leu Asn Ser Ala Glu Cys Tyr Tyr Pro Glu Arg Asn Glu
                485                 490                 495

Trp Arg Met Ile Thr Pro Met Asn Thr Ile Arg Ser Gly Ala Gly Val
            500                 505                 510

Cys Val Leu His Asn Cys Ile Tyr Ala Ala Gly Gly Tyr Asp Gly Gln
        515                 520                 525

Asp Gln Leu Asn Ser Val Glu Arg Tyr Asp Val Glu Thr Glu Thr Trp
    530                 535                 540

Thr Phe Val Ala Pro Met Arg His His Arg Ser Ala Leu Gly Ile Thr
545                 550                 555                 560

Val His Gln Gly Lys Ile Tyr Val Leu Gly Gly Tyr Asp Gly His Thr
                565                 570                 575

Phe Leu Asp Ser Val Glu Cys Tyr Asp Pro Asp Ser Asp Thr Trp Ser
            580                 585                 590
```

```
Glu Val Thr Arg Met Thr Ser Gly Arg Ser Gly Val Gly Val Ala Val
        595                 600                 605

Thr Met Glu Pro Cys Arg Lys Gln Ile Asp Gln Gln Asn Cys Thr Cys
    610                 615                 620


<210> SEQ ID NO 37
<211> LENGTH: 624
<212> TYPE: PRT
<213> ORGANISM: Mus musculus

<400> SEQUENCE: 37

Met Gln Pro Glu Pro Lys Leu Ser Gly Ala Pro Arg Ser Ser Gln Phe
1               5                   10                  15

Leu Pro Leu Trp Ser Lys Cys Pro Glu Gly Ala Gly Asp Ala Val Met
            20                  25                  30

Tyr Ala Ser Thr Glu Cys Lys Ala Glu Val Thr Pro Ser Gln Asp Gly
        35                  40                  45

Asn Arg Thr Phe Ser Tyr Thr Leu Glu Asp His Thr Lys Gln Ala Phe
    50                  55                  60

Gly Val Met Asn Glu Leu Arg Leu Ser Gln Gln Leu Cys Asp Val Thr
65                  70                  75                  80

Leu Gln Val Lys Tyr Glu Asp Ile Pro Ala Ala Gln Phe Met Ala His
                85                  90                  95

Lys Val Val Leu Ala Ser Ser Ser Pro Val Phe Lys Ala Met Phe Thr
            100                 105                 110

Asn Gly Leu Arg Glu Gln Gly Met Glu Val Val Ser Ile Glu Gly Ile
        115                 120                 125

His Pro Lys Val Met Glu Arg Leu Ile Glu Phe Ala Tyr Thr Ala Ser
    130                 135                 140

Ile Ser Val Gly Glu Lys Cys Val Leu His Val Met Asn Gly Ala Val
145                 150                 155                 160

Met Tyr Gln Ile Asp Ser Val Val Arg Ala Cys Ser Asp Phe Leu Val
                165                 170                 175

Gln Gln Leu Asp Pro Ser Asn Ala Ile Gly Ile Ala Asn Phe Ala Glu
            180                 185                 190

Gln Ile Gly Cys Thr Glu Leu His Gln Arg Ala Arg Glu Tyr Ile Tyr
        195                 200                 205

Met His Phe Gly Glu Val Ala Lys Gln Glu Glu Phe Phe Asn Leu Ser
    210                 215                 220

His Cys Gln Leu Ala Thr Leu Ile Ser Arg Asp Asp Leu Asn Val Arg
225                 230                 235                 240

Cys Glu Ser Glu Val Phe His Ala Cys Ile Asp Trp Val Lys Tyr Asp
                245                 250                 255

Cys Pro Gln Arg Arg Phe Tyr Val Gln Ala Leu Leu Arg Ala Val Arg
            260                 265                 270

Cys His Ala Leu Thr Pro Arg Phe Leu Gln Thr Gln Leu Gln Lys Cys
        275                 280                 285

Glu Ile Leu Gln Ala Asp Ala Arg Cys Lys Asp Tyr Leu Val Gln Ile
    290                 295                 300

Phe Gln Glu Leu Thr Leu His Lys Pro Thr Gln Ala Val Pro Cys Arg
305                 310                 315                 320

Ala Pro Lys Val Gly Arg Leu Ile Tyr Thr Ala Gly Gly Tyr Phe Arg
                325                 330                 335

Gln Ser Leu Ser Tyr Leu Glu Ala Tyr Asn Pro Ser Asn Gly Ser Trp
```

-continued

```
            340                 345                 350

Leu Arg Leu Ala Asp Leu Gln Val Pro Arg Ser Gly Leu Ala Gly Cys
        355                 360                 365

Val Val Gly Gly Leu Leu Tyr Ala Val Gly Gly Arg Asn Asn Ser Pro
    370                 375                 380

Asp Gly Asn Thr Asp Ser Ser Ala Leu Asp Cys Tyr Asn Pro Met Thr
385                 390                 395                 400

Asn Gln Trp Ser Pro Cys Ala Ser Met Ser Val Pro Arg Asn Arg Ile
                405                 410                 415

Gly Val Gly Val Ile Asp Gly His Ile Tyr Ala Val Gly Gly Ser His
            420                 425                 430

Gly Cys Ile His His Ser Ser Val Glu Arg Tyr Glu Pro Glu Arg Asp
        435                 440                 445

Glu Trp His Leu Val Ala Pro Met Leu Thr Arg Arg Ile Gly Val Gly
    450                 455                 460

Val Ala Val Leu Asn Arg Leu Leu Tyr Ala Val Gly Gly Phe Asp Gly
465                 470                 475                 480

Thr Asn Arg Leu Asn Ser Ala Glu Cys Tyr Tyr Pro Glu Arg Asn Glu
                485                 490                 495

Trp Arg Met Ile Thr Pro Met Asn Thr Ile Arg Ser Gly Ala Gly Val
            500                 505                 510

Cys Val Leu His Asn Cys Ile Tyr Ala Ala Gly Gly Tyr Asp Gly Gln
        515                 520                 525

Asp Gln Leu Asn Ser Val Glu Arg Tyr Asp Val Glu Thr Glu Thr Trp
    530                 535                 540

Thr Phe Val Ala Pro Met Arg His His Arg Ser Ala Leu Gly Ile Thr
545                 550                 555                 560

Val His Gln Gly Lys Ile Tyr Val Leu Gly Gly Tyr Asp Gly His Thr
                565                 570                 575

Phe Leu Asp Ser Val Glu Cys Tyr Asp Pro Asp Ser Asp Thr Trp Ser
            580                 585                 590

Glu Val Thr Arg Met Thr Ser Gly Arg Ser Gly Val Gly Val Ala Val
        595                 600                 605

Thr Met Glu Pro Cys Arg Lys Gln Ile Asp Gln Gln Asn Cys Thr Cys
    610                 615                 620


<210> SEQ ID NO 38
<211> LENGTH: 624
<212> TYPE: PRT
<213> ORGANISM: Mus musculus

<400> SEQUENCE: 38

Met Gln Pro Glu Pro Lys Leu Ser Gly Ala Pro Arg Ser Ser Gln Phe
1               5                   10                  15

Leu Pro Leu Trp Ser Lys Cys Pro Glu Gly Ala Gly Asp Ala Val Met
            20                  25                  30

Tyr Ala Ser Thr Glu Cys Lys Ala Glu Val Thr Pro Ser Gln Asp Gly
        35                  40                  45

Asn Arg Thr Phe Ser Tyr Thr Leu Glu Asp His Thr Lys Gln Ala Phe
    50                  55                  60

Gly Val Met Asn Glu Leu Arg Leu Ser Gln Gln Leu Cys Asp Val Thr
65                  70                  75                  80

Leu Gln Val Lys Tyr Glu Asp Ile Pro Ala Ala Gln Phe Met Ala His
                85                  90                  95
```

-continued

Lys Val Val Leu Ala Ser Ser Ser Pro Val Phe Lys Ala Met Phe Thr
100 105 110

Asn Gly Leu Arg Glu Gln Gly Met Glu Val Val Ser Ile Glu Gly Ile
115 120 125

His Pro Lys Val Met Glu Arg Leu Ile Glu Phe Ala Tyr Thr Ala Ser
130 135 140

Ile Ser Val Gly Glu Lys Cys Val Leu His Val Met Asn Gly Ala Val
145 150 155 160

Met Tyr Gln Ile Asp Ser Val Val Arg Ala Cys Ser Asp Phe Leu Val
165 170 175

Gln Gln Leu Asp Pro Ser Asn Ala Ile Gly Ile Ala Asn Phe Ala Glu
180 185 190

Gln Ile Gly Cys Thr Glu Leu His Gln Arg Ala Arg Glu Tyr Ile Tyr
195 200 205

Met His Phe Gly Glu Val Ala Lys Gln Glu Glu Phe Phe Asn Leu Ser
210 215 220

His Cys Gln Leu Ala Thr Leu Ile Ser Arg Asp Asp Leu Asn Val Arg
225 230 235 240

Cys Glu Ser Glu Val Phe His Ala Cys Ile Asp Trp Val Lys Tyr Asp
245 250 255

Cys Pro Gln Arg Arg Phe Tyr Val Gln Ala Leu Leu Arg Ala Val Arg
260 265 270

Cys His Ala Leu Thr Pro Arg Phe Leu Gln Thr Gln Leu Gln Lys Cys
275 280 285

Glu Ile Leu Gln Ala Asp Ala Arg Cys Lys Asp Tyr Leu Val Gln Ile
290 295 300

Phe Gln Glu Leu Thr Leu His Lys Pro Thr Gln Ala Val Pro Cys Arg
305 310 315 320

Ala Pro Lys Val Gly Arg Leu Ile Tyr Thr Ala Gly Gly Tyr Phe Arg
325 330 335

Gln Ser Leu Ser Tyr Leu Glu Ala Tyr Asn Pro Ser Asn Gly Ser Trp
340 345 350

Leu Arg Leu Ala Asp Leu Gln Val Pro Arg Ser Gly Leu Ala Gly Cys
355 360 365

Val Val Gly Gly Leu Leu Tyr Ala Val Gly Gly Arg Asn Asn Ser Pro
370 375 380

Asp Gly Asn Thr Asp Ser Ser Ala Leu Asp Cys Tyr Asn Pro Met Thr
385 390 395 400

Asn Gln Trp Ser Pro Cys Ala Ser Met Ser Val Pro Arg Asn Arg Ile
405 410 415

Gly Val Gly Val Ile Asp Gly His Ile Tyr Ala Val Gly Gly Ser His
420 425 430

Gly Cys Ile His His Ser Ser Val Glu Arg Tyr Glu Pro Glu Arg Asp
435 440 445

Glu Trp His Leu Val Ala Pro Met Leu Thr Arg Arg Ile Gly Val Gly
450 455 460

Val Ala Val Leu Asn Arg Leu Leu Tyr Ala Val Gly Gly Phe Asp Gly
465 470 475 480

Thr Asn Arg Leu Asn Ser Ala Glu Cys Tyr Tyr Pro Glu Arg Asn Glu
485 490 495

Trp Arg Met Ile Thr Pro Met Asn Thr Ile Arg Ser Gly Ala Gly Val
500 505 510

Cys Val Leu His Asn Cys Ile Tyr Ala Ala Gly Gly Tyr Asp Gly Gln 515 520 525

Asp Gln Leu Asn Ser Val Glu Arg Tyr Asp Val Glu Thr Glu Thr Trp
530 535 540

Thr Phe Val Ala Pro Met Arg His His Arg Ser Ala Leu Gly Ile Thr
545 550 555 560

Val His Gln Gly Lys Ile Tyr Val Leu Gly Gly Tyr Asp Gly His Thr
565 570 575

Phe Leu Asp Ser Val Glu Cys Tyr Asp Pro Asp Ser Asp Thr Trp Ser
580 585 590

Glu Val Thr Arg Met Thr Ser Gly Arg Ser Gly Val Gly Val Ala Val
595 600 605

Thr Met Glu Pro Cys Arg Lys Gln Ile Asp Gln Gln Asn Cys Thr Cys
610 615 620

<210> SEQ ID NO 39
<211> LENGTH: 624
<212> TYPE: PRT
<213> ORGANISM: Mus musculus

<400> SEQUENCE: 39

Met Gln Pro Glu Pro Lys Leu Ser Gly Ala Pro Arg Ser Ser Gln Phe
1 5 10 15

Leu Pro Leu Trp Ser Lys Cys Pro Glu Gly Ala Gly Asp Ala Val Met
20 25 30

Tyr Ala Ser Thr Glu Cys Lys Ala Glu Val Thr Pro Ser Gln Asp Gly
35 40 45

Asn Arg Thr Phe Ser Tyr Thr Leu Glu Asp His Thr Lys Gln Ala Phe
50 55 60

Gly Val Met Asn Glu Leu Arg Leu Ser Gln Gln Leu Cys Asp Val Thr
65 70 75 80

Leu Gln Val Lys Tyr Glu Asp Ile Pro Ala Ala Gln Phe Met Ala His
85 90 95

Lys Val Val Leu Ala Ser Ser Ser Pro Val Phe Lys Ala Met Phe Thr
100 105 110

Asn Gly Leu Arg Glu Gln Gly Met Glu Val Val Ser Ile Glu Gly Ile
115 120 125

His Pro Lys Val Met Glu Arg Leu Ile Glu Phe Ala Tyr Thr Ala Ser
130 135 140

Ile Ser Val Gly Glu Lys Cys Val Leu His Val Met Asn Gly Ala Val
145 150 155 160

Met Tyr Gln Ile Asp Ser Val Val Arg Ala Cys Ser Asp Phe Leu Val
165 170 175

Gln Gln Leu Asp Pro Ser Asn Ala Ile Gly Ile Ala Asn Phe Ala Glu
180 185 190

Gln Ile Gly Cys Thr Glu Leu His Gln Arg Ala Arg Glu Tyr Ile Tyr
195 200 205

Met His Phe Gly Glu Val Ala Lys Gln Glu Glu Phe Phe Asn Leu Ser
210 215 220

His Cys Gln Leu Ala Thr Leu Ile Ser Arg Asp Asp Leu Asn Val Arg
225 230 235 240

Cys Glu Ser Glu Val Phe His Ala Cys Ile Asp Trp Val Lys Tyr Asp
245 250 255

Cys Pro Gln Arg Arg Phe Tyr Val Gln Ala Leu Leu Arg Ala Val Arg
260 265 270

-continued

```
Cys His Ala Leu Thr Pro Arg Phe Leu Gln Thr Gln Leu Gln Lys Cys
        275                 280                 285

Glu Ile Leu Gln Ala Asp Ala Arg Cys Lys Asp Tyr Leu Val Gln Ile
    290                 295                 300

Phe Gln Glu Leu Thr Leu His Lys Pro Thr Gln Ala Val Pro Cys Arg
305                 310                 315                 320

Ala Pro Lys Val Gly Arg Leu Ile Tyr Thr Ala Gly Gly Tyr Phe Arg
                325                 330                 335

Gln Ser Leu Ser Tyr Leu Glu Ala Tyr Asn Pro Ser Asn Gly Ser Trp
            340                 345                 350

Leu Arg Leu Ala Asp Leu Gln Val Pro Arg Ser Gly Leu Ala Gly Cys
        355                 360                 365

Val Val Gly Gly Leu Leu Tyr Ala Val Gly Gly Arg Asn Asn Ser Pro
    370                 375                 380

Asp Gly Asn Thr Asp Ser Ser Ala Leu Asp Cys Tyr Asn Pro Met Thr
385                 390                 395                 400

Asn Gln Trp Ser Pro Cys Ala Ser Met Ser Val Pro Arg Asn Arg Ile
                405                 410                 415

Gly Val Gly Val Ile Asp Gly His Ile Tyr Ala Val Gly Gly Ser His
            420                 425                 430

Gly Cys Ile His His Ser Ser Val Glu Arg Tyr Glu Pro Glu Arg Asp
        435                 440                 445

Glu Trp His Leu Val Ala Pro Met Leu Thr Arg Arg Ile Gly Val Gly
    450                 455                 460

Val Ala Val Leu Asn Arg Leu Leu Tyr Ala Val Gly Gly Phe Asp Gly
465                 470                 475                 480

Thr Asn Arg Leu Asn Ser Ala Glu Cys Tyr Tyr Pro Glu Arg Asn Glu
                485                 490                 495

Trp Arg Met Ile Thr Pro Met Asn Thr Ile Arg Ser Gly Ala Gly Val
            500                 505                 510

Cys Val Leu His Asn Cys Ile Tyr Ala Ala Gly Gly Tyr Asp Gly Gln
        515                 520                 525

Asp Gln Leu Asn Ser Val Glu Arg Tyr Asp Val Glu Thr Glu Thr Trp
    530                 535                 540

Thr Phe Val Ala Pro Met Arg His His Arg Ser Ala Leu Gly Ile Thr
545                 550                 555                 560

Val His Gln Gly Lys Ile Tyr Val Leu Gly Gly Tyr Asp Gly His Thr
                565                 570                 575

Phe Leu Asp Ser Val Glu Cys Tyr Asp Pro Asp Ser Asp Thr Trp Ser
            580                 585                 590

Glu Val Thr Arg Met Thr Ser Gly Arg Ser Gly Val Gly Val Ala Val
        595                 600                 605

Thr Met Glu Pro Cys Arg Lys Gln Ile Asp Gln Gln Asn Cys Thr Cys
    610                 615                 620
```